US008557540B2

(12) United States Patent
Burlew et al.

(10) Patent No.: US 8,557,540 B2
(45) Date of Patent: Oct. 15, 2013

(54) METHODS AND SYSTEMS FOR REMOVING UNDISSOLVED SOLIDS PRIOR TO EXTRACTIVE FERMENTATION IN THE PRODUCTION OF BUTANOL

(75) Inventors: Keith H. Burlew, Middletown, DE (US); Michael Charles Grady, Oaklyn, NJ (US); John W. Hallam, Bear, DE (US); David J. Lowe, Wilmington, DE (US); Brian Michael Roesch, Middletown, DE (US); Joseph J. Zaher, Newark, DE (US)

(73) Assignee: Butamax (TM) Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 13/163,243

(22) Filed: Jun. 17, 2011

(65) Prior Publication Data

US 2012/0164302 A1 Jun. 28, 2012

Related U.S. Application Data

(60) Provisional application No. 61/356,290, filed on Jun. 18, 2010, provisional application No. 61/368,451, filed on Jul. 28, 2010, provisional application No. 61/368,436, filed on Jul. 28, 2010, provisional application No. 61/368,444, filed on Jul. 28, 2010, provisional application No. 61/368,429, filed on Jul. 28, 2010, provisional application No. 61/379,546, filed on Sep. 2, 2010, provisional application No. 61/440,034, filed on Feb. 7, 2011.

(51) Int. Cl.

| | |
|---|---|
| ***C12P 7/16*** | (2006.01) |
| ***C12P 7/04*** | (2006.01) |
| ***C12P 7/06*** | (2006.01) |
| ***C12P 1/00*** | (2006.01) |
| ***C12M 1/00*** | (2006.01) |
| ***C12M 3/00*** | (2006.01) |
| ***A23J 1/14*** | (2006.01) |

(52) U.S. Cl.

USPC .......... 435/41; 435/157; 435/161; 435/294.1; 435/160; 426/656

(58) Field of Classification Search

None

See application file for complete search history.

(56) References Cited

U.S. PATENT DOCUMENTS

| | | | | |
|---|---|---|---|---|
| 4,491,522 | A | 1/1985 | Ishida et al. | |
| 4,865,973 | A * | 9/1989 | Kollerup et al. | 435/43 |
| 5,221,357 | A | 6/1993 | Brink | |
| 5,514,583 | A | 5/1996 | Picataggio et al. | |
| 5,712,133 | A | 1/1998 | Picataggio et al. | |
| 6,509,051 | B1 | 1/2003 | Wills | |
| 6,660,506 | B2 | 12/2003 | Nguyen et al. | |
| 6,703,227 | B2 | 3/2004 | Jakel et al. | |
| 6,732,454 | B2 | 5/2004 | Anderson et al. | |
| 6,766,595 | B2 | 7/2004 | Anderson | |
| 6,996,917 | B2 | 2/2006 | Anderson | |
| 7,083,954 | B2 | 8/2006 | Jakel et al. | |
| 7,148,366 | B2 | 12/2006 | Cheryan | |
| 7,223,575 | B2 | 5/2007 | Zhang et al. | |
| 7,455,997 | B2 | 11/2008 | Hughes | |
| 7,481,890 | B2 | 1/2009 | Cheryan | |
| 7,608,729 | B2 | 10/2009 | Winsness et al. | |
| 7,666,282 | B2 | 2/2010 | Sylvester et al. | |
| 7,741,119 | B2 | 6/2010 | Viitanen et al. | |
| 7,851,188 | B2 | 12/2010 | Donaldson et al. | |
| 7,888,082 | B2 | 2/2011 | Verser et al. | |
| 2005/0272134 | A1 | 12/2005 | Hughes | |
| 2006/0173169 | A1 | 8/2006 | Cheryan | |
| 2007/0014905 | A1 * | 1/2007 | Chen et al. | 426/490 |
| 2007/0031918 | A1 | 2/2007 | Dunson, Jr. et al. | |
| 2007/0092957 | A1 * | 4/2007 | Donaldson et al. | 435/157 |
| 2008/0032344 | A1 | 2/2008 | Fallavollita | |
| 2008/0121742 | A1 | 5/2008 | Foster | |
| 2008/0261230 | A1 | 10/2008 | Liao et al. | |
| 2009/0029432 | A1 * | 1/2009 | Abbas et al. | 435/165 |
| 2009/0061490 | A1 | 3/2009 | Edwards et al. | |
| 2009/0163376 | A1 | 6/2009 | Li et al. | |
| 2009/0171129 | A1 | 7/2009 | Evanko et al. | |
| 2009/0176286 | A1 | 7/2009 | O'Connor et al. | |
| 2009/0181153 | A1 | 7/2009 | Bendorf et al. | |
| 2009/0203099 | A1 | 8/2009 | Caimi et al. | |
| 2009/0209009 | A1 | 8/2009 | Tolan et al. | |

(Continued)

FOREIGN PATENT DOCUMENTS

| | | |
|---|---|---|
| DE | 102006040567 | 3/2008 |
| WO | 9528476 | 10/1995 |

(Continued)

OTHER PUBLICATIONS

Davison, BH et al. Continuous Direct Solvent Extranction of Butanol in a Fermenting Fluidized-Bed Bioreactor with Immobilized Clostridium acetobutylicum. Applied Biochemistry and Biotechnology. 1993 vol. 39/40. p. 415-426.*

Gunt Hamburg. Thermal Processing Engineering. Gunt Hamburg. 2009. p. 1.*

Machine Translation of DE102006040567; 2008, 15 pages.*

International Search Report for PCT/US2009/046278, 5 pages; mailing date Mar. 3, 2010.*

Ohgren, K et al. Simultaneous saccharification and co-fermentation of glucose and xylose in steam-pretreated corn stover at high fiber content with Saccharomyces cerevisiae TMB3400. Journal of Bacteriology. 2006. 126. p. 488-498.*

U.S. Appl. No. 13/227,016, filed Sep. 7, 2011.

Feldmann, et al., Pentose Metabolism in Zymomonas Mobilis Wildtype and Recombinant Strains, Applied Microbiology and Biotechnology, 1992, 354-361, 38.

(Continued)

*Primary Examiner* — David J Steadman
*Assistant Examiner* — Paul Holland
(74) *Attorney, Agent, or Firm* — Christine M. Lhulier

(57) ABSTRACT

A method and system for efficiently producing a fermentative product alcohol such as butanol utilizing in situ product extraction are provided. The efficiency is obtained through separating undissolved solids after liquefying a given feedstock to create a feedstock and prior to fermentation, for example, through centrifugation. Removal of the undissolved solids avoids problems associated with having the undissolved solids present during in situ production extraction, and thereby increases the efficiency of the alcohol production.

21 Claims, 13 Drawing Sheets

(56) References Cited

U.S. PATENT DOCUMENTS

| | | | |
|---|---|---|---|
| 2009/0246846 | A1 | 10/2009 | Viitanen et al. |
| 2009/0259078 | A1 | 10/2009 | Schucker |
| 2009/0269823 | A1 | 10/2009 | Bramucci et al. |
| 2009/0305363 | A1 | 12/2009 | Anthony et al. |
| 2009/0305370 | A1 | 12/2009 | Grady et al. |
| 2010/0058649 | A1 | 3/2010 | Bootsma |
| 2010/0081154 | A1 | 4/2010 | Flint et al. |
| 2010/0092603 | A1 | 4/2010 | Bruinsma et al. |
| 2010/0144001 | A1 | 6/2010 | Horton |
| 2010/0196980 | A1 | 8/2010 | Smith et al. |
| 2010/0197519 | A1 | 8/2010 | Li et al. |
| 2010/0273228 | A1 | 10/2010 | Sant'Anna et al. |
| 2010/0319424 | A1 | 12/2010 | Wietgrefe |
| 2011/0008863 | A1 | 1/2011 | Zhu et al. |
| 2011/0124060 | A1 | 5/2011 | Anthony et al. |
| 2011/0244536 | A1 | 10/2011 | Nagarajan et al. |
| 2012/0015416 | A1 | 1/2012 | Anthony et al. |
| 2012/0051980 | A1 | 3/2012 | Gallop et al. |

FOREIGN PATENT DOCUMENTS

| | | |
|---|---|---|
| WO | 2008025522 | 3/2008 |
| WO | 2008086115 | 7/2008 |
| WO | WO2009015333 | 1/2009 |
| WO | 2009026706 | 3/2009 |
| WO | 2009149270 | 10/2009 |
| WO | 2010075241 | 7/2010 |
| WO | 2011020082 | 2/2011 |
| WO | WO2012036857 | 3/2012 |

OTHER PUBLICATIONS

Hahnai, et al., Engineered synthetic Pathway for Isopropanol Production in *Escherichia coli*, Applied Environmental Microbiology, 2007, 7814-7818, 73.

Lynd, Microbial Cellulose Utilization: Fundamentals and Biotechnology, Microbiology Molecular Biological Review, 2002, 506-577, 66.

Methods in Yeast Genetics, 2005 Cold Spring Harbor Laboratory Press, Cold Spring Harbor, NY, pp. 201-202.

Ohta, et al., Genetic Improvement of *Escherichia coli* for Ethanol Production: Chromosomal Integration of Zymomonas Mobilis Genes Encoding Pyruvate Decarboxylase and Alcohol dehydrogenase II, Applied Environmental Microbiology, 199, 893-900, 57, 1991.

Shen et al., Metabolic Engineering of *Escherichia coli* for 1-Butanol and 1-Propanol Production via the Keto-acid Pathways, Metabolic Engineering, 2008, 312-320, 10.

Underwood, et al., Flux through Citrate synthase Limits the Growth of Ethanologenic *Escherichia coli* KO11 during Xylose Fermentation, Applied Environmental Microbiology, 2002, 1071-1081, 68.

Zhang, et al., Metabolic Engineering of a Pentose Metabolism Pathway in Ethanologenic Zymomonas Mobilis, Science 267:240-243, 1995.

Singh et al., Extraction of Oil from Corn Distillers Dried Grains with Solubles, Transactions of the ASAE, vol. 41(6) 1775-1777, 1998.

International Search Report and Written Opinion of corresponding PCT/US2011/040899 mailed Dec. 28, 2011.

* cited by examiner

METHODS AND SYSTEMS FOR REMOVING UNDISSOLVED SOLIDS PRIOR TO EXTRACTIVE FERMENTATION IN THE PRODUCTION OF BUTANOL

This application claims the benefit of U.S. Provisional Application No. 61/356,290, filed on Jun. 18, 2010; U.S. Provisional Application No. 61/368,451, filed on Jul. 28, 2010; U.S. Provisional Application No. 61/368,436, filed on Jul. 28, 2010; U.S. Provisional Application No. 61/368,444, filed on Jul. 28, 2010; U.S. Provisional Application No. 61/368,429, filed on Jul. 28, 2010; U.S. Provisional Application No. 61/379,546, filed on Sep. 2, 2010; and U.S. Provisional Application No. 61/440,034, filed on Feb. 7, 2011; U.S. patent application Ser. No. 13/160,766, filed on Jun. 15, 2011; the entire contents of which are all herein incorporated by reference.

The Sequence Listing associated with this application is filed in electronic form via EFS-Web and hereby incorporated by reference into the specification in its entirety.

FIELD OF THE INVENTION

The present invention relates to processes and systems for removing undissolved solids from a fermentor feed stream in the production of fermentative alcohols such as butanol.

BACKGROUND OF THE INVENTION

Background Art

Butanol is an important industrial chemical with a variety of applications, including use as a fuel additive, as a feedstock chemical in the plastics industry, and as a food-grade extractant in the food and flavor industry. Accordingly, there is a high demand for butanol, as well as for efficient and environmentally friendly production methods.

Production of butanol utilizing fermentation by microorganisms is one such environmentally friendly production method. Some microorganisms that produce butanol in high yields also have low butanol toxicity thresholds, such that butanol needs to be removed from the fermentor as it is being produced. In situ product removal (ISPR) may be used to remove butanol from the fermentor as it is produced, thereby allowing the microorganism to produce butanol at high yields. One method for ISPR that has been described in the art is liquid-liquid extraction (U.S. Patent Application Publication No. 2009/0305370). In order to be technically and economically viable, liquid-liquid extraction requires contact between the extractant and the fermentation broth for efficient mass transfer; phase separation of the extractant from the fermentation broth (during and after fermentation); and/or efficient recovery and recycle of the solvent and minimal degradation and/or contamination of the extractant over a long-term operation.

When the aqueous stream entering the fermentor contains undissolved solids from the feedstock, the undissolved solids interfere with the requirements noted above for liquid-liquid extraction to be technically and economically viable by increasing capital and operating costs. In particular, the presence of the undissolved solids during extractive fermentation may lower the mass transfer coefficient inside the fermentor, impede phase separation in the fermentor, may result in the accumulation of oil (e.g., corn oil) from the undissolved solids in the extractant leading to reduced extraction efficiency over time, may increase the loss of solvent because it becomes trapped in solids ultimately removed as Dried Distillers' Grains with Solubles (DDGS), may slow the disengagement of extractant drops from the fermentation broth, and/or may result in a lower fermentor volume efficiency. Thus, there is a continuing need to develop more efficient methods and systems for producing product alcohols such as butanol through extractive fermentation.

The present invention satisfies the above need and provides methods and systems for producing product alcohols such as butanol by decreasing the amount of undissolved solids that are fed to the fermentor.

BRIEF SUMMARY OF THE INVENTION

The present invention relates to processes and systems for removing undissolved solids from a fermentor feed stream in the production of fermentative alcohols such as butanol.

The present invention is directed to a method comprising providing a biomass feedstock slurry comprising fermentable carbon source, undissolved solids, and water; separating at least a portion of the undissolved solids from said slurry whereby (i) an aqueous solution comprising fermentable carbon source and (ii) a wet cake co-product comprising solids are, generated; and adding the aqueous solution to a fermentation broth comprising recombinant microorganisms in a fermentation vessel whereby a fermentative product is produced; wherein the biomass processing productivity is improved. In some embodiments, the improved biomass processing productivity comprises improved fermentative product and co-product recoverability relative to a fermentative product produced in the presence of undissolved solids. In some embodiments, the improved biomass processing productivity includes one or more of increased process stream recyclability, increased fermentor volume efficiency, and increased biomass feedstock load feeding. In some embodiments, the method further comprising contacting the fermentation broth with an extractant wherein the extractant has increased extraction efficiency relative to a fermentation broth comprising undissolved solids. In some embodiments, increased extraction efficiency includes one or more of stabilized partition coefficient of the extractant, enhanced phase separation of the extractant from the fermentation broth, enhanced liquid-liquid mass transfer coefficient, increased extractant recovery and recyclability, and preserved extractant for recovery and recycle. In some embodiments, the extractant is an organic extractant. In some embodiments, the extractant comprises one or more immiscible organic extractants selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof. In some embodiments, the extractant comprises $C_{12}$ to $C_{22}$ fatty acids derived from corn oil. In some embodiments, the undissolved solids are separated from feedstock slurry by decanter bowl centrifugation, Tricanter® (three-phase centrifuge) centrifugation, disk stack centrifugation, filtering centrifugation, decanter centrifugation, filtration, vacuum filtration, beltfilter, pressure filtration, filtration using a screen, screen separation, grating, porous grating, flotation, hydroclone, filter press, sciewpress, gravity settler, vortex separator, or combination thereof. In some embodiments, the method further comprising the step of liquefying a feedstock to create a biomass feedstock slurry; wherein the feedstock is selected from corn grain, corn, cobs, crop residues such as corn husks, corn stover, grasses, corn, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, and mixtures thereof. In some embodiments, the feedstock is corn. In some embodiments, the feedstock is fractionated of unfractionated. In some embodiments, the feedstock is wet milled or dry milled. In some embodiments, the method further comprising the step of increasing the reaction temperature during liquefaction. In some embodiments, the feedstock slurry comprises oil from the feedstock and said oil is separated from the slurry. In some embodiments, the wet cake comprises feedstock oil. In some embodiments, the wet cake is washed with water to recover oligosaccharides present in the wet cake. In some embodiments, the recovered oligosaccharides are added to the fermentation vessel. In some embodiments, the wet cake is further processed to provide an improved co-product. In some embodiments, the co-product is further processed to form an animal feed product. In some embodiments, the wet cake is washed with solvent to recover oil present in the wet cake. In some embodiments, the solvent is selected from hexane, butanol, isobutanol, isohexane, ethanol, and petroleum distillates. In some embodiments, the fermentative product is a product alcohol selected from the group consisting of methanol, ethanol, propanol, butanol, pentanol, and isomers thereof In some embodiments, the recombinant microorganism comprises an engineered butanol biosynthetic pathway. In some embodiments, the method further comprising at least partially vaporizing the fermentation broth and product and optionally $CO_2$ wherein a vapor stream is produced and recover the, product from the vapor stream. In some embodiments, the method further comprises contacting the vapor stream with an absorption liquid phase wherein at least a portion of the vapor stream is absorbed into the absorption liquid phase; wherein the temperature of the onset of the absorption of the vapor stream into the absorption liquid phase is greater than the temperature of the onset of condensation of the vapor stream in the absence of the absorption liquid phase. In some embodiments, the vaporizing and contacting, steps are carried out under vacuum conditions. In some embodiments, the separating a substantial portion of the undissolved solids from said slurry provides for a higher vapor pressure of the fermentation broth relative to a fermentation broth comprising undissolved solids. In some embodiments, the higher vapor pressure provides for more efficient vaporization product recovery. In some embodiments, the more efficient vaporization product recovery includes one or more of lower capital investment, smaller vaporization, absorption, compression, and refrigeration equipment, improved mass transfer rates, less energy for vaporization, and lower absorbent flow rate.

The present invention is also directed to method for producing butanol comprising providing a feedstock; liquefying the feedstock to create a feedstock slurry, wherein the feedstock slurry comprises oligosaccharides, oil, and undissolved solids; separating undissolved solids from the feedstock slurry to create (i) an aqueous solution comprising oligosaccharides, (ii) a wet cake comprising undissolved solids, and (iii) an oil phase; contacting the aqueous solution with a fermentation broth in a fermentor; fermenting the oligosaccharides in the fermentor to produce butanol; and performing in situ removal of the butanol from the fermentation broth as the butanol is produced, wherein removal of the undissolved solids from the feedstock slurry increases the efficiency of the butanol production. In some embodiments, the feedstock is corn and the oil is corn oil. In some embodiments, the undissolved solids comprise genn, fiber, and gluten. In some embodiments, the method further comprises dry milling the feedstock. In some embodiments, the corn is unfractionated. In some embodiments, the undissolved solids are separated by decanter bowl centrifugation, Tricanter® (three-phase centrifuge) centrifugation, disk stack centrifugation, filtering centrifugation, decanter centrifugation, filtration, vacuum filtration, beltfilter, pressure filtration, filtration using a screen, screen separation, grating, porous grating, flotation, hydroclone, filter press, sciewpress, gravity settler, vortex separator, or combination thereof. In some embodiments, the step of separating undissolved solids from the feedstock slurry comprises centrifuging the feedstock slurry. In some embodiments, centrifuging the feedstock slurry separates the feedstock into a first liquid phase comprising the aqueous solution, a solid phase comprising the wet cake, and a second liquid phase comprising the oil. In some embodimenis, the wet cake is washed with water to recover oligosaccharides present in the wet cake. In some embodiments, the in situ removal comprises liquid-liquid extraction. In some embodiments, an extractant for the liquid-liquid extraction is an organic extractant. In some embodiments, saccharification of the oligosaccharides in the aqueous solution occurs simultaneously with fermenting the oligosaccharides in the ferrnentor. In some embodiments, the method further comprises the step of increasing the reaction temperattne during liquefaction. In some embodiments, the method further comprises saccharifying the oligosaccharides prior to fermenting the oligosaccharides in the fermentor. In some embodiments, the step of removing undissolved solids from the feedstock slurry comprises centrifuging the feedstock slurry. In some embodiments, centrifuging the feedstock slurry occurs prior to saccharifying the sugar. In some embodiments, fermentation broth comprises a recombinant microorganism comprising a butanol biosynthetic pathway. In some embodiments, the butanol is isobutanol. In some embodiments, the step of removing undissolved solids from the feedstock slurry increases the efficiency of the butanol production by increasing a liquid-liquid mass transfer coefficient of the butanol from the fermentation broth to the extractant; increases the efficiency of the butanol production by increasing an extraction efficiency of the butanol with an extractant; increases the efficiency of the butanol production by increasing a rate of phase separation between the fermentation broth and an extractant; increases the efficiency of the butanol production by increasing recovery and recycling of an extractant; or increases the efficiency of the butanol production by decreasing a flow rate of an extractant. The present invention is also directed to a system for producing butanol comprising a liquefaction vessel configured to liquefy a feedstock to create a feedstock slurry, the liquefaction vessel comprising: an inlet for receiving the feedstock; and an outlet for discharging a feedstock slurry, wherein the feedstock slurry comprises sugar and undissolved solids; a centrifuge configured to remove the undissolved solids from the feedstock slurry to create (i) an aqueous solution comprising the sugar and (ii) a wet cake comprising the portion of the undissolved solids, the centrifuge comprising: an inlet for receiving the feedstock slurry; a first outlet for discharging the aqueous solution; and a second outlet for discharging the wet cake; and a fermentor configured to ferment the aqueous solution to produce butanol, the fermentor comprising: a first inlet for receiving the aqueous solution; a second inlet for receiving an extractant; a first outlet for discharging the extractant rich with butanol; and a second outlet for discharging fermentation broth. In some embodiments, the centrifuge further comprises a third outlet for discharging an oil created while removing the undissolved solids from the feedstock slurry. In some embodiments, the apparatus further comprises a saccharification vessel configured to saccharify the sugar in the feedstock slurry, the saccharification vessel comprising: an inlet for receiving the feedstock slurry; and an outlet for discharging the feedstock slurry. In some embodiments, the apparatus further comprises a saccharification vessel configured to saccharify the sugar in the aqueous solution, the saccharification vessel comprising: an inlet for receiving the aqueous solution; and an outlet for discharging the aqueous solution. In some embodiments, the apparatus further comprises a dry mill configured to grind the feedstock, the dry mill comprising: an inlet for receiving the feedstock; and an outlet for discharging ground feedstock.

The present invention is also directed to a composition comprising: 20-35 wt % crude protein, 1-20 wt % crude fat, 0-5 wt % triglycerides, 4-10 wt % fatty acids, and 2-6 wt % fatty acid isobutyl esters. The present invention is also directed to a composition comprising: 25-31 wt % crude protein, 6-10 wt % crude fat, 4-8 wt % triglycerides, 0-2 wt % fatty acids, and 1-3 wt % fatty acid isobutyl esters. The present invention is also directed to a composition comprising: 20-35 wt % crude protein, 1-20 wt % crude fat, 0-5 wt % triglycerides, 4-10 wt % fatty acids, and 2-6 wt % fatty acid isobutyl esters. The present invention is also directed to a composition comprising: 26-34 wt % crude protein, 15-25 wt % crude fat, 12-20 wt % triglycerides, 1-2 wt % fatty acids, 2-4 wt % fatty acid isobutyl esters, 1-2 wt % lysine, 11-23 wt % NDF, and 5-11 wt % ADF.

In some embodiments, a method comprising: (a) providing a feedstock slurry comprising fermentable carbon and undissolved solids from said biomass and water; (b) separating a substantial portion of the undissolved solids from said slurry whereby (i) an aqueous solution comprising fermentable carbon and (ii) a wet cake co-product comprising solids are generated; and (c) adding the aqueous solution to a fermentation broth comprising recombinant microorganisms in a fermentation vessel whereby a fermentative product is produced; wherein the biomass processing productivity is improved. In some embodiments, the improved biomass processing productivity comprises improved fermentative product and co-product recoverability relative to a fermentative product produced in the presence of undissolved solids. In some embodiments, the improved biomass processing productivity includes one or more of increased process stream recyclability, increased fermentor volume efficiency and increased corn load feeding. In some embodiments, the increased process stream recyclability includes one or more of fermentative recombinant microorganism recycle, water recycle, and energy efficiency.

In some embodiments, the process can also include (d) contacting the fermentation broth of (c) with an extractant wherein the extractant has increased extraction efficiency relative to a fermentation broth comprising undissolved solids. In some embodiments, the increased extraction efficiency includes one or more of stabilized partition coefficient, enhanced phase separation, enhanced mass transfer coefficient, and increased process stream recyclability. In some embodiments, increased extraction efficiency includes one or more of stabilized partition coefficient of the extractant, enhanced phase separation of the extractant from the fermentation broth, enhanced liquid-liquid mass transfer coefficient, and increased extractant recovery and recyclability. In some embodiments, the increased extraction efficiency includes preserved extractant for recycle.

In some embodiments, the aqueous solution has a viscosity of less than about 20 cps. In some embodiments, the aqueous solution contains less than about 20 g/L monomeric glucose.

In some embodiments, the improved product recoverability provides for improved recombinant microorganism tolerance to the product. In some embodiments, the improved tolerance is provided by one or more of removal of inhibitors with the undissolved solids or increased liquid-liquid mass transfer coefficient. In some embodiments, the improved extractant efficiency provides for improved recombinant microorganism tolerance. In some embodiments, the improved recombinant microorganism tolerance is provided by extraction of inhibitors, by-products, and metabolites.

In some embodiments, the feedstock slurry comprises oil from the feedstock and said oil is separated from the slurry in step (b). In some embodiments, the wet cake comprises feedstock oil in an amount of less than about 20% of dry solids content of the wet cake.

In some embodiments, the substantial portion of undissolved solids separated from the feedstock slurry in step (b) is at least about 75% by weight of undissolved solids. In some embodiments, the substantial portion of undissolved solids separated from the feedstock slurry in step (b) is at least about 90% by weight of undissolved solids. In some embodiments, the substantial portion of undissolved solids separated from the feedstock slurry in step (b) is at least about 95% by weight of undissolved solids. In some embodiments, step (b) comprises centrifuging the feedstock slurry. In some embodiments, centrifuging the feedstock slurry separates the feedstock into a first liquid phase comprising the aqueous solution and a solid phase comprising the wet cake. In some embodiments, the wet cake is washed with water to recover sugar or sugar source present in the wet cake. In some embodiments, the liquid phase comprising the aqueous solution is centrifuged more than once.

In some embodiments, the extractant is an organic extractant. In some embodiments, the extractant comprises one or more immiscible organic extractants selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof.

In some embodiments, the fermentative recombinant microorganism is a bacteria or yeast cell.

In some embodiments, the product is a product alcohol selected from the group consisting of butanol and isomers thereof.

In some embodiments, the method also includes (d) at least partially vaporizing the fermentation broth and product of (c) and optionally $CO_2$ wherein a vapor stream is produced and recover the product from the vapor stream. In some embodiments, the method also includes contacting the vapor stream with an absorption liquid phase wherein at least a portion of the vapor stream is absorbed into the absorption liquid phase, wherein the temperature of the onset of the absorption of the vapor stream into the absorption liquid phase is greater than the temperature of the onset of condensation of the vapor stream in the absence of the absorption liquid phase. In some embodiments, the vaporizing and contacting steps are carried out under vacuum conditions. In some embodiments, the separating a substantial portion of the undissolved solids from said slurry may provide for a higher vapor pressure of the fermentation broth relative to a fermentation broth comprising undissolved solids. In some embodiments, the higher vapor pressure provides for more efficient vaporization product recovery. In some embodiments, the more efficient vaporization product recovery includes one or more of lower capital investment, smaller vaporization, absorption, compression, and refrigeration equipment, improved mass transfer rates, less energy for vaporization, and lower absorbent flow rate.

In some embodiments, separating a substantial portion of the undissolved solids is performed such that starch loss to the undissolved solids is minimized. In some embodiments, the starch loss is minimized by performing one or more optimization operations including temperature control, enzyme concentration, pH, particle size of ground corn, and reaction time during liquefaction; centrifugation operating conditions; and wet cake wash conditions.

In some embodiments, the wet cake is further processed to provide an improved co-product. In some embodiments, the co-product is further processed to DDGS. In some embodiments, the DDGS has an improved product profile comprising less feedstock oil relative to DDGS produced in the presence of undissolved solids. In some embodiments, the DDGS has an improved product profile such that the DDGS is produced with minimal contaminating contact with the fermentation broth, the recombinant microorganism, fermentative products, and extractant. In some embodiments, DDGS produced by the above methods meets dietary labeling requirements for organic animal feed.

In some embodiments, a fermentation broth includes a fermentative product portion and a corn oil portion in a ratio of at least about 4:1 by weight, wherein said broth is substantially free of undissolved solids. In some embodiments, the corn oil portion contains at least about 15 weight % free fatty acids. In some embodiments, the fermentation broth contains no more than about 15% by weight of undissolved solids. In some embodiments, the fermentation broth contains no more than about 10% by weight of undissolved solids. In some embodiments, the fermentation broth contains no more than about 5% by weight of undissolved solids.

In some embodiments, a centrifuge product profile includes a layer of undissolved solids, a corn oil layer and a supernatant layer comprising fermentable sugars, wherein a ratio fermentable sugars in the supernatant layer to undissolved solids in the undissolved solids layer on a weight basis is in a range from about 2:1 to about 5:1; a ratio of fermentable sugars in the supernatant layer to corn oil in the corn oil layer on a weight basis is in a range from about 10:1 to about 50:1; and a ratio of undissolved solids in the undissolved solids layer to corn oil in the corn oil layer on a weight basis is in a range from about 2:1 to about 25:1.

In some embodiments, a method for producing butanol includes the steps of (a) providing a corn feedstock; (b) liquefying the corn feedstock to create a feedstock slurry, wherein the feedstock slurry comprises sugar, corn oil, and undissolved solids; (c) removing undissolved solids from the feedstock slurry to create (i) an aqueous solution comprising sugar, (ii) a wet cake comprising undissolved solids, and (iii) a free corn oil phase; (d) contacting the aqueous solution with a broth in a fermentor; (e) fermenting the sugar in the fermentor to produce butanol; and (f) performing in situ removal of the butanol from the broth as the butanol is produced, wherein removal of the undissolved solids from the feedstock slurry increases the efficiency of the butanol production. In some embodiments, the undissolved solids comprise germ, fiber, and gluten. In some embodiments, the method also includes dry milling the corn feedstock. In some embodiments, the corn is unfractionated.

In some embodiments, step (c) comprises centrifuging the feedstock slurry. In some embodiments, centrifuging the feedstock slurry separates the feedstock slurry into a first liquid phase comprising the aqueous solution, a solid phase comprising the wet cake, and a second liquid phase comprising the free corn oil. In some embodiments, the wet cake is washed with water to recover sugar present in the wet cake. In some embodiments, the liquid phase comprising the aqueous solution is centrifuged more than once. In some embodiments, at least about 75% by weight of the undissolved solids are removed from the feedstock slurry in step (c). In some embodiments, at least about 90% by weight of the undissolved solids are removed from the feedstock slurry in step (c). In some embodiments, at least about 95% by weight of the undissolved solids are removed from the feedstock slurry in step (c).

In some embodiments, the in situ removal comprises liquid-liquid extraction. In some embodiments, an extractant for the liquid-liquid extraction is an organic extractant. In some embodiments, the organic extractant comprises oleyl alcohol.

In some embodiments, the broth comprises a microorganism. In some embodiments, the microorganism is a bacteria or yeast cell.

In some embodiments, a portion of the broth exits the fermentor and the method further comprises separating the yeast present in the portion of the broth therefrom and returning the separated yeast to the fermentor. In some embodiments, the portion of the broth comprises no more than about 25% by weight of the undissolved solids present in the feedstock slurry. In some embodiments, the portion of the broth comprises no more than about 10% by weight of the undissolved solids present in the feedstock slurry. In some embodiments, the portion of the broth comprises no more than about 5% by weight of the undissolved solids present in the feedstock slurry.

In some embodiments, saccharification of the sugar in the aqueous solution occurs simultaneously with fermenting the sugar in the fermentor. In some embodiments, the method also includes saccharifying the sugar prior to fermenting the sugar in the fermentor. In some embodiments, step (c) includes centrifuging the feedstock slurry. In some embodiments, centrifuging the feedstock slurry occurs prior to saccharifying the sugar. In some embodiments, centrifuging the feedstock slurry occurs after saccharifying the sugar.

In some embodiments, the butanol is isobutanol. In some embodiments, step (c) increases the efficiency of the butanol production by increasing a liquid-liquid mass transfer coefficient of the butanol from the broth to the extractant. In some embodiments, step (c) increases the efficiency of the butanol production by increasing an extraction efficiency of the butanol with an extractant. In some embodiments, step (c) increases the efficiency of the butanol production by increasing a rate of phase separation between the broth and an extractant. In some embodiments, step (c) increases the efficiency of the butanol production by increasing recovery and recycling of an extractant. In some embodiments, step (c) increases the efficiency of the butanol production by decreasing a flow rate of an extractant.

In some embodiments, step (c) includes one or more of stabilized partition coefficient of the extractant, increased fermentor volume frequency, increased corn load feeding, increased fermentative recombinant microorganism recycle, increased water recycle, increased energy efficiency, improved recombinant microorganism tolerance to the butanol, lowered aqueous phase titer, and improved value of DDGS.

In some embodiments, a system for producing butanol includes (a) a liquefaction vessel configured to liquefy a feedstock to create a feedstock slurry, the liquefaction vessel comprising an inlet for receiving the feedstock, an outlet for discharging a feedstock slurry, wherein the feedstock slurry comprises sugar and undissolved solids; (b) a centrifuge configured to remove the undissolved solids from the feedstock slurry to create (i) an aqueous solution comprising the sugar and (ii) a wet cake comprising the portion of the undissolved solids, the centrifuge comprising an inlet for receiving the feedstock slurry, a first outlet for discharging the aqueous solution, and a second outlet for discharging the wet cake; and (c) a fermentor for fermenting the aqueous solution in the fermentor to produce butanol, the fermentor comprising a first inlet for receiving the aqueous solution, a second inlet for receiving an extractant, and a first outlet for discharging the extractant rich with butanol and a second outlet for discharging fermentation broth. In some embodiments, the centrifuge further comprises a third outlet for discharging an oil created while removing the undissolved solids from the feedstock slurry. In some embodiments, the system also includes a saccharification vessel configured to saccharify the sugar in the feedstock slurry, the saccharification vessel comprising an inlet for receiving the feedstock slurry and an outlet for discharging the feedstock slurry. In some embodiments, the system also includes a saccharification vessel configured to saccharify the sugar in the aqueous solution, the saccharification vessel comprising an inlet for receiving the aqueous and an outlet for discharging the aqueous solution. In some embodiments, the system also includes a dry mill configured to grind the feedstock, the dry mill comprising an inlet for receiving the feedstock and an outlet for discharging ground feedstock.

In some embodiments, a wet cake formed in a centrifuge from a corn mash slurry, wherein the wet cake comprises undissolved solids, includes at least about 75% by weight of the undissolved solids present in the corn mash slurry. In some embodiments, the wet cake includes at least about 90% by weight of the undissolved solids present in the corn mash slurry. In some embodiments, the wet cake includes at least about 95% by weight of the undissolved solids present in the corn mash slurry.

In some embodiments, an aqueous solution formed in a centrifuge from a corn mash slurry, wherein the aqueous solution comprises undissolved solids, includes no more than about 25% by weight of the undissolved solids present in the corn mash slurry. In some embodiments, the aqueous solution includes no more than about 10% by weight of the undissolved solids present in the corn mash slurry. In some embodiments, the aqueous solution includes no more than about 5% by weight of the undissolved solids present in the corn mash slurry.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 1 schematically illustrates an exemplary method and system of the present invention, in which undissolved solids are removed in a centrifuge after liquefaction and before fermentation.

FIG. 2 schematically illustrates an exemplary alternative method and system of the present invention, in which feedstock is milled.

FIG. 3 schematically illustrates another exemplary alternative method and system of the present invention, in which the centrifuge discharges an oil stream.

FIG. 4 schematically illustrates another exemplary alternative method and system of the present invention, in which a saccharification vessel is placed between the centrifuge and the fermentor.

FIG. 5 schematically illustrates another exemplary alternative method and system of the present invention, in which a saccharification vessel is placed between the liquefaction vessel and the centrifuge.

FIG. 6 schematically illustrates another exemplary alternative method and system of the present invention, in which two centrifuges are utilized in series to remove the undissolved solids.

FIG. 7 illustrates the effect of the presence of undissolved corn mash solids on the overall volumetric mass transfer coefficient, $k_L a$, for the transfer of i-BuOH from an aqueous solution of liquefied corn starch (i.e., oligosaccharides) to a dispersion of oleyl alcohol droplets flowing up through a bubble column when a nozzle with an inner diameter of 2.03 mm is used to disperse the oleyl alcohol.

FIG. 8 illustrates the effect of the presence of undissolved corn mash solids on the overall volumetric mass transfer coefficient, $k_L a$, for the transfer of i-BuOH from an aqueous solution of liquefied corn starch (i.e., oligosaccharides) to a dispersion of oleyl alcohol droplets flowing up through a bubble column when a nozzle with an inner diameter of 0.76 mm is used to disperse the oleyl alcohol.

FIG. 9 illustrates the position of the liquid-liquid interface in the fermentation sample tubes as a function of (gravity) settling time. Phase separation data shown for run times: 5.3, 29.3, 53.3, and 70.3 hrs run time. Sample data from extractive-fermentation where solids were removed from the mash feed, and OA was the solvent (2010Y035).

DETAILED DESCRIPTION OF THE INVENTION

Figure 1:
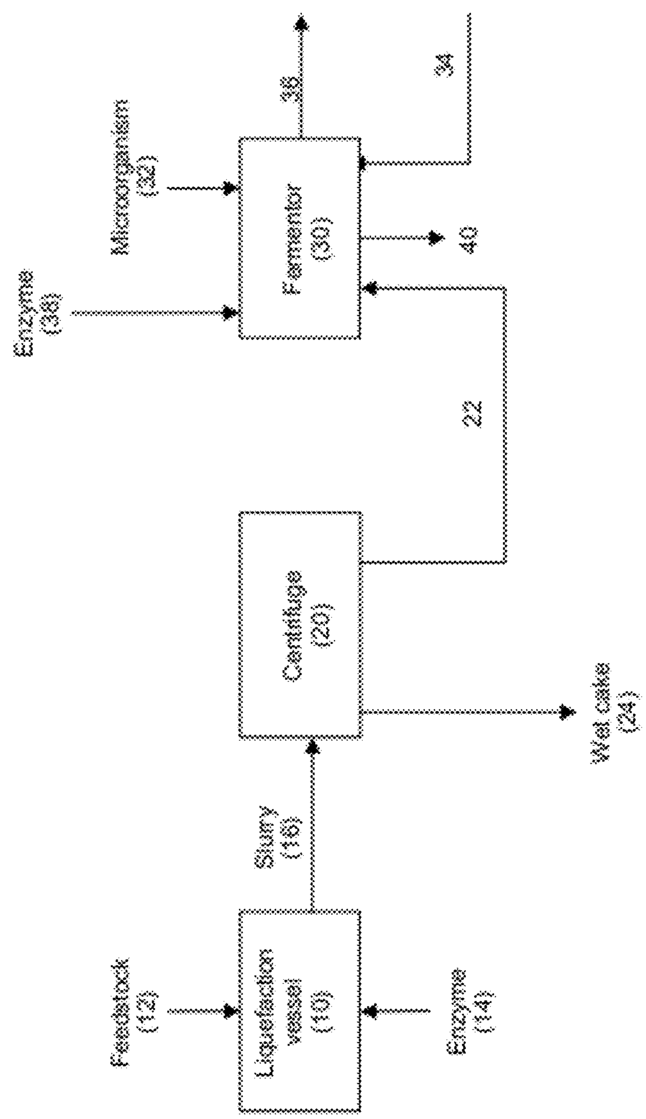

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents, and other references mentioned herein are incorporated by reference in their entireties for all purposes.

In order to further define this invention, the following terms and definitions are herein provided.

As used herein, the terms “comprises,” “comprising,” “includes,” “including,” “has,” “having,” “contains,” or “containing,” or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, “or” refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles “a” and “an” preceding an element or component of the invention are intended to be nonrestrictive regarding the number of instances, i.e., occurrences of the element or component. Therefore “a” or “an” should be read to include one or at least one, and the singular word form of the element or component also includes the plural unless the number is obviously meant to be singular.

The term “invention” or “present invention” as used herein is a non-limiting term and is not intended to refer to any single embodiment of the particular invention but encompasses all possible embodiments as described in the application.

As used herein, the term “about” modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term “about” also encompasses amounts that differ due to different equilibrium conditions for a composition resulting from a particular initial mixture. Whether or not modified by the term “about,” the claims include equivalents to the quantities. In one embodiment, the term “about” means within 10% of the reported numerical value, alternatively within 5% of the reported numerical value.

“Biomass” as used herein refers to a natural product containing hydrolyzable polysaccharides that provide fermentable sugars including any sugars and starch derived from natural resources such as corn, sugar cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass can comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation such as by milling, treating, and/or liquefying and comprises fermentable sugar and may comprise water. For example, cellulosic and/or lignocellulosic biomass may be processed to obtain a hydrolysate containing fermentable sugars by any method known to one skilled in the art. A low ammonia pretreatment is disclosed in U.S. Patent Application Publication No. 2007/0031918A1, which is herein incorporated by reference. Enzymatic saccharification of cellulosic and/or lignocellulosic biomass typically makes use of an enzyme consortium for breaking down cellulose and hemicellulose to produce a hydrolysate containing sugars including glucose, xylose, and arabinose. (Saccharification enzymes suitable for cellulosic and/or lignocellulosic biomass are reviewed in Lynd, et al. (Microbiol. Mol. Biol. Rev. 66:506-577, 2002).

Dried Distillers' Grains with Solubles (DDGS) as used herein refers to a co-product or by-product from a fermentation of a feedstock or biomass (e.g., fermentation of grain or grain mixture that produces a product alcohol). In some embodiments, DDGS may also refer to an animal feed produced from a process of making a product alcohol (e.g., butanol, isobutanol, etc.).

“Fermentable carbon source” or “fermentable carbon substrate” as used herein means a carbon source capable of being metabolized by microorganisms. Suitable fermentable carbon sources include, but are not limited to, monosaccharides such as glucose or fructose; disaccharides such as lactose or sucrose; oligosaccharides; polysaccharides such as starch or cellulose; one carbon substrates; and mixtures thereof.

“Fermentable sugar” as used herein refers to one or more sugars capable of being metabolized by the microorganisms disclosed herein for the production of fermentative alcohol.

“Feedstock” as used herein means a feed in a fermentation process, the feed containing a fermentable carbon source with or without undissolved solids, and where applicable, the feed containing the fermentable carbon source before or after the fermentable carbon source has been liberated from starch or obtained from the break down of complex sugars by further processing such as by liquefaction, saccharification, or other process. Feedstock includes or is derived from a biomass. Suitable feedstocks include, but are not limited to, rye, wheat, corn, corn mash, cane, cane mash, barley, cellulosic material, lignocellulosic material, or mixtures thereof. Where reference is made to “feedstock oil,” it will be appreciated that the term encompasses the oil produced from a given feedstock.

“Fermentation broth” as used herein means the mixture of water, sugars (fermentable carbon sources), dissolved solids, optionally microorganisms producing alcohol, product alcohol, and all other constituents of the material held in the fermentation vessel in which product alcohol is being made by the reaction of sugars to alcohol, water, and carbon dioxide ($CO_2$) by the microorganisms present. From time to time as used herein, the term “fermentation medium” and “fermented mixture” can be used synonymously with “fermentation broth.”

“Fermentation vessel” as used herein means the vessel in which the fermentation reaction is carried out whereby product alcohol such as butanol is made from sugars. The term “fermentor” can be used synonymously herein with “fermentation vessel.”

“Saccharification vessel” as used herein means the vessel in which saccharification (i.e., the break down of oligosaccharides into monosaccharides) is carried out. Where fermentation and saccharification occur simultaneously, the saccharification vessel and the fermentation vessels may be the same vessel.

As used herein, “saccharification enzyme” means one or more enzymes that are capable of hydrolyzing polysaccharides and/or oligosaccharides, for example, alpha-1,4-glucosidic bonds of glycogen, or starch. Saccharification enzymes may include enzymes capable of hydrolyzing cellulosic or ligncellulosic materials as well.

“Liquefaction vessel” as used herein means the vessel in which liquefaction is carried out. Liquefaction is the process in which oligosaccharides are liberated from the feedstock. In embodiments where the feedstock is corn, oligosaccharides are liberated from the corn starch content during liquefaction.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

"Undissolved solids" as used herein means non-fermentable portions of feedstock which are not dissolved in the liquid phase, for example, germ, fiber, and gluten. For example, the non-fermentable portions of feedstock include the portion of feedstock that remains as solids and can absorb liquid from the fermentation broth.

"Extractant" as used herein means an organic solvent used to extract any butanol isomer.

"In Situ Product Removal (ISPR)" as used herein means the selective removal of a specific fermentation product from a biological process such as fermentation to control the product concentration in the biological process as the product is produced.

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. "Alcohol" is also used herein with reference to a product alcohol.

"Butanol" as used herein refers with specificity to the butanol isomers 1-butanol (1-BuOH), 2-butanol (2-BuOH), tertiary-butanol (tert-BuOH), and/or isobutanol (iBuOH, i-BuOH, or I-BUOH), either individually or as mixtures thereof.

"Propanol" as used herein refers to the propanol isomers isopropanol or 1-propanol.

"Pentanol" as used herein refers to the pentanol isomers 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

The term "aqueous phase titer" as used herein refers to the concentration of a particular alcohol (e.g., butanol) in the fermentation broth.

The term "effective titer" as used herein refers to the total amount of a particular alcohol (e.g., butanol) produced by fermentation or alcohol equivalent of the alcohol ester produced by alcohol esterification per liter of fermentation medium.

The terms "water-immiscible" or "insoluble" refer to a chemical component such as an extractant or solvent, which is incapable of mixing with an aqueous solution such as a fermentation broth, in such a manner as to form one liquid phase.

The term "aqueous phase" as used herein refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase" as used herein refers to the non-aqueous phase of a biphasic mixture obtained by contacting a fermentation broth with a water-immiscible organic extractant.

The present invention provides systems and methods for producing a fermentative product such as a product alcohol, through fermentation as well as increasing biomass processing productivity and cost effectiveness. In some embodiments, the product alcohol is butanol. A feedstock can be liquefied to create a feedstock slurry, wherein the feedstock slurry includes soluble sugar and undissolved solids. If the feedstock slurry is fed directly to the fermentor, the undissolved solids may interfere with efficient removal and recovery of a product alcohol such as butanol from the fermentor. In particular, when liquid-liquid extraction is utilized to extract butanol from the fermentation broth, the presence of the undissolved particulates may cause system inefficiencies including, but not limited to, decreasing the mass transfer rate of the butanol to the extractant by interfering with the contact between the extractant and the fermentation broth; creating an emulsion in the fermentor and thereby interfering with good phase separation of the extractant and the fermentation broth; reducing the efficiency of recovering and recycling the extractant because at least a portion of the extractant and butanol becomes "trapped" in the solids which are ultimately removed as Distillers' Dried Grains with Solubles (DDGS); a lower fermentor volume efficiency because there are solids taking up volume in the fermentor and because there is a slower disengagement of the extractant from the fermentation broth; and shortening the life cycle of the extractant by contamination with corn oil. All of these effects result in higher capital and operating costs. In addition, the extractant "trapped" in the DDGS may detract from DDGS value and qualification for sale as animal feed. Thus, in order to avoid and/or minimize these problems, at least a portion of the undissolved particles (or solids) are removed from the feedstock slurry prior to the addition of sugar present in the feedstock slurry to the fermentor. Extraction activity and the efficiency of the butanol production are increased when extraction is performed on a fermentation broth containing an aqueous solution wherein undissolved particles have been removed relative to extraction performed on a fermentation broth containing an aqueous solution wherein undissolved particles have not been removed.

The systems and methods of the present invention will be described with reference to the Figures. In some embodiments, as shown, for example, in FIG. 1, the system includes a liquefaction vessel 10 configured to liquefy a feedstock to create a feedstock slurry.

In particular, a feedstock 12 can be introduced to an inlet in liquefaction vessel 10. Feedstock 12 can be any suitable biomass material known in the industry including, but not limited to, rye, wheat, cane, or corn, that contains a fermentable carbon source such as starch.

The process of liquefying feedstock 12 involves hydrolysis of starch in feedstock 12 into water-soluble sugars and is a conventional process. Any known liquefying processes, as well as the corresponding liquefaction vessel, normally utilized by the industry can be used including, but not limited to, the acid process, the acid-enzyme process, or the enzyme process. Such processes can be used alone or in combination. In some embodiments, the enzyme process can be utilized and an appropriate enzyme 14, for example, alpha-amylase, is introduced to an inlet in liquefaction vessel 10. Water can also be introduced to the liquefaction vessel 10.

The process of liquefying feedstock 12 creates a feedstock slurry 16 that includes sugar (e.g., fermentable carbon) and undissolved solids from the feedstock or biomass. The undissolved solids are non-fermentable portions of feedstock 12. In some embodiments, feedstock 12 can be corn, such as dry milled, unfractionated corn kernels, and the undissolved particles can include germ, fiber, and gluten. Feedstock slurry 16 can be discharged from an outlet of liquefaction vessel 10. In some embodiments, feedstock 12 is corn or corn kernels and feedstock slurry 16 is a corn mash slurry.

A centrifuge 20 configured to remove the undissolved solids from feedstock slurry 16 has an inlet for receiving feedstock slurry 16. Centrifuge 20 agitates or spins feedstock slurry 16 to create a liquid phase or aqueous solution 22 and a solid phase or wet cake 24.

Aqueous solution 22 can include the sugar, for example, in the form of oligosaccharides, and water. Aqueous solution can comprise at least about 10% by weight oligosaccharides, at least about 20% by weight of oligosaccharides, or at least about 30% by weight of oligosaccharides. Aqueous solution 22 can be discharged out an outlet located near the top of centrifuge 20. Aqueous solution can have a viscosity of less than about 20 centipoise. The aqueous solution can comprise less than about 20 g/L of monomeric glucose, more preferably less than about 10 g/L, or less than about 5 g/L of monomeric glucose. Suitable methodology to determine the amount of monomeric glucose is well known in the art. Such suitable methods known in the art include HPLC.

Wet cake 24 can include the undissolved solids. Wet cake 24 can be discharged from an outlet located near the bottom of centrifuge 20. Wet cake 24 can also include a portion of the sugar and water. Wet cake 24 can be washed with additional water in centrifuge 20 once aqueous solution 22 has been discharged from centrifuge 20. Alternatively, wet cake 24 can be washed with additional water in a separate centrifuge. Washing wet cake 24 will recover the sugar or sugar source (e.g., oligosaccharides) present in the wet cake, and the recovered sugar and water can be recycled to the liquefaction vessel 10. After washing, wet cake 24 can be dried to form Dried Distillers' Grains with Solubles (DDGS) through any suitable known process. The formation of the DDGS from wet cake 24 formed in centrifuge 20 has several benefits. Since the undissolved solids do not go to the fermentor, extractant and/or butanol are not trapped in the DDGS, DDGS is not subjected to the conditions of the fermentor, and DDGS does not contact the microorganisms present in the fermentor. All these effects provide benefits to subsequent processing and selling of DDGS, for example as animal feed.

Centrifuge 20 can be any conventional centrifuge utilized, in the industry, including, for example, a decanter bowl centrifuge, Tricanter® (three-phase centrifuge) centrifuge, disk stack centrifuge, filtering centrifuge, or decanter centrifuge. In some embodiments, removal of the undissolved solids from feedstock slurry 16 can be accomplished by filtration, vacuum filtration, beltfilter, pressure filtration, filtration using a screen, screen separation, grates or grating, porous grating, flotation, hydroclone, filter press, screwpress, gravity settler, vortex separator, or any method that may be used to separate solids from liquids. In one embodiment, undissolved solids may be removed from corn mash to form two product streams, for example, an aqueous solution of oligosaccharides which contains a lower concentration of solids as compared to corn mash and a wet cake which contains a higher concentration of solids as compared to corn mash. In addition, a third stream containing corn oil may be generated if a Tricanter® (three-phase centrifuge) centrifuge is utilized for solids removal from corn mash. As such, a number of product streams may be generated by using different separation techniques or a combination thereof.

In some embodiments, wet cake 24 is a composition formed from feedstock slurry 16, for example, a corn mash slurry, in centrifuge 20 wherein wet cake 24 includes at least about 50% by weight of the undissolved particles present in the feedstock slurry, at least about 55% by weight of the undissolved particles present in the feedstock slurry, at least about 60% by weight of the undissolved particles present in the feedstock slurry, at least about 65% by weight of the undissolved particles present in the feedstock slurry, at least about 70% by weight of the undissolved particles present in the feedstock slurry, at least about 75% by weight of the undissolved particles present in the feedstock slurry, at least about 80% by weight of the undissolved particles present in the feedstock slurry, at least about 85% by weight of the undissolved particles present in the feedstock slurry, at least about 90% by weight of the undissolved particles present in the feedstock slurry, at least about 95% by weight of the undissolved particles present in the feedstock slurry, or about 99% by weight of the undissolved particles present in the feedstock slurry.

In some embodiments, aqueous solution 22 formed from feedstock slurry 16, for example, a corn mash slurry, in centrifuge 20 includes no more than about 50% by weight of the undissolved particles present in the feedstock slurry, no more than about 45% by weight of the undissolved particles present in the feedstock slurry, no more than about 40% by weight of the undissolved particles present in the feedstock slurry, no more than about 35% by weight of the undissolved particles present in the feedstock slurry, no more than about 30% by weight of the undissolved particles present in the feedstock slurry, no more than about 25% by weight of the undissolved particles present in the feedstock slurry, no more than about 20% by weight of the undissolved particles present in the feedstock slurry, no more than about 15% by weight of the undissolved particles present in the feedstock slurry, no more than about 10% by weight of the undissolved particles present in the feedstock slurry, no more than about 5% by weight of the undissolved particles present in the feedstock slurry, or about 1% by weight of the undissolved particles present in the feedstock slurry.

A fermentor 30 configured to ferment aqueous solution 22 to produce butanol has an inlet for receiving aqueous solution 22. Fermentor 30 can include a fermentation broth. A microorganism 32 selected from the group of bacteria, cyanobacteria, filamentous fungi, and yeasts is introduced to fermentor 30 to be included in the fermentation broth. In some embodiments, microorganism 32 can be a bacteria such as *E. coli*. In some embodiments, microorganism 32 can be *S. cerevisiae*. Microorganism 32 consumes the sugar in aqueous solution 22 and produces butanol. The production of butanol utilizing fermentation with a microorganism, as well as microorganisms that produce a high yield of butanol, is known and is disclosed, for example, in U.S. Patent Application Publication No. 2009/0305370, the disclosure of which is hereby incorporated in its entirety. In some embodiments, microorganism 32 can be a fermentative recombinant microorganism.

In some embodiments, the microorganism 32 is engineered to contain a biosynthetic pathway. In some embodiments, the biosynthetic pathway is a butanol biosynthetic pathway. In some embodiments, the biosynthetic pathway converts pyruvate to a fermentative product. In some embodiments, the biosynthetic pathway comprises at least one heterologous polynucleotide encoding a polypeptide which catalyzes a substrate to product conversion of the biosynthetic pathway. In some embodiments, each substrate to product conversion of the biosynthetic pathway is catalyzed by a polypeptide encoded by a heterologous polynucleotide.

In situ product removal (ISPR) can be utilized to remove butanol from fermentor 30 as the butanol is produced by the microorganism, for example, by liquid-liquid extraction. Liquid-liquid extraction is described briefly below and can be performed according to the processes described in U.S.

Patent Application Publication No. 2009/0305370, the disclosure of which is hereby incorporated in its entirety.

Fermentor 30 has an inlet for receiving an extractant 34. Extractant 34 can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof. The extractant may also be an organic extractant selected from the group consisting of saturated, mono-unsaturated, poly-unsaturated (and mixtures thereof) $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, and mixtures thereof. Extractant 34 can be an organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof. Extractant 34 contacts the fermentation broth and butanol present in the fermentation broth is transferred to extractant 34. A stream 36 of extractant rich with butanol is discharged through an outlet in fermentor 30. Butanol is subsequently separated from the extractant in stream 36 using conventional techniques. Feed stream may be added to fermentor 30. Fermentor 30 can be any suitable fermentor known in the art.

In some embodiments, simultaneous saccharification and fermentation can occur inside fermentor 30. Any known saccharification process normally utilized by the industry can be used including, but not limited to, the acid process, the acid-enzyme process, or the enzyme process. In some embodiments, an enzyme 38 such as glucoamylase, can be introduced to an inlet in fermentor 30 in order to break down sugars in the form of oligosaccharides present in aqueous solution 22 into monosaccharides.

In some embodiments, fermentation broth 40 can be discharged from an outlet in fermentor 30. The discharged fermentation broth 40 can include microorganism 32 such as a yeast. Microorganism 32 can be easily separated from the fermentation broth 40, for example, in a centrifuge (not shown). Microorganism 32 can then be recycled to fermentor 30 which over time can increase the production rate of butanol, thereby resulting in an increase in the efficiency of the butanol production.

When a portion of fermentation broth 40 exits fermentor 30, fermentation broth 40 includes no more than about 50% by weight of the undissolved particles present in the feedstock slurry, no more than about 45% by weight of the undissolved particles present in the feedstock slurry, no more than about 40% by weight of the undissolved particles present in the feedstock slurry, no more than about 35% by weight of the undissolved particles present in the feedstock slurry, no more than about 30% by weight of the undissolved particles present in the feedstock slurry, no more than about 25% by weight of the undissolved particles present in the feedstock slurry, no more than about 20% by weight of the undissolved particles present in the feedstock slurry, no more than about 15% by weight of the undissolved particles present in the feedstock slurry, no more than about 10% by weight of the undissolved particles present in the feedstock slurry, no more than about 5% by weight of the undissolved particles present in the feedstock slurry, or no more than about 1% by weight of the undissolved particles present in the feedstock slurry.

Figure 2:
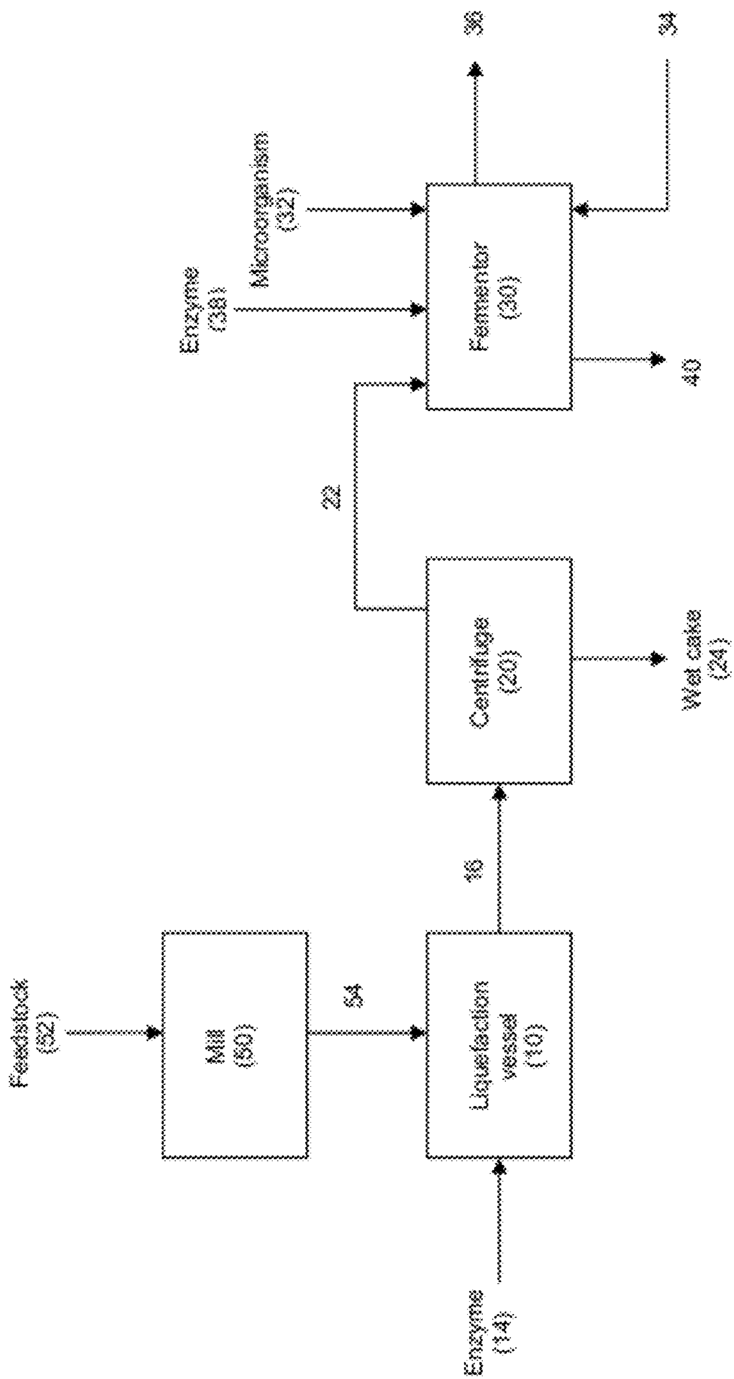

In some embodiments, as shown for example in FIG. 2, the systems and processes of the present invention can include a mill 50 configured to dry mill a feedstock 52. Feedstock 52 can be the same as feedstock 12 from FIG. 1 and can enter mill 50 through an inlet. Mill 50 can mill or grind feedstock 52. In some embodiments, feedstock 52 can be unfractionated. In some embodiments, feedstock 52 can be unfractionated corn kernels. Mill 50 can be any suitable known mill, for example, a hammer mill. Dry milled feedstock 54 is discharged from mill 50 through an outlet and enters liquefaction vessel 10. The remainder of FIG. 2 is identical to FIG. 1 and is not described again. In other embodiments, the feedstock can be fractionated and/or wet milled as is known in the industry as an alternative to being unfractionated and/or dry milled.

Wet milling is a multi-step process that separates a biomass (e.g., corn) into its key components (germ, pericarp fiber, starch, and gluten) in order to capture value from each co-product separately. This process gives a purified starch stream; however, it is costly and includes the separation of the biomass into its non-starch components which is unnecessary for fermentative alcohol production. Fractionation removes fiber and germ, which contains a majority of the lipids present in ground whole corn resulting in a fractionated corn that has a higher starch (endosperm) content. Dry fractionation does not separate the germ from fiber and therefore, it is less expensive than wet milling. However, fractionation does not remove the entirety of the fiber or germ, and does not result in total elimination of solids. Furthermore, there is some loss of starch in fractionation. Wet milling of corn is more expensive than dry fractionation, but dry fractionation is more expensive than dry grinding of unfractionated corn.

Figure 3:
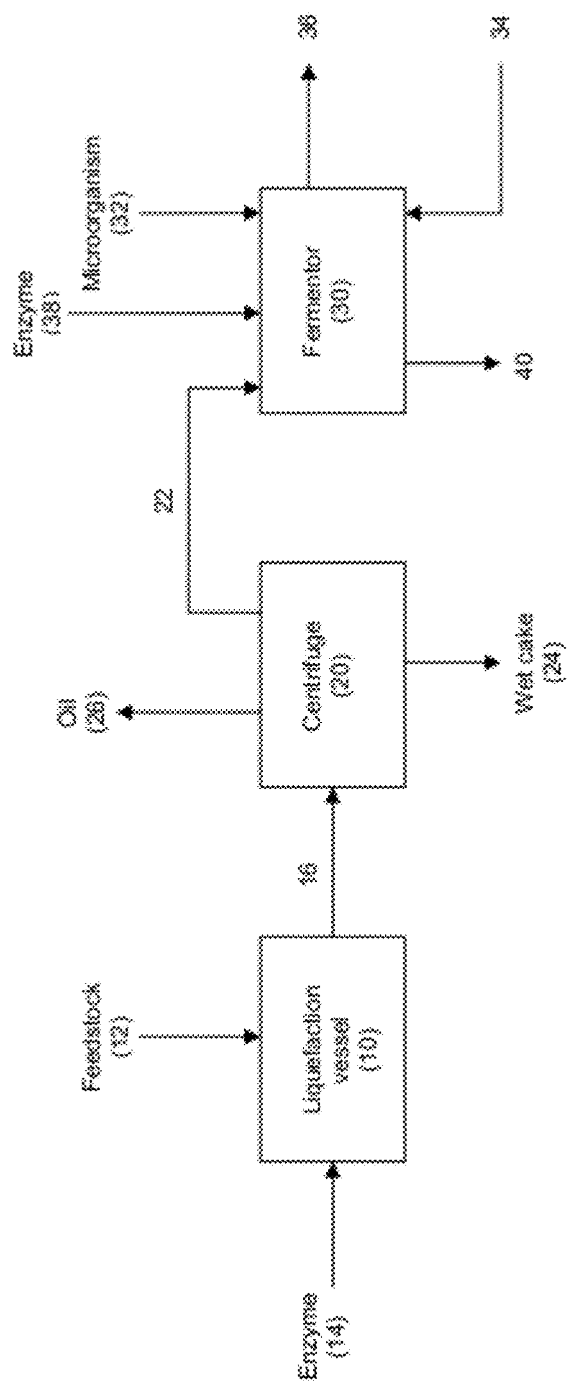

In some embodiments, as shown, for example, in FIG. 3, the systems and processes of the present invention can include discharging an oil 26 from an outlet of centrifuge 20. FIG. 3 is identical to FIG. 1, except for oil stream 26 exiting centrifuge 20 and therefore will not be described in detail again.

Feedstock slurry 16 is separated into a first liquid phase or aqueous solution 22 containing the fermentable sugar, a solid phase or wet cake 24 containing the undissolved solid, and a second liquid phase containing oil 26 which may exit centrifuge 20. In some embodiments, feedstock 12 is corn and oil 26 is free corn oil. The term free corn oil as used herein means corn oil that is freed from the corn germ. Any suitable conventional centrifuge can be used to discharge aqueous solution 22, wet cake 24, and oil 26, for example, a Tricanter® (three-phase centrifuge) centrifuge. In some embodiments, a portion of the oil from feedstock 12 such as corn oil when the feedstock is corn, remains in wet cake 24. In such instances, wet cake 24 includes corn oil in an amount of less than about 20% by weight of dry solids content of wet cake 24.

In some embodiments, when feedstock 12 (e.g., corn) and corn oil 26 is removed from centrifuge 20, the fermentation broth in fermentor 30 includes a reduced amount of corn oil. For example, the fermentation broth, substantially free of undissolved solid, can include a product alcohol portion (e.g., butanol) and an oil portion (e.g., corn oil) in a ratio of at least about 4:1 on a weight basis. The corn oil can contain at least 15% by weight of free fatty acids, for example, 16.7% by weigh of free fatty acids. In some embodiments, the fermentation broth has no more than about 25% by weight of undissolved solids, the fermentation broth has no more than about 15% by weight of undissolved solids, the fermentation broth has no more than about 10% by weight of undissolved solids, the fermentation broth has no more than about 5% by weight of undissolved solids, the fermentation broth has no more than about 1% by weight of undissolved solids, or the fermentation broth has no more than about 0.5% by weight of undissolved solids.

In some embodiments, centrifuge 20 produces a product profile including a layer of undissolved solids, a layer of oil (e.g., corn oil), and a supernatant layer including the fermentable sugars. The ratio of fermentable sugars in the supernatant layer to undissolved solids in the undissolved solids layer on a weight base can be in a range from about 2:1 to about 5:1; the ratio of fermentable sugars in the supernatant layer to corn oil in the corn oil layer on a weight basis can be in a range from about 10:1 to about 50:1; and/or the ratio of undissolved solids in the undissolved solids layer to corn oil in the corn oil layer on a weight basis can be in a range from about 2:1 to about 25:1.

In some embodiments, the system and process of FIG. 2 can be modified to include discharge of an oil stream from centrifuge 20 as discussed above in connection to the system and process of FIG. 3.

If oil 26 is not discharged separately it may be removed with wet cake 24. When wet cake 24 is removed via centrifuge 20, in some embodiments, a portion of the oil from feedstock 12, such as corn oil when the feedstock is corn, remains in wet cake 24. Wet cake 24 can be washed with additional water in the centrifuge once aqueous solution 22 has been discharged from the centrifuge 20. Washing wet cake 24 will recover the sugar (e.g., oligosaccharides) present in the wet cake and the recovered sugar and water can be recycled to the liquefaction vessel 10. After washing, wet cake 24 may be combined with solubles and then dried to form Dried Distillers' Grains with Solubles (DDGS) through any suitable known process. The formation of the DDGS from wet cake 24 formed in centrifuge 20 has several benefits. Since the undissolved solids do not go to the fermentation vessel, the DDGS does not have trapped extractant and/or product alcohol such as butanol, it is not subjected to the conditions of the fermentation vessel, and it does not contact the microorganisms present in the fermentation vessel. All these benefits make it easier to process and sell DDGS, for example, as animal feed. In some embodiments, oil 26 is not discharged separately from wet cake 24, but rather oil 26 is included as part of wet cake 24 and is ultimately present in the DDGS. In such instances, the oil can be separated from the DDGS and converted to an ISPR extractant for subsequent use in the same or different alcohol fermentation process.

Oil 26 may be separated from DDGS using any suitable known process including, for example, a solvent extraction process. In one embodiment of the invention, DDGS are loaded into an extraction vessel and washed with a solvent such as hexane to remove oil 26. Other solvents that may be utilized include, for example, isobutanol, isohexane, ethanol, petroleum distillates such as petroleum ether, or mixtures thereof. After oil 26 extraction, DDGS may be treated to remove any residual solvent. For example, DDGS may be heated to vaporize any residual solvent using any method known in the art. Following solvent removal, DDGS may be subjected to a drying process to remove any residual water. The processed DDGS may be used as a feed supplement for animals such as poultry, livestock, and domestic pets.

After extraction from DDGS, the resulting oil 26 and solvent mixture may be collected for separation of oil 26 from the solvent. In one embodiment, the oil 26/solvent mixture may be processed by evaporation whereby the solvent is evaporated and may be collected and recycled. The recovered oil may be converted to an ISPR extractant for subsequent use in the same or different alcohol fermentation process.

Removal of the oil component of the feedstock is advantageous to butanol production because oil present in the fermentor can break down into fatty acids and glycerin. The glycerin can accumulate in the water and reduce the amount of water that is available for recycling throughout the system. Thus, removal of the oil component of the feedstock increases the efficiency of the product alcohol production by increasing the amount of water that can be recycled through the system.

Figure 4:
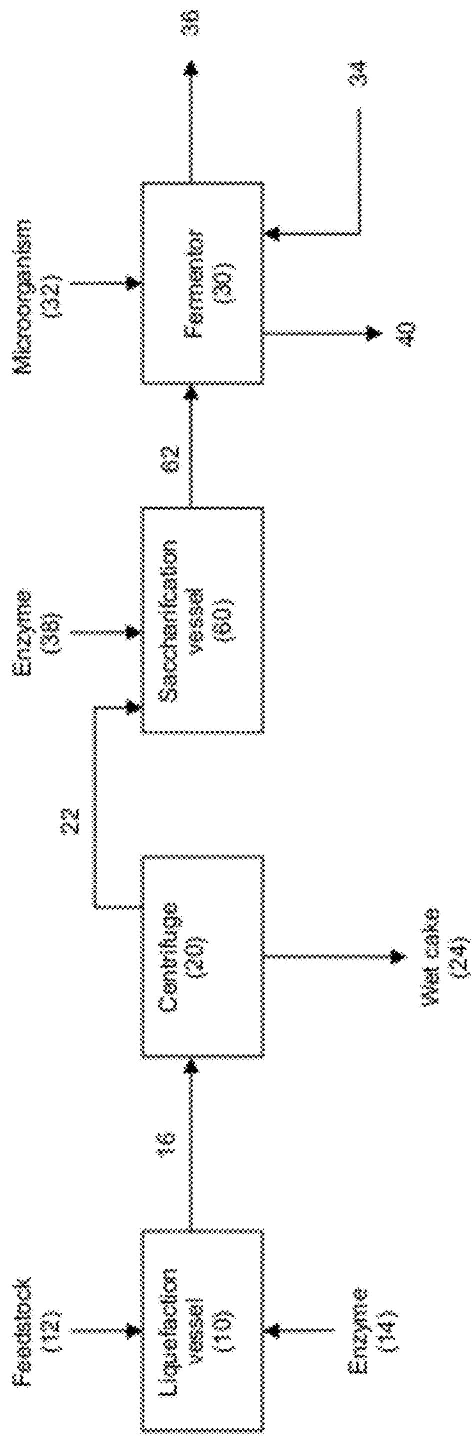
Figure 5:
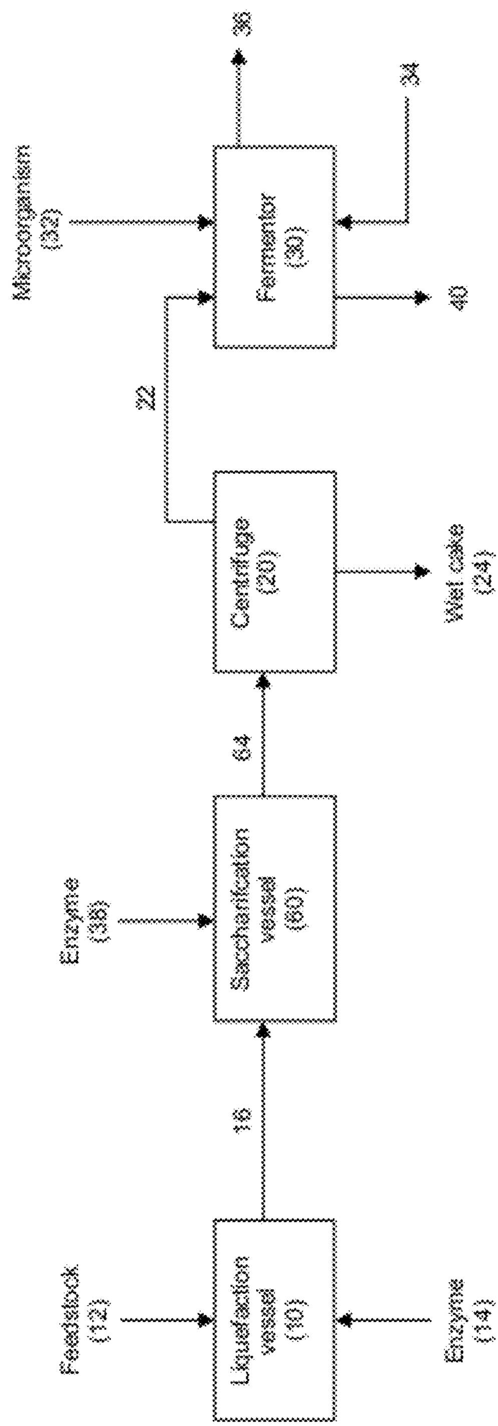

In some embodiments, as shown, for example, in FIGS. 4 and 5, saccharification can occur in a separate saccharification vessel 60 which is located between centrifuge 20 and fermentor 30 (FIG. 4) or between liquefaction vessel 10 and centrifuge 20 (FIG. 5). FIGS. 4 and 5 are identical to FIG. 1 except for the inclusion of a separate saccharification vessel 60 and that fermentor 30 does not receive enzyme 38.

As discussed above, any known saccharification processes normally utilized by the industry can be used including, but not limited to, the acid process, the acid-enzyme process, or the enzyme process. Saccharification vessel 60 can be any suitable known saccharification vessels. In some embodiments, an enzyme 38 such as glucoamylase, can be introduced to an inlet in saccharification vessel 60 in order to break sugars in the form of oligosaccharides into monosaccharides. For example, in FIG. 4, oligosaccharides present in aqueous stream 22 discharged from centrifuge 20 and received in saccharification vessel 60 through an inlet are broken down into monosaccharides. Thus, an aqueous solution 62 containing monosaccharides is discharged from saccharification vessel 60 through an outlet and received in fermentor 30. Alternatively, as shown in FIG. 5, oligosaccharides present in feedstock slurry 16 discharged from liquefaction vessel 10 and received in saccharification vessel 60 through an inlet are broken down into monosaccharides. Thus, a feedstock slurry 64 containing monosaccharides is discharged from saccharification vessel 60 through an outlet and received in centrifuge 20.

In some embodiments, the system and processes of FIGS. 2 and 3 can be modified to include a separate saccharification vessel 60 as discussed above in connection to the systems and processes of FIGS. 4 and 5.

Figure 6:
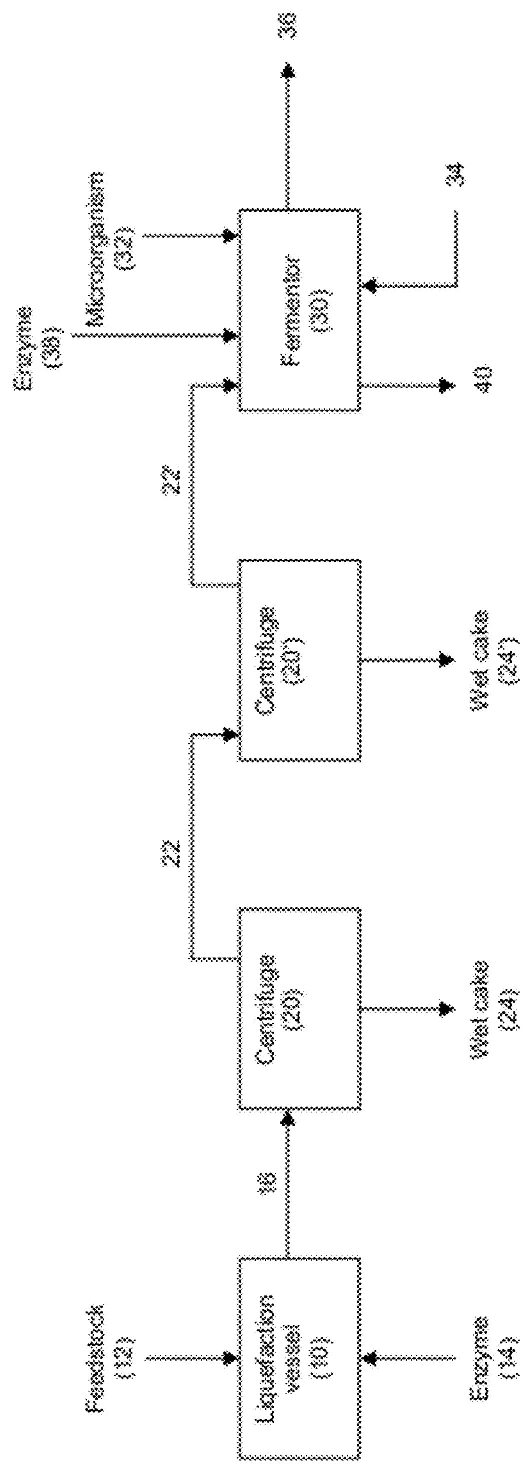

In some embodiments, as shown, for example, in FIG. 6, the systems and processes of the present invention can include a series of two or more centrifuges. FIG. 6 is identical to FIG. 1, except for the addition of a second centrifuge 20' and therefore will not be described in detail again.

Aqueous solution 22 discharged from centrifuge 20 can be received in an inlet of centrifuge 20'. Centrifuge 20' can be identical to centrifuge 20 and can operate in the same manner. Centrifuge 20' can remove undissolved solids not separated from aqueous solution 22 in centrifuge 20 to create (i) an aqueous stream 22' similar to aqueous stream 22, but containing reduced amounts of undissolved solids in comparison to aqueous stream 22 and (ii) a wet cake 24' similar to wet cake 24. Aqueous stream 22' can then be introduced to fermentor 30. In some embodiments, there can be one or more additional centrifuges after centrifuge 20'.

In some embodiments, the systems and processes of FIGS. 2-6 can be modified to include additional centrifuges for removing undissolved solids as discussed above in connection to the systems and processes of FIG. 6.

In some embodiments, fermentation broth 40 can be discharged from an outlet in fermentor 30. The absence or minimization of the undissolved solids exiting fermentor 30 with fermentation broth 40 has several additional benefits. For example, the need for units and operations in the downstream processing can be eliminated such as, for example, a beer column or distillation column, thereby resulting in an increased efficiency for the product alcohol production. Also, some or all of the whole stillage centrifuges may be eliminated as a result of less undissolved solids in the final broth exiting the fermentor.

The processes and systems disclosed in FIGS. 1-6 include removing the undissolved solids from feedstock slurry 16 and as a result, improve the processing productivity of biomass and cost effectiveness. The improved productivity can include having an increased efficiency of butanol production and/or an increased extraction activity relative to processes and systems that do not remove undissolved solids prior to fermentation.

As discussed above, the undissolved solids may be further processed to generate other by-products such as DDGS or fatty acid esters. For example, fatty acid esters may be recovered to increase the yield of carbohydrate to product alcohol (e.g., butanol). This may be accomplished by using a solvent to extract fatty acid esters from, for example, the by-product formed by combining and mixing several by-product streams and drying the product of the combining and mixing steps. Such a solvent-based extraction system for recovering corn oil triglyceride from DDGS is described in U.S. Patent Application Publication No. 2010/0092603, the teachings of which are incorporated by reference herein.

In one embodiment of solvent extraction of fatty acid esters, solids may be separated from whole stillage ("separated solids") since that stream would contain the largest portion, by far, of fatty acid esters in uncombined by-product streams. These separated solids may then be fed into an extractor and washed with solvent. In one embodiment, the separated solids are turned at least once in order to ensure that all sides of the separated solids are washed with solvent. After washing, the resulting mixture of lipid and solvent, known as miscella, is collected for separation of the extracted lipid from the solvent. For example, the resulting mixture of lipid and solvent may be deposited to a separator for further processing. During the extraction process, as the solvent washes over the separated solids, the solvent not only brings lipid into solution, but it collects fine, solid particles. These "fines" are generally undesirable impurities in the miscella and in one embodiment, the miscella may be discharged from the extractor or separator through a device that separates or scrubs the fines from the miscella.

In order to separate the lipid and the solvent contained in the miscella, the miscella may be subjected to a distillation step. In this step, the miscella can, for example, be processed through an evaporator which heats the miscella to a temperature that is high enough to cause vaporization of the solvent, but is not sufficiently high to adversely affect or vaporize the extracted lipid. As the solvent evaporates, it may be collected, for example, in a condenser, and recycled for future use. Separation of the solvent from the miscella results in a stock of crude lipid which may be further processed to separate water, fatty acid esters (e.g., fatty acid isobutyl esters), fatty acids, and triglycerides.

After extraction of the lipids, the solids may be conveyed out of the extractor and subjected to a stripping process that removes residual solvent. Recovery of residual solvent is important to process economics. In one embodiment, the wet solids can be conveyed in a vapor tight environment to preserve and collect solvent that transiently evaporates from the wet solids as it is conveyed into the desolventizer. As the solids enter the desolventizer, they may be heated to vaporize and remove the residual solvent. In order to heat the solids, the desolventizer may include a mechanism for distributing the solids over one or more trays, and the solids may be heated directly, such as through direct contact with heated air or steam, or indirectly, such as by heating the tray carrying the meal. In order to facilitate transfer of the solids from one tray to another, the trays carrying the solids may include openings that allow the solids to pass from one tray to the next. From the desolventizer, the solids may be conveyed to, optionally, a mixer where the solids are mixed with other by-products before being conveyed into a dryer. In this example, the solids are fed to a desolventizer where the solids are contacted by steam. In one embodiment, the flows of steam and solids in the desolventizer may be countercurrent. The solids may then exit the desolventizer and may be fed to a dryer or optionally a mixer where various by-products may be mixed. Vapor exiting the desolventizer may be condensed and optionally mixed with miscella and then fed to a decanter. The water-rich phase exiting the decanter may be fed to a distillation column where hexane is removed from the water-rich stream. In one embodiment, the hexane-depleted water rich stream exits the bottom of the distillation column and may be recycled back to the fermentation process, for example, it may be used to slurry the ground corn solids. In another embodiment, the overhead and bottom products may be recycled to the fermentation process. For example, the lipid-rich bottoms may be added to the feed of a hydrolyzer. The overheads may be, for example, condensed and fed to a decanter. The hexane rich stream exiting this decanter can optionally be used as part of the solvent feed to the extractor. The water-rich phase exiting this decanter may be fed to the column that strips hexane out of water. As one skilled in the art can appreciate, the methods of the present invention may be modified in a variety of ways to optimize the fermentation process for the production of a product alcohol such as butanol.

In a further embodiment, by-products (or co-products) may be derived from the mash used in the fermentation process. For example, corn oil may be separated from mash and this corn oil may contain triglycerides, free fatty acids, diglycerides, monoglycerides, and phospholipids (see, e.g., Example 20). The corn oil may optionally be added to other by-products (or co-products) at different rates and thus, for example, creating the ability to vary the amount of triglyceride in the resulting byproduct. In this manner, the fat content of the resulting by-product could be controlled, for example, to yield a lower fat, high protein animal feed that would better suit the needs of dairy cows compared to a high fat product.

In one embodiment, crude corn oil separated from mash may be further processed into edible oil for consumer use, or it could also be used as a component of animal feed because its high triglyceride content would make it an excellent source of metabolizable energy. In another embodiment, it could also be used as feedstock for biodiesel or renewable diesel.

In one embodiment, extractant by-product may be used, all or in part, as a component of an animal feed by-product or it can be used as feedstock for biodiesel or renewable diesel.

In a further embodiment, solids may be separated from mash and may comprise triglycerides and free fatty acids. These solids (or stream) may be used as an animal feed, either recovered as discharge from centrifugation or after drying. The solids (or wet cake) may be particularly suited as feed for ruminants (e.g., dairy cows) because of its high content of available lysine and by-pass or rumen undegradable protein. For example, these solids may be of particular value in a high protein, low fat feed. In another embodiment, these solids may be used as a base, that is, other by-products such as syrup may be added to the solids to form a product that may be used as an animal feed. In another embodiment, different amounts of other by-products may be added to the solids to tailor the properties of the resulting product to meet the needs of a certain animal species.

The composition of solids separated from whole stillage as described in Example 21 may include, for example, crude protein, fatty acid, and fatty acid isobutyl esters. In one embodiment, this composition (or by-product) may be used, wet or dry, as an animal feed where, for example, a high protein (e.g., high lysine), low fat, and high fiber content is desired. In another embodiment, fat may be added to this composition, for example, from another by-product stream if a higher fat, low fiber animal feed is desired. In one embodiment, this higher fat, low fiber animal feed may be used for swine or poultry. In a further embodiment, a non-aqueous composition of Condensed Distillers Solubles (CDS) (see, e.g., Example 21) may include, for example, protein, fatty acids, and fatty acid isobutyl esters as well as other dissolved and suspended solids such as salts and carbohydrates. This CDS composition may be used, for example, as animal feed, either wet or dry, where a high protein, low fat, high mineral salt feed component is desired. In one embodiment, this composition may be used as a component of a dairy cow ration.

In another embodiment, oil from the fermentation process may be recovered by evaporation. This non-aqueous composition may comprise fatty acid isobutyl esters and fatty acids (see, e.g., Example 20) and this composition (or stream) may be fed to a hydrolyser to recover isobutanol and fatty acids. In a further embodiment, this stream may be used as feedstock for biodiesel production.

The various streams generated by the production of an alcohol (e.g., butanol) via a fermentation process may be combined in many ways to generate a number of co-products. For example, if crude corn from mash is used to generate fatty acids to be utilized as extractant and lipid is extracted by evaporators for other purposes, then the remaining streams may be combined and processed to create a co-product composition comprising crude protein, crude fat, triglycerides, fatty acid, and fatty acid isobutyl ester. In one embodiment, this composition may comprise at least about 20-35 wt % crude protein, at least about 1-20 wt % crude fat, at least about 0-5 wt % triglycerides, at least about 4-10 wt % fatty acid, and at least about 2-6 wt % fatty acid isobutyl ester. In one particular embodiment, the co-product composition may comprise about 25 wt % crude protein, about 10 wt % crude fat, about 0.5 wt % triglycerides, about 6 wt % fatty acid, and about 4 wt % fatty acid isobutyl ester.

In another embodiment, the lipid is extracted by evaporators and the fatty acids are used for other purposes and about 50 wt % of the crude corn from mash and the remaining streams are combined and processed, the resulting co-product composition may comprise crude protein, crude fat, triglycerides, fatty acid, and fatty acid isobutyl ester. In one embodiment, this composition may comprise at least about 25-31 wt % crude protein, at least about 6-10 wt % crude fat, at least about 4-8 wt % triglycerides, at least about 0-2 wt % fatty acid, and at least about 1-3 wt % fatty acid isobutyl ester. In one particular embodiment, the co-product composition may comprise about 28 wt % crude protein, about 8 wt % crude fat, about 6 wt % triglycerides, about 0.7 wt % fatty acid, and about 1 wt % fatty acid isobutyl ester.

In another embodiment, the solids separated from whole stillage and 50 wt % of the corn oil extracted from mash are combined and the resulting co-product composition may comprise crude protein, crude fat, triglycerides, fatty acid, fatty acid isobutyl ester, lysine, neutral detergent fiber (NDF), and acid detergent fiber (ADF). In one embodiment, this composition may comprise at least about 26-34 wt % crude protein, at least about 15-25 wt % crude fat, at least about 12-20 wt % triglycerides, at least about 1-2 wt % fatty acid, at least about 2-4 wt % fatty acid isobutyl ester, at least about 1-2 wt % lysine, at least about 11-23 wt % NDF, and at least about 5-11 wt % ADF. In one particular embodiment, the co-product composition may comprise about 29 wt % crude protein, about 21 wt % crude fat, about 16 wt % triglycerides, about 1 wt % fatty acid, about 3 wt % fatty acid isobutyl ester, about 1 wt % lysine, about 17 wt % NDF, and about 8 wt % ADF. The high fat, triglyceride, and lysine content and the lower fiber content of this co-product composition may be desirable as feed for swine and poultry.

As described above, the various streams generated by the production of an alcohol (e.g., butanol) via a fermentation process may be combined in many ways to generate a co-product composition comprising crude protein, crude fat, triglycerides, fatty acid, and fatty acid isobutyl ester. For example, a composition comprising at least about 6% crude fat and at least about 28% crude protein may be utilized as an animal feed product for dairy animals. A composition comprising at least about 6% crude fat and at least about 26% crude protein may be utilized as an animal feed product for feedlot cattle whereas a composition comprising at least about 1% crude fat and at least about 27% crude protein may be utilized as an animal feed product for wintering cattle. A composition comprising at least about 13% crude fat and at least about 27% crude protein may be utilized as an animal feed product for poultry. A composition comprising at least about 18% crude fat and at least about 22% crude protein may be utilized as an animal feed product for monogastric animals. Thus, the various streams may be combined in such a way as to customize a feed product for a specific animal species.

As described above, the various streams generated by the production of an alcohol (e.g., butanol) via a fermentation process may be combined in many ways to generate a co-product composition comprising crude protein, crude fat, triglycerides, fatty acid, and fatty acid isobutyl ester. For example, a composition comprising at least about 6% crude fat and at least about 28% crude protein may be utilized as an animal feed product for dairy animals. A composition comprising at least about 6% crude fat and at least about 26% crude protein may be utilized as an animal feed product for feedlot cattle whereas a composition comprising at least about 1% crude fat and at least about 27% crude protein may be utilized as an animal feed product for wintering cattle. A composition comprising at least about 13% crude fat and at least about 27% crude protein may be utilized as an animal feed product for poultry. A composition comprising at least about 18% crude fat and at least about 22% crude protein may be utilized as an animal feed product for monogastric animals. Thus, the various streams may be combined in such a way as to customize a feed product for a specific animal species.

In one embodiment, one or more streams generated by the production of an alcohol (e.g., butanol) via a fermentation process may be combined in many ways to generate a composition comprising at least about 90% COFA which may be used as fuel source such as biodiesel.

As an example of one embodiment of the methods of the invention, milled grain (e.g., corn processed by hammer mill) and one or more enzymes are combined to generate a slurried grain. This slurried grain is cooked, liquified, and flashed with flash vapor resulting in a cooked mash. The cooked mash is then filtered to remove suspended solids, generating a wet cake and a filtrate. The filtration may be accomplished by several methods such as centrifugation, screening, or vacuum filtration and this filtration step may remove at least about 80% to at least about 99% of the suspended solids from the mash.

The wet cake is reslurried with water and refiltered to remove additional starch, generating a washed filter cake. The reslurry process may be repeated a number of times, for example, one to five times. The water used to reslurry the wet cake may be recycled water generated during the fermentation process. The filtrate produced by the reslurry/refiltration process may be returned to the initial mix step to form a slurry with the milled grain. The filtrate may be heated or cooled prior to the mix step.

The washed filter cake may be reslurried with beer at a number of stages during the production process. For example, the washed filter cake may be reslurried with beer after the fermentor, before the preflash column, or at the feedpoint to the distillers grain dryer. The washed filter cake may be dried separately from other by-products or may be used directly as wet cake for generation of DDGS.

The filtrate produced as a result of the initial mix step may be further processed as described herein. For example, the filtrate may be heated with steam or process to process heat exchange. A saccharification enzyme may be added to the filtrate and the dissolved starch of the filtrate may be partially or completely saccharified. The saccharified filtrate may be cooled by a number of means such as process to process exchange, exchange with cooling water, or exchange with chilled water.

The cooled filtrate may then be added to a fermentor as well as a microorganism that is suitable for alcohol production, for example, a recombinant yeast capable of producing butanol. In addition, ammonia and recycle streams may also be added to the fermentor. This process may include at least one fermentor, at least two fermentors, at least three fermentors, or at least four fermentors. Carbon dioxide generated during the fermentation may be vented to a scrubber in order to reduce air emissions (e.g., butanol air emissions) and to increase product yield.

Solvent may be added to the fermentor via a recycled loop or may be added directly into the fermentor. The solvent may be one or more organic compounds which have the ability to dissolve or react with the alcohol (e.g., butanol) and may have limited solubility in water. The solvent may be taken from the fermentor continually as a single liquid phase or as a two liquid phase material, or the solvent may be withdrawn batchwise as a single or two liquid phase material.

Beer may be degassed. The beer may be heated before degassing, for example, by process to process exchange with hot mash or process to process exchange with preflash column overheads. Vapors may be vented to a condenser and then, to a scrubber. Degassed beer may be heated further, for example, by process to process heat exchange with other streams in the distillation area.

Preheated beer and solvent may enter a preflash column which may be retrofit from a beer column of a conventional dry grind fuel ethanol plant. This column may be operated at sub-atmospheric pressure, driven by water vapor taken from an evaporator train or from the mash cook step. The overheads of the preflash column may be condensed by heat exchange with some combination of cooling water and process to process heat exchange including heat exchange with the preflash column feed. The liquid condensate may be directed to an alcohol/water decanter (e.g., butanol/water decanter).

The preflash column bottoms may be advanced to a solvent decanter. The preflash column bottoms may be substantially stripped of free alcohol (e.g., butanol). The decanter may be a still well, a centrifuge, or a hydroclone. Water is substantially separated from the solvent phase in this decanter, generating a water phase. The water phase including suspended and dissolved solids may be centrifuged to produce a wet cake and thin stillage. The wet cake may be combined with other streams and dried to produce DDGS, it may be dried and sold separate from other streams which produce DDGS, or it may be sold as a wet cake. The water phase may be split to provide a backset which is used in part to reslurry the filter cake described above. The split also provides thin stillage which may be pumped to evaporators for further processing.

The organic phase produced in the solvent decanter may be an ester of an alcohol (e.g., butanol). The solvent may be hydrolyzed to regenerate reactive solvent and to recover additional alcohol (e.g., butanol). Alternatively, the organic phase may be filtered and sold as a product. Hydrolysis may be thermal driven, homogeneously catalyzed, or heterogeneously catalyzed. The heat input to this process may be a fired heater, hot oil, electrical heat input, or high pressure steam. Water added to drive the hydrolysis may be from a recycled water stream, fresh water, or steam.

Cooled hydrolyzed solvent may be pumped into a sub-atmospheric solvent column where it may be substantially stripped of alcohol (e.g., butanol) with steam. This steam may be water vapor from evaporators, it may be steam from the flash step of the mash process, or it may be steam from a boiler (see, e.g., U.S. Patent Application Publication No. 2009/0171129, incorporated herein by reference). A rectifier column from a conventional dry grind ethanol plant may be suitable as a solvent column. The rectifier column may be modified to serve as a solvent column. The bottoms of the solvent column may be cooled, for example, by cooling water or process to process heat exchange. The cooled bottoms may be decanted to remove residual water and this water may be recycled to other steps with the process or recycled to the mash step.

The solvent column overheads may be cooled by exchange with cooling water or by process to process heat exchange, and the condensate may be directed to a vented alcohol water decanter (e.g., butanol/water decanter) which may be shared with the preflash column overheads. Other mixed water and alcohol (e.g., butanol) streams may be added to this decanter including the scrubber bottoms and condensate from the degas step. The vent which comprises carbon dioxide, may be directed to a water scrubber. The aqueous layer of this decanter may also be fed to the solvent column or may be stripped of alcohol (e.g., butanol) in a small dedicated distillation column. The aqueous layer may be preheated by process to process exchange with the preflash column overheads, solvent column overheads, or solvent column bottoms. This dedicated column may be modified from the side stripper of a conventional dry grind fuel ethanol process.

The organic layer of the alcohol/water decanter (e.g., butanol/water decanter) may be pumped to an alcohol (e.g., butanol) column. This column may be a super-atmospheric column and may be driven by steam condensation within a reboiler. The feed to the column may be heated by process to process heat exchange in order to reduce the energy demand to operate the column. This process to process heat exchanger may include a partial condenser of the preflash column, a partial condenser of a solvent column, the product of the hydrolyzer, water vapor from the evaporators, or the butanol column bottoms. The condensate of the alcohol (e.g., butanol) column vapor may be cooled and may be returned to the alcohol/water decanter (e.g., butanol/water decanter). The alcohol (e.g., butanol) column bottoms may be cooled by process to process heat exchange including exchange with the alcohol (e.g., butanol) column feed and may be further cooled with cooling water, filtered, and are sold as product alcohol (e.g., butanol).

Thin stillage generated from the preflash column bottoms as described above may be directed to a multiple effect evaporator. This evaporator may have two, three, or more stages. The evaporator may have a configuration of four bodies by two effects similar to the conventional design of a fuel ethanol plant, it may have three bodies by three effects, or it may have other configurations. Thin stillage may enter at any of the effects. At least one of the first effect bodies may be heated with vapor from the super-atmospheric alcohol (e.g., butanol) column. The vapor may be taken from the lowest pressure effect to provide heat in the form of water vapor to the sub-atmospheric preflash column and solvent column. Syrup from the evaporators may be added to the distiller's grain dryer.

Carbon dioxide emissions from the fermentor, degasser, alcohol/water decanter (e.g., butanol/water decanter) and other sources may be directed to a water scrubber. The water supplied to the top of this scrubber may be fresh makeup water or may be recycled water. The recycled water may be treated (e.g., biologically digested) to remove volatile organic compounds and may be chilled. Scrubber bottoms may be sent to the alcohol/water decanter (e.g., butanol/water decanter), to the solvent column, or may be used with other recycled water to reslurry the wet cake described above. Condensate from the evaporators may be treated with anaerobic biological digestion or other processes to purify the water before recycling to reslurry the filter cakes.

If corn is used as the source of the milled grain, corn oil may be separated from the process streams at any of several points. For example, a centrifuge may be operated to produce a corn oil stream following filtration of the cooked mash or the preflash column water phase centrifuge may be operated to produce a corn oil stream. Intermediate concentration syrup or final syrup may be centrifuged to produce a corn oil stream.

In another example of an embodiment of the methods of the invention, the material discharged from the fermentor may be processed in a separation system that involves devices such as a centrifuge, settler, hydrocyclone, etc., and combinations thereof to effect the recovery of live yeast in a concentrated form that can be recycled for reuse in a subsequent fermentation batch either directly or after some re-conditioning. This separation system may also produce an organic stream that comprises fatty esters (e.g. isobutyl fatty esters) and an alcohol (e.g., butanol) produced from the fermentation and an aqueous stream containing only trace levels of immiscible organics. This aqueous stream may be used either before or after it is stripped of the alcohol (e.g., butanol) content to re-pulp and pump the low starch solids that was separated and washed from liquefied mash. This has the advantage of avoiding what might otherwise be a long belt-driven conveying system to transfer these solids from the liquefaction area to the grain drying and syrup blend area. Furthermore, this whole stillage that results after the alcohol (e.g., butanol) has been stripped will need to be separated into thin stillage and wet cake fractions either using existing or new separation devices and this thin stillage will form in part the backset that returns to combine with cook water for preparing a new batch of fermentable mash. Another advantage of this embodiment is that any residual dissolved starch that was retained in the moisture of the solids separated from the liquefied mash would in part be captured and recovered through this backset. Alternatively, the yeast contained in the solids stream may be considered nonviable and may be redispersed in the aqueous stream and this combined stream distilled of any alcohol (e.g., butanol) content remaining from fermentation. Non viable organisms may further be separated for use as a nutrient in the propagation process.

In another embodiment, the multi-phase material may leave the bottom of the pre-flash column and may be processed in a separation system as described above. The concentrated solids may be redispersed in the aqueous stream and this combined stream may be used to re-pulp and pump the low starch solids that were separated and washed from liquefied mash.

The process described above as well as other processes described herein may be demonstrated using computational modeling such as Aspen modeling (see, e.g., U.S. Pat. No. 7,666,282). For example, the commercial modeling software Aspen Plus® (Aspen Technology, Inc., Burlington, Mass.) may be use in conjunction with physical property databases such as DIPPR (Design Institute for Physical Property Research), available from American Institute of Chemical Engineers, Inc. (New York, N.Y.) to develop an Aspen model for an integrated butanol fermentation, purification, and water management process. This process modeling can perform many fundamental engineering calculations, for example, mass and energy balances, vapor/liquid equilibrium, and reaction rate computations. In order to generate an Aspen model, information input may include, for example, experimental data, water content and composition of feedstock, temperature for mash cooking and flashing, saccharification conditions (e.g., enzyme feed, starch conversion, temperature, pressure), fermentation conditions (e.g., microorganism feed, glucose conversion, temperature, pressure), degassing conditions, solvent columns, preflash columns, condensers, evaporators, centrifuges, etc.

The processes and systems described above can lead to increased extraction activity and/or efficiency in the product alcohol production as a result of the removal of the undissolved solids. For example, extractive fermentation without the presence of the undissolved solids can lead to higher mass transfer rate of the product alcohol from the fermentation broth to the extractant, better phase separation of the extractant from the fermentation inside or external to the fermentor, and lower hold up of the extractant as a result of higher extractant droplet rise velocities. Also, for example, the extractant droplets held up in the fermentation broth during fermentation will disengage from the fermentation broth faster and more completely, thereby resulting in less free extractant in the fermentation broth and can decrease the amount of extractant lost in the process. In addition, for example, the microorganism can be recycled and additional equipment in the downstream processing can be eliminated, such as for example, a beer column and/or some or all of the whole stillage centrifuges. Further, for example, the possibility of extractant being lost in the DDGS is removed. Also, for example, the ability to recycle the microorganism can increase the overall rate of product alcohol production, lower the overall titer requirement, and/or lower the aqueous titer requirement, thereby leading to a healthier microorganism and a higher production rate. In addition, for example, it can be possible to eliminate an agitator in the fermentor to reduce capital costs; to increase the fermentor productivity since the volume is used more efficiently because the extractant hold up is minimized and the undissolved solids are not present; and/or to use continuous fermentation or smaller fermentors in a greenfield plant.

Examples of increased extraction efficiency can include, for example, a stabilized partition coefficient, enhanced (e.g., quicker or more complete) phase separation, enhanced liquid-liquid mass transfer coefficient, operation at a lower titer, increased process stream recyclability, increased fermentation volume efficiency, increased feedstock (e.g., corn) load feeding, increased butanol titer tolerance of the microorganism (e.g., a recombinant microorganism), water recycling, reduction in energy, increased recycling of extractant, and/or recycling of the microorganism.

For example, the volume of the fermentor taken up by solids will be decreased. Thus, the effective volume of the fermentor available for the fermentation can be increased. In some embodiments, the volume of the fermentor available for the fermentation is increased by at least about 10%.

For example, there can be a stabilization in partition coefficient. Because the corn oil in the fermentor can be reduced by removing the solids from the feedstock slurry prior to fermentation, the extractant is exposed to less corn oil which combines with the extractant and may lower the partition coefficient if present in sufficient amount. Therefore, reduction of the corn oil introduced into the fermentor results in a more stable partition coefficient of the extractant phase in the fermentor. In some embodiments, the partition coefficient is decreased by less than about 10% over 10 fermentation cycles.

For example, there can be an increase in the extraction efficiency of the butanol with extractant because there will be a higher mass transfer rate (e.g., in the form of a higher mass transfer coefficient) of the product alcohol from the fermentation broth to the extractant, thereby resulting in an increased efficiency of product alcohol production. In some embodiments, the mass transfer coefficient is increased at least 2-fold (see Examples 4 and 5).

In addition, there can be an increase in phase separation between the fermentation broth and the extractant that reduces the likelihood of the formation of an emulsion, thereby resulting in an increased efficiency of product alcohol production. For example, the phase separation can occur more quickly or can be more complete. In some embodiments, a phase separation may occur where previously no appreciable phase separation was observed in 24 hours. In some embodiments, the phase separation occurs at least about 2× as quickly, at least about 5× as quickly, or at least about 10× as quickly as compared to the phase separation where solids have not been removed (see Examples 6 and 7).

Further, there can be an increase in the recovery and recycling of the extractant. The extractant will not be "trapped" in the solids which may ultimately be removed as DDGS, thereby resulting in an increased efficiency of product alcohol production (see Examples 8 and 9). Also, there will be less dilution of the extractant with corn oil, and there may be less degradation of the extractant (see Example 10).

Also, the flow rate of the extractant can be reduced which will lower operating costs, thereby resulting in an increased efficiency of product alcohol production.

Further still, hold up of the extractant will be decreased as a result of extractant droplets rising at a higher velocity, thereby resulting in an increased efficiency of product alcohol production. Reducing the amount of undissolved solids in the fermentor will also result in an increased efficiency of product alcohol production.

In addition, an agitator can be removed from the fermentor because it is no longer needed to suspend the undissolved solids, thereby reducing capital costs and energy, and increasing the efficiency of the product alcohol production.

In some embodiments, fermentation broth 40 can be discharged from an outlet in fermentor 30. The absence or minimization of the undissolved solids exiting fermentor 30 with fermentation broth 40 has several additional benefits. For example, the need for units and operations in the downstream processing can be eliminated such as, for example, a beer column or distillation column, thereby resulting in an increased efficiency for the product alcohol production. Furthermore, since the undissolved solids are not present in fermentation broth 40 exiting fermentor 30, there is no DDGS formed with "trapped" extractant. Also, some or all of the whole stillage centrifuges may be eliminated as a result of less undissolved solids in the final broth exiting the fermentor.

As described above, the methods of the present invention provide a number of benefits that can result in improved production (e.g., batch or continuous) of a product alcohol such as butanol. For example, the improvement in mass transfer enables operation at a lower aqueous titer resulting in a "healthier" microorganism. A better phase separation can lead to improved fermentor volume efficiency as well as the possibility of processing less reactor contents through beer columns, distillation columns, etc. In addition, there is less solvent loss via solids and there is the possibility of cell recycling. The methods of the present invention may also provide a higher quality of DDGS.

In addition, the methods described herein provide for the removal of oil (e.g., corn oil) prior to fermentation which would then allow the controlled addition of oil to the fermentation. Furthermore, the removal of oil prior to fermentation would allow some flexibility in the amount of oil present in DDGS. That is, oil may be added in different amounts to DDGS resulting in the production of DDGS with different fat contents depending on the nutritional needs of a particular animal species.

Recombinant Microorganisms and Butanol Biosynthetic Pathways

While not wishing to be bound by theory, it is believed that the processes described herein are useful in conjunction with any alcohol producing microorganism, particularly recombinant microorganisms which produce alcohol at titers above their tolerance levels.

Alcohol-producing microorganisms are known in the art. For example, fermentative oxidation of methane by methanotrophic bacteria (e.g., *Methylosinus trichosporium*) produces methanol, and contacting methanol (a $C_1$ alkyl alcohol) with a carboxylic acid and a catalyst capable of esterifying the carboxylic acid with methanol forms a methanol ester of the carboxylic acid. The yeast strain CEN.PK113-7D (CBS 8340, the Centraal Buro voor Schimmelculture; van Dijken, et al., Enzyme Microb. Techno. 26:706-714, 2000) can produce ethanol, and contacting ethanol with a carboxylic acid and a catalyst capable of esterifying the carboxylic acid with the ethanol forms ethyl ester (see, e.g., Example 36).

Recombinant microorganisms which produce alcohol are also known in the art (e.g., Ohta, et al., Appl. Environ. Microbiol. 57:893-900, 1991; Underwood, et al., Appl. Environ. Microbiol. 68:1071-1081, 2002; Shen and Liao, Metab. Eng. 10:312-320, 2008; Hahnai, et al., Appl. Environ. Microbiol. 73:7814-7818, 2007; U.S. Pat. No. 5,514,583; U.S. Pat. No. 5,712,133; PCT Application Publication No. WO 1995/028476; Feldmann, et al., Appl. Microbiol. Biotechnol. 38: 354-361, 1992; Zhang, et al., Science 267:240-243, 1995; U.S. Patent Application Publication No. 2007/0031918 A1; U.S. Pat. No. 7,223,575; U.S. Pat. No. 7,741,119; U.S. Pat. No. 7,851,188; U.S. Patent Application Publication No. 2009/0203099 A1; U.S. Patent Application Publication No. 2009/0246846 A1; and PCT Application Publication No. WO 2010/075241, which are all herein incorporated by reference).

Suitable recombinant microorganisms capable of producing butanol are known in the art, and certain suitable microorganisms capable of producing butanol are described herein. Recombinant microorganisms to produce butanol via a biosynthetic pathway can include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevi-*

*bacterium, Schizosaccharomyces, Kluyveromyces, Yarrowia, Pichia, Candida, Hansenula, Issatchenkia*, or *Saccharomyces*. In one embodiment, recombinant microorganisms can be selected from the group consisting of *Escherichia coli, Lactobacillus plantarum, Kluyveromyces lactis, Kluyveromyces marxianus* and *Saccharomyces cerevisiae*. In one embodiment, the recombinant microorganism is yeast. In one embodiment, the recombinant microorganism is crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii*, and *Candida glabrata*.

In some embodiments, the host cell is *Saccharomyces cerevisiae. S. cerevisiae* yeast are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™Gold yeast, Thermosacc® yeast, BG-1, PE-2, CAT-1, CBS7959, CBS7960, and CBS7961.

The production of butanol utilizing fermentation with a microorganism, as well as microorganisms which produce butanol, is disclosed, for example, in U.S. Patent Application Publication No. 2009/0305370, herein incorporated by reference. In some embodiments, microorganisms comprise a butanol biosynthetic pathway. In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism. In some embodiments, the microorganism comprises a reduction or elimination of pyruvate decarboxylase activity. Microorganisms substantially free of pyruvate decarboxylase activity are described in US Application Publication No. 2009/0305363, herein incorporated by reference. Microorganisms substantially free of an enzyme having NAD-dependent glycerol-3-phosphate dehydrogenase activity such as GPD2 are also described therein.

Suitable biosynthetic pathways for production of butanol are known in the art, and certain suitable pathways are described herein. In some embodiments, the butanol biosynthetic pathway comprises at least one gene that is heterologous to the host cell. In some embodiments, the butanol biosynthetic pathway comprises more than one gene that is heterologous to the host cell. In some embodiments, the butanol biosynthetic pathway comprises heterologous genes encoding polypeptides corresponding to every step of a biosynthetic pathway.

Certain suitable proteins having the ability to catalyze indicated substrate to product conversions are described herein and other suitable proteins are provided in the art. For example, U.S. Patent Application Publication Nos. 2008/0261230, 2009/0163376, and 2010/0197519, incorporated herein by reference, describe acetohydroxy acid isomeroreductases; U.S. Patent Application Publication No. 2010/0081154, incorporated by reference, describes dihydroxy-acid dehydratases; an alcohol dehydrogenase is described in U.S. Patent Application Publication No. 2009/0269823, incorporated herein by reference.

It is well understood by one skilled in the art that many levels of sequence identity are useful in identifying polypeptides from other species, wherein such polypeptides have the same or similar function or activity and are suitable for use in the recombinant microorganisms described herein. Useful examples of percent identities include, but are not limited to, 75%, 80%, 85%, 90%, or 95%, or any integer percentage from 75% to 100% may be useful in describing the present invention such as 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

Suitable strains include those described in certain applications cited and incorporated by reference herein as well as in U.S. Provisional Application Ser. No. 61/380,563, filed on Sep. 7, 2010. Construction of certain suitable strains including those used in the Examples, is provided herein.

Construction of *Saccharomyces cerevisiae* Strain BP1083 ("NGCI-070"; PNY1504)

The strain BP1064 was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, PDC6, and GPD2. BP1064 was transformed with plasmids pYZ090 (SEQ ID NO: 1, described in U.S. Provisional Application Ser. No. 61/246,844) and pLH468 (SEQ ID NO: 2) to create strain NGCI-070 (BP1083, PNY1504).

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion or if flanked by loxP sites, was removed using Cre recombinase.

The scarless deletion procedure was adapted from Akada, et al., (Yeast 23:399-405, 2006). In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3' 500 bp of the target gene (Fragment C). Fragments A and C were used for integration of the cassette into the chromosome by homologous recombination. Fragment B (500 bp long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted. For integration of genes using this method, the gene to be integrated was included in the PCR cassette between fragments A and B.

URA3 Deletion

To delete the endogenous URA3 coding region, a ura3::loxP-kanMX-loxP cassette was PCR-amplified from pLA54 template DNA (SEQ ID NO: 3). pLA54 contains the *K. lactis* TEF1 promoter and kanMX marker, and is flanked by loxP sites to allow recombination with Cre recombinase and removal of the marker. PCR was done using Phusion® DNA polymerase (New England BioLabs Inc., Ipswich, Mass.) and primers BK505 and BK506 (SEQ ID NOs: 4 and 5). The URA3 portion of each primer was derived from the 5' region upstream of the URA3 promoter and 3' region downstream of the coding region such that integration of the loxP-kanMX-loxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 μg/mL) at 30° C. Transformants were screened to verify correct integration by PCR using primers LA468 and LA492 (SEQ ID NOs: 6 and 7) and designated CEN.PK 113-7D Δura3::kanMX.

HIS3 Deletion

The four fragments for the PCR cassette for the scarless HIS3 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact, kit (Qiagen, Valencia, Calif.). HIS3 Fragment A was amplified with primer oBP452 (SEQ ID NO: 14) and primer oBP453 (SEQ ID NO: 15) containing a 5' tail with homology to the 5' end of HIS3 Fragment B. HIS3 Fragment B was amplified with primer oBP454 (SEQ ID NO: 16) containing a 5' tail with homology to the 3' end of HIS3 Fragment A, and primer oBP455 (SEQ ID NO: 17) containing a 5' tail with homology to the 5' end of HIS3 Fragment U. HIS3 Fragment U was amplified with primer oBP456 (SEQ ID NO: 18) containing a 5' tail with homology to the 3' end of HIS3 Fragment B, and primer oBP457 (SEQ ID NO: 19) containing a 5' tail with homology to the 5' end of HIS3 Fragment C. HIS3 Fragment C was amplified with primer oBP458 (SEQ ID NO: 20) containing a 5' tail with homology to the 3' end of HIS3 Fragment U, and primer oBP459 (SEQ ID NO: 21). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 14) and oBP455 (SEQ ID NO: 17). HIS3 Fragment UC was created by overlapping PCR by mixing HIS3 Fragment U and HIS3 Fragment C and amplifying with primers oBP456 (SEQ ID NO: 18) and oBP459 (SEQ ID NO: 21). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 14) and oBP459 (SEQ ID NO: 21). The PCR product was purified with a PCR Purification kit (Qiagen, Valencia, Calif.).

Competent cells of CEN.PK 113-7D Δura3::kanMX were made and transformed with the HIS3 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a his3 knockout were screened for by PCR with primers oBP460 (SEQ ID NO: 22) and oBP461 (SEQ ID NO: 23) using genomic DNA prepared with a Gentra® Puregene® Yeast/Bact. kit (Qiagen, Valencia, Calif.). A correct transformant was selected as strain CEN.PK 113-7D Δura3::kanMX Δhis3::URA3.

KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 66, described in U.S. Provisional Application No. 61/290,639) using a Frozen-EZ Yeast Transformation II™ kit (Zymo Research Corporation, Irvine, Calif.) and plating on synthetic complete medium lacking histidine and uracil supplemented with 2% glucose at 30° C. Transformants were grown in YP supplemented with 1% galactose at 30° C. for ~6 hours to induce the Cre recombinase and KanMX marker excision and plated onto YPD (2% glucose) plates at 30° C. for recovery. An isolate was grown overnight in YPD and plated on synthetic complete medium containing 5-fluoro-orotic acid (5-FOA, 0.1%) at 30° C. to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying growth on YPD+G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 24) and oBP451 (SEQ ID NO: 25) for Δura3 and primers oBP460 (SEQ ID NO: 22) and oBP461 (SEQ ID NO: 23) for Δhis3 using genomic DNA prepared with a Gentra® Puregene® Yeast/Bact. kit (Qiagen, Valencia, Calif.).

PDC6 Deletion

The four fragments for the PCR cassette for the scarless PDC6 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC6 Fragment A was amplified with primer oBP440 (SEQ ID NO: 26) and primer oBP441 (SEQ ID NO: 27) containing a 5' tail with homology to the 5' end of PDC6 Fragment B. PDC6 Fragment B was amplified with primer oBP442 (SEQ ID NO: 28), containing a 5' tail with homology to the 3' end of PDC6 Fragment A, and primer oBP443 (SEQ ID NO: 29) containing a 5' tail with homology to the 5' end of PDC6 Fragment U. PDC6 Fragment U was amplified with primer oBP444 (SEQ ID NO: 30) containing a 5' tail with homology to the 3' end of PDC6 Fragment B, and primer oBP445 (SEQ ID NO: 31) containing a 5' tail with homology to the 5' end of PDC6 Fragment C. PDC6 Fragment C was amplified with primer oBP446 (SEQ ID NO: 32) containing a 5' tail with homology to the 3' end of PDC6 Fragment U, and primer oBP447 (SEQ ID NO: 33). PCR products were purified with a PCR Purification kit (Qiagen, Valencia, Calif.). PDC6 Fragment AB was created by overlapping PCR by mixing PDC6 Fragment A and PDC6 Fragment B and amplifying with primers oBP440 (SEQ ID NO: 26) and oBP443 (SEQ ID NO: 29). PDC6 Fragment UC was created by overlapping PCR by mixing PDC6 Fragment U and PDC6 Fragment C and amplifying with primers oBP444 (SEQ ID NO: 30) and oBP447 (SEQ ID NO: 33). The resulting PCR products were purified on an agarose gel followed by a Gel Extraction kit (Qiagen, Valencia, Calif.). The PDC6

ABUC cassette was created by overlapping PCR by mixing PDC6 Fragment AB and PDC6 Fragment UC and amplifying with primers oBP440 (SEQ ID NO: 26) and oBP447 (SEQ ID NO: 33). The PCR product was purified with a PCR Purification kit (Qiagen, Valencia, Calif.).

Competent cells of CEN.PK 113-7D Δura3::loxP Δhis3 were made and transformed with the PDC6 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc6 knockout were screened for by PCR with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0.1%) at 30° C. to select for isolates that lost the URA3 marker. The deletion and marker removal were confirmed by PCR and sequencing with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). The absence of the PDC6 gene from the isolate was demonstrated by a negative PCR result using primers specific for the coding sequence of PDC6, oBP554 (SEQ ID NO: 36) and oBP555 (SEQ ID NO: 37). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC No. 700610. The A fragment followed by the ilvD coding region from *Streptococcus mutans* for the PCR cassette for the PDC1 deletion-ilvDSm integration was amplified using Phusion® High Fidelity PCR Master Mix (New England BioLabs Inc., Ipswich, Mass.) and NYLA83 genomic DNA as template, prepared with a Gentra® Puregene® Yeast/Bact. kit (Qiagen, Valencia, Calif.). NYLA83 is a strain (construction described in U.S. App. Pub. NO. 20110124060, incorporated herein by reference in its entirety) which carries the PDC1 deletion-ilvDSm integration described in U.S. Patent Application Publication No. 2009/0305363 (herein incorporated by reference in its entirety). PDC1 Fragment A-ilvDSm (SEQ ID NO: 69) was amplified with primer oBP513 (SEQ ID NO: 38) and primer oBP515 (SEQ ID NO: 39) containing a 5' tail with homology to the 5' end of PDC1 Fragment B. The B, U, and C fragments for the PCR cassette for the PDC1 deletion-ilvDSm integration were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC1 Fragment B was amplified with primer oBP516 (SEQ ID NO: 40) containing a 5' tail with homology to the 3' end of PDC1 Fragment A-ilvDSm, and primer oBP517 (SEQ ID NO: 41) containing a 5' tail with homology to the 5' end of PDC1 Fragment U. PDC1 Fragment U was amplified with primer oBP518 (SEQ ID NO: 42) containing a 5' tail with homology to the 3' end of PDC1 Fragment B, and primer oBP519 (SEQ ID NO: 43) containing a 5' tail with homology to the 5' end of PDC1 Fragment C. PDC1 Fragment C was amplified with primer oBP520 (SEQ ID NO: 44), containing a 5' tail with homology to the 3' end of PDC1 Fragment U, and primer oBP521 (SEQ ID NO: 45). PCR products were purified with a PCR Purification kit (Qiagen, Valencia, Calif. PDC1 Fragment A-ilvDSm-B was created by overlapping PCR by mixing PDC1 Fragment A-ilvDSm and PDC1 Fragment B and amplifying with primers oBP513 (SEQ ID NO: 38) and oBP517 (SEQ ID NO: 41). PDC1 Fragment UC was created by overlapping PCR by mixing PDC1 Fragment U and PDC1 Fragment C and amplifying with primers oBP518 (SEQ ID NO: 42) and oBP521 (SEQ ID NO: 45). The resulting PCR products were purified on an agarose gel followed by a Gel Extraction kit (Qiagen, Valencia, Calif.). The PDC1 A-ilvDSm-BUC cassette (SEQ ID NO: 70) was created by overlapping PCR by mixing PDC1 Fragment A-ilvDSm-B and PDC1 Fragment UC and amplifying with primers oBP513 (SEQ ID NO: 38) and oBP521 (SEQ ID NO: 45). The PCR product was purified with a PCR Purification kit (Qiagen, Valencia, Calif.).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc1 knockout ilvDSm integration were screened for by PCR with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The absence of the PDC1 gene from the isolate was demonstrated by a negative PCR result using primers specific for the coding sequence of PDC1, oBP550 (SEQ ID NO: 48) and oBP551 (SEQ ID NO: 49). A correct transformant was selected as strain CEN.PK 113-7D Δura3::loxP Δhis3 Δpdc6 Δpdc1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1%) at 30° C. to select for isolates that lost the URA3 marker. The deletion of PDC1, integration of ilvDSm, and marker removal were confirmed by PCR and sequencing with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter xylosoxidans*. A segment of the PCR cassette for the PDC5 deletion-sadB integration was first cloned into plasmid pUC19-URA3MCS.

pUC19-URA3MCS is pUC19 based and contains the sequence of the URA3 gene from *Saccaromyces cerevisiae* situated within a multiple cloning site (MCS). pUC19 contains the pMB1 replicon and a gene coding for beta-lactamase for replication and selection in *Escherichia coli*. In addition to the coding sequence for URA3, the sequences from upstream and downstream of this gene were included for expression of the URA3 gene in yeast. The vector can be used for cloning purposes and can be used as a yeast integration vector.

The DNA encompassing the URA3 coding region along with 250 bp upstream and 150 bp downstream of the URA3 coding region from *Saccaromyces* cerevisiae CEN.PK 113-7D genomic DNA was amplified with primers oBP438 (SEQ ID NO: 12) containing BamHI, AscI, PmeI, and FseI restriction sites, and oBP439 (SEQ ID NO: 13) containing XbaI, Pad, and NotI restriction sites, using Phusion® High Fidelity PCR Master Mix (New England BioLabs Inc., Ipswich, Mass.). Genomic DNA was prepared using a Gentra® Puregene® Yeast/Bact. kit (Qiagen, Valencia, Calif.). The PCR product and pUC19 (SEQ ID NO: 71) were ligated with T4 DNA ligase after digestion with BamHI and XbaI to create vector pUC19-URA3MCS. The vector was confirmed by PCR and sequencing with primers oBP264 (SEQ ID NO: 10) and oBP265 (SEQ ID NO: 11).

The coding sequence of sadB and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 67) as template with primer oBP530 (SEQ ID NO: 50) containing an AscI restriction site, and primer oBP531 (SEQ ID NO: 51) containing a 5' tail with homology to the 5' end of PDC5 Fragment B. PDC5 Fragment B was amplified with primer oBP532 (SEQ ID NO: 52) containing a 5' tail with homology to the 3' end of sadB, and primer oBP533 (SEQ ID NO: 53) containing a PmeI restriction site. PCR products were purified with a PCR Purification kit (Qiagen, Valencia, Calif.). sadB-PDC5 Fragment B was created by overlapping PCR by mixing the sadB and PDC5 Fragment B PCR products and amplifying with primers oBP530 (SEQ ID NO: 50) and oBP533 (SEQ ID NO: 53). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 54) and oBP546 (SEQ ID NO: 55) containing a 5' tail with homology to the 5' end of PDC5 Fragment C. PDC5 Fragment C was amplified with primer oBP547 (SEQ ID NO: 56) containing a 5' tail with homology to the 3' end of PDC5 sadB-Fragment B-Fragment U, and primer oBP539 (SEQ ID NO: 57). PCR products were purified with a PCR Purification kit (Qiagen, Valencia, Calif.). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 54) and oBP539 (SEQ ID NO: 57). The resulting PCR product was purified on an agarose gel followed by a Gel Extraction kit (Qiagen, Valencia, Calif.). The PDC5 A-sadB-BUC cassette (SEQ ID NO: 72) was created by amplifying PDC5 sadB-Fragment B-Fragment U-Fragment C with primers oBP542 (SEQ ID NO: 58) containing a 5' tail with homology to the 50 nucleotides immediately upstream of the native PDC5 coding sequence, and oBP539 (SEQ ID NO: 57). The PCR product was purified with a PCR Purification kit (Qiagen, Valencia, Calif.).

Competent cells of CEN.PK 113-7D Δura3::loxP Δhis3 Δpdc6 Δpdc1::ilvDSm were made and transformed with the PDC5 A-sadB-BUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol (no glucose) at 30° C. Transformants with a pdc5 knockout sadB integration were screened for by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The absence of the PDC5 gene from the isolate was demonstrated by a negative PCR result using primers specific for the coding sequence of PDC5, oBP552 (SEQ ID NO: 61) and oBP553 (SEQ ID NO: 62). A correct transformant was selected as strain CEN.PK 113-7D Δura3::loxP Δhis3 Δpdc6 Δpdc1::ilvDSm Δpdc5::sadB-URA3.

CEN.PK 113-7D Δura3::loxP Δhis3 Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30° C. to select for isolates that lost the URA3 marker. The deletion of PDC5, integration of sadB, and marker removal were confirmed by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm Δpdc5::sadB and designated as BP913.

GPD2 Deletion

To delete the endogenous GPD2 coding region, a gpd2::loxP-URA3-loxP cassette (SEQ ID NO: 73) was PCR-amplified using loxP-URA3-loxP (SEQ ID NO: 68) as template DNA. loxP-URA3-loxP contains the URA3 marker from (ATCC No. 77107) flanked by loxP recombinase sites. PCR was done using Phusion® DNA polymerase (New England BioLabs Inc., Ipswich, Mass.) and primers LA512 and LA513 (SEQ ID NOs: 8 and 9). The GPD2 portion of each primer was derived from the 5' region upstream of the GPD2 coding region and 3' region downstream of the coding region such that integration of the loxP-URA3-loxP marker resulted in replacement of the GPD2 coding region. The PCR product was transformed into BP913 and transformants were selected on synthetic complete media lacking uracil supplemented with 1% ethanol (no glucose). Transformants were screened to verify correct integration by PCR using primers oBP582 and AA270 (SEQ ID NOs: 63 and 64).

The URA3 marker was recycled by transformation with pRS423::PGAL1-cre (SEQ ID NO: 66) and plating on synthetic complete media lacking histidine supplemented with 1% ethanol at 30° C. Transformants were streaked on synthetic complete medium supplemented with 1% ethanol and containing 5-fluoro-orotic acid (0.1%) and incubated at 30° C. to select for isolates that lost the URA3 marker. 5-FOA resistant isolates were grown in YPE (1% ethanol) for removal of the pRS423::PGAL1-cre plasmid. The deletion and marker removal were confirmed by PCR with primers oBP582 (SEQ ID NO: 63) and oBP591 (SEQ ID NO: 65). The correct isolate was selected as strain CEN.PK 113-7D Δura3::loxP Δhis3 Δpdc6 Δpdc1::ilvDSm Δpdc5::sadB Δgpd2::loxP and designated as PNY1503 (BP1064).

BP1064 was transformed with plasmids pYZ090 (SEQ ID NO: 1) and pLH468 (SEQ ID NO: 2) to create strain NGCI-070 (BP1083; PNY1504).

Further, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following nonlimiting examples will further illustrate the invention. It should be understood that, while the following examples involve corn as feedstock, other biomass sources can be used for feedstock without departing from the present invention.

As used herein, the meaning of abbreviations used was as follows: "g" means gram(s), "kg" means kilogram(s), "L" means liter(s), "mL" means milliliter(s), "μL" means microliter(s), "mL/L" means milliliter(s) per liter, "mL/min" means milliliter(s) per min, "DI" means deionized, "uM" means micrometer(s), "nm" means nanometer(s), "w/v" means weight/volume, "OD" means optical density, "$OD_{600}$" means optical density at a wavelength of 600 nM, "dcw" means dry cell weight, "rpm" means revolutions per minute, "° C." means degree(s) Celsius, "° C./min" means degrees Celsius per minute, "slpm" means standard liter(s) per minute, "ppm" means part per million, "pdc" means pyruvate decarboxylase enzyme followed by the enzyme number.

Example 1

Preparation of Corn Mash

Approximately 100 kg of liquefied corn mash was prepared in three equivalent batches using a 30 L glass, jacketed resin kettle. The kettle was set up with mechanical agitation, temperature control, and pH control. The protocol used for all three batches was as follows: (a) mixing ground corn with tap water (30 wt % corn on a dry basis), (b) heating the slurry to 55° C. while agitating, (c) adjusting pH of the slurry to 5.8 with either NaOH or $H_2SO_4$, (d) adding alpha-amylase (0.02 wt % on a dry corn basis), (e) heating the slurry to 85° C., (f) adjusting pH to 5.8, (g) holding the slurry at 85° C. for 2 hrs while maintaining pH at 5.8, and (h) cooling the slurry to 25° C.

The corn used was whole kernel yellow corn from Pioneer (3335). It was ground in a hammer-mill using a 1 mm screen. The moisture content of the ground corn was measured to be 12 wt %, and the starch content of the ground corn was measured to be 71.4 wt % on a dry corn basis. The alpha-amylase enzyme was Liquozyme® SC DS available from Novozymes (Franklinton, N.C.). The total amounts of the ingredients used for all three batches combined were: 33.9 kg of ground corn (12% moisture), 65.4 kg of tap water, and 0.006 kg of Liquozyme® SC DS. A total of 0.297 kg of NaOH (17 wt %) was added to control pH. No $H_2SO_4$ was required. The total amount of liquefied corn mash recovered from the three 30 L batches was 99.4 kg.

Example 2

Solids Removal

The solids were removed from the mash produced in Example 1 by centrifugation in a large floor centrifuge which contained six 1 L bottles. 73.4 kg of mash was centrifuged at 8000 rpm for 20 min at 25° C. yielding 44.4 kg of centrate and 26.9 kg of wet cake. It was determined that the centrate contained <1 wt % suspended solids, and that the wet cake contained approximately 18 wt % suspended solids. This implies that the original liquefied mash contained approximately 7 wt % suspended solids. This is consistent with the corn loading and starch content of the corn used assuming most of the starch was liquefied. If all of the starch was liquefied, the 44.4 kg of centrate recovered directly from the centrifuge would have contained approximately 23 wt % dissolved oligosaccharides (liquefied starch). About 0.6 kg of i-BuOH was added to 35.4 kg of centrate to preserve it. The resulting 36.0 kg of centrate, which contained 1.6 wt % i-BuOH, was used as a stock solution.

Example 3

Effect of Undissolved Solids on the Rate of Mass Transfer

The following experiment was performed to measure the effect of undissolved solids on the rate of mass transfer of i-BuOH from an aqueous phase that simulates the composition of a fermentation broth derived from corn mash, which is approximately half way through an SSF (simultaneous saccharification and fermentation) fermentation (i.e., ca. 50% conversion of the oligosaccharides) in order to mimic the average composition of the liquid phase for an SSF batch. The centrate from Example 2 mimics the liquid phase composition at the beginning of SSF. Therefore, a portion of it was diluted with an equal amount of $H_2O$ on a mass basis to generate centrate that mimics SSF at about 50% conversion. More i-BuOH was added to bring the final concentration of i-BuOH in the diluted centrate to 3.0 wt % (ca. 30 g/L).

The diluted centrate was prepared as follows: 18 kg of the centrate stock solution from Example 2 which contained 1.6 wt % i-BuOH, was mixed with 18 kg of tap water and 0.82 kg of i-BuOH was added. The resulting 36.8 kg solution of diluted centrate consisted of approximately 11 wt % oligosaccharides and approximately 30 g/L of i-BuOH. This solution mimics the liquid phase of a corn mash fermentation (SSF) at approximately 50% conversion of the oligosaccharides and an aqueous titer of 30 g/L i-BuOH.

Example 4

Effect of Removing Undissolved Solids on Mass Transfer

Mass transfer tests were conducted using the solution obtained in Example 3 as the aqueous phase to mimic mass transfer performance in a broth derived from liquefied corn mash after most of the undissolved solids are removed. The objective of the mass transfer tests was to measure the effect of undissolved solids on the overall volumetric mass transfer coefficient ($k_La$) for the transfer of i-BuOH from a simulated broth, derived from liquefied corn mash, to a dispersion of solvent (extractant) droplets rising up through the simulated broth. Correlations of $k_La$ with key design of operating parameters can be used to scale up mass transfer operations. Examples of parameters that should be held constant as much as possible in order to generate correlations of $k_La$ from smaller scale data which are useful for scale up are the physical properties of both phases and design parameters that determine droplet size (e.g., nozzle diameter, velocity of the phase to be dispersed through the nozzle).

A 6 inch diameter, 7 foot tall glass, jacketed column was used to measure the $k_La$ for the transfer of i-BuOH from an aqueous solution of oligosaccharides (derived from liquefied corn mash), both with and without suspended mash solids, to a dispersion of oleyl alcohol (OA) droplets rising up through the simulated broth. i-BuOH was added to the aqueous phase to give an initial concentration of i-BuOH of approximately 30 g/L. A certain amount of the aqueous phase (typically about 35 kg) which contained approximately 11 wt % oligosaccharides and approximately 30 g/L of i-BuOH, was charged to the column, and the column was heated to 30° C. by flowing warm $H_2O$ through the jacket. There was no flow of aqueous phase in or out of the column during the test.

Fresh oleyl alcohol (80/85% grade from Cognis) was sparged into the bottom of the column through a single nozzle to create a dispersion of extractant droplets which flowed up through the aqueous phase. After reaching the top of the aqueous phase, the extractant drops formed a separate organic phase which then overflowed from the top of the column and was collected into a receiver. Typically, 3 to 5 gallons of OA flowed through the column for a single test.

Samples of the aqueous phase were pulled from the column at several times throughout the test, and a composite sample of the total "rich" OA collected from the overflow was pulled at the end of the test. All samples were analyzed for i-BuOH using a HP-6890 GC. The concentration profile for i-BuOH in the aqueous phase (i.e., i-BuOH concentration versus time) was used to calculate the $k_La$ at the given set of operating conditions. The final composite sample of the total "rich" OA collected during the test was used to check the mass balance for i-BuOH.

The nozzle size and nozzle velocity (average velocity of OA through the feed nozzle) were varied to observe their effects on the $k_La$. A series of tests were done using an aqueous solution of oligosaccharides (diluted centrate obtained from liquefied corn mash) with the mash solids removed. A similar series of tests were done using the same aqueous solution of oligosaccharides after adding the mash solids back to simulate liquefied corn mash (including the undissolved solids) at the middle of SSF. It is noted that under some operating conditions (e.g., higher OA flow rates), poor phase separation was obtained at the top of the column which made it difficult to obtain a representative composite sample of the total "rich" OA collected during the test. It is also noted that under some operating conditions, samples of the aqueous phase contained a significant amount of organic phase. Special sample handling and preparation techniques were employed to obtain a sample of the aqueous phase that was as representative as possible of the aqueous phase in the column at the time the sample was pulled.

It was determined that the aqueous phase in the column was "well mixed" for all practical purposes because the concentration of i-BuOH did not vary much along the length of the column at a given point in time. Assuming the solvent droplet phase is also well mixed, the overall mass transfer of i-BuOH from the aqueous phase to the solvent phase in the column can be approximated by the following equation:

$$r_B = k_La\left(C_{B,broth} - \frac{C_{B,solvent}}{K_B}\right) \tag{1}$$

where, $r_B$=total mass of i-BuOH transferred from the aqueous phase to the solvent phase per unit time per unit volume of the aqueous phase, grams i-BuOH/Liter aqueous phase/hr or g/L/hr.

$k_La$=overall volumetric mass transfer coefficient describing the mass transfer of i-BuOH from the aqueous phase to the solvent phase, $hr^{-1}$.

$C_{B,broth}$=average concentration of i-BuOH in the simulated broth (aqueous) phase over the entire test, grams i-BuOH/Liter aqueous phase or g/L.

$C_{B,solvent}$=average concentration of i-BuOH in the solvent phase over the entire test, grams i-BuOH/Liter solvent phase or g/L.

$K_B$=average equilibrium distribution coefficient for i-BuOH between the solvent and aqueous phase, (grams i-BuOH/Liter solvent phase)/(grams i-BuOH/Liter aqueous phase).

The parameters $r_B$, $C_{B,broth}$, and $C_{B,solvent}$ were calculated for each test from the concentration data obtained from the samples of the aqueous and solvent phases. The parameter $K_B$ was independently measured by mixing aqueous centrate from liquefied corn mash, OA, and i-BuOH and vigorously mixing the system until the two liquid phases were at equilibrium. The concentration of i-BuOH was measured in both phases to determine $K_B$. After $r_B$, $C_{B,broth}$, $C_{B,solvent}$, and $K_B$ were determined for a given test, the $k_La$ could be calculated by rearranging Equation (1):

$$k_La = \frac{r_B}{\left(C_{B,broth} - \frac{C_{B,solvent}}{K_B}\right)} \tag{2}$$

Mass transfer tests were conducted with two different size nozzles at nozzle velocities ranging from 5 ft/s to 21 ft/s using the diluted centrate (solids removed) as the aqueous phase. Three tests were done using a nozzle that has an inner diameter (ID) of 0.76 mm, and three tests were done using a nozzle that has an ID of 2.03 mm. All tests were conducted at 30° C. in the 6 inch diameter column described above using OA as the solvent. The equilibrium distribution coefficient for i-BuOH between OA and the diluted centrate which was obtained from liquefied corn mash by removing the solids, was measured to be approximately 5. The results of the mass transfer tests using diluted centrate (with the solids removed) are shown in Table 1.

TABLE 1

| | 41 Diluted Centrate from Liq'd Mash, Solids Removed | 42 Diluted Centrate from Liq'd Mash, Solids Removed | 43 Diluted Centrate from Liq'd Mash, Solids Removed | 44 Diluted Centrate from Liq'd Mash, Solids Removed | 45 Diluted Centrate from Liq'd Mash, Solids Removed | 46 Diluted Centrate from Liq'd Mash, Solids Removed |
|---|---|---|---|---|---|---|
| MASS TRANSFER TEST CONDITIONS: | | | | | | |
| Aqueous Phase | 36.0 | 35.0 | 34.3 | 32.0 | 28.0 | 28.6 |
| Volume of Aqueous Phase, L: | | | | | | |
| Solvent Feed Rate, g/min: | 33.2 | 79.5 | 145.3 | 237.7 | 507.7 | 875 |
| Superficial Liq. Velocity (Us), ft/hr: | 0.42 | 1.01 | 1.84 | 3.02 | 6.45 | 11.11 |

TABLE 1-continued

| | 41 Diluted Centrate from Liq'd Mash, Solids Removed | 42 Diluted Centrate from Liq'd Mash, Solids Removed | 43 Diluted Centrate from Liq'd Mash, Solids Removed | 44 Diluted Centrate from Liq'd Mash, Solids Removed | 45 Diluted Centrate from Liq'd Mash, Solids Removed | 46 Diluted Centrate from Liq'd Mash, Solids Removed |
|---|---|---|---|---|---|---|
| Nozzle I.D., mm: | 0.76 | 0.76 | 0.76 | 2.03 | 2.03 | 2.03 |
| Nozzle Velocity, ft/s | 4.7 | 11.3 | 20.6 | 4.7 | 10.1 | 17.4 |
| MASS TRANSFER RESULTS: | | | | | | |
| Initial [i-B] in Aq. Phase, g/L: | 28.2 | 27.0 | 29.1 | 31.3 | 38.7 | 30.1 |
| Final [i-B] in Aq. Phase, g/L: | 25.7 | 14.8 | 14.7 | 24.8 | 11.5 | 5.4 |
| Rich OA collected, kg: | 4.05 | 7.47 | 6.03 | 7.37 | 12.82 | 14.0 |
| [i-B] in OA collected, wt %: | 2.22 | 5.72 | 8.17 | 2.83 | 5.93 | 5.04 |
| Test time, min: | 122 | 94 | 41.5 | 31.0 | 25.3 | 16.0 |
| Overall i-BuOH M.T. Rate, g/L/hr | 1.23 | 7.81 | 20.76 | 12.62 | 64.52 | 92.52 |
| kLa, hr^(−1) | 0.05 | 0.70 | 2.58 | 0.54 | 4.29 | 10.06 |
| (kLa/Us) | 0.12 | 0.69 | 1.40 | 0.18 | 0.67 | 0.91 |

Example 5

Effect of Undissolved Solids on Mass Transfer

An aqueous phase that simulates a fermentation broth from liquefied corn mash (containing undissolved solids) half way through SSF was synthesized by adding some of the wet cake from Example 2 (which was initially obtained from removing the solids from liquefied corn mash) to diluted centrate (which was used for the mass transfer tests describe above in Example 4). Some water was also added to dilute the liquid phase held up in the wet cake because this liquid has the same composition as the concentrated centrate. 17.8 kg of diluted supernate, 13.0 kg of wet cake (contains ~18 wt % undissolved mash solids), 5.0 kg $H_2O$, and 0.83 kg of i-BuOH were mixed together yielding 36.6 kg of a slurry containing approximately 6.3 wt % undissolved solids and a liquid phase consisting of approximately 13 wt % liquefied starch and approximately 2.4 wt % i-BuOH (balance $H_2O$). This slurry mimics the composition of a fermentation broth half way through SSF of corn to i-BuOH at approximately 30% corn loadings because the level of undissolved solids and oligosaccharides found in these types of broths is approximately 6-8 wt % and 10-12 wt %, respectively.

Mass transfer tests were conducted with two different size nozzles at nozzle velocities ranging from 5 ft/s to 22 ft/s using the slurry of diluted centrate and undissolved mash solids as the aqueous phase. Three tests were done using a nozzle that has an ID of 0.76 mm, and three tests were done using a nozzle that has an ID of 2.03 mm. All tests were conducted at 30° C. in the 6 inch diameter column described above using OA as the solvent. The results of the mass transfer tests using the slurry of diluted centrate and undissolved mash solids are shown in Table 2.

TABLE 2

| | 52 Diluted Centrate from Liq'd Mash, +6.3 wt % Solids | 53 Diluted Centrate from Liq'd Mash, +6.3 wt % Solids | 54 Diluted Centrate from Liq'd Mash, +6.3 wt % Solids | 49 Diluted Centrate from Liq'd Mash, +6.3 wt % Solids | 50 Diluted Centrate from Liq'd Mash, +6.3 wt % Solids | 51 Diluted Centrate from Liq'd Mash, +6.3 wt % Solids |
|---|---|---|---|---|---|---|
| MASS TRANSFER TEST CONDITIONS: | | | | | | |
| Aqueous Phase Volume of Aqueous Phase, L: | 35.5 | 35.5 | 32.5 | 31.5 | 30 | 31.6 |
| Solvent Feed Rate, g/min: | 40 | 64 | 157 | 249 | 549 | 853 |
| Superficial Liq. Velocity (Us), ft/hr: | 0.51 | 0.81 | 1.99 | 3.16 | 6.97 | 10.83 |
| Nozzle I.D., mm: | 0.76 | 0.76 | 0.76 | 2.03 | 2.03 | 2.03 |
| Nozzle Velocity, ft/s | 5.7 | 9.1 | 22.3 | 4.9 | 10.9 | 17.0 |
| MASS TRANSFER RESULTS: | | | | | | |
| Initial [i-B] in Aq. Phase, g/L: | 28.1 | 26.0 | 26.2 | 27.6 | 26.3 | 36.8 |
| Final [i-B] in Aq. Phase, g/L: | 26.3 | 23.8 | 14.0 | 24.6 | 13.8 | 16.1 |
| Rich OA collected, kg: | 6.02 | 5.75 | 10.23 | 15.05 | 16.58 | 13.22 |
| [i-B] in OA collected, wt %: | 1.05 | 1.35 | 3.86 | 0.68 | 2.30 | 5.00 |
| Test time, min: | 150 | 90 | 65 | 60 | 30 | 15.5 |
| Overall i-BuOH M.T. Rate, g/L/hr | 0.71 | 1.46 | 11.2 | 3.0 | 25.0 | 80.0 |
| kLa, hr^(−1) | 0.03 | 0.06 | 0.83 | 0.12 | 1.55 | 4.45 |
| (kLa/Us) | 0.06 | 0.07 | 0.42 | 0.04 | 0.22 | 0.41 |

Figure 7:
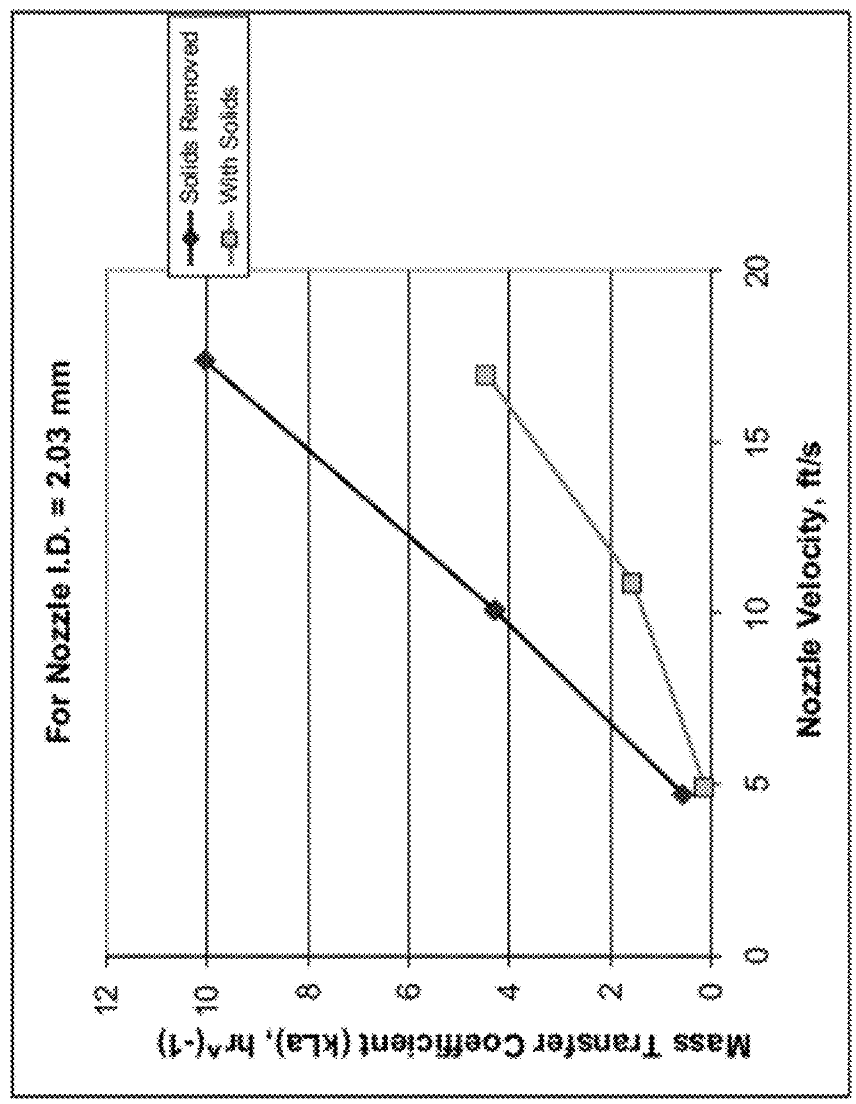

FIG. 7 illustrates the effect of the presence of undissolved corn mash solids on the overall volumetric mass transfer coefficient, $k_L a$, for the transfer of i-BuOH from an aqueous solution of liquefied corn starch (i.e., oligosaccharides) to a dispersion of oleyl alcohol droplets flowing up through a bubble column. The OA was fed to the column through a 2.03 mm ID nozzle. It was discovered that the ratio of the $k_L a$ for a system where the solids have been removed to the $k_La$ for a system where the solids have not been removed is 2 to 5 depending on the nozzle velocity for a 2.03 mm nozzle.

Figure 8:
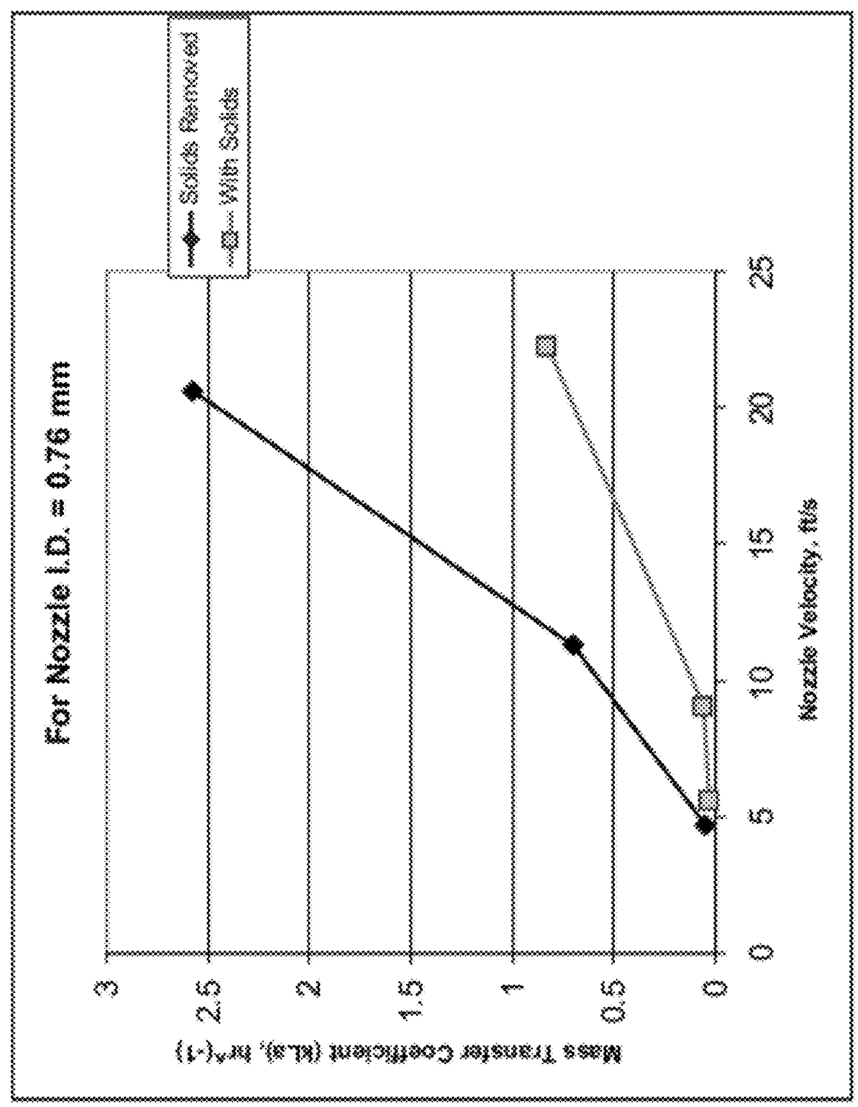

FIG. 8 illustrates the effect of the presence of undissolved corn mash solids on the overall volumetric mass transfer coefficient, $k_La$, for the transfer of i-BuOH from an aqueous solution of liquefied corn starch (i.e., oligosaccharides) to a dispersion of oleyl alcohol droplets flowing up through a bubble column. The OA was fed to the column through a 0.76 mm ID nozzle. It was discovered that the ratio of the $k_La$ for a system where the solids have been removed to the $k_La$ for a system where the solids have not been removed is 2 to 4 depending on the nozzle velocity for a 0.76 mm nozzle.

Example 6

Effect of Removing Undissolved Solids on Phase Separation Between an Aqueous Phase and a Solvent Phase This example illustrates improved phase separation between an aqueous solution of oligosaccharides derived from liquefied corn mash from which undissolved solids have been removed and a solvent phase as compared to an aqueous solution of oligosaccharides derived from liquefied corn mash from which no undissolved solids have been removed and the same solvent. Both systems contained i-BuOH. Adequate separation of the solvent phase from the aqueous phase is important for liquid-liquid extraction to be a viable separation method for practicing in-situ product removal (ISPR).

Approximately 900 g of liquefied corn mash was prepared in a 1 L glass, jacketed resin kettle. The kettle was set up with mechanical agitation, temperature control, and pH control. The following protocol was used: mixed ground corn with tap water (26 wt % corn on a dry basis), heated the slurry to 55° C. while agitating, adjusted pH to 5.8 with either NaOH or $H_2SO_4$, added alpha-amylase (0.02 wt % on a dry corn basis), continued heating to 85° C., adjusted pH to 5.8, held at 85° C. for 2 hrs while maintaining pH at 5.8, cool to 25° C. The corn used was whole kernel yellow corn from Pioneer (3335). It was ground in a hammer-mill using a 1 mm screen. The moisture content of the ground corn was measured to be 12 wt %, and the starch content of the ground corn was measured to be 71.4 wt % on a dry corn basis. The alpha-amylase enzyme was Liquozyme® SC DS from Novozymes (Franklinton, N.C.). The total amounts of the ingredients used were: 265.9 g of ground corn (12% moisture), 634.3 g of tap water, and 0.056 g of Liquozyme® SC DS. The total amount of liquefied corn mash recovered was 883.5 g.

Part of the liquefied corn mash was used directly, without removing undissolved solids, to prepare the aqueous phase for phase separation tests involving solids. Part of the liquefied corn mash was centrifuged to remove most of the undissolved solids and used to prepare the aqueous phase for phase separation tests involving the absence of solids.

The solids were removed from the mash by centrifugation in a large floor centrifuge. 583.5 g of mash was centrifuged at 5000 rpm for 20 min at 35° C. yielding 394.4 g of centrate and 189.0 g of wet cake. It was determined that the centrate contained approximately 0.5 wt % suspended solids, and that the wet cake contained approximately 20 wt % suspended solids. This implies that the original liquefied mash contained approximately 7 wt % suspended solids. This is consistent with the corn loading and starch content of the corn used assuming most of the starch was liquefied. If all of the starch was liquefied, the centrate recovered directly from the centrifuge would have contained approximately 20 wt % dissolved oligosaccharides (liquefied starch) on a solids-free basis.

The objective of the phase separation test was to measure the effect of undissolved solids on the degree of phase separation between a solvent phase and an aqueous phase that simulates a broth that is derived from liquefied corn mash. The aqueous liquid phase contained about 20 wt % oligosaccharides, and the organic phase contained oleyl alcohol (OA) in all tests. Furthermore, i-BuOH was added to all tests to give approximately 25 g/L in the aqueous phase when the phases were at equilibrium. Two shake tests were performed. The aqueous phase for the first test (with solids) was prepared by mixing 60.0 g of liquefied corn mash with 3.5 g of i-BuOH. The aqueous phase for the second test (solids removed) was prepared by mixing 60.0 g of centrate which was obtained from the liquefied corn mash by removing the solids, with 3.5 g of i-BuOH. 15.0 g of oleyl alcohol (80/85% grade from Cognis) was added to each of the shake test bottles. The OA formed a separate liquid phase on top of the aqueous phase in both bottles resulting in a mass ratio of phases: Aq Phase/Solvent Phase to be about 1/4. Both bottles were shaken vigorously for 2 minutes to intimately contact the aqueous and organic phases and enable the i-BuOH to approach equilibrium between the two phases. The bottles were allowed to set for 1 hour. Photographs were taken at various times (0, 15, 30, and 60 minutes) to observe the effect of undissolved solids on phase separation in systems that contain an aqueous phase derived from liquefied corn mash, a solvent phase containing OA, and i-BuOH. Time zero (0) corresponds to the time immediately after the two minute shake period was complete.

The degree of separation between the organic (solvent) phase and the aqueous phase as a function of time for the system with solids (from liquefied corn mash) and the system where solids were removed (liquid centrate from liquefied corn mash) appeared about the same in both systems at any point in time. The organic phase was a slightly darker and cloudier, and the interface was a little less distinct (thicker "rag" layer around the interface) for the case with solids. However, for an extractive fermentation where the solvent is operated continuously, the composition of the top of the organic phase is of interest for the process downstream of the extractive fermentation wherein the next step is a distillation.

It may be advantageous to minimize the amount of microorganisms in the top of the organic phase because the microorganisms will be thermally deactivated in the distillation column. It may be advantageous to minimize the amount of undissolved solvents in the top of the organic phase because they could plug the distillation column, foul the reboiler, cause poor phase separation in the solvent/water decanter located at the base of the column, or any combination of the previously mentioned concerns. It may be advantageous to minimize the amount of phase water in the top of the organic phase. Phase water is water that exists as a separate aqueous phase. Additional amounts of aqueous phase will increase the loading and energy requirement in the distillation column. Ten milliliter samples were removed from the top of the organic layers from the "With Solids" and "Solids Removed" bottles, and both samples were centrifuged to reveal and compare the composition of the organic phases in the "With Solids" and "Solids Removed" bottles after 60 minutes of settling time. The results show that the "organic phases" at the end of both shake tests contained some undesired phase(s) (both organic phases are cloudy). However, the results also show that the top layer from the phase separation test involving centrate, from which solids were removed, contained essentially no undissolved solids. On the other hand, undissolved solids are clearly seen at the bottom of the 10 mL sample pulled from the top of the organic phase of the test involving mash. It was estimated that 3% of the sample pulled from the top of the organic layer wash mash solids. If the rich solvent phase exiting the fermentor of an extractive fermentation process contained 3% undissolved solids, one or more of the following problems could occur: loss of significant amount of microorganisms, fouling of solvent column reboiler, plugging of solvent column. The results also show that the top layer from the phase separation test involving centrate contained less phase water. Table 3 shows an estimate of the relative amount of phases that were dispersed throughout the upper "organic" layers in both shake test bottles after 60 minutes of settling time.

TABLE 3

Approximate composition of organic (top) layer from shake tests after 60 minutes

| | Top Layer from "With Solids" Shake Test | Top Layer from "Solids Removed" Shake Test |
|---|---|---|
| Organic (solvent) Phase: | 82% | 87% |
| Aqueous (water) Phase: | 15% | 13% |
| Undissolved Solids: | 3% | 0% |

This example shows that removing most of the undissolved solids from liquefied corn mash results in improved phase separation after the liquid, aqueous phase obtained from the mash is contacted with a solvent, such as oleyl alcohol. This example shows that the upper phase obtained after phase separation will contain significantly less undissolved solids if the solids are removed first before contacting the liquid part of mash with an organic solvent. This demonstrates advantages of minimizing the undissolved solids content of mash in the upper ("organic") layer of the phase separation for an extractive fermentation.

Example 7

Effect of Removing Undissolved Solids on Phase Separation Between an Aqueous Phase and a Solvent Phase Similar to Example 6, this example illustrates improved phase separation between an aqueous solution of oligosaccharides derived from liquefied corn mash from which undissolved solids have been removed, and a solvent phase as compared to an aqueous solution of oligosaccharides derived from liquefied corn mash from which no undissolved solids have been removed and the same solvent. Both systems contained i-BuOH. Adequate separation of the solvent phase from the aqueous phase is important for liquid-liquid extraction to be a viable separation method for practicing in-situ product removal (ISPR).

The same mixtures prepared for Example 6 were used in this example. The only difference was that the samples were allowed to sit for several days after completion of sample preparation as described in Example 6 before repeating the phase separation shake test described in this example. The sample labeled "with solids" consisted of liquefied corn mash, i-BuOH, and oleyl alcohol. The sample labeled "solids removed" consisted of centrate which was produced by removing most of the undissolved solids from liquefied corn mash, i-BuOH, and oleyl alcohol. The liquefied mash contained approximately 7 wt % suspended solids, and the centrate produced from the mash contained approximately 0.5 wt % suspended solids. If all of the starch in the ground corn was liquefied, the liquid phase in the liquefied mash and the centrate produced from the mash would have contained approximately 20 wt % dissolved oligosaccharides (liquefied starch) on a solids-free basis. Both samples contained oleyl alcohol in an amount to give a mass ratio of phases: Solvent Phase/Aq Phase to be about 1/4. Furthermore, i-BuOH was added to all tests to give approximately 25 g/L in the aqueous phase when the phases were at equilibrium.

The objective of the phase separation test was to measure the effect of undissolved solids on the degree of phase separation between a solvent phase (containing OA) and an aqueous phase derived from liquefied corn mash (with and without solids) after the multi-phase mixtures aged at room temperature for several days to mimic the potential change in properties of the system through out an extractive fermentation. Two shake tests were performed. Both bottles were shaken vigorously for 2 minutes to intimately contact the aqueous and organic phases. The bottles were allowed to sit for 1 hour. Photographs were taken at various times (0, 2, 5, 10, 20, and 60 minutes) to observe the effect of undissolved solids on phase separation in these systems which had aged for several days. Time zero (0) corresponds to the time immediately after the bottles were placed on the bench.

Phase separation started to occur in the sample where solids were removed after two minutes. It appeared that almost complete phase separation had occurred in the sample where solids had been removed after only 5-10 minutes based on the fact that the organic phase occupied approximately 25% of the total volume of the two phase mixture. It would be expected that complete separation would be indicated if the organic phase occupied approximately 20% of the total volume, since that corresponds to the initial ratio of phases. No apparent phase separation occurred in the sample where solids were not removed even after one hour.

The composition of the upper phase for both samples was also compared. The composition of the upper phase has implications for the process downstream of the extractive fermentation wherein the next step is a distillation. It is advantageous to minimize the amount of microorganisms in the top of the organic phase because the microorganisms will be thermally deactivated in the distillation column. Another component to minimize in the top of the organic phase is the amount of undissolved solids because the solids could plug the distillation column, foul the reboiler, cause poor phase separation in the solvent/water decanter located at the base of the column, or any combination of the previously mentioned concerns. In addition, another component to minimize in the top of the organic phase is the amount of phase water which is water that exists as a separate aqueous phase, because this additional amount of aqueous phase will increase the loading and energy requirement in the subsequent distillation column.

Ten milliliter samples were removed from the top of the organic layers from the "With Solids" and "Solids Removed" bottles, and both samples were centrifuged to reveal and compare the composition of the organic phases in the "With Solids" and "Solids Removed" bottles after 60 minutes of settling time. The composition of the sample pulled from the top of the "With Solids" sample confirms that essentially no phase separation occurred in that sample within 60 minutes. Specifically, the ratio of the solvent phase to total aqueous phase (aqueous liquid+suspended solids) in the sample pulled from the top of the "With Solids" shake test bottle is approximately 1/4 w/w, which is the same ratio used to prepare the sample prior to the test. Also, the amount of undissolved solids in the sample pulled from the top of the "With Solids" shake test bottle is approximately the same as what is found in liquefied corn mash, which shows that essentially no solids settled in this shake test bottle within 60 minutes. On the other hand, the top layer from the phase separation test involving centrate ("Solids Removed") from which solids were removed, contained essentially no undissolved solids. The results also show that the top layer from the phase separation test involving centrate contained less phase water. This is indicated by the fact that the ratio of the solvent phase to aqueous phase in that sample bottle is approximately 1/1 w/w, which shows that the organic phase was enriched with solvent (OA) in the test where solids were removed. Table 4 shows an estimate of the relative amount of phases that were dispersed throughout the upper "organic" layers in both shake test bottles after 60 minutes of settling time.

TABLE 4

Approximate composition of organic (top) layer from shake tests after 60 minutes

| | Top Layer from "With Solids" Shake Test | Top Layer from "Solids Removed" Shake Test |
|---|---|---|
| Organic (solvent) Phase: | 19% | 50% |
| Aqueous (water) Phase: | 47% | 50% |
| Undissolved Solids: | 34% | 0% |

This example shows that removing undissolved solids from liquefied corn mash that contains i-BuOH, contacting it with a solvent phase, letting it set for several days, and mixing the phases again results in improved phase separation when compared to a sample where undissolved solids were not removed from the liquefied mash. In fact, this example shows that essentially no phase separation occurs in the sample where undissolved solids were not removed even after 60 minutes. This example shows that the upper phase obtained after phase separation contains significantly less undissolved solids if the solids are removed first before contacting the liquid part of mash with an organic solvent. This is important because two of the most important species that should be minimized in the upper ("organic") layer of the phase separation for an extractive fermentation are the level of microorganisms and the level of undissolved solids from mash. The previous example showed that removing solids from liquefied corn mash results in improved phase separation shortly after the aqueous phase is contacted with a solvent phase. This would allow extractive fermentation to be viable at earlier times in the fermentation. This example also shows that removing solids from liquefied corn mash results in improved phase separation in aged samples that contain an aqueous phase (oligosaccharide solution with solids removed) that has been contacted with a solvent phase. This would also allow extractive fermentation to be viable at later times in the fermentation.

Example 8

Effect of Removing Undissolved Solids on the Loss of ISPR Extraction Solvent —Disk Stack Centrifuge This example demonstrates the potential for reducing solvent losses via DDGS generated by the extractive fermentation process by removing undissolved solids from the corn mash prior to fermentation using a semi-continuous disk-stack centrifuge.

Approximately 216 kg of liquefied corn mash was prepared in a jacketed stainless steel reactor. The reactor was set up with mechanical agitation, temperature control, and pH control. The protocol used was as follows: mixed ground corn with tap water (25 wt % corn on a dry basis), heated the slurry to 55° C. while agitating at 400 rpm, adjusted pH to 5.8 with either NaOH or $H_2SO_4$, added alpha-amylase (0.02 wt % on a dry corn basis), continued heating to 85° C., adjusted pH to 5.8, held at 85° C. for 30 minutes while maintaining pH at 5.8, heated to 121° C. using live steam injection, held at 121° C. for 30 minutes to simulate a jet cooker, cooled to 85° C., adjusted pH to 5.8, added second charge of alpha-amylase (0.02 wt % on a dry corn basis), held at 85° C. for 60 minutes while maintaining pH at 5.8 to complete liquefaction. The mash was then cooled to 60° C. and transferred to the centrifuge feed tank.

The corn used was whole kernel yellow corn from Pioneer (3335). It was ground in a hammer-mill using a 1 mm screen. The moisture content of the ground corn was measured to be 12 wt %, and the starch content of the ground corn was measured to be 71.4 wt % on a dry corn basis. The alpha-amylase enzyme was Liquozyme® SC DS from Novozymes (Franklinton, N.C.). The amounts of the ingredients used were: 61.8 kg of ground corn (12% moisture), 147.3 kg of tap water, a solution of 0.0109 kg of Liquozyme® SC DS in 1 kg of water for first alpha-amylase charge, another solution of 0.0109 kg of Liquozyme® SC DS in 1 kg of water for second alpha-amylase charge (after the cook stage). About 5 kg of $H_2O$ was added to the batch via steam condensate during the cook stage. A total of 0.25 kg of NaOH (12.5 wt %) and 0.12 kg of $H_2SO_4$ (12.5 wt %) were added throughout the run to control pH. The total amount of liquefied corn mash recovered was 216 kg.

The composition of the final liquefied corn mash slurry was estimated to be approximately 7 wt % undissolved solids and 93 wt % liquid. The liquid phase contained about 19 wt % (190 g/L) liquefied starch (soluble oligosaccharides). The rheology of the mash is important regarding the ability to separate the slurry into its components. The liquid phase in the mash was determined to be a Newtonian fluid with a viscosity of about 5.5 cP at 30° C. The mash slurry was determined to be a shear-thinning fluid with a bulk viscosity of about 10 to 70 cP at 85° C. depending on shear rate.

209 kg (190 L) of the liquefied mash was centrifuged using an Alfa Laval disk-stack split-bowl centrifuge. The centrifuge operated in semi-batch mode with continuous feed, continuous centrate outlet, and batch discharge of the wet cake. Liquefied corn mash was continuously fed at a rate of 1 L/minute, clarified centrate was removed continuously, and wet cake was periodically discharged every 4 minutes. To determine an appropriate discharge interval for the solids from the disk stack, a sample of the mash to be fed to the disk stack was centrifuged in a high-speed lab centrifuge. Mash (48.5 g) was spun at 11,000 rpm (about 21,000 g's) for about 10 minutes at room temperature. Clarified centrate (36.1 g) and 12.4 g of pellet (wet cake) were recovered. It was determined that the clarified centrate contained about 0.3 wt % undissolved solids and that the pellet (wet cake) contained about 27 wt % undissolved solids. Based on this data, a discharge interval of 4 minutes was chosen for operation of the disk stack centrifuge.

The disk stack centrifuge was operated at 9000 rpm (6100 g's) with a liquefied corn mash feed rate of 1 L/min and about 60° C. Mash (209 kg) was separated into 155 kg of clarified centrate and 55 kg of wet cake. The split, defined as (amount of centrate)/(amount of mash fed), achieved by the semi-continuous disk stack was similar to the split achieved in the batch centrifuge. The split for the disk stack semi-batch centrifuge operating at 6100 g's, 1 L/min feed rate, and 4 minutes discharge interval was (155 kg/209 kg)=74%, and the split for the lab batch centrifuge operating at 21,000 g's for 10 minutes was (36.1 g/48.5 g)=74%.

A 45 mL sample of the clarified centrate recovered from the disk stack centrifuge was spun down in a lab centrifuge at 21,000 g's for 10 minutes to estimate the level of suspended solids in the centrate. About 0.15-0.3 g of undissolved solids were recovered from the 45 mL of centrate. This corresponds to 0.3-0.7 wt % undissolved solids in the centrate which is about a ten-fold reduction in undissolved solids from mash fed to the centrifuge. It is reasonable to assume that the ISPR extraction solvent losses via DDGS could be reduced by about an order of magnitude if the level of undissolved solids present in extractive fermentation is reduced by an order of magnitude using some solid/liquid separation device or combination of devices to remove suspended solids from the corn mash before fermentation. Minimizing solvent losses via DDGS is an important factor in the economics and DDGS quality for an extractive fermentation process.

Example 9

Effect of Removing Undissolved Solids on the Loss of ISPR Extraction Solvent —Bottle Spin Test This example demonstrates the potential for reducing solvent losses via DDGS generated by the extractive fermentation process by removing undissolved solids from the corn mash prior to fermentation using a centrifuge.

A lab-scale bottle spin test was performed using liquefied corn mash. The test simulates the operating conditions of a typical decanter centrifuge used to remove undissolved solids from whole stillage in a commercial ethanol (EtOH) plant. Decanter centrifuges in commercial EtOH plants typically operate at a relative centrifugal force (RCF) of about 3000 g's and a whole stillage residence time of about 30 seconds. These centrifuges typically remove about 90% of the suspended solids in whole stillage which contains about 5% to 6% suspended solids (after the beer column), resulting in thin stillage which contains about 0.5% suspended solids.

Liquefied corn mash was made according to the protocol described in Example 6. About 10 mL of mash was placed in a centrifuge tube. The sample was centrifuged at an RCF of about 3000 g's (4400 rpm rotor speed) for a total of 1 minute. The sample spent about 30-40 seconds at 3000 g's and a total of 20-30 seconds at speeds less than 3000 g's due to speeding up and slowing down of the centrifuge. The sample temperature was about 60° C.

The 10 mL of mash which contained about 7 wt % suspended solids was separated into about 6.25 mL of clarified centrate and 3.75 mL of wet cake (pellet at the bottom of the centrifuge tube). The split, defined as (amount of centrate)/(amount of original mash charged), achieved by the bottle spin test was about 62%. It was determined that the clarified centrate contained about 0.5 wt % suspended solids which is more than a ten-fold decrease in suspend solids compared to the level of suspended solids in the original mash. It was also determined that the clarified pellet contained about 18 wt % suspended solids.

Table 5 summarizes the suspended (undissolved) solids mass balance for the bottle spin test at conditions representative of the operation of a decanter centrifuge to convert whole stillage to thin stillage in a commercial EtOH process. All values given in Table 5 are approximate.

TABLE 5

| | Volume, mL | Suspend Solids, wt % |
|---|---|---|
| Liquified Corn Mash charge: | 10 | 7% |
| Clarified Centrate: | 6.25 | 0.5% |
| Wet Cake (pellet): | 3.75 | 18% |

Performance Summary

| | |
|---|---|
| Split: | 62% |
| Centrate Clarity: | 0.5 wt % suspended solids |
| Cake (pellet) Dryness: | 18 wt % suspended solids |
| % Removal of Suspended Solids: | 95% removal from liquefied mash |

It was also determined that the centrate contained about 190 g/L of dissolved oligosaccharides (liquefied starch). This is consistent with the assumption that most of the starch in the ground corn was liquefied (i.e., hydrolyzed to soluble oligosaccharides) in the liquefaction process based on the corn loading used (about 26 wt % on a dry corn basis) and the starch content of the corn used to produce the liquefied mash (about 71.4 wt % starch on a dry corn basis). Hydrolyzing most of the starch in the ground corn at a 26% dry corn loading will result in about 7 wt % suspended (undissolved) solids in the liquefied corn mash charged to the centrifuge used for the bottle spin test.

The fact that the clarified centrate contained only about 0.5 wt % undissolved solids indicates that the conditions used in the bottle spin test resulted in more than a ten-fold reduction in undissolved solids from mash charged. If this same solids removal performance could be achieved by a continuous decanter centrifuge before fermentation, it is reasonable to assume that the ISPR extraction solvent losses in the DDGS could be reduced by about an order of magnitude. Minimizing solvent losses via DDGS is an important factor in the economics and DDGS quality for an extractive fermentation process.

Example 10

Removal of Corn Oil by Removing Undissolved Solids

This example demonstrates the potential to remove and recover corn oil from corn mash by removing the undissolved solids prior to fermentation. The effectiveness of the extraction solvent may be improved if corn oil is removed via removal of the undissolved solids. In addition, removal of corn oil via removal of the undissolved solids may also minimize any reduction in solvent partition coefficient and potentially resulting an improved extractive fermentation process.

Approximately 1000 g of liquefied corn mash was prepared in a 1 L glass, jacketed resin kettle. The kettle was set up with mechanical agitation, temperature control, and pH control. The following protocol was used: mixed ground corn with tap water (26 wt % corn on a dry basis), heated the slurry to 55° C. while agitating, adjusted pH to 5.8 with either NaOH or $H_2SO_4$, added alpha-amylase (0.02 wt % on a dry corn basis), continued heating to 85° C., adjusted pH to 5.8, held at 85° C. for 2 hrs while maintaining pH at 5.8, cool to 25° C. The corn used was whole kernel yellow corn from Pioneer (3335). It was ground in a hammer-mill using a 1 mm screen. The moisture content of the ground corn was measured to be about 11.7 wt %, and the starch content of the ground corn was measured to be about 71.4 wt % on a dry corn basis. The alpha-amylase enzyme was Liquozyme® SC DS from Novozymes (Franklinton, N.C.). The total amounts of the ingredients used were: 294.5 g of ground corn (11.7% moisture), 705.5 g of tap water, and 0.059 g of Liquozyme® SC DS. Water (4.3 g) was added to dilute the enzyme, and a total of 2.3 g of 20% NaOH solution was added to control pH. About 952 g of mash was recovered.

The liquefied corn mash was centrifuged at 5000 rpm (7260 g's) for 30 minutes at 40° C. to remove the undissolved solids from the aqueous solution of oligosaccharides. Removing the solids by centrifugation also resulted in the removal of free corn oil as a separate organic liquid layer on top of the aqueous phase. Approximately 1.5 g of corn oil was recovered from the organic layer floating on top of the aqueous phase. It was determined by hexane extraction that the ground corn used to produce the liquefied mash contained about 3.5 wt % corn oil on a dry corn basis. This corresponds to about 9 g of corn oil fed to the liquefaction process with the ground corn.

After recovering the corn oil from the liquefied mash, the aqueous solution of oligosaccharides was decanted away from the wet cake. About 617 g of liquefied starch solution was recovered leaving about 334 g of wet cake. The wet cake contained most of the undissolved solids that were in the liquefied mash. The liquefied starch solution contained about 0.2 wt % undissolved solids. The wet cake contained about 21 wt % undissolved solids. The wet cake was washed with 1000 g of tap water to remove the oligosaccharides still in the cake. This was done by mixing the cake with the water to form a slurry. The slurry was then centrifuged under the same conditions used to centrifuge the original mash in order to recover the washed solids. Removing the washed solids by centrifuging the wash slurry also resulted in the removal of some additional free corn oil that must have remained with the original wet cake produced from the liquefied mash. This additional corn oil was observed as a separate, thin, organic liquid layer on top of the aqueous phase of the centrifuged wash mixture. Approximately 1 g of additional corn oil was recovered from the wash process.

The wet solids were washed two more times using a 1000 g of tap water each time to remove essentially all of the liquefied starch. No visible additional corn oil was removed from the 2nd and 3rd water washes of the mash solids. The final washed solids were dried in a vacuum oven overnight at 80° C. and about 20 inches Hg vacuum. The amount of corn oil remaining in the dry solids, presumably still in the germ, was determined by hexane extraction. It was measured that a 3.60 g sample of relatively dry solids (about 2 wt % moisture) contained 0.22 g of corn oil. This result corresponds to 0.0624 g corn oil/g dry solids. This was for washed solids which means there are no residual oligosaccharides in the wet solids. After centrifuging the liquefied corn mash to separate the layer of free corn oil and the aqueous solution of oligosaccharides from the wet cake, it was determined that about 334 g of wet cake containing about 21 wt % undissolved solids remained. This corresponds to the wet cake comprising about 70.1 g of undissolved solids. At 0.0624 g corn oil/g dry solids, the solids in the wet cake should contain about 4.4 g of corn oil.

In summary, approximately 1.5 g of free corn oil was recovered by centrifuging the liquefied mash. An additional 1 g of free corn oil was recovered by centrifuging the first (water) wash slurry which was generated to wash the original wet cake produced from the mash. Finally, it was determined that the washed solids still contained about 4.4 g of corn oil. It was also determined that the corn charged to the liquefaction contained about 9 g of corn oil. Therefore, a total of 6.9 g of corn oil was recovered from the following process steps: liquefaction, removal of solids from liquefied mash, washing of the solids from the mash, and the final washed solids. Consequently, approximately 76% of the total corn oil in the corn fed to liquefaction was recovered during the liquefaction and solids removal process described here.

Example 11

Extractive Fermentation Using Mash and Centrate as the Sugar Source

This example describes extractive fermentations performed using corn mash and corn mash centrate as the sugar source. Corn mash centrate was produced by removing undissolved solids from the corn mash prior to fermentation. Four extractive fermentations were conducted side-by side, two with liquefied corn mash as the sugar source (solids not removed) and two with liquefied mash centrate (aqueous solution of oligosaccharides) obtained by removing most of the undissolved solids from liquefied corn mash. Oleyl alcohol (OA) was added to two of the fermentations, one with solids and one with solids removed, to extract the product (i-BuOH) from the broth as it was formed. A mixture of corn oil fatty acids (COFA) was added to the other two of the fermentations, one with solids and one with solids removed, to extract the product from the broth as it was formed. The COFA was made by hydrolyzing corn oil. The purpose of these fermentations was to test the effect of removing solids on phase separation between the solvent and broth (see Example 11) and to measure the amount of residual solvent trapped in the undissolved solids recovered from fermentation broths where solids were or were not removed (see Example 12).

Preparation of Liquified Corn Mash

Approximately 31 kg of liquefied corn mash was prepared in a 30 L jacketed glass resin kettle. The reactor was outfitted with mechanical agitation, temperature control, and pH control. The protocol used was as follows: mix ground corn with tap water (40 wt % corn on a dry basis), heat the slurry to 55° C. while agitating at 250 rpm, adjust pH to 5.8 with either NaOH or $H_2SO_4$, add a dilute aqueous solution of alpha-amylase (0.16 wt % on a dry corn basis), hold at 55° C. for 60 minutes, heat to 95° C., adjust pH to 5.8, hold at 95° C. for 120 minutes while maintaining pH at 5.8 to complete liquefaction. The mash was transferred into sterile centrifuge bottles to prevent contamination.

The corn used was whole kernel yellow corn from Pioneer. It was ground in a pilot-scale hammer-mill using a 1 mm screen. The moisture content of the ground corn was measured to be about 12 wt %, and the starch content of the ground corn was measured to be about 71.4 wt % on a dry corn basis. The alpha-amylase enzyme used was Spezyme® Fred-L (Genencor®, Palo Alto, Calif.). The amounts of the ingredients used were: 14.1 kg of ground corn (12% moisture), 16.9 kg of tap water, a solution of alpha-amylase consisting of 19.5 g of Spezyme® Fred-L in 2.0 kg of water. The alpha-amylase was sterile filtered. A total of 0.21 kg of NaOH (17 wt %) was added throughout the run to control pH.

It was estimated that the liquefied corn mash contained approximately 28 wt % (about 280 g/L) of liquefied starch based on the corn loading used, starch content of the corn, and assuming all the starch was hydrolyzed during liquefaction. The mash was prepared with a higher concentration of oligosaccharides than was desired in the fermentations to allow for dilution when adding the nutrients, inoculum, glucoamylase, and base to the initial fermentation broth. After dilution by addition of nutrients, inoculum, glucoamylase, and base, the expected total initial soluble sugars in the mash (solids not removed) was about 250 g/L.

About 13.9 kg of the liquefied mash was centrifuged using a bottle centrifuge which contained six 1 L bottles. The centrifuge was operated at 5000 rpm (7260 RCF) for 20 minutes at room temperature. The mash was separated into about 5.5 kg of clarified centrate and about 8.4 kg of wet cake (the pellet at the bottom of the centrifuge bottles). The split, defined as (amount of centrate)/(amount of mash fed), was about (5.5 kg/13.9 kg)=40%.

Solids were not removed from the mash charged to the 2010Y034 and 2010Y036 fermentations described below. The centrate charged to fermentations 2010Y033 and 2010Y035 (also described below) was produced by removing (by centrifugation) most of the suspended solids from mash according to the protocols above.

General Methods for Fermentation

Seed Flask Growth

A *Saccharomyces cerevisiae* strain that was engineered to produce isobutanol from a carbohydrate source, with pdc1 deleted, pdc5 deleted, and pdc6 deleted was grown to 0.55-1.1 g/L dcw ($OD_{600}$ 1.3-2.6—Thermo Helios a Thermo Fisher Scientific Inc., Waltham, Mass.) in seed flasks from a frozen culture. The culture was grown at 26° C. in an incubator rotating at 300 rpm. The frozen culture was previously stored at −80° C. The composition of the first seed flask medium was:

- 3.0 g/L dextrose
- 3.0 g/L ethanol, anhydrous
- 3.7 g/L ForMedium™ Synthetic Complete Amino Acid (Kaiser) Drop-Out: without HIS, without URA (Reference No. DSCK162CK)
- 6.7 g/L Difco Yeast Nitrogen Base without amino acids (No. 291920).

Twelve milliliters from the first seed flask culture was transferred to a 2 L flask and grown at 30° C. in an incubator rotating at 300 rpm. The second seed flask has 220 mL of the following medium:

- 30.0 g/L dextrose
- 5.0 g/L ethanol, anhydrous
- 3.7 g/L ForMedium™ Synthetic Complete Amino Acid (Kaiser) Drop-Out: without HIS, without URA (Reference No. DSCK162CK)
- 6.7 g/L Difco Yeast Nitrogen Base without amino acids (No. 291920)
- 0.2M MES Buffer titrated to pH 5.5-6.0.

The culture was grown to 0.55-1.1 g/L dcw ($OD_{600}$ 1.3-2.6). An addition of 30 mL of a solution containing 200 g/L peptone and 100 g/L yeast extract was added at this cell concentration. Then an addition of 300 mL of 0.2 uM filter sterilized Cognis, 90-95% oleyl alcohol was added to the flask. The culture continues to grow to >4 g/L dcw ($OD_{600}$>10) before being harvested and added to the fermentation.

Fermentation Preparation

Initial Fermentor Preparation

A glass jacked, 2 L fermentor (Sartorius AG, Goettingen, Germany) was charged with liquefied mash either with or without solids (centrate). A pH probe (Hamilton Easyferm Plus K8, part number: 238627, Hamilton Bonaduz AG, Bonaduz, Switzerland) was calibrated through the Sartorius DCU-3 Control Tower Calibration menu. The zero was calibrated at pH=7. The span was calibrated at pH=4. The probe was then placed into the fermentor, through the stainless steel head plate. A dissolved oxygen probe ($pO_2$ probe) was also placed into the fermentor through the head plate. Tubing used for delivering nutrients, seed culture, extracting solvent, and base were attached to the head plate and the ends were foiled. The entire fermentor was placed into a Steris (Steris Corporation, Mentor, Ohio) autoclave and sterilized in a liquid cycle for 30 minutes.

The fermentor was removed from the autoclave and placed on a load cell. The jacket water supply and return line was connected to the house water and clean drain, respectively. The condenser cooling water in and water out lines were connected to a 6-L recirculating temperature bath running at 7° C. The vent line that transfers the gas from the fermentor was connected to a transfer line that was connected to a Thermo mass spectrometer (Prima dB, Thermo Fisher Scientific Inc., Waltham, Mass.). The sparger line was connected to the gas supply line. The tubing for adding nutrients, extract solvent, seed culture, and base was plumbed through pumps or clamped closed. The autoclaved material, 0.9% w/v NaCl was drained prior to the addition of liquefied mash.

Lipase Treatment Post-Liquefaction

The fermentor temperature was set to 55° C. instead of 30° C. after the liquefaction cycle was complete (Liquefaction). The pH was manually controlled at pH=5.8 by making bolus additions of acid or base when needed. A lipase enzyme stock solution was added to the fermentor to a final lipase concentration of 10 ppm. The fermentor was held at 55° C., 300 rpm, and 0.3 slpm $N_2$ overlay for >6 hrs. After the Lipase Treatment was complete the fermentor temperature was set to 30° C.

Nutrient Addition Prior to Inoculation

Added 7.0 mL/L (post-inoculation volume) of ethanol (200 proof, anhydrous) just prior to inoculation. Add thiamine to 20 mg/L final concentration just prior to inoculation. Add 100 mg/L nicotinic acid just prior to inoculation.

Fermentor Inoculation

The fermentors $pO_2$ probe was calibrated to zero while $N_2$ was being added to the fermentor. The fermentors $pO_2$ probe was calibrated to its span with sterile air sparging at 300 rpm. The fermentor was inoculated after the second seed flask was >4 g/L dcw. The shake flask was removed from the incubator/shaker for 5 minutes allowing a phase separation of the oleyl alcohol phase and the aqueous phase. The 55 mL of the aqueous phase was transferred to a sterile, inoculation bottle. The inoculum was pumped into the fermentor through a peristaltic pump.

Oleyl Alcohol or Corn Oil Fatty Acids Addition after Inoculation

Added 1 L/L (post-inoculation volume) of oleyl alcohol or corn oil fatty acids immediately after inoculation Fermentor Operating Conditions The fermentor was operated at 30° C. for the entire growth and production stages. The pH was allowed to drop from a pH between 5.7-5.9 to a control set-point of 5.2 without adding any acid. The pH was controlled for the remainder of the growth and production stage at a pH=5.2 with ammonium hydroxide. Sterile air was added to the fermentor, through the sparger, at 0.3 slpm for the remainder of the growth and production stages. The $pO_2$ was set to be controlled at 3.0% by the Sartorius DCU-3 Control Box PID control loop, using stir control only, with the stirrer minimum being set to 300 rpm and the maximum being set to 2000 rpm. The glucose was supplied through simultaneous saccharification and fermentation of the liquified corn mash by adding a $\alpha$-amylase (glucoamylase). The glucose was kept excess (1-50 g/L) for as long as starch was available for saccharification.

Analytical

Gas Analysis

Process air was analyzed on a Thermo Prima (Thermo Fisher Scientific Inc., Waltham, Mass.) mass spectrometer. This was the same process air that was sterilized and then added to each fermentor. Each fermentor's off-gas was analyzed on the same mass spectrometer. This Thermo Prima dB has a calibration check run every Monday morning at 6:00 am. The calibration check was scheduled through the Gas Works v1.0 (Thermo Fisher Scientific Inc., Waltham, Mass.) software associated with the mass spec. The gas calibrated for were:

| GAS | Calibration Concentration mole % | Cal Frequency |
|---|---|---|
| Nitrogen | 78% | weekly |
| Oxygen | 21% | weekly |
| Isobutanol | 0.2% | yearly |
| Argon | 1% | weekly |
| Carbon Dioxide | 0.03% | weekly |

Carbon dioxide was checked at 5% and 15% during calibration cycle with other known bottled gases. Oxygen was checked at 15% with other known bottled gases. Based on the analysis of the off-gas of each fermentor, the amount of isobutanol stripped, oxygen consumed, and carbon dioxide respired into the off-gas was measured by using the mass spectrometer's mole fraction analysis and gas flow rates (mass flow controller) into the fermentor. Calculate the gassing rate per hour and then integrating that rate over the course of the fermentation.

Biomass Measurement

A 0.08% Trypan Blue solution was prepared from a 1:5 dilution of 0.4% Trypan Blue in NaCl (VWR BDH8721-0) with 1×PBS. A 1.0 mL sample was pulled from a fermentor and placed in a 1.5 mL Eppendorf centrifuge tube and centrifuged in an Eppendorf, 5415C at 14,000 rpm for 5 minutes. After centrifugation, the top solvent layer was removed with an m200 Variable Channel BioHit pipette with 20-200 μL BioHit pipette tips. Care was made not to remove the layer between the solvent and aqueous layers. Once the solvent layer was removed, the sample was re-suspended using a Vortex-Genie® set at 2700 rpm.

A series of dilutions were required to get cells into the ideal concentration for hemacytometer counts. If OD was 10, a 1:20 dilution would be performed to achieve 0.5 OD which would give the ideal amount of cells to be counted per square, 20-30. In order to reduce inaccuracy in the dilution, due to corn solids, multiple dilutions with cut 100-1000 μL BioHit pipette tips was required. Approximately, 1 cm was cut off the tips to increase the opening which will prevent the tip from clogging. For a 1:20 final dilution, an initial 1:1 dilution of fermentation sample and 0.9% NaCl solution was done. Then a 1:1 dilution of previous solution and 0.9% NaCl solution, then finally a 1:5 dilution with the previous solution and Trypan Blue Solution. Samples were vortexed between each dilution and cut tips were rinsed into the 0.9% NaCl and Trypan Blue solutions.

The cover slip was carefully placed on top of the, Hausser Scientific Bright-Line 1492, hemacytometer. 10 uL was drawn up of the final Trypan Blue dilution with an m20 Variable Channel BioHit pipette with 2-20 μL BioHit pipette tips and injected into the hemacytometer. The hemacytometer was placed on the Zeis Axioskop 40 microscope at 40× magnification. The center quadrant is broken into 25 squares, the four corner and center squares in both chambers were then counted and recorded. After both chambers were counted the average was taken and multiplied by the dilution factor (20), then by 25 for the number for squares in the quadrant in the hemacytometer and then divided by 0.0001 mL, which is the volume of the quadrant that was counted. The sum of this calculation is the number cells per mL.

LC Analysis of Fermentation Products in the Aqueous Phase

Samples were refrigerated until ready for processing. Samples were removed from refrigeration for one hour to bring to room temperature. Approximately 300 uL of sample was transferred with a m1000 Variable Channel BioHit pipette with 100-1000 μL BioHit pipette tips into a 0.2 um centrifuge filter (Nanosep MF modified nylon centrifuge filter), then centrifuged using a Eppendorf 5415C for five minutes at 14,000 rpm. Approximately 200 uL of filtered sample was transferred into a 1.8 auto sampler vial with a 250 uL glass vial insert with polymer feet. A screw cap with PTFE septa, was used to cap the vial before vortexing the sample with a Vortex-Genie® set at 2700 rpm.

Sample was then run on Agilent 1200 series LC equipped with binary, isocratic pumps, vacuum degasser, heated column compartment, sampler cooling system, UV DAD detector and RI detector. The column used was an Aminex HPX-87H, 300×7.8 with a Bio-Rad Cation H refill, 30×4.6 guard column. Column temperature was 40° C., with a mobile phase of 0.01 N sulfuric acid, at a flow rate of 0.6 mL/min for 40 minutes. Results are shown in Table 6.

TABLE 6

Retention times of fermentation products in aqueous phase

| HPLC 302/310 Normalized to 10 μL injections | FW | RID Retention Time, min | Range of Standards, g/L | UV Retention Time, min |
|---|---|---|---|---|
| citric acid | 192.12 | 8.025 | 0.3-17 | 7.616 |
| glucose | 180.16 | 8.83 | 0.5-71 | |
| pyruvic acid (Na) | 110.04 | 9.388 | 0.1-5.2 | 8.5 |
| A-Kiv (Na) | 138.1 | 9.91 | 0.07-5.0 | 8.55 |
| 2,3-dihydroxyisovaleric acid (Na) | 156.1 | 10.972 | 0.2-8.8 | 10.529 |
| succinic acid | 118.09 | 11.561 | 0.3-16 | 11.216 |
| lactic acid (Li) | 96.01 | 12.343 | 0.3-17 | 11.948 |
| glycerol | 92.09 | 12.974 | 0.8-39 | |
| formic acid | 46.03 | 13.686 | 0.2-13 | 13.232 |
| acetate (Na) | 82.03 | 14.914 | 0.5-16 | 14.563 |
| meso-butanediol | 90.12 | 17.583 | 0.1-19 | |
| (+/−)-2,3-butanediol | 90.12 | 18.4 | 0.2-19 | |
| isobutyric acid | 88.11 | 19.685 | 0.1-8.0 | 19.277 |
| ethanol | 46.07 | 21.401 | 0.5-34 | |
| isobutyraldehyde | 72.11 | 27.64 | 0.01-0.11 | |
| isobutanol | 74.12 | 32.276 | 0.2-15 | |
| 3-OH-2-butanone (acetoin) | 88.11 | | 0.1-11 | 17.151 |

GC Analysis of Fermentation Products in the Solvent Phase

Samples were refrigerated until ready for processing. Samples were removed from refrigerator for one hour to bring to room temperature. Approximately 150 uL of sample was transferred using a m1000 Variable Channel BioHit pipette with 100-1000 μL BioHit pipette tips into a 1.8 auto sampler vial with a 250 uL glass vial insert with polymer feet. A screw cap with PTFE septa was used to cap the vial.

Sample was then run on Agilent 7890A GC with a 7683B injector and a G2614A auto sampler. The column was a HP-InnoWax column (30 m×0.32 mm ID, 0.25 μm film). The carrier gas was helium at a flow rate of 1.5 mL/min measured at 45° C. with constant head pressure; injector split was 1:50 at 225° C.; oven temperature was 45° C. for 1.5 min, 45° C. to 160° C. at 10° C./min for 0 min, then 230° C. at 35° C./min for 14 minutes for a run time of 29 minutes. Flame ionization detection was used at 260° C. with 40 mL/min helium makeup gas. Results are shown in Table 7.

TABLE 7

Retention times of fermentation products in solvent phase

| GC 302/310 Normalized to 10 µL injections | FW | Solvent Retention Time, min | Range of Standards, g/L |
|---|---|---|---|
| isobutyraldehyde | 72.11 | 2.75 | 0.7-10.4 |
| ethanol | 46.07 | 3.62 | 0.5-34 |
| isobutanol | 74.12 | 5.53 | 0.2-16 |
| 3-OH-2-butanone (acetoin) | 88.11 | 8.29 | 0.1-11 |
| (+/−)-2,3-butanediol | 90.12 | 10.94 | 0.1-19 |
| isobutyric acid | 88.11 | 11.907 | 0.1-7.9 |
| meso-butanediol | 90.12 | 11.26 | 0.1-6.5 |
| glycerol | 92.09 | 16.99 | 0.8-9 |

Samples analyzed for fatty acid butyl esters were run on Agilent 6890 GC with a 7683B injector and a G2614A auto sampler. The column was a HP-DB-FFAP column (15 meters×0.53 mm ID (Megabore), 1-micron film thickness column (30 m×0.32 mm ID, 0.25 µm film). The carrier gas was helium at a flow rate of 3.7 mL/min measured at 45° C. with constant head pressure; injector split was 1:50 at 225° C.; oven temperature was 100° C. for 2.0 min, 100° C. to 250° C. at 10° C./min, then 250° C. for 9 min for a run time of 26 minutes. Flame ionization detection was used at 300° C. with 40 mL/min helium makeup gas. The following GC standards (Nu-Chek Prep; Elysian, Minn.) were used to confirm the identity of fatty acid isobutyl ester products: iso-butyl palmitate, iso-butyl stearate, iso-butyl oleate, iso-butyl linoleate, iso-butyl linolenate, iso-butyl arachidate.

Example 11A

Experiment identifier 2010Y033 included: Seed Flask Growth method, Initial Fermentor Preparation method with corn mash that excludes solids, Lipase Treatment Post-Liquefaction, Nutrient Addition Prior to Inoculation method, Fermentor Inoculation method, Fermentor Operating Conditions method, and all of the Analytical methods. Corn oil fatty acid was added in a single batch between 0.1-1.0 hr after inoculation. The butanologen was CEN.PK113-7D Δura3::loxP Δhis3 Δpdc6 Δpdc1::ilvDSm Δpdc5::sadB Δgpd2::loxP/pYZ090+pLH468 (NGCI-070).

Example 11B

Experiment identifier 2010Y034 included: Seed Flask Growth method, Initial Fermentor Preparation method with corn mash that includes solids, Lipase Treatment Post-Liquefaction, Nutrient Addition Prior to Inoculation method, Fermentor Inoculation method, Fermentor Operating Conditions method, and all of the Analytical methods. Corn oil fatty acid was added in a single batch between 0.1-1.0 hr after inoculation. The butanologen was CEN.PK113-7D Δura3::loxP Δhis3 Δpdc6 Δpdc1::ilvDSm Δpdc5::sadB Δgpd2::loxP/pYZ090+pLH468 (NGCI-070).

Example 11C

Experiment identifier 2010Y035 included: Seed Flask Growth method, Initial Fermentor Preparation method with corn mash that excludes solids, Nutrient Addition Prior to Inoculation method, Fermentor Inoculation method, Fermentor Operating Conditions method, and all of the Analytical methods. Oleyl alcohol was added in a single batch between 0.1-1.0 hr after inoculation. The butanologen was CEN.PK113-7D Δura3::loxP Δhis3 Δpdc6 Δpdc1::ilvDSm Δpdc5::sadB Δgpd2::loxP/pYZ090+pLH468 (NGCI-070).

Example 11D

Experiment identifier 2010Y036 included: Seed Flask Growth method, Initial Fermentor Preparation method with corn mash that includes solids, Nutrient Addition Prior to Inoculation method, Fermentor Inoculation method, Fermentor Operating Conditions method, and all of the Analytical methods. Oleyl alcohol was added in a single batch between 0.1-1.0 hr after inoculation. The butanologen was CEN.PK113-7D Δura3::loxP Δhis3 Δpdc6 Δpdc1::ilvDSm Δpdc5::sadB Δgpd2::loxP/pYZ090+pLH468 (NGCI-070).

Results for Examples 11A-11D are shown in Table 8

TABLE 8

Fermentation conditions and results for Examples 11A-11D

| Example # | Experimental ID | Active Lipase | Post-Liquefaction Undissolved Solids Removed | Extracting Solvent | Glucose Equivalents Charged g/kg | g/kg glucose consumed at EOR | Effective isobutanol g/L |
|---|---|---|---|---|---|---|---|
| 11A | 2010Y033 | Yes | Yes | Corn oil fatty acids | 257 | 257 | 30.9 |
| 11B | 2010Y034 | Yes | No | Corn oil fatty acids | 239 | 239 | 17.3 |
| 11C | 2010Y035 | No | Yes | Oleyl alcohol | 263 | 72 | 15.7 |
| 11D | 2010Y036 | No | No | Oleyl alcohol | 241 | 101 | 20 |

Example 12

Effect of Removing Undissolved Solids from the Fermentor Feed on Improvement in Fermentor Volume Efficiency This example demonstrates the effect of removing undissolved solids from the mash prior to fermentation on fermentor volume efficiency. Undissolved solids in corn mash occupy at least 5% of the mash volume depending on corn loading and content starch content. Removing solids before fermentation enables at least 5% more sugar to be charged to the fermentor thus increasing batch productivity.

It was estimated that the liquefied corn mash produced in Example 10 contained approximately 28 wt % (280 g/L) liquefied starch based on the corn loading used (40% dry corn basis), starch content of the corn (71.4% dry corn basis), and assuming all the starch was hydrolyzed to soluble oligosaccharides during liquefaction. The mash was prepared with a higher concentration of oligosaccharides than was desired in the fermentations as described in Example 11 to allow for dilution when adding the nutrients, inoculum, glucoamylase, and base to the initial fermentation broth. The mash was diluted by approximately 10% after adding these ingredients. Therefore, the expected concentration of liquefied starch in the mash (including solids) at the beginning of fermentations 2010Y034 and 2010Y036 was about 250 g/L. The actual glucose equivalents charged to the 2010Y034 and 2010Y036 fermentations was measured to be 239 g/kg and 241 g/kg, respectively (see Table 8). By comparison, the glucose equivalents charged to the 2010Y033 and 2010Y035 fermentations was measured to be 257 g/kg and 263 g/kg, respectively. Note that the feed to these fermentations was centrate (mash from which most of the solids had been removed). Approximately 1.2 L of the sugar source (mash or centrate) was charged to each fermentation. Therefore, based on this data, approximately 8.3% more sugar was charged to the fermentors which used centrate (2010Y033 and 2010Y035) compared to mash (2010Y034 and 2010Y036). These results demonstrate that removing undissolved solids from corn mash prior to fermentation can result in a significant increase in sugar charged per unit volume. This implies that when solids are present, they occupy valuable fermentor volume. If solids are removed from the feed, more sugar may be added ("fit") to the fermentor due to the absence of undissolved solids. This example demonstrates that fermentor volume efficiency can be significantly improved by removing undissolved solids from the mash prior to fermentation.

Example 13

Effect of Removing Undissolved Solids on Phase Separation Between the Extraction Solvent and the Broth

Extractive Fermentation

This example demonstrates improved separation between the solvent phase and the broth phase during and after an extractive fermentation process by removing undissolved solids from the corn mash prior to fermentation. Two extractive fermentations were conducted side-by side, one with liquefied corn mash as the sugar source (solids not removed) and one with centrate (aqueous solution of oligosaccharides) which was generated by removing most of the undissolved solids from liquefied corn mash. Oleyl alcohol (OA) was added to both fermentations to extract the product (i-BuOH) from the broth as it was formed. The fermentation broth referred to in this example where solids were not removed from the feed (used corn mash) was 2010Y036 as described in Example 10. The fermentation broth referred to in this example where solids were removed from the feed (used centrate produced from corn mash) was 2010Y035 as described in Example 10. Oleyl alcohol was the extraction solvent used in both fermentations. The rate and degree of phase separation was measured and compared throughout the fermentations as well as for the final fermentation broths. Adequate phase separation in an extractive fermentation process can lead to minimal loss of the microorganism and minimal solvent losses as well lower capital and operating cost of downstream processing.

Phase Separation Between Solvent and Broth Phases During Fermentation

Approximately 10 mL samples were pulled from each fermentor at 5.3, 29.3, 53.3, and 70.3 hrs, and phase separation was compared for the samples from the fermentation where solids were removed (2010Y035) from the samples and where solids were not removed (2010Y036). Phase separation was observed and compared for all samples from all run times by allowing the samples to set for about 2 hrs and tracking the position of the liquid-liquid interface. Essentially no phase separation was observed for any of the samples pulled from the fermentation where solids were not removed. Phase separation was observed for all samples from the fermentation where solids were removed from the liquefied corn mash prior to fermentation. Separation started to occur within about 10-15 minutes of pulling the samples from the run where solids were removed for all fermentation times and continued to improve over a 2 hr period of time. Phase separation started to occur in the sample pulled at 5.3 hrs fermentation run time from the centrate fermentation (solids removed) after about 7 minutes of settling time. Phase separation started to occur in the sample pulled at 53.3 hrs from the centrate fermentation (solids removed) after about 17 minutes of settling time.

Figure 9:
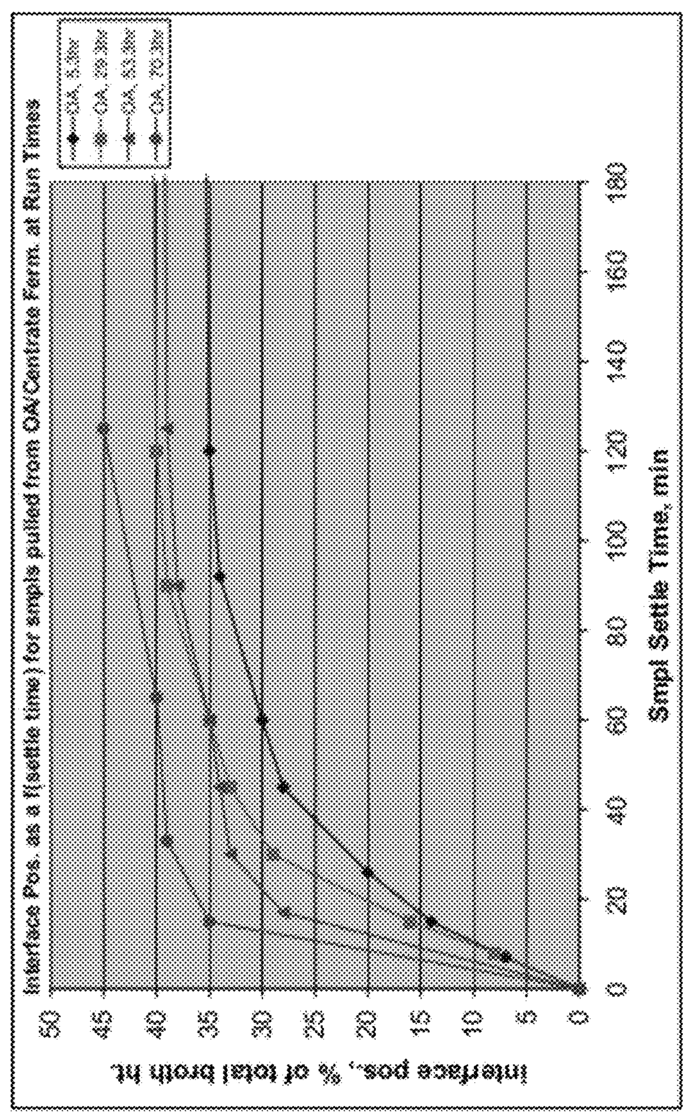

FIG. 9 is a plot of the position of the liquid-liquid interface in the fermentation sample tubes as a function of (gravity) settling time. The data is for the samples pulled from the extractive fermentation where centrate was fed (solids removed from corn mash) as the sugar source and OA was the ISPR extraction solvent (run 2010Y035 in Example 10). The phase separation data in this plot is for samples pulled at 5.3, 29.3, 53.3, and 70.3 hrs run time from fermentation 2010Y035. The interface position is reported as a percentage of the total broth height in the sample tube. For example, the interface position in the sample pulled at 5.3 hrs run time from the 2010Y035 fermentation (centrate/OA) increased from the bottom of the sample tube (no separation) to 3.5 mL after 120 minutes of settling time. There was about 10 mL of total broth in that particular sample tube. Therefore, the interface position for that sample was reported as 35% in FIG. 9. Similarly, the interface position in the sample pulled at 53.3 hrs run time from the 2010Y035 fermentation (centrate/OA) increased from the bottom of the sample tube (no separation) to about 3.9 mL after 125 minutes of settling time. There was about 10 mL of total broth in that particular sample tube. Therefore, the interface position for that sample was reported as 39% in FIG. 9.

Phase Separation Between Solvent and Broth Phases after Completing Fermentation

Figure 10:
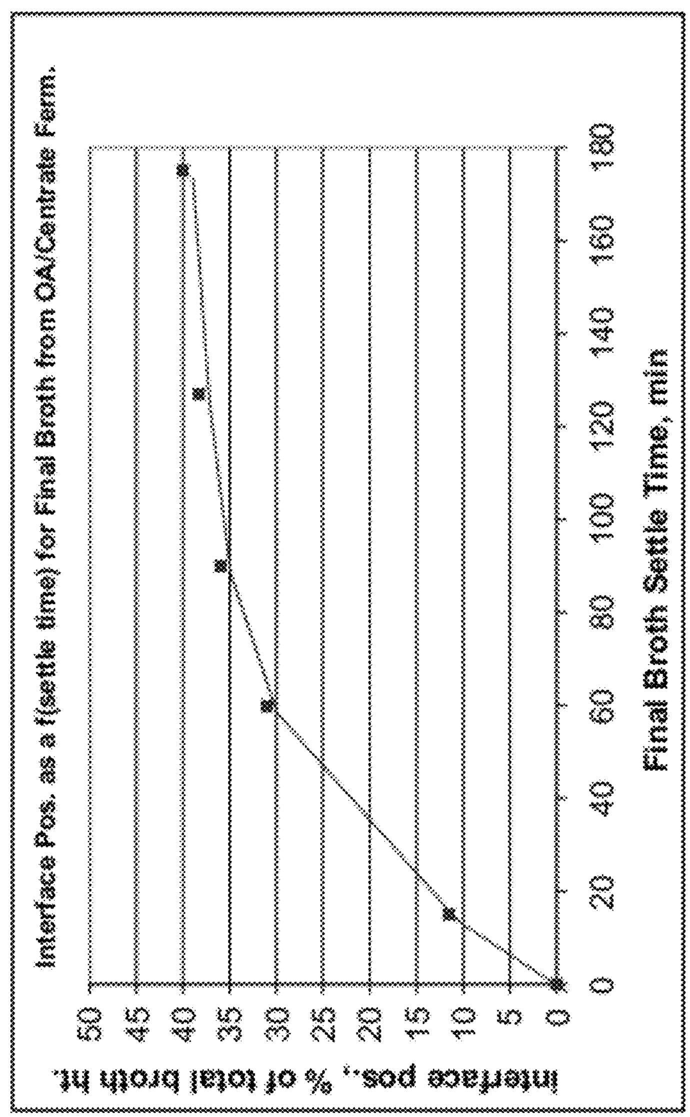
FIG. 10 illustrates the position of the liquid-liquid interface of the final fermentation broth as a function of (gravity) settling time. Data from extractive-fermentation where solids were removed from the mash feed, and OA was the solvent (2010Y035).

After 70 hrs of run time, the fermentations were stopped, and the two broths from the OA extractive fermentations were transferred to separate 2 L glass graduated cylinders. The separation of the solvent and broth phases were observed and compared. Almost no phase separation was observed after about 3 hrs for the broth where solids were not removed prior to fermentation (run 2010Y036). Phase separation was observed for the broth where solids were removed from the liquefied corn mash prior to fermentation (run 2010Y035). Separation started to occur after about 15 minutes of settling time and continued to improve over a 3 hr period of time. After 15 minutes, a liquid-liquid interface was established at a level that was about 10% of the total height of the two phase mixture. This indicates that the aqueous phase splits out from the dispersion first and starts to accumulate at the bottom of the mixture. As time proceeded, more aqueous phase accumulated at the bottom of the mixture causing the position of the interface to rise. After about 3 hrs of settling time, the interface had increased to a level that was about 40% of the total height of the two phase mixture. This indicates that almost complete phase separation had occurred after about 3 hrs of (gravity) settling time for the final two phase broth where solids were removed based on the amounts of centrate and OA initially charged to the fermentation. Approximately equal volumes of initial centrate and solvent were charged to both fermentations. Approximately 1.2 L of liquefied corn mash and approximately 1.1 L of OA were charged to fermentation 2010Y036. Approximately 1.2 L of centrate, which was produced from the same batch of mash, and approximately 1.1 L of OA were charged to fermentation 2010Y035. After accounting for the fact that approximately 100 g/kg of the initial sugar in the aqueous phase was consumed and the fact that about 75% of the i-BuOH produced was in the solvent phase, it would be expected that the relative volumes of the final aqueous and organic phases would be about 1:1 if complete separation occurred. FIG. 10 is a plot of the liquid-liquid interface position as a function of (gravity) settling time for the final two phase broth from the extractive fermentation where solids were removed (2010Y035). The interface position is reported as a percentage of the total broth height in the 2 L graduated cylinder used to observe phase separation of the final broth. The interface position of the final broth from the 2010Y035 fermentation increased from the bottom of the graduated cylinder (no separation) to a level that was about 40% of the total height of the two phase mixture after 175 min of settling time. Therefore, almost complete separation of the two phases in the final broth occurred after 3 hrs of settling time. An interface position of approximately 50% would correspond to complete separation.

A 10 mL sample was pulled from the top of the organic phase of the final broth (which had settled for about 3 hrs) from the fermentation where solids had been removed. The sample was spun in a high-speed lab centrifuge to determine the amount of aqueous phase that was present in the organic phase after allowing the broth to settle for 3 hrs. The results showed that about 90% of the top layer of the final broth was solvent phase. About 10% of the top layer of the final broth was aqueous phase, including a relatively small amount of undissolved solids. Some solids were located at the bottom of the aqueous phase (more dense than the aqueous phase) and also a small amount of solids accumulated at the liquid-liquid interface.

A 10 mL sample was also pulled from the bottom phase of the final broth (which had settled for about 3 hrs) from the fermentation where solids had been removed. The sample was spun in a high-speed lab centrifuge to determine the amount of organic phase that was present in the aqueous phase after allowing the broth to settle for 3 hrs. It was determined that essentially no organic phase was present in the bottom (aqueous) phase of the final broth from the fermentation from which solids had been removed after the broth had settled for 3 hrs. These results confirm that almost complete phase separation had occurred for the final broth from the fermentation where solids had been removed. Almost no phase separation was apparent for the final broth from the fermentation where solids had not been removed. This data implies that removing solids from liquefied corn mash before extractive fermentation may enable a significant improvement in phase separation during and after fermentation resulting in less loss of the microorganism, undissolved solids, and water to downstream processing.

A 10 mL sample was pulled from the top of the final broth from the fermentation from which solids had not been removed after the broth had set for about 3 hrs. The sample was spun in a high-speed lab centrifuge to determine the relative amount of solvent and aqueous phases at the top of the final broth. This broth contained all solids from the liquefied corn mash solids. About half of the sample was aqueous phase, and about half was organic phase. The aqueous phase contained significantly more undissolved solids (from the liquefied mash) compared to the sample of the top layer from the broth where solids were removed. The amounts of aqueous and solvent phases in this sample are approximately the same indicating that essentially no phase separation occurred in the final broth where solids were not removed (even after 3 hrs of settling time). This data implies that if solids are not removed from liquefied corn mash before an extractive fermentation, little to no phase separation is likely to occur during and after fermentation. This could result in a significant loss of the microorganism, undissolved solids, and water to downstream processing.

Example 14

Effect of Removing Undissolved Solids on the Loss of ISPR Extraction Solvent —Extractive Fermentation This example demonstrates the potential for reducing solvent losses with the DDGS out the back end of an extractive fermentation process by removing undissolved solids from the corn mash prior to fermentation. Example 10 described two extractive fermentations conducted side-by side, one with liquefied corn mash as the sugar source (2010Y036—solids not removed) and one with liquefied mash centrate (2010Y035—aqueous solution of oligosaccharides) obtained by removing most of the undissolved solids from liquefied corn mash. Oleyl alcohol (OA) was added to both fermentations to extract the product isobutanol (i-BuOH) from the broth as it was formed. The amount of residual solvent trapped in the undissolved solids recovered from the final fermentation broths was measured and compared.

After completion of the fermentations 2010Y035 and 2010Y036 described in Example 10, the broths were harvested and used to conduct the phase separation tests described in Example 11. Then the undissolved solids (fines from the corn mash that did not get removed prior to fermentation) were recovered from each broth and analyzed for total extractable oils. The oil recovered from each lot of solids was analyzed for OA and corn oil. The following protocol was followed for both broths:

The broth was centrifuged to separate the organic, aqueous, and solid phases.

The organic and aqueous phases were decanted away from the solids leaving a wet cake at the bottom of the centrifuge bottle.

The wet cake was thoroughly washed with water to remove essentially all of the dissolved solids held up in the cake, such as residual oligosaccharides, glucose, salts, enzymes, etc.

The washed wet cake was dried in a vacuum oven overnight (house-vacuum at 80° C.) to remove essentially all of the water in the cake.

A portion of the dry solids was thoroughly contacted with hexane in a Soxhlet extractor to remove the oil from the solids.

The oil recovered from the solids was analyzed by GC to determine the relative amount of OA and corn oil present in the oil recovered from the solids.

A particle size distribution (PSD) was measured for the solids recovered from both fermentation broths.

The data for the recovery and hexane extraction of the undissolved solids from both fermentation broths is shown in Table 8. The data shows that approximately the same amount of oil was absorbed by the solids (per unit mass of solids) in both fermentations.

TABLE 8

| | Fermentation ID: | |
|---|---|---|
| | 2010Y036 | 2010Y035 |
| Solids removed from liquefied mash before fermentation | No (mash) | Yes (centrate) |
| Washed wet cake recovered after removing organic phase, aqueous phase, and washing the wet cake with water, g: | 290.6 g | 15.6 g |
| Dry solids content in washed wet cake, wt %: | 23.6% | 25.8% |
| Dry solids recovered from washed wet cake, g: | 68.1 g | 4.02 g |
| Dry solids charged to Soxhlet, g: | 20.11 g | 3.91 g |
| Dry Content of solids charged to Soxhlet via moisture analysis, wt %: | 97.9% | 98.1% |
| Total oil recovered from Soxhlet hexane extraction, g: | 2.30 g | 0.25 g |
| Oil content of solids (dry solids basis), g oil per g of dry solids: | 0.12 g oil/g dry solids | 0.07 g oil/g dry solids |
| Fraction of oil extracted from solids that is OA (approximate value), wt %: | 76% | 74% |

Example 15

Recovery of Soluble Starch from a Wet Cake Generated from the Removal of Solids from Liquefied Corn Mash by Washing the Wet Cake with Water —Two Stage Process This example demonstrated the recovery of soluble starch from a wet cake by washing the cake twice with water, where the cake was generated by centrifuging liquified mash. Liquefied corn mash was fed to a continuous decanter centrifuge to produce a centrate stream (C-1) and a wet cake (WC-1). The centrate was a relatively solids-free, aqueous solution of soluble starch, and the wet cake was concentrated in solids compared to the feed mash. A portion of the wet cake was mixed with hot water to form a slurry (S-1). The slurry was pumped back through the decanter centrifuge to produce a wash water centrate (C-2) and a washed wet cake (WC-2). C-2 was a relatively solids-free, dilute aqueous solution of soluble starch. The concentration of soluble starch in C-2 was less than the concentration of soluble starch in the centrate produced from the separation of mash. The liquid phase held up in WC-2 was more dilute in starch than the liquid in the wet cake produced from the separation of mash. The washed wet cake (WC-2) was mixed with hot water to form a slurry (S-2). The ratio of water charged to the amount of soluble starch in the wet cake charged was the same in both wash steps. The second wash slurry was pumped back through the decanter centrifuge to produce a second wash water centrate (C-3) and a wet cake (WC-3) that had been washed twice. C-3 was a relatively solids-free, dilute aqueous solution of soluble starch. The concentration of soluble starch in C-3 was less than the concentration of soluble starch in the centrate produced in the first wash stage (C-2), and thus the liquid phase held up in WC-3 (second washed wet cake) was more dilute in starch than in WC-2 (first washed wet cake). The total soluble starch in the two wash centrates (C-2 and C-3) is the starch that was recovered and could be recycled back to liquefaction. The soluble starch in the liquid held up in the final washed wet cake is much less that in the wet cake produced in the original separation of the mash.

Production of Liquefied Corn Mash

Approximately 1000 gallons of liquefied corn mash was produced in a continuous dry-grind liquefaction system consisting of a hammer mill, slurry mixer, slurry tank, and liquefaction tank. Ground corn, water, and alpha-amylase were fed continuously. The reactors were outfitted with mechanical agitation, temperature control, and pH control using either ammonia or sulfuric acid. The reaction conditions were as follows:

Hammer mill screen size: 7/64"

Feed Rates to Slurry Mixer
- Ground Corn: 560 lbm/hr (14.1 wt % moisture)
- Process Water: 16.6 lbm/min (200 F)
- Alpha-Amylase: 61 g/hr (Genecor: Spezyme® ALPHA)

Slurry Tank Conditions:
- Temperature: 185° F. (85° C.)
- pH: 5.8
- Residence Time: 0.5 hr
- Dry Corn Loading: 31 wt %
- Enzyme Loading: 0.028 wt % (dry corn basis)

Liquefaction Tank Conditions:
- Temperature: 185° F. (85° C.)
- pH: 5.8
- Residence Time: about 3 hrs
- No additional enzyme added.

The production rate of liquefied corn mash was about 3 gpm. The starch content of the ground corn was measured to be about 70 wt % on a dry corn basis. The total solids (TS) of the liquefied mash was about 31 wt %, and the total suspended solids (TSS) was approximately 7 wt %. The liquid phase contained about 23-24 wt % liquefied starch as measured by HPLC (soluble oligosaccharides).

The liquefied mash was centrifuged in a continuous decanter centrifuge at the following conditions:

Bowl Speed: 5000 rpm (about 3600 g's)

Differential Speed: 15 rpm

Weir Diameter: 185 mm (weir plate removed)

Feed Rate: Varied from 5-20 gpm.

Approximately 850 gal of centrate and approximately 1400 lbm of wet cake were produced by centrifuging the mash. The total solids in the wet cake were measured to be about 46.3% (suspended+dissolved) by moisture balance. Knowing that the liquid phase contained about 23 wt % soluble starch, it was estimated that the total suspended solids in the wet cake was about 28 wt %. It was estimated that the wet cake contained approximately 12% of the soluble starch that was present in the liquefied mash prior to the centrifuge operation.

Recovery of Soluble Starch from Wet Cake by Washing the Solids with Water—1st Wash About 707 lbm of the wet cake recovered from separation of the liquefied mash was mixed with 165 gal of hot (91° C.) water in a 300 gallon stainless steel vessel. The resulting slurry was mixed for about 30 minutes. The slurry was continuously fed to a decanter centrifuge to remove the washed solids from the slurry. The centrifuge used to separate the wash slurry was the same one used to remove solids from the liquefied mash above, and it was rinsed with fresh water before feeding the slurry. The centrifuge was operated at the following conditions to remove solids from the wash slurry:

Bowl Speed: 5000 rpm (about 3600 g's)
Differential Speed: 5 rpm
Weir Diameter: 185 mm (weir plate removed)
Feed Rate: 5 gpm.

Approximately 600 lbm of washed wet cake was produced by the centrifuge, but only 400 lbm were recovered due to loss of material. The total solids in the wet cake were measured to be about 36.7% (suspended+dissolved) by moisture balance. The total soluble starch (sum of glucose, DP2, DP3, and DP4+) in the liquid phase of the slurry and in the wash water centrate (obtained from the slurry) was measured to be about 6.7 wt % and 6.9 wt %, respectively, by HPLC. DP2 refers to a dextrose polymer containing two glucose units (glucose dimer). DP3 refers to a dextrose polymer containing three glucose units (glucose trimer). DP4+ refers to a dextrose polymer containing four or more glucose units (glucose tetramer and higher). This confirmed that a well mixed dilution wash stage was achieved. Therefore, the concentration of soluble starch in the liquid phase held up in the washed wet cake must have been about 6.8 wt % (by mass balance) for this dilution wash. Based on the total solids and dissolved oligosaccharide data, it was estimated that the total suspended solids in the washed wet cake was about 32 wt %. It was estimated that the washed wet cake contained approximately 2.6% of the soluble starch that was present in the original liquefied mash if all 600 lbm of the cake produced by the centrifuge could have been washed. This represents about a 78% reduction in soluble starch in the washed wet cake compared to the mash wet cake prior to washing. If the wet cake produced from the separation of liquefied mash was not washed, about 12% of the total starch in the mash would be lost as soluble (liquefied) starch. If the wet cake produced from the separation of mash is washed with water at the conditions demonstrated in this example, 2.6% of the total starch from the mash would be lost as soluble (liquefied) starch.

About 400 lbm of the washed wet cake recovered from the first reslurry wash of the liquefied mash wet cake was mixed with 110 gal of hot (90° C.) water in a 300 gallon stainless steel vessel. The resulting slurry was mixed for about 30 minutes. The slurry was continuously fed to a decanter centrifuge to remove the washed solids from the slurry. The centrifuge used to separate the second wash slurry was the same one used in the first wash above, and it was rinsed with fresh water before feeding the second wash slurry. The centrifuge was operated at the following conditions to remove solids from the wash slurry:

Bowl Speed: 5000 rpm (about 3600 g's)
Differential Speed: 5 rpm
Weir Diameter: 185 mm (weir plate removed)
Feed Rate: 4 gpm.

Approximately 322 lbm of washed wet cake was produced by the centrifuge. The total solids in the wet cake from the second wash were measured to be about 37.4% (suspended+dissolved) by moisture balance. The total soluble starch (sum of glucose, DP2, DP3, and DP4+) in the liquid phase of the slurry and in the wash water centrate (obtained from the slurry) was measured to be about 1.6 wt % and 1.6 wt %, respectively, by HPLC. This confirmed that a well mixed dilution wash stage was achieved in the second wash. Therefore, the concentration of soluble starch in the liquid phase held up in the washed wet cake must have been about 1.6 wt % (by mass balance) for this dilution wash. Based on the total solids and dissolved oligosaccharide data, it was estimated that the total suspended solids in the washed wet cake was about 36 wt %. It was estimated that the washed wet cake contained approximately 0.5% of the soluble starch that was present in the original liquefied mash if all 600 lbm of the cake produced in the first wash stage could have been washed. This represents an overall reduction in soluble starch in the doubly washed wet cake compared to the mash wet cake prior to washing of about 96%. If the wet cake produced from the separation of liquefied mash was not washed, about 12% of the total starch in the mash would be lost as soluble (liquefied) starch. If the wet cake produced from the separation of mash is washed twice with water at the conditions demonstrated in this example, 0.5% of the total starch from the mash would be lost as soluble (liquefied) starch.

Example 16

Effect of High Temperature Stage During Liquefaction on the Conversion of Starch in Corn Solids to Soluble (Liquefied) Starch This example demonstrates that operating liquefaction with a high temperature (or "cook") stage at some time in the middle of the reaction can result in higher conversion of the starch in corn solids to soluble (liquefied) starch. The "cook" stage demonstrated in this example involves raising the liquefaction temperature at some point after liquefaction starts, holding at the higher temperature for some period of time, and then lowering the temperature back to the original value to complete liquefaction.

A. Procedure to Measure Unhydrolyzed Starch Remaining in Solids after Liquefaction Liquefied corn mash was prepared in one run according to the protocol in Example 1 (no intermediate high temperature stage). Liquefied corn mash was prepared in another run at the same conditions as in the first run except for the addition of an intermediate high temperature stage. The mash from both runs was worked up according to the following steps. It was centrifuged to separate the aqueous solution of liquefied starch from the undissolved solids. The aqueous solution of liquefied starch was decanted off to recover the wet cake. The wet cake contained most of the undissolved solids from the mash, but the solids were still wet with liquefied starch solution. The wet cake was thoroughly washed with water, and the subsequent slurry was centrifuged to separate the aqueous layer from the undissolved solids. The cake was washed a total of five times with enough water to remove approximately all of the soluble starch that was held up in the original wet cake recovered from liquefaction. Consequently, the liquid phase held up in the final washed wet cake consisted of water containing essentially no soluble starch.

The final washed wet cake was reslurried in water, and large excesses of both alpha-amylase and glucoamylase were added. The slurry was mixed for at least 24 hrs while controlling temperature and pH to enable the alpha-amylase to convert essentially all the unhydrolyzed starch remaining in the undissolved solids to soluble oligosaccharides. The soluble oligosaccharides generated from the residual starch (which was not hydrolyzed during liquefaction at the conditions of interest) were subsequently converted to glucose by the glucoamylase present. Glucose concentration was tracked with time by HPLC to make sure all the oligosaccharides generated from the residual starch were converted to glucose and that the glucose concentration was no longer increasing with time.

B. Production of Liquefied Corn Mash

Two batches of liquefied corn mash were prepared (approximately 1 L each) at 85° C. using Liquozyme® SC DS (alpha-amylase from Novozymes, Franklinton, N.C.). Both batches operated at 85° C. for a little more than 2 hrs. However, a "cook" period was added in the middle of the second batch ("Batch 2"). The temperature profile for Batch 2 was about 30 minutes at 85° C., raising the temperature from 85° C. to 101° C., holding at 101° C. for about 30 minutes, cooling down to 85° C., and continuing liquefaction for another 120 minutes. The ground corn used in both batches was the same as in Example 1. A corn loading of 26 wt % (dry corn basis) was used in both batches. The total amount of enzyme used in both runs corresponded to 0.08 wt % (dry corn basis). The pH was controlled at 5.8 during both liquefaction runs. The liquefactions were carried out in a glass, jacketed resin kettle. The kettle was set up with mechanical agitation, temperature control, and pH control.

The following protocol was followed to prepare liquefied corn mash for Batch 1:

- The alpha-amylase was diluted in tap water (0.418 g enzyme in 20.802 g water)
- Charged 704.5 g tap water to the kettle
- Turned on agitator
- Made first charge of ground corn, 198 g
- Heated to 55° C. while agitating
- Adjusted pH to 5.8 using $H_2SO_4$ or NaOH
- Made first charge of alpha-amylase solution, 7.111 g
- Heated to 85° C.
- Held at 85° C. for 30 minutes
- Made second charge of alpha-amylase solution, 3.501 g
- Made second charge of ground corn, 97.5 g
- Continued to run at 85° C. for another 100 minutes.
- After the liquefaction was complete, cooled to 60° C.
- Dumped reactor and recovered 998.5 g of liquefied mash.

The following protocol was followed to prepare liquified corn mash for Batch 2:

- The alpha-amylase was diluted in tap water (0.3366 g enzyme in 16.642 g water)
- Charged 562.6 g tap water to the kettle
- Turned on agitator
- Charged ground corn, 237.5 g
- Heated to 55° C. while agitating
- Adjusted pH to 5.8 using dilute $H_2SO_4$ or NaOH
- Made first charge of alpha-amylase solution, 4.25 g
- Heated to 85° C.
- Held at 85° C. for 30 minutes
- Heated to 101° C.
- Held at 101° C. for 30 minutes
- Lowered temperature of mash back to 85° C.
- Adjusted pH to 5.8 using dilute $H_2SO_4$ or NaOH
- Made second charge of alpha-amylase solution, 4.2439 g
- Continued to run at 85° C. for another 120 minutes.
- After the liquefaction was complete, cooled to 60° C.

C. Removal of Undissolved Solids from the Liquified Mash and Washing of the Wet Cake with Water to Remove Soluble Starch Most of the solids were removed from both batches of liquefied mash by centrifuging them in a large floor centrifuge at 5000 rpm for 20 minutes at room temperature. Centrifugation of 500 g of mash from Batch 1 yielded 334.1 g of centrate and 165.9 g of wet cake. Centrifugation of 872 g of mash from Batch 2 yielded 654.7 g of centrate and 217 g of wet cake. The wet cakes recovered from each batch of liquefied mash were washed five times with tap water to remove essentially all of the soluble starch held up in the cakes. The washes were performed in the same bottle used to centrifuge the original mash to avoid transferring the cake between containers. For each wash stage, the cake was mixed with water, and the resulting wash slurry was centrifuged (5000 rpm for 20 minutes) at room temperature. This was done for all five wash stages performed on the wet cakes recovered from both batches of mash. Approximately 165 g of water was used in each of the five washes of the wet cake from Batch 1 resulting in a total of 828.7 g of water used to wash the wet cake from Batch 1. Approximately 500 g of water was used in each of the five washes of the wet cake from Batch 2 resulting in a total of 2500 g of water used to wash the wet cake from Batch 2. The total wash centrate recovered from all five water washes of the wet cake from Batch 1 was 893.1 g. The total wash centrate recovered from all five water washes of the wet cake from Batch 2 was 2566.3 g. The final washed wet cake recovered from Batch 1 was 101.5 g, and the final washed wet cake recovered from Batch 2 was 151.0 g. The final washed wet cakes obtained from each batch contained essentially no soluble starch; therefore, the liquid held up in each cake was primarily water. The total solids (TS) of the wet cakes was measured using a moisture balance. The total solids of the wet cake from Batch 1 was 21.63 wt %, and the TS for the wet cake from Batch 2 was 23.66 wt %.

D. Liquefaction/Saccharification of Washed Wet Cake to Determine the Level of Unhydrolyzed Starch Remaining in the Undissolved Solids after Liquefaction The level of unhydrolyzed starch remaining in the solids present in both washed wet cakes was measured by reslurrying the cakes in water and adding excess alpha-amylase and excess glucoamylase. The alpha-amylase converts residual unhydrolyzed starch in the solids to soluble oligosaccharides which dissolve in the aqueous phase of the slurry. The glucoamylase subsequently converts the soluble oligosaccharides generated by the alpha-amylase to glucose. The reactions were run at 55° C. (maximum recommended temperature for the glucoamylase) for at least 24 hrs to ensure all of the residual starch in the solids was converted to soluble oligosaccharides and that all the soluble oligosaccharides were converted to glucose. The residual unhydrolyzed starch that was in the solids, which is the starch that did not get hydrolyzed during liquefaction, can be calculated from the amount of glucose generated by this procedure.

The alpha-amylase and glucoamylase enzymes used in the following protocols were Liquozyme® SC DS and Spirizyme® Fuel, respectively (Novozymes, Franklinton, N.C.). The vessel used to treat the washed wet cakes was a 250 mL jacketed glass resin kettle equipped with mechanical agitation, temperature control, and pH control. The amount of Liquozyme® used corresponds to an enzyme loading of 0.08 wt % on a "dry corn basis." The amount of Spirizyme® used corresponds to an enzyme loading of 0.2 wt % on a "dry corn basis." This basis is defined as the amount of ground corn required to give the amount of undissolved solids held up in the washed cakes assuming all the starch is hydrolyzed to soluble oligosaccharides. The undissolved solids held up in the washed cakes are considered to be mostly the non-starch, non-fermentable part of the corn. These enzyme loadings are at least four times higher than is required to give complete liquefaction and saccharification at 26% corn loading. The enzymes were used in large excess to ensure complete hydrolysis of the residual starch in the solids and complete conversion of the oligosaccharides to glucose.

The following protocol was followed to determine the level of unhydrolyzed starch in the solids present in the washed wet cake from Batch 1 mash:

- The alpha-amylase was diluted in tap water (0.1297 g enzyme in 10.3607 g water)
- The glucoamylase was diluted in tap water (0.3212 g enzyme in 15.6054 g water)
- Charged 132 g tap water to the kettle
- Turned on agitator Charged 68 g of the washed wet cake produced from liquefaction Batch 1 (TS=21.63 wt %)

Heated to 55° C. while agitating

Adjusted pH to 5.5 using dilute $H_2SO_4$ or NaOH

Charged alpha-amylase solution, 3.4992 g

Charged glucoamylase solution, 5.319 g

Run at 55° C. for 24 hrs while controlling pH at 5.5 and periodically sample the slurry for glucose.

The following protocol was followed to determine the level of unhydrolyzed starch in the solids present in the washed wet cake from Batch 2.

The alpha-amylase was diluted in tap water (0.2384 g enzyme in 11.709 g water)

The glucoamylase was diluted in tap water (0.3509 g enzyme in 17.5538 g water)

Charged 154.3 g tap water to the kettle

Turned on agitator

Charged 70.7 g of the washed wet cake produced from liquefaction Batch 1 (TS=23.66 wt %)

Heated to 55° C. while agitating

Adjusted pH to 5.5 using dilute $H_2SO_4$ or NaOH

Charged alpha-amylase solution, 2.393 g

Charged glucoamylase solution, 5.9701 g

Run at 55° C. for 24 hrs while controlling pH at 5.5 and periodically sample the slurry for glucose.

Figure 11:
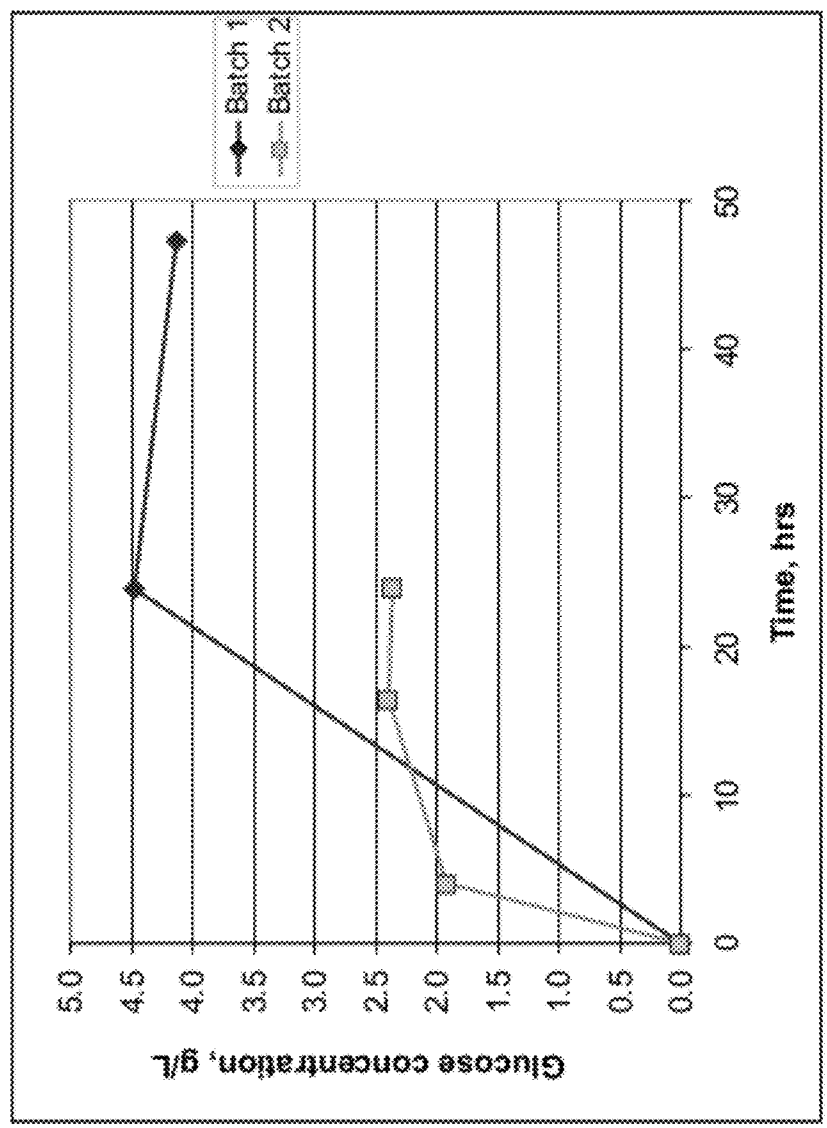
FIG. 11 illustrate the concentration of glucose in the aqueous phase of the slurries as a function of time for Batch 1 and Batch 2.

Comparison of Results for the Liquefaction/Saccharification of the Washed Wet Cakes As described above, the washed wet cakes from Batches 1 and 2 were re-slurried in water, and large excesses of both alpha-amylase and glucoamylase were added to the slurries in order to hydrolyze any starch remaining in the solids and convert it to glucose. FIG. 11 shows the concentration of glucose in the aqueous phase of the slurries as a function of time.

The glucose concentration increased with time and leveled out at a maximum value at approximately 24 hrs for both reactions. The slight decrease in glucose between 24 and 48 hrs could have been from microbial contamination; therefore, the maximum level of glucose reached in each system was used to calculate the level of residual unhydrolyzed starch that was in the solids of the washed wet cake. The maximum level of glucose reached by reacting (in the presence of alpha-amylase and glucoamylase) the washed wet cake obtained from the Batch 1 liquefaction was 4.48 g/L. By comparison, the maximum level of glucose reached by reacting (in the presence of alpha-amylase and glucoamylase) the washed wet cake obtained from the Batch 2 liquefaction was 2.39 g/L.

The level of residual unhydrolyzed starch that was in the undissolved solids in the liquefied mash (that did not get hydrolyzed during liquefaction) was calculated based on the glucose data obtained from the washed wet cake obtained from the corresponding batch of mash.

Liquefaction Batch 1: The residual unhydrolyzed starch in the solids corresponds to 2.1% of the total starch in the corn fed to liquefaction. This implies that 2.1% of the starch in the corn was not hydrolyzed during Batch 1 liquefaction conditions. No intermediate high temperature ("cook") stage occurred during liquefaction Batch 1.

Liquefaction Batch 2: The residual unhydrolyzed starch in the solids corresponds to 1.1% of the total starch in the corn fed to liquefaction. This implies that 1.1% of the starch in the corn was not hydrolyzed during Batch 2 liquefaction conditions. A high temperature ("cook") stage did occur during liquefaction Batch 2.

This example demonstrates that the addition of a high temperature "cook" stage at some time during the liquefaction could result in higher starch conversion. This will result in less residual unhydrolyzed starch remaining in the undissolved solids in the liquefied corn mash and will lead to less starch loss in a process where undissolved solids are removed from the mash prior to liquefaction.

Example 17

Effect of High Temperature Stage During Liquefaction on the Conversion of Starch in Corn Solids to Soluble (Liquefied) Starch Two batches of liquefied corn mash (Batch 3 and Batch 4) were prepared at 85° C. using Liquozyme® SC DS (alpha-amylase from Novozymes, Franklinton, N.C.). Both batches operated at 85° C. for a little more than 2 hrs. However, a "cook" period was added in the middle of Batch 4. The temperature profile for Batch 4 was about 30 minutes at 85° C., raising the temperature from 85° C. to 121° C., holding at 121° C. for about 30 minutes, cooling down to 85° C., and continuing liquefaction for another 90 minutes. The ground corn used in both batches was the same as in Example 1. A corn loading of 26 wt % (dry corn basis) was used in both batches. The total amount of enzyme used in both runs corresponded to 0.04 wt % (dry corn basis). The pH was controlled at 5.8 during both liquefaction runs. The liquefaction for Batch 3 was carried out in a 1 L glass, jacketed resin kettle, and the liquefaction for Batch 4 was carried out in a 200 L stainless steel fermentor. Both reactors were outfitted with mechanical agitation, temperature control, and pH control.

The experimental conditions for this example were similar to those described for Example 14 with the following differences:

For the Production of Liquefied Corn Mash for Batch 3: 0.211 g of alpha-amylase was diluted in 10.403 g tap water. The first charge of alpha-amylase solution was 3.556 g. The second charge of alpha-amylase solution was 1.755 g and the reaction was allowed to continue to run at 85° C. for another 90 minutes.

For the Production of Liquefied Corn Mash for Batch 4: 22 g of alpha-amylase was diluted in 2 kg tap water, 147.9 kg of tap water was charged to the fermentor, and 61.8 kg of ground corn was charged. The first charge of alpha-amylase solution was 1.0 kg, the reaction was heated to 85° C. and held at 85° C. for 30 minutes, then the reaction was heated to 121° C. and held at 121° C. for 30 minutes. The second charge of alpha-amylase solution was 1 kg and the reaction was allowed to continue to run at 85° C. for another 90 minutes.

Removal of Undissolved Solids from the Liquefied Mash and Washing of the Wet Cake with Water to Remove Soluble Starch Most of the solids were removed from both batches of liquefied mash by centrifuging them in a large floor centrifuge at 5000 rpm for 15 minutes at room temperature. Centrifugation of 500.1 g of mash from Batch 3 yielded 337.2 g of centrate and 162.9 g of wet cake. Centrifugation of 509.7 g of mash from Batch 4 yielded 346.3 g of centrate and 163.4 g of wet cake. The wet cakes recovered from each batch of liquefied mash were washed five times with tap water to remove essentially all of the soluble starch held up in the cakes. The washes were performed in the same bottle used to centrifuge the original mash to avoid transferring the cake between containers. For each wash stage, the cake was mixed with water, and the resulting wash slurry was centrifuged (5000 rpm for 15 min) at room temperature. This was done for all five wash stages performed on the wet cakes recovered from both batches of mash. Approximately 164 g of water was used in each of the five washes of the wet cake from Batch 3 resulting in a total of 819.8 g of water used to wash the wet cake from Batch 3. Approximately 400 g of water was used in each of the five washes of the wet cake from Batch 4 resulting in a total of 2000 g of water used to wash the wet cake from Batch 4. The total wash centrate recovered from all five water washes of the wet cake from Batch 3 was 879.5 g. The total wash centrate recovered from all five water washes of the wet cake from Batch 4 was 2048.8 g. The final washed wet cake recovered from Batch 3 was 103.2 g, and the final washed wet cake recovered from Batch 4 was 114.6 g. The final washed wet cakes obtained from each batch contained essentially no soluble starch; therefore, the liquid held up in each cake was primarily water. The total solids (TS) of the wet cakes was measured using a moisture balance. The total solids of the wet cake from Batch 3 was 21.88 wt %, and the TS for the wet cake from Batch 4 was 18.1 wt %.

The experimental conditions for this example were similar to those described for Example 14 with the following differences:

For the Liquefaction/Saccharification of Washed Wet Cake to Determine the Level of Unhydrolyzed Starch Remaining in the Undissolved Solids after Liquefaction for Batch 3: 68 g of the washed wet cake produced from liquefaction of Batch 3 was charged (TS=21.88 wt %). 3.4984 g of alpha-amylase solution and 5.3042 g of glucoamylase was charged. The reaction was ran at 55° C. for 47 hrs while controlling pH at 5.5 and periodically sampling the slurry for glucose.

For the Liquefaction/Saccharification of Washed Wet Cake to Determine the Level of Unhydrolyzed Starch Remaining in the Undissolved Solids after Liquefaction for Batch 4: 0.1663 g of alpha-amylase was diluted in 13.8139 g tap water, and 0.213 g of glucoamylase was diluted in 20.8002 g tap water. 117.8 g of tap water was charged to the kettle. 82.24 g of the washed wet cake produced from liquefaction of Batch 4 was charged (TS=18.1 wt %). 3.4952 g of alpha-amylase solution and 10.510 g of glucoamylase was charged. The reaction was ran at 55° C. for 50 hrs while controlling pH at 5.5 and periodically sampling the slurry for glucose.

Figure 12:
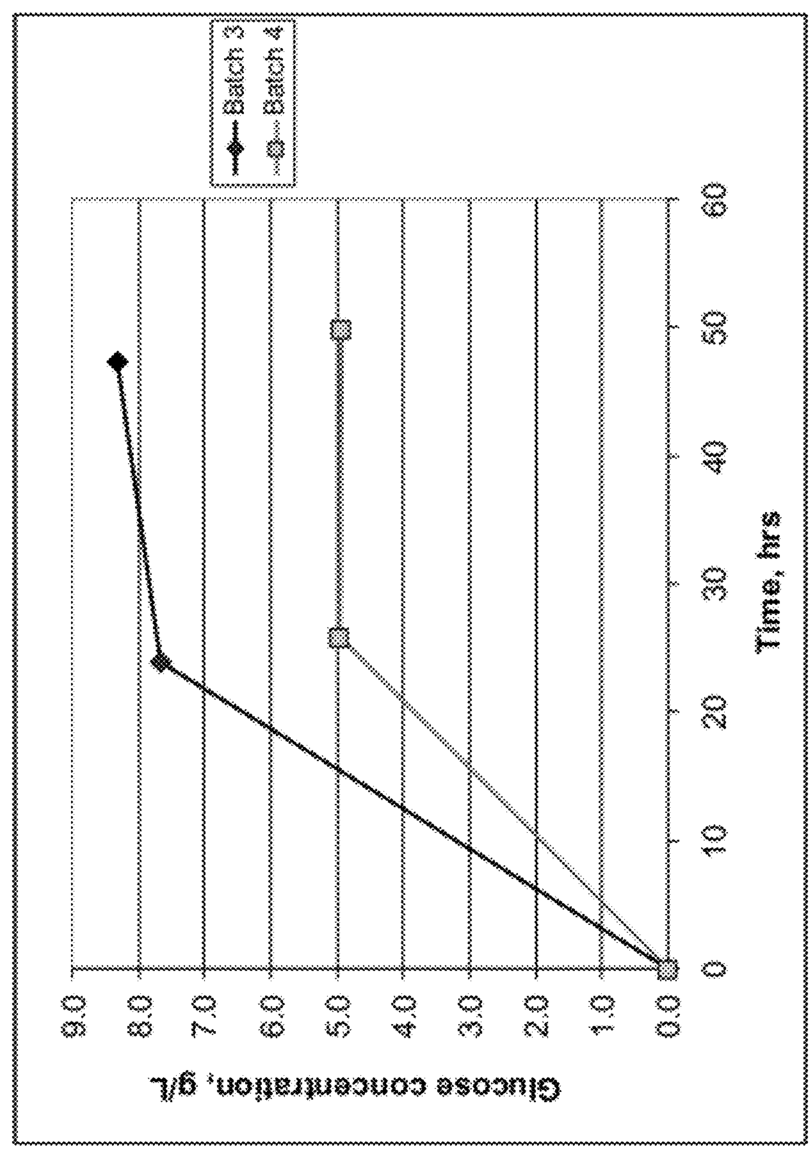
FIG. 12 illustrates concentration of glucose in the aqueous phase of the slurries as a function of time for Batch 3 and Batch 4.

Comparison of Results for the Liquefaction/Saccharification of the Washed Wet Cakes As described above, the washed wet cakes from Batches 3 and 4 were re-slurried in water, and large excesses of both alpha-amylase and glucoamylase were added to the slurries in order to hydrolyze any starch remaining in the solids and convert it to glucose. FIG. 12 shows the concentration of glucose in the aqueous phase of the slurries as a function of time.

The glucose concentration increased with time and leveled out at a maximum value at approximately 26 hrs for the washed wet cake from Batch 3. For the Batch 4 washed wet cake, the glucose concentration continued to increase slightly between 24 hrs and 47 hrs. It is assumed that the glucose concentration measured at 47 hrs for the Batch 4 wet cake is approximately equal to the maximum value. The maximum level of glucose reached by reacting (in the presence of alpha-amylase and glucoamylase) the washed wet cake obtained from the Batch 3 liquefaction was 8.33 g/L. By comparison, the maximum level of glucose reached by reacting (in the presence of alpha-amylase and glucoamylase) the washed wet cake obtained from the Batch 4 liquefaction was 4.92 g/L.

The level of residual unhydrolyzed starch that was in the undissolved solids in the liquefied mash (that did not get hydrolyzed during liquefaction) was calculated based on the glucose data obtained from "hydrolyzing" the washed wet cake (in the presence of excess alpha-amylase and glucoamylase) obtained from the corresponding batch of mash.

Liquefaction Batch 3: The residual unhydrolyzed starch in the solids corresponds to 3.8% of the total starch in the corn fed to liquefaction. This implies that 3.8% of the starch in the corn was not hydrolyzed during Batch 3 liquefaction conditions. No intermediate high temperature ("cook") stage occurred during liquefaction Batch 3.

Liquefaction Batch 4: The residual unhydrolyzed starch in the solids corresponds to 2.2% of the total starch in the corn fed to liquefaction. This implies that 2.2% of the starch in the corn was not hydrolyzed during Batch 4 liquefaction conditions. A high temperature ("cook") stage did occur during liquefaction Batch 4.

This example demonstrates that the addition of a high temperature "cook" stage at some time during the liquefaction could result in higher starch conversion. This will result in less residual unhydrolyzed starch remaining in the undissolved solids in the liquefied corn mash and will lead to less starch loss in a process where undissolved solids are removed from the mash prior to liquefaction.

Summary and Comparison of Examples 16 and 17

Liquefaction conditions can influence the conversion of starch in the corn solids to soluble (liquefied) starch. Possible liquefaction conditions that could affect the conversion of starch in the ground corn to soluble starch are temperature, enzyme (alpha-amylase) loading, and +/−a high temperature ("cook") stage occurs at some time during liquefaction. Examples 16 and 17 demonstrated that implementing a high temperature ("cook") stage at some time during liquefaction can result in higher conversion of starch in the corn solids to soluble (liquefied) starch. The high temperature stage in the liquefactions described in Examples 16 and 17 involved raising the liquefaction temperature at some point after liquefaction starts, holding at the higher temperature for some period of time, and then lowering the temperature back to the original value to complete liquefaction.

The liquefaction reactions compared in Example 16 were run at a different enzyme loading than the reactions compared in Example 17. These examples demonstrate the effect of two key liquefaction conditions on starch conversion: (1) enzyme loading, and (2) +/−a high temperature stage is applied at some time during liquefaction.

The conditions used to prepare the four batches of liquefied corn mash described in Examples 16 and 17 are summarized below and in Table 9.

Conditions common for all batches:

Liquefaction temperature—85° C.

Total time at liquefaction temperature—approximately 2 hrs

Screen size used to grind corn—1 mm pH—5.8

Dry corn loading—26%

Alpha-amylase—Liquozyme® SC DS (Novozymes, Franklinton, N.C.).

TABLE 9

| | Batch 1 | Batch 2 | Batch 3 | Batch 4 |
|---|---|---|---|---|
| Described in Example: | 16 | 16 | 17 | 17 |
| High Temperature Stage Implemented | No | Yes | No | Yes |
| Temperature of High Temperature Stage, C: | NA | 101° C. | NA | 121° C. |
| Total Enzyme Loading, wt % (dry corn basis): | 0.08% | 0.08% | 0.04% | 0.04% |

TABLE 9-continued

| | Batch 1 | Batch 2 | Batch 3 | Batch 4 |
|---|---|---|---|---|
| Residual Unhydrolyzed Starch in Undissolved Solids after Liquefaction (as a percentage of total starch in corn feed): | 2.1% | 1.1% | 3.8% | 2.3% |

The temperature profile for Batches 2 and 4 was (all values are approximate): 85° C. for 30 minutes, High Temperature Stage for 30 minutes, 85° C. for 90 min. Half the enzyme was added before the initial 85° C. period, and half was added after the high temperature stage for the final 85° C. period.

Figure 13:
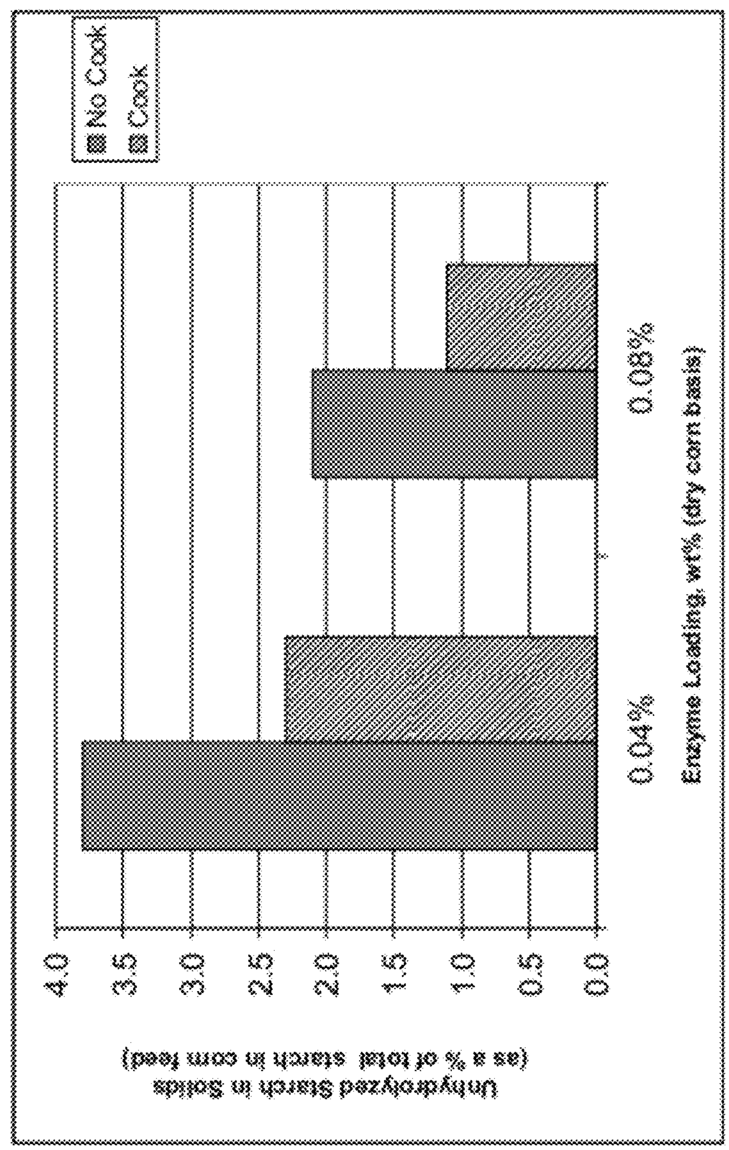
FIG. 13 illustrates the effect of enzyme loading and +/−a high temperature stage was applied at some time during the liquefaction on starch conversion.

FIG. 13 illustrates the effect of enzyme loading and +/−a high temperature stage was applied at some time during the liquefaction on starch conversion. The level of residual unhydrolyzed starch in the solids is the starch that was not hydrolyzed during the liquefaction conditions of interest. FIG. 13 shows that the level of unhydrolyzed starch in the solids was reduced by almost half by applying a high temperature ("cook") stage at some point during the liquefaction. This was demonstrated at two different enzyme loadings. The data in FIG. 13 also shows that doubling the enzyme loading resulted in almost half the level of unhydrolyzed starch remaining in the solids whether a high temperature stage was applied during liquefaction or not. These examples demonstrate that operating liquefaction with a higher enzyme (alpha-amylase) loading and/or the addition of a high temperature ("cook") stage at some time during the reaction could result in a significant reduction in residual unhydrolyzed starch in the undissolved solids present in the liquefied corn mash and can reduce the loss of starch in a process where undissolved solids are removed from the mash prior to liquefaction. Any residual starch in the solids after liquefaction will not have the opportunity to hydrolyze during fermentation in a process where solids are removed prior to fermentation.

Example 18

Screen Separation of Starch and Nonsolubles Following 85° C. Enzyme Digestion Mash (301 grams) prepared per the method described in Example 1 were maintained at pH 5.8 using drops of NaOH solution when adjustment was necessary, treated with a vendor-specified dose of approximately 0.064 grams of Liquozyme® alpha-amylase enzyme (Novozyme, Franklinton, N.C.) and held at 85° C. for five hours. The product was refrigerated.

Refrigerated product was warmed to approximately 50° C. and 48 g was poured onto a filter assembly containing a 100 mesh screen and connected to a house vacuum source at between −15 in Hg and −20 in Hg. The screen dish had an exposed screen surface area of 44 cm2 and was sealed inside a plastic filter housing provided by Nalgene® (Thermo Fisher Scientific, Rochester, N.Y.). The slurry was filtered to form a wet cake on the screen and a yellow cloudy filtrate of 40.4 g in the receiver bottle. The wet cake was immediately washed in place with water and then discontinued while the vacuum source continued to pull any free moisture through the final washed cake. Filtration was ended when dripping ceased from the underside of the filter. An additional 28.5 g of wash filtrate were collected over 3 stages where the final stage of filtrate revealed the least color and turbidity. The final wet cake mass of 7.6 g was air dried to 2.1 g over 24 hours at room temperature. The 2.1 g were determined to contain 7.73% water after drying with a heat lamp. The vacuum filtration of this experiment produced a wet cake containing 25% total dry solids.

A sample of filtrate was combined with oleyl alcohol at room temperature, vigorously mixed and allowed to settle. The interface was restored in approximately 15 minutes but a hazy rag layer remained.

Lugol's solution (starch indicator) consisting of 1 g of >99.99% (trace metals basis) iodine, 2 g of ReagentPlus® grade (>99%) potassium iodide (both from Sigma-Aldrich, St. Louis, Mo.), and 17 g of house deionized water in the amount of one drop was added to samples of the filtrate, dried cake solids reslurried in water and a control sample of water. The filtrate turned dark blue or purple, the solids slurry turned very dark blue and the water became light amber in color. Any color darker than amber indicates presence of oligosaccharides greater than 12 units long.

This experiment illustrated that most suspended solids could be separated from starch solution prepared as described above at a moderate rate on a 100 mesh screen and that starch remains with the filter cake solids. This is an indication of incomplete washing of the cake where a portion of hydrolyzed starch is left behind.

This experiment was repeated with 156 grams of mash on a 63 mm diameter 100 mesh screen. The maximum temperature was 102° C., the enzyme was Spezyme® and the slurry was held above 85° C. for three hours. The screening rate was measured and determined to be 0.004 or less gallons per minute per square foot of screen area.

Example 19

Screen Separation of Starch and Nonsolubles Following 115° C. Enzyme Digestion House deionized water (200 g) were charged into an open Parr Model 4635 1 liter pressure vessel (Moline, Ill.) and heated to a temperature of 85° C. The water was agitated with a magnetic stir bar. Dry ground corn (90 g) prepared as described in Example 1 were added spoon-wise. The pH was raised from 5.2 to near 6.0 with stock aqueous ammonia solution. Approximately 0.064 grams of Liquozyme® solution were added with a small calibrated pipette. The lid of the pressure vessel was sealed and the vessel was pressurized to 50 psig with house nitrogen. The agitated mixture was heated to 110° C. within 6 minutes and held between 106 to 116° C. for a total of 20 minutes. The heating was reduced, the pressure was relieved, and the vessel was opened. An additional 0.064 g of Liquozyme® was added and the temperature was held at 63-75° C. for an additional 142 minutes.

A small amount of the slurry was taken from the Parr vessel and gravity screened through a stack of 100, 140, and 170 mesh screens. Solids were retained only on the 100 mesh screen.

A portion, about 40%, of the slurry was transferred while hot onto the top of a dual screen assembly of 100 and 200 mesh dishes of 75 millimeter diameter. Some gravity filtration took place. Vacuum, between −15 and −20 inches of mercury, was pulled on the filtrate receiver and steady filtration was established. The filtrate was yellow and cloudy but with a stable dispersion. The cake surface was exposed within 5 minutes. The cake was washed with a spray of deionized water for 2-3 minutes and repeated with a change of receiver until the turbidity of the filtrate was constant—a total of five sprayings. The screens were examined with the conclusion that all solids were on the 100 mesh screen and none were on the 200 mesh. The wet cake was 5 mm thick. The wet cake mass was determined to be 18.9 g and the combined filtrate masses were 192 g.

The remaining mass of slurry was transferred to the filter assembly with a 100 mesh screen in place at 65° C. and filtered over 5-10 minutes. The cake was washed with a spray of deionized water for 3-4 minutes and repeated with a change of receiver until the turbidity of the filtrate was constant—a total of eight sprayings. Vacuum was continued until no more drops were observed falling from the underside of the filter. The wet cake was 8 mm thick and 75 mm in diameter with a mass of 36.6 g. The combined filtrates weighed 261 g.

Three vials were tested for starch per the method described above. One vial contained water and the other two contained samples of wet cake slurried in deionized water. All vials turned yellow-amber in color. This was interpreted to mean that the filter cake was washed free of oligosaccharides of starch. These solids were later analyzed rigorously using prolonged liquefaction and subsequent saccharification to confirm that on a glucose basis, the wet cake contained no more than 0.2% of the total starch that was in the original corn.

A sample of filtrate was combined with oleyl alcohol in a vial, vigorously mixed and allowed to settle. A clear oil layer was quickly attained and the interface was well defined with little rag layer. This example illustrated that in a process in which corn mash is heated to hydrothermal conditions of ~110° C. for 20 minutes of cooking and further liquefied for more than two hours at 85° C. before being filtered and washed, the total filtrate contains essentially all starch supplied in the grain. Furthermore, no significant interference is observed between the oleyl alcohol and the impurities contained in the filtrate.

This experiment was repeated with 247 grams of mash on a 75 mm diameter 80 mesh screen. The maximum cook temperature was 115° C., the enzyme was Liquozyme® and the slurry was held at or above 85° C. for three hours. The screening rate was measured and determined to be more than 0.1 gallons per minute per square foot of screen area.

Example 20

Lipid Analysis

Lipid analysis was conducted by conversion of the various fatty acid-containing compound classes to fatty acid methyl esters ("FAMEs") by transesterification. Glycerides and phospholipids were transesterified using sodium methoxide in methanol. Glycerides, phospholipids, and free fatty acids were transesterified using acetyl chloride in methanol. The resulting FAMEs were analyzed by gas chromatography using an Agilent 7890 GC fitted with a 30-m×0.25 mm (i.d.) OMEGAWAX™ (Supelco, SigmaAldrich, St. Louis, Mo.) column after dilution in toluene/hexane (2:3). The oven temperature was increased from 160° C. to 200° C. at 5° C./min then 200° C. to 250° C. (hold for 10 min) at 10° C./min. FAME peaks recorded via GC analysis were identified by their retention times, when compared to that of known methyl esters (MEs), and quantitated by comparing the FAME peak areas with that of the internal standard (C15:0 triglyceride, taken through the transesterification procedure with the sample) of known amount. Thus, the approximate amount (mg) of any fatty acid FAME ("mg FAME") is calculated according to the formula: (area of the FAME peak for the specified fatty acid/area of the 15:0 FAME peak)*(mg of the internal standard C15:0 FAME). The FAME result can then be corrected to mg of the corresponding fatty acid by dividing by the appropriate molecular weight conversion factor of 1.052. All internal and reference standards are obtained from Nu-Chek Prep, Inc.

The fatty acid results obtained for samples transesterified using sodium methoxide in methanol are converted to the corresponding triglyceride levels by multiplying the molecular weight conversion factor of 1.045. Triglycerides generally account for approximately 80 to 90% of the glycerides in the samples studies for this example, with the remainder being diglycerides. Monoglyceride and phospholipid contents are generally negligible. The total fatty acid results obtained for a sample transesterified using acetyl chloride in methanol are corrected for glyceride content by subtracting the fatty acids determined for the same sample using the sodium methoxide procedure. The result is the free fatty acid content of the sample.

The distribution of the glyceride content (monoglycerides, diglycerides, triglycerides, and phospholipids) is determined using thin layer chromatography. A solution of the oil dissolved in 6:1 chloroform/methanol is spotted near the bottom of a glass plate precoated with silica gel. The spot is then chromatographed up the plate using a 70:30:1 hexane/diethyl ether/acetic acid solvent system. Separated spots corresponding to monoglycerides, diglycerides, triglycerides, and phospholipids are then detected by staining the plate with iodine vapor. The spots are then scraped off the plate, transesterified using the acetyl chloride in methanol procedure, and analyzed by gas chromatography. The ratios of the totaled peak areas for each spot to the totaled peak areas for all the spots are the distribution of the various glycerides.

Example 21

This example illustrated the removal of solids from stillage and extraction by desolventizer to recover fatty acids, esters, and triglycerides from the solids. During fermentation, solids are separated from whole stillage and fed to a desolventizer where they are contacted with 1.1 tons/hr of steam. The flow rates for the whole stillage wet cake (extractor feed), solvent, the extractor miscella, and extractor discharge solids are as shown in Table 10. Table values are short tons/hr.

TABLE 10

| | Solids from whole stillage | Solvent | Miscella | Extractor discharge solids |
|---|---|---|---|---|
| Fatty acids | 0.099 | 0 | 0.0982 | 0.001 |
| Undissolved solids | 17.857 | 0 | 0.0009 | 17.856 |
| Fatty acid butyl esters | 2.866 | 0 | 2.837 | 0.0287 |
| Hexane | 0 | 11.02 | 10.467 | 0.555 |
| Triglyceride | 0.992 | 0 | 0.982 | 0.0099 |
| Water | 29.762 | 0 | 29.464 | 0.297 |

Solids exiting the desolventizer are fed to a dryer. The vapor exiting the desolventizer contains 0.55 tons/hr of hexane and 1.102 tons/hr of water. This stream is condensed and fed to a decanter. The water-rich phase exiting the decanter contains about 360 ppm of hexane. This stream is fed to a distillation column where the hexane is removed from the water-rich stream. The hexane enriched stream exiting the top of the distillation column is condensed and fed to the decanter. The organic-rich stream exiting the decanter is fed to a distillation column. Steam (11.02 tons/hr) is fed to the bottom of the distillation column. The composition of the overhead and bottom products for this column are shown in Table 11. Table values are tons/hr.

TABLE 11

| | Bottoms | Overheads |
|---|---|---|
| Fatty acids | 0.0981 | 0 |
| Fatty acid butyl esters | 2.8232 | 0 |
| Hexane | 0.0011 | 11.12 |
| Triglyceride | 0.9812 | 0 |
| Water | 0 | 11.02 |

Example 22

This example illustrates the recovery of by-products from mash. Corn oil separated from mash under the conditions described in Example 10 with the exception that a Tricanter® (three-phase centrifuge) centrifuge (Flottweg Z23-4 bowl diameter, 230 mm, length to diameter ratio 4:1) was used with these conditions:

Bowl Speed: 5000 rpm

Differential Speed: 10 rpm

Feed Rate: 3 gpm

Phase Separator Disk: 138 mm.

The corn oil separate had 81% triglycerides, 6% free fatty acids, 4% diglyceride, and 5% total of phospholipids and monoglycerides as determined by the methods described in Example 18 and thin layer chromatography.

The solids separated from mash under the conditions described above had a moisture content of 58% as determined by weight loss upon drying and had 1.2% triglycerides and 0.27% free fatty acids as determined by the method described in Example 18.

The composition of solids separated from whole stillage, oil extracted between evaporator stages, by-product extractant and Condensed Distillers Solubles (CDS) in Table 14 were calculated assuming the composition of whole stillage shown in Table 12 and the assumptions in Table 13 (separation at a Tricanter ® (three-phase centrifuge) centrifuge. The values of Table 11 were obtained from an Aspen Plus.RTM. model (Aspen Technology, Inc., Burlington, Mass.). This model assumes that corn oil is not extracted from mash. It is estimated that the protein content on a dry basis of cells, dissolved solids, and suspended solids is approximately 50%, 22%, and 35.5%, respectively. The composition of by-product extractant is estimated to be 70.7% fatty acid and 29.3% fatty acid isobutyl ester on a dry basis.

TABLE 12

| Component | Mass % |
|---|---|
| Water | 57.386% |
| Cells | 0.502% |
| Fatty acids | 6.737% |
| Isobutyl esters of fatty acids | 30.817% |
| Triglyceride | 0.035% |
| Suspended solids | 0.416% |
| Dissolved solids | 4.107% |

TABLE 13

| | Hydrolyzer feed | Thin stillage | Solids |
|---|---|---|---|
| Organics | 99.175% | 0.75% | 0.08% |
| Water and dissolved solids | 1% | 96% | 3% |
| Suspended solids and cells | 1% | 2% | 97% |

TABLE 14

| Stream | C. protein | triglyceride | FFA | FABE |
|---|---|---|---|---|
| Whole stillage wet cake | 40% | trace | 0.5% | 2.2% |
| Oil at evaporator | 0% | 0.08% | 16.1% | 73.8% |
| CDS | 22% | trace % | 0.37% | 1.71% |

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing a fermentation product and an animal feed co-product comprising:

providing a feedstock, wherein the feedstock comprises sugar, oil, gluten, and fiber;

milling the feedstock in a dry-grind liquefaction system comprising a hammer mill and liquefaction vessel and liquefying the feedstock to create a feedstock slurry, wherein the feedstock slurry comprises sugar, liquid oil, and undissolved solids, wherein said undissolved solids comprise gluten and fiber;

separating said undissolved solids and the liquid oil from the feedstock slurry in a single vessel, to create: an aqueous solution comprising sugar (i), a wet cake comprising the undissolved solids (ii), and the liquid oil (iii);

recovering the aqueous solution (i), the wet cake (ii), and the liquid oil (iii) as separate streams from the single vessel;

contacting the recovered aqueous solution (i) with a fermentation broth in a fermentor;

fermenting the sugar in the aqueous solution (i) in the fermentor to produce the fermentation product; and processing the wet cake (ii) to produce the animal feed co-product.

2. The method of claim 1, wherein the feedstock is corn and the liquid oil is corn oil.

3. The method of claim 2, wherein a ratio of undissolved solids in the wet cake to corn oil in the liquid oil on a weight basis is in a range from 2:1 to 25:1.

4. The method of claim 2, wherein the corn is unfractionated.

5. The method of claim 1, wherein the undissolved solids, the aqueous solution, and the liquid oil are separated by three-phase centrifuge centrifugation, disk stack centrifugation, flotation, hydroclone, gravity settler, or vortex separator.

6. The method of claim 1, wherein the step of separating the undissolved solids and the liquid oil from the feedstock slurry in a single vessel comprises centrifuging the feedstock slurry.

7. The method of claim 1, wherein the wet cake is washed with water to recover oligosaccharides present in the wet cake.

8. The method of claim 1, further comprising performing in situ removal of the fermentation product from the fermentation broth as the fermentation product is produced.

9. The method of claim 8, wherein the in situ removal comprises liquid-liquid extraction.

10. The method of claim 9, wherein an extractant for the liquid-liquid extraction is an organic extractant.

11. The method of claim 10, wherein the extractant comprises one or more immiscible organic extractants selected from the group consisting of $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof.

12. The method of claim 11, wherein the extractant comprises $C_{12}$ to $C_{22}$ fatty acids derived from corn oil.

13. The method of claim 1, further comprising saccharifying the sugar in the aqueous solution simultaneously with fermenting the sugar in the fermentor.

14. The method of claim 1, wherein the animal feed co-product comprises at least 22% by weight protein.

15. The method of claim 1, further comprising saccharifying the sugar prior to fermenting the sugar in the fermentor.

16. The method of claim 15, wherein the step of separating the undissolved solids and the liquid oil from the feedstock slurry comprises centrifuging the feedstock slurry.

17. The method of claim 16, wherein centrifuging the feedstock slurry occurs prior to saccharifying the sugar.

18. The method of claim 1, wherein the fermentation broth comprises a recombinant microorganism comprising a butanol biosynthetic pathway.

19. The method of 18, wherein the fermentation product is isobutanol.

20. The method of 19, wherein the step of recovering undissolved solids from the feedstock slurry increases the efficiency of the isobutanol production by increasing a liquid-liquid mass transfer coefficient of the isobutanol from the fermentation broth to an extractant; increases the efficiency of the isobutanol production by increasing an extraction efficiency of the isobutanol with an extractant; increases the efficiency of the isobutanol production by increasing a rate of phase separation between the fermentation broth and an extractant; increases the efficiency of the isobutanol production by increasing recovery and recycling of an extractant; increases the efficiency of the isobutanol production by decreasing a flow rate of an extractant; or combinations thereof.

21. The method of claim 1, wherein the fermentation product is selected from the group consisting of methanol, ethanol, propanol, butanol, pentanol, and isomers thereof.

* * * * *

SEQUENCE LISTING

```
<160> NUMBER OF SEQ ID NOS: 73

<210> SEQ ID NO 1
<211> LENGTH: 11856
<212> TYPE: DNA
<213> ORGANISM: Artificial sequence
<220> FEATURE:
<223> OTHER INFORMATION: Plasmid

<400> SEQUENCE: 1

tcccattacc gacatttggg cgctatacgt gcatatgttc atgtatgtat ctgtatttaa     60

aacacttttg tattattttt cctcatatat gtgtataggt ttatacggat gatttaatta    120

ttacttcacc accctttatt tcaggctgat atcttagcct tgttactagt tagaaaaaga    180

catttttgct gtcagtcact gtcaagagat tcttttgctg gcatttcttc tagaagcaaa    240

aagagcgatg cgtcttttcc gctgaaccgt tccagcaaaa aagactacca acgcaatatg    300
```

```
gattgtcaga atcatataaa agagaagcaa ataactcctt gtcttgtatc aattgcatta    360
taatatcttc ttgttagtgc aatatcatat agaagtcatc gaaatagata ttaagaaaaa    420
caaactgtac aatcaatcaa tcaatcatcg ctgaggatgt tgacaaaagc aacaaaagaa    480
caaaaatccc ttgtgaaaaa cagaggggcg gagcttgttg ttgattgctt agtggagcaa    540
ggtgtcacac atgtatttgg cattccaggt gcaaaaattg atgcggtatt tgacgcttta    600
caagataaag gacctgaaat tatcgttgcc cggcacgaac aaaacgcagc attcatggcc    660
caagcagtcg gccgtttaac tggaaaaccg ggagtcgtgt tagtcacatc aggaccgggt    720
gcctctaact tggcaacagg cctgctgaca gcgaacactg aaggagaccc tgtcgttgcg    780
cttgctggaa acgtgatccg tgcagatcgt ttaaaacgga cacatcaatc tttggataat    840
gcggcgctat tccagccgat tacaaaatac agtgtagaag ttcaagatgt aaaaaatata    900
ccggaagctg ttacaaatgc atttaggata gcgtcagcag ggcaggctgg ggccgctttt    960
gtgagctttc cgcaagatgt tgtgaatgaa gtcacaaata cgaaaaacgt gcgtgctgtt   1020
gcagcgccaa aactcggtcc tgcagcagat gatgcaatca gtgcggccat agcaaaaatc   1080
caaacagcaa aacttcctgt cgttttggtc ggcatgaaag gcggaagacc ggaagcaatt   1140
aaagcggttc gcaagctttt gaaaaaggtt cagcttccat ttgttgaaac atatcaagct   1200
gccggtaccc tttctagaga tttagaggat caatattttg gccgtatcgg tttgttccgc   1260
aaccagcctg gcgatttact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga aagtggaatt tgcagagcgt   1500
gagcagaaaa tcctttctga tttaaaacaa tatatgcatg aaggtgagca ggtgcctgca   1560
gattggaaat cagacagagc gcaccctctt gaaatcgtta aagagttgcg taatgcagtc   1620
gatgatcatg ttacagtaac ttgcgatatc ggttcgcacg ccatttggat gtcacgttat   1680
ttccgcagct acgagccgtt aacattaatg atcagtaacg gtatgcaaac actcggcgtt   1740
gcgcttcctt gggcaatcgg cgcttcattg gtgaaaccgg gagaaaaagt ggtttctgtc   1800
tctggtgacg gcggtttctt attctcagca atggaattag agacagcagt tcgactaaaa   1860
gcaccaattg tacacattgt atggaacgac agcacatatg acatggttgc attccagcaa   1920
ttgaaaaaat ataaccgtac atctgcggtc gatttcggaa atatcgatat cgtgaaatat   1980
gcggaaagct tcggagcaac tggcttgcgc gtagaatcac cagaccagct ggcagatgtt   2040
ctgcgtcaag gcatgaacgc tgaaggtcct gtcatcatcg atgtcccggt tgactacagt   2100
gataacatta atttagcaag tgacaagctt ccgaaagaat tcggggaact catgaaaacg   2160
aaagctctct agttaattaa tcatgtaatt agttatgtca cgcttacatt cacgccctcc   2220
ccccacatcc gctctaaccg aaaaggaagg agttagacaa cctgaagtct aggtccctat   2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgcac ctggtaaaac ctctagtgga   2460
gtagtagatg taatcaatga agcggaagcc aaaagaccag agtagaggcc tatagaagaa   2520
actgcgatac cttttgtgat ggctaaacaa acagacatct tttatatgt ttttacttct    2580
gtatatcgtg aagtagtaag tgataagcga atttggctaa gaacgttgta agtgaacaag   2640
ggacctcttt tgcctttcaa aaaaggatta aatggagtta atcattgaga tttagttttc   2700
```

```
gttagattct gtatccctaa ataactccct tacccgacgg gaaggcacaa aagacttgaa   2760
taatagcaaa cggccagtag ccaagaccaa ataatactag agttaactga tggtcttaaa   2820
caggcattac gtggtgaact ccaagaccaa tatacaaaat atcgataagt tattcttgcc   2880
caccaattta aggagcctac atcaggacag tagtaccatt cctcagagaa gaggtataca   2940
taacaagaaa atcgcgtgaa caccttatat aacttagccc gttattgagc taaaaaacct   3000
tgcaaaattt cctatgaata agaatacttc agacgtgata aaaatttact ttctaactct   3060
tctcacgctg cccctatctg ttcttccgct ctaccgtgag aaataaagca tcgagtacgg   3120
cagttcgctg tcactgaact aaaacaataa ggctagttcg aatgatgaac ttgcttgctg   3180
tcaaacttct gagttgccgc tgatgtgaca ctgtgacaat aaattcaaac cggttatagc   3240
ggtctcctcc ggtaccggtt ctgccacctc caatagagct cagtaggagt cagaacctct   3300
gcggtggctg tcagtgactc atccgcgttt cgtaagttgt gcgcgtgcac atttcgcccg   3360
ttcccgctca tcttgcagca ggcggaaatt ttcatcacgc tgtaggacgc aaaaaaaaaa   3420
taattaatcg tacaagaatc ttggaaaaaa aattgaaaaa ttttgtataa aagggatgac   3480
ctaacttgac tcaatggctt ttacacccag tattttccct ttccttgttt gttacaatta   3540
tagaagcaag acaaaaacat atagacaacc tattcctagg agttatattt ttttacccta   3600
ccagcaatat aagtaaaaaa ctgtttaaac agtatggcag ttacaatgta ttatgaagat   3660
gatgtagaag tatcagcact tgctggaaag caaattgcag taatcggtta tggttcacaa   3720
ggacatgctc acgcacagaa tttgcgtgat tctggtcaca acgttatcat tggtgtgcgc   3780
cacggaaaat cttttgataa agcaaaagaa gatggctttg aaacatttga agtaggagaa   3840
gcagtagcta aagctgatgt tattatggtt ttggcaccag atgaacttca acaatccatt   3900
tatgaagagg acatcaaacc aaacttgaaa gcaggttcag cacttggttt tgctcacgga   3960
tttaatatcc attttggcta tattaaagta ccagaagacg ttgacgtctt tatggttgcg   4020
cctaaggctc caggtcacct tgtccgtcgg acttatactg aaggttttgg tacaccagct   4080
ttgtttgttt cacaccaaaa tgcaagtggt catgcgcgtg aaatcgcaat ggattgggcc   4140
aaaggaattg gttgtgctcg agtgggaatt attgaaacaa cttttaaaga agaaacagaa   4200
gaagatttgt ttggagaaca agctgttcta tgtggaggtt tgacagcact tgttgaagcc   4260
ggttttgaaa cactgacaga agctggatac gctggcgaat tggcttactt tgaagttttg   4320
cacgaaatga aattgattgt tgacctcatg tatgaaggtg gttttactaa aatgcgtcaa   4380
tccatctcaa atactgctga gtttggcgat tatgtgactg gtccacggat tattactgac   4440
gaagttaaaa agaatatgaa gcttgttttg gctgatattc aatctggaaa atttgctcaa   4500
gatttcgttg atgacttcaa agcggggcgt ccaaaattaa tagcctatcg cgaagctgca   4560
aaaaatcttg aaattgaaaa aattggggca gagctacgtc aagcaatgcc attcacacaa   4620
tctggtgatg acgatgcctt taaaatctat cagtaaggcc ctgcaggcca gaggaaaata   4680
atatcaagtg ctggaaactt tttctcttgg aatttttgca acatcaagtc atagtcaatt   4740
gaattgaccc aatttcacat ttaagatttt tttttttca tccgacatac atctgtacac   4800
taggaagccc tgtttttctg aagcagcttc aaatatatat attttttaca tatttattat   4860
gattcaatga acaatctaat taaatcgaaa acaagaaccg aaacgcgaat aaataattta   4920
tttagatggt gacaagtgta taagtcctca tcgggacagc tacgatttct ctttcggttt   4980
tggctgagct actggttgct gtgacgcagc ggcattagcg cggcgttatg agctaccctc   5040
gtggcctgaa agatggcggg aataaagcgg aactaaaaat tactgactga gccatattga   5100
```

```
ggtcaatttg tcaactcgtc aagtcacgtt tggtggacgg cccctttcca acgaatcgta   5160
tatactaaca tgcgcgcgct tcctatatac acatatacat atatatatat atatatatgt   5220
gtgcgtgtat gtgtacacct gtatttaatt tccttactcg cgggtttttc tttttctca   5280
attcttggct tcctctttct cgagcggacc ggatcctccg cggtgccggc agatctattt   5340
aaatggcgcg ccgacgtcag gtggcacttt tcggggaaat gtgcgcggaa cccctatttg   5400
tttatttttc taaatacatt caaatatgta tccgctcatg agacaataac cctgataaat   5460
gcttcaataa tattgaaaaa ggaagagtat gagtattcaa catttccgtg tcgcccttat   5520
tccctttttt gcggcatttt gccttcctgt ttttgctcac ccagaaacgc tggtgaaagt   5580
aaaagatgct gaagatcagt tgggtgcacg agtgggttac atcgaactgg atctcaacag   5640
cggtaagatc cttgagagtt ttcgccccga agaacgtttt ccaatgatga gcacttttaa   5700
agttctgcta tgtggcgcgg tattatcccg tattgacgcc gggcaagagc aactcggtcg   5760
ccgcatacac tattctcaga atgacttggt tgagtactca ccagtcacag aaaagcatct   5820
tacggatggc atgacagtaa gagaattatg cagtgctgcc ataaccatga gtgataacac   5880
tgcggccaac ttacttctga caacgatcgg aggaccgaag gagctaaccg cttttttgca   5940
caacatgggg gatcatgtaa ctcgccttga tcgttgggaa ccggagctga atgaagccat   6000
accaaacgac gagcgtgaca ccacgatgcc tgtagcaatg gcaacaacgt tgcgcaaact   6060
attaactggc gaactactta ctctagcttc ccggcaacaa ttaatagact ggatggaggc   6120
ggataaagtt gcaggaccac ttctgcgctc ggcccttccg gctggctggt ttattgctga   6180
taaatctgga gccggtgagc gtgggtctcg cggtatcatt gcagcactgg ggccagatgg   6240
taagccctcc cgtatcgtag ttatctacac gacggggagt caggcaacta tggatgaacg   6300
aaatagacag atcgctgaga taggtgcctc actgattaag cattggtaac tgtcagacca   6360
agtttactca tatatacttt agattgattt aaaacttcat ttttaattta aaaggatcta   6420
ggtgaagatc ctttttgata atctcatgac caaaatccct taacgtgagt tttcgttcca   6480
ctgagcgtca gaccccgtag aaaagatcaa aggatcttct tgagatcctt tttttctgcg   6540
cgtaatctgc tgcttgcaaa caaaaaaacc accgctacca gcggtggttt gtttgccgga   6600
tcaagagcta ccaactcttt ttccgaaggt aactggcttc agcagagcgc agataccaaa   6660
tactgttctt ctagtgtagc cgtagttagg ccaccacttc aagaactctg tagcaccgcc   6720
tacatacctc gctctgctaa tcctgttacc agtggctgct gccagtggcg ataagtcgtg   6780
tcttaccggg ttggactcaa gacgatagtt accggataag gcgcagcggt cgggctgaac   6840
ggggggttcg tgcacacagc ccagcttgga gcgaacgacc tacaccgaac tgagatacct   6900
acagcgtgag ctatgagaaa gcgccacgct tcccgaaggg agaaaggcgg acaggtatcc   6960
ggtaagcggc agggtcggaa caggagagcg cacgagggag cttccagggg gaaacgcctg   7020
gtatctttat agtcctgtcg ggtttcgcca cctctgactt gagcgtcgat ttttgtgatg   7080
ctcgtcaggg gggcggagcc tatggaaaaa cgccagcaac gcggcctttt tacggttcct   7140
ggccttttgc tggccttttg ctcacatgtt ctttcctgcg ttatcccctg attctgtgga   7200
taaccgtatt accgcctttg agtgagctga taccgctcgc cgcagccgaa cgaccgagcg   7260
cagcgagtca gtgagcgagg aagcggaaga gcgcccaata cgcaaaccgc ctctccccgc   7320
gcgttggccg attcattaat gcagctggca cgacaggttt cccgactgga aagcgggcag   7380
tgagcgcaac gcaattaatg tgagttagct cactcattag gcaccccagg ctttacactt   7440
tatgcttccg gctcgtatgt tgtgtggaat tgtgagcgga taacaatttc acacaggaaa   7500
```

```
cagctatgac catgattacg ccaagctttt tctttccaat tttttttttt tcgtcattat   7560
aaaaatcatt acgaccgaga ttcccgggta ataactgata taattaaatt gaagctctaa   7620
tttgtgagtt tagtatacat gcatttactt ataatacagt tttttagttt tgctggccgc   7680
atcttctcaa atatgcttcc cagcctgctt ttctgtaacg ttcaccctct accttagcat   7740
cccttccctt tgcaaatagt cctcttccaa caataataat gtcagatcct gtagagacca   7800
catcatccac ggttctatac tgttgaccca atgcgtctcc cttgtcatct aaacccacac   7860
cgggtgtcat aatcaaccaa tcgtaacctt catctcttcc acccatgtct ctttgagcaa   7920
taaagccgat aacaaaatct ttgtcgctct tcgcaatgtc aacagtaccc ttagtatatt   7980
ctccagtaga tagggagccc ttgcatgaca attctgctaa catcaaaagg cctctaggtt   8040
cctttgttac ttcttctgcc gcctgcttca aaccgctaac aatacctggg cccaccacac   8100
cgtgtgcatt cgtaatgtct gcccattctg ctattctgta tacacccgca gagtactgca   8160
atttgactgt attaccaatg tcagcaaatt ttctgtcttc gaagagtaaa aaattgtact   8220
tggcggataa tgcctttagc ggcttaactg tgccctccat ggaaaaatca gtcaagatat   8280
ccacatgtgt ttttagtaaa caaattttgg gacctaatgc ttcaactaac tccagtaatt   8340
ccttggtggt acgaacatcc aatgaagcac acaagtttgt ttgcttttcg tgcatgatat   8400
taaatagctt ggcagcaaca ggactaggat gagtagcagc acgttcctta tatgtagctt   8460
tcgacatgat ttatcttcgt ttcctgcagg tttttgttct gtgcagttgg gttaagaata   8520
ctgggcaatt tcatgtttct tcaacactac atatgcgtat atataccaat ctaagtctgt   8580
gctccttcct tcgttcttcc ttctgttcgg agattaccga atcaaaaaaa tttcaaggaa   8640
accgaaatca aaaaaaagaa taaaaaaaaa atgatgaatt gaaaagcttg catgcctgca   8700
ggtcgactct agtatactcc gtctactgta cgatacactt ccgctcaggt ccttgtcctt   8760
taacgaggcc ttaccactct tttgttactc tattgatcca gctcagcaaa ggcagtgtga   8820
tctaagattc tatcttcgcg atgtagtaaa actagctaga ccgagaaaga gactagaaat   8880
gcaaaaggca cttctacaat ggctgccatc attattatcc gatgtgacgc tgcatttttt   8940
tttttttttt tttttttttt tttttttttt tttttttttt ttttttgtac aaatatcata   9000
aaaaaagaga atctttttaa gcaaggattt tcttaacttc ttcggcgaca gcatcaccga   9060
cttcggtggt actgttggaa ccacctaaat caccagttct gatacctgca tccaaaacct   9120
ttttaactgc atcttcaatg gctttacctt cttcaggcaa gttcaatgac aatttcaaca   9180
tcattgcagc agacaagata gtggcgatag ggttgacctt attctttggc aaatctggag   9240
cggaaccatg gcatggttcg tacaaaccaa atgcggtgtt cttgtctggc aaagaggcca   9300
aggacgcaga tggcaacaaa cccaaggagc ctgggataac ggaggcttca tcggagatga   9360
tatcaccaaa catgttgctg gtgattataa taccatttag gtgggttggg ttcttaacta   9420
ggatcatggc ggcagaatca atcaattgat gttgaacttt caatgtaggg aattcgttct   9480
tgatggtttc ctccacagtt tttctccata atcttgaaga ggccaaaaca ttagctttat   9540
ccaaggacca aataggcaat ggtggctcat gttgtagggc catgaaagcg gccattcttg   9600
tgattctttg cacttctgga acggtgtatt gttcactatc ccaagcgaca ccatcaccat   9660
cgtcttcctt tctcttacca aagtaaatac ctcccactaa ttctctaaca acaacgaagt   9720
cagtaccttt agcaaattgt ggcttgattg gagataagtc taaaagagag tcggatgcaa   9780
agttacatgg tcttaagttg gcgtacaatt gaagttcttt acggattttt agtaaacctt   9840
gttcaggtct aacactaccg gtaccccatt taggaccacc cacagcacct aacaaaacgg   9900
```

```
catcagcctt cttggaggct tccagcgcct catctggaag tggaacacct gtagcatcga    9960

tagcagcacc accaattaaa tgattttcga aatcgaactt gacattggaa cgaacatcag   10020

aaatagcttt aagaacctta atggcttcgg ctgtgatttc ttgaccaacg tggtcacctg   10080

gcaaaacgac gatcttctta ggggcagaca ttacaatggt atatccttga aatatatata   10140

aaaaaaaaaa aaaaaaaaaa aaaaaaaaat gcagcttctc aatgatattc gaatacgctt   10200

tgaggagata cagcctaata tccgacaaac tgttttacag atttacgatc gtacttgtta   10260

cccatcattg aattttgaac atccgaacct gggagttttc cctgaaacag atagtatatt   10320

tgaacctgta taataatata tagtctagcg ctttacggaa gacaatgtat gtatttcggt   10380

tcctggagaa actattgcat ctattgcata ggtaatcttg cacgtcgcat ccccggttca   10440

ttttctgcgt ttccatcttg cacttcaata gcatatcttt gttaacgaag catctgtgct   10500

tcattttgta gaacaaaaat gcaacgcgag agcgctaatt tttcaaacaa agaatctgag   10560

ctgcattttt acagaacaga aatgcaacgc gaaagcgcta ttttaccaac gaagaatctg   10620

tgcttcattt ttgtaaaaca aaaatgcaac gcgagagcgc taatttttca aacaaagaat   10680

ctgagctgca tttttacaga acagaaatgc aacgcgagag cgctatttta ccaacaaaga   10740

atctatactt cttttttgtt ctacaaaaat gcatcccgag agcgctattt ttctaacaaa   10800

gcatcttaga ttactttttt tctcctttgt gcgctctata atgcagtctc ttgataactt   10860

tttgcactgt aggtccgtta aggttagaag aaggctactt tggtgtctat tttctcttcc   10920

ataaaaaaag cctgactcca cttcccgcgt ttactgatta ctagcgaagc tgcgggtgca   10980

ttttttcaag ataaaggcat ccccgattat attctatacc gatgtggatt gcgcatactt   11040

tgtgaacaga aagtgatagc gttgatgatt cttcattggt cagaaaatta tgaacggttt   11100

cttctatttt gtctctatat actacgtata ggaaatgttt acattttcgt attgttttcg   11160

attcactcta tgaatagttc ttactacaat ttttttgtct aaagagtaat actagagata   11220

aacataaaaa atgtagaggt cgagtttaga tgcaagttca aggagcgaaa ggtggatggg   11280

taggttatat agggatatag cacagagata tatagcaaag agatactttt gagcaatgtt   11340

tgtggaagcg gtattcgcaa tattttagta gctcgttaca gtccggtgcg tttttggttt   11400

tttgaaagtg cgtcttcaga gcgcttttgg ttttcaaaag cgctctgaag ttcctatact   11460

ttctagagaa taggaacttc ggaataggaa cttcaaagcg tttccgaaaa cgagcgcttc   11520

cgaaaatgca acgcgagctg cgcacataca gctcactgtt cacgtcgcac ctatatctgc   11580

gtgttgcctg tatatatata tacatgagaa gaacggcata gtgcgtgttt atgcttaaat   11640

gcgtacttat atgcgtctat ttatgtagga tgaaaggtag tctagtacct cctgtgatat   11700

tatcccattc catgcggggt atcgtatgct tccttcagca ctacccttta gctgttctat   11760

atgctgccac tcctcaattg gattagtctc atccttcaat gctatcattt cctttgatat   11820

tggatcatat gcatagtacc gagaaactag aggatc                             11856
```

<210> SEQ ID NO 2
<211> LENGTH: 15539
<212> TYPE: DNA
<213> ORGANISM: Artificial sequence
<220> FEATURE:
<223> OTHER INFORMATION: Plasmid

<400> SEQUENCE: 2

```
tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120
```

-continued

```
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctctag tacactctat atttttttat gcctcggtaa tgattttcat    360
tttttttttt ccacctagcg gatgactctt ttttttttctt agcgattggc attatcacat    420
aatgaattat acattatata aagtaatgtg atttcttcga agaatatact aaaaaatgag    480
caggcaagat aaacgaaggc aaagatgaca gagcagaaag ccctagtaaa gcgtattaca    540
aatgaaacca agattcagat tgcgatctct ttaaagggtg gtcccctagc gatagagcac    600
tcgatcttcc cagaaaaaga ggcagaagca gtagcagaac aggccacaca atcgcaagtg    660
attaacgtcc acacaggtat agggtttctg gaccatatga tacatgctct ggccaagcat    720
tccggctggt cgctaatcgt tgagtgcatt ggtgacttac acatagacga ccatcacacc    780
actgaagact gcgggattgc tctcggtcaa gcttttaaag aggccctagg ggccgtgcgt    840
ggagtaaaaa ggtttggatc aggatttgcg cctttggatg aggcactttc cagagcggtg    900
gtagatcttt cgaacaggcc gtacgcagtt gtcgaacttg gtttgcaaag ggagaaagta    960
ggagatctct cttgcgagat gatcccgcat ttcttgaaa gctttgcaga ggctagcaga   1020
attaccctcc acgttgattg tctgcgaggc aagaatgatc atcaccgtag tgagagtgcg   1080
ttcaaggctc ttgcggttgc cataagagaa gccacctcgc ccaatggtac caacgatgtt   1140
ccctccacca aaggtgttct tatgtagtga caccgattat ttaaagctgc agcatacgat   1200
atatatacat gtgtatatat gtatacctat gaatgtcagt aagtatgtat acgaacagta   1260
tgatactgaa gatgacaagg taatgcatca ttctatacgt gtcattctga acgaggcgcg   1320
ctttcctttt ttcttttttgc tttttctttt tttttctctt gaactcgacg gatctatgcg   1380
gtgtgaaata ccgcacagat gcgtaaggag aaaataccgc atcaggaaat tgtaagcgtt   1440
aatattttgt taaaattcgc gttaaatttt tgttaaatca gctcattttt taaccaatag   1500
gccgaaatcg gcaaaatccc ttataaatca aaagaataga ccgagatagg gttgagtgtt   1560
gttccagttt ggaacaagag tccactatta aagaacgtgg actccaacgt caaagggcga   1620
aaaaccgtct atcagggcga tggcccacta cgtgaaccat caccctaatc aagttttttg   1680
gggtcgaggt gccgtaaagc actaaatcgg aaccctaaag ggagcccccg atttagagct   1740
tgacggggaa agccggcgaa cgtggcgaga aaggaaggga agaaagcgaa aggagcgggc   1800
gctagggcgc tggcaagtgt agcggtcacg ctgcgcgtaa ccaccacacc cgccgcgctt   1860
aatgcgccgc tacagggcgc gtccattcgc cattcaggct gcgcaactgt tgggaagggc   1920
gcggtgcggg cctcttcgct attacgccag ctggcgaaag ggggatgtgc tgcaaggcga   1980
ttaagttggg taacgccagg gttttcccag tcacgacgtt gtaaaacgac ggccagtgag   2040
cgcgcgtaat acgactcact atagggcgaa ttgggtaccg ggcccccccct cgaggtcgac   2100
ggcgcgccac tggtagagag cgactttgta tgccccaatt gcgaaacccg cgatatcctt   2160
ctcgattctt tagtacccga ccaggacaag gaaaaggagg tcgaaacgtt tttgaagaaa   2220
caagaggaac tacacggaag ctctaaagat ggcaaccagc cagaaactaa gaaaatgaag   2280
ttgatggatc caactggcac cgctggcttg aacaacaata ccagccttcc aacttctgta   2340
aataacggcg gtacgccagt gccaccagta ccgttacctt tcggtatacc tcctttcccc   2400
atgtttccaa tgcccttcat gcctccaacg gctactatca caaatcctca tcaagctgac   2460
gcaagcccta agaaatgaat aacaatactg acagtactaa ataattgcct acttggcttc   2520
```

```
acatacgttg catacgtcga tatagataat aatgataatg acagcaggat tatcgtaata   2580
cgtaatagct gaaaatctca aaaatgtgtg ggtcattacg taaataatga taggaatggg   2640
attcttctat ttttcctttt tccattctag cagccgtcgg gaaaacgtgg catcctctct   2700
ttcgggctca attggagtca cgctgccgtg agcatcctct ctttccatat ctaacaactg   2760
agcacgtaac caatggaaaa gcatgagctt agcgttgctc caaaaaagta ttggatggtt   2820
aataccattt gtctgttctc ttctgacttt gactcctcaa aaaaaaaaat ctacaatcaa   2880
cagatcgctt caattacgcc ctcacaaaaa ctttttttcct tcttcttcgc ccacgttaaa   2940
ttttatccct catgttgtct aacggatttc tgcacttgat ttattataaa aagacaaaga   3000
cataatactt ctctatcaat ttcagttatt gttcttcctt gcgttattct tctgttcttc   3060
tttttctttt gtcatatata accataacca agtaatacat attcaaacta gtatgactga   3120
caaaaaaact cttaaagact taagaaatcg tagttctgtt tacgattcaa tggttaaatc   3180
acctaatcgt gctatgttgc gtgcaactgg tatgcaagat gaagactttg aaaaacctat   3240
cgtcggtgtc atttcaactt gggctgaaaa cacaccttgt aatatccact tacatgactt   3300
tggtaaacta gccaaagtcg gtgttaagga agctggtgct tggccagttc agttcggaac   3360
aatcacggtt tctgatggaa tcgccatggg aacccaagga atgcgtttct ccttgacatc   3420
tcgtgatatt attgcagatt ctattgaagc agccatggga ggtcataatg cggatgcttt   3480
tgtagccatt ggcggttgtg ataaaaacat gcccggttct gttatcgcta tggctaacat   3540
ggatatccca gccatttttg cttacggcgg aacaattgca cctggtaatt tagacggcaa   3600
agatatcgat ttagtctctg tctttgaagg tgtcggccat tggaaccacg gcgatatgac   3660
caaagaagaa gttaaagctt tggaatgtaa tgcttgtccc ggtcctggag gctgcggtgg   3720
tatgtatact gctaacacaa tggcgacagc tattgaagtt ttgggactta gccttccggg   3780
ttcatcttct cacccggctg aatccgcaga aaagaaagca gatattgaag aagctggtcg   3840
cgctgttgtc aaaatgctcg aaatgggctt aaaaccttct gacattttaa cgcgtgaagc   3900
ttttgaagat gctattactg taactatggc tctgggaggt tcaaccaact caacccttca   3960
cctcttagct attgcccatg ctgctaatgt ggaattgaca cttgatgatt tcaatacttt   4020
ccaagaaaaa gttcctcatt tggctgattt gaaaccttct ggtcaatatg tattccaaga   4080
cctttacaag gtcggagggg taccagcagt tatgaaatat ctccttaaaa atggcttcct   4140
tcatggtgac cgtatcactt gtactggcaa aacagtcgct gaaaatttga aggcttttga   4200
tgatttaaca cctggtcaaa aggttattat gccgcttgaa aatcctaaac gtgaagatgg   4260
tccgctcatt attctccatg gtaacttggc tccagacggt gccgttgcca aagtttctgg   4320
tgtaaaagtg cgtcgtcatg tcggtcctgc taaggtcttt aattctgaag aagaagccat   4380
tgaagctgtc ttgaatgatg atattgttga tggtgatgtt gttgtcgtac gttttgtagg   4440
accaaagggc ggtcctggta tgcctgaaat gctttccctt tcatcaatga ttgttggtaa   4500
agggcaaggt gaaaaagttg cccttctgac agatggccgc ttctcaggtg gtacttatgg   4560
tcttgtcgtg ggtcatatcg ctcctgaagc acaagatggc ggtccaatcg cctacctgca   4620
aacaggagac atagtcacta ttgaccaaga cactaaggaa ttacactttg atatctccga   4680
tgaagagtta aaacatcgtc aagagaccat tgaattgcca ccgctctatt cacgcggtat   4740
ccttggtaaa tatgctcaca tcgtttcgtc tgcttctagg ggagccgtaa cagacttttg   4800
gaagcctgaa gaaactggca aaaaatgttg tcctggttgc tgtggttaag cggccgcgtt   4860
aattcaaatt aattgatata gtttttttaat gagtattgaa tctgtttaga aataatggaa   4920
```

```
tattatttt atttatttat ttatattatt ggtcggctct tttcttctga aggtcaatga   4980
caaaatgata tgaaggaaat aatgatttct aaaattttac aacgtaagat atttttacaa   5040
aagcctagct catcttttgt catgcactat tttactcacg cttgaaatta acggccagtc   5100
cactgcggag tcatttcaaa gtcatcctaa tcgatctatc gtttttgata gctcattttg   5160
gagttcgcga ttgtcttctg ttattcacaa ctgttttaat tttatttca ttctggaact   5220
cttcgagttc tttgtaaagt ctttcatagt agcttacttt atcctccaac atatttaact   5280
tcatgtcaat ttcggctctt aaattttcca catcatcaag ttcaacatca tcttttaact   5340
tgaatttatt ctctagctct tccaaccaag cctcattgct ccttgattta ctggtgaaaa   5400
gtgatacact ttgcgcgcaa tccaggtcaa aactttcctg caaagaattc accaatttct   5460
cgacatcata gtacaatttg ttttgttctc ccatcacaat ttaatatacc tgatggattc   5520
ttatgaagcg ctgggtaatg gacgtgtcac tctacttcgc ctttttccct actcctttta   5580
gtacggaaga caatgctaat aaataagagg gtaataataa tattattaat cggcaaaaaa   5640
gattaaacgc caagcgttta attatcagaa agcaaacgtc gtaccaatcc ttgaatgctt   5700
cccaattgta tattaagagt catcacagca acatattctt gttattaaat taattattat   5760
tgatttttga tattgtataa aaaaaccaaa tatgtataaa aaaagtgaat aaaaaatacc   5820
aagtatggag aaatatatta gaagtctata cgttaaacca cccgggcccc ccctcgaggt   5880
cgacggtatc gataagcttg atatcgaatt cctgcagccc gggggatcca ctagttctag   5940
agcggccgct ctagaactag taccacaggt gttgtcctct gaggacataa aatacacacc   6000
gagattcatc aactcattgc tggagttagc atatctacaa ttgggtgaaa tggggagcga   6060
tttgcaggca tttgctcggc atgccggtag aggtgtggtc aataagagcg acctcatgct   6120
atacctgaga aagcaacctg acctacagga aagagttact caagaataag aattttcgtt   6180
ttaaaaccta agagtcactt taaaatttgt atacacttat ttttttata acttatttaa   6240
taataaaaat cataaatcat aagaaattcg cttactctta attaatcaaa aagttaaaat   6300
tgtacgaata gattcaccac ttcttaacaa atcaaaccct tcattgattt tctcgaatgg   6360
caatacatgt gtaattaaag gatcaagagc aaacttcttc gccataaagt cggcaacaag   6420
ttttggaaca ctatccttgc tcttaaaacc gccaaatata gctcccttcc atgtacgacc   6480
gcttagcaac agcataggat tcatcgacaa attttgtgaa tcaggaggaa cacctacgat   6540
cacactgact ccatatgcct cttgacagca ggacaacgca gttaccatag tatcaagacg   6600
gcctataact tcaaaagaga aatcaactcc accgtttgac atttcagtaa ggacttcttg   6660
tattggtttc ttataatctt gagggttaac acattcagta gccccgacct ccttagcttt   6720
tgcaaatttg tccttattga tgtctacacc tataatcctc gctgcgcctg cagctttaca   6780
ccccataata acgcttagtc ctactcctcc taaaccgaat actgcacaag tcgaaccctg   6840
tgtaaccttt gcaactttaa ctgcggaacc gtaaccggtg gaaaatccgc accctatcaa   6900
gcaaactttt tccagtggtg aagctgcatc gattttagcg acagatatct cgtccaccac   6960
tgtgtattgg gaaaatgtag aagtaccaag gaaatggtgt ataggtttcc ctctgcatgt   7020
aaatctgctt gtaccatcct gcatagtacc tctaggcata gacaaatcat ttttaaggca   7080
gaaattaccc tcaggatgtt tgcagactct acacttacca cattgaggag tgaacagtgg   7140
gatcacttta tcaccaggac gaacagtggt aacaccttca cctatggatt caacgattcc   7200
ggcagcctcg tgtcccgcga ttactggcaa aggagtaact agagtgccac tcaccacatg   7260
gtcgtcggat ctacagattc cggtggcaac catcttgatt ctaacctcgt gtgcttttgg   7320
```

```
tggcgctact tctacttctt ctatgctaaa cggctttttc tcttcccaca aaactgccgc   7380
tttacactta ataactttac cggctgttga catcctcagc tagctattgt aatatgtgtg   7440
tttgtttgga ttattaagaa gaataattac aaaaaaaatt acaaaggaag gtaattacaa   7500
cagaattaag aaaggacaag aaggaggaag agaatcagtt cattatttct tctttgttat   7560
ataacaaacc caagtagcga tttggccata cattaaaagt tgagaaccac cctccctggc   7620
aacagccaca actcgttacc attgttcatc acgatcatga aactcgctgt cagctgaaat   7680
ttcacctcag tggatctctc tttttattct tcatcgttcc actaaccttt ttccatcagc   7740
tggcagggaa cggaaagtgg aatcccattt agcgagcttc ctcttttctt caagaaaaga   7800
cgaagcttgt gtgtgggtgc gcgcgctagt atctttccac attaagaaat ataccataaa   7860
ggttacttag acatcactat ggctatatat atatatatat atatatgtaa cttagcacca   7920
tcgcgcgtgc atcactgcat gtgttaaccg aaaagtttgg cgaacacttc accgacacgg   7980
tcatttagat ctgtcgtctg cattgcacgt cccttagcct taaatcctag gcgggagcat   8040
tctcgtgtaa ttgtgcagcc tgcgtagcaa ctcaacatag cgtagtctac ccagtttttc   8100
aagggtttat cgttagaaga ttctcccttt tcttcctgct cacaaatctt aaagtcatac   8160
attgcacgac taaatgcaag catgcggatc cccccgggctg caggaattcg atatcaagct   8220
tatcgatacc gtcgactggc cattaatctt tcccatatta gatttcgcca agccatgaaa   8280
gttcaagaaa ggtctttaga cgaattaccc ttcatttctc aaactggcgt caagggatcc   8340
tggtatggtt ttatcgtttt atttctggtt cttatagcat cgttttggac ttctctgttc   8400
ccattaggcg gttcaggagc cagcgcagaa tcattctttg aaggatactt atcctttcca   8460
attttgattg tctgttacgt tggacataaa ctgtatacta gaaattggac tttgatggtg   8520
aaactagaag atatggatct tgataccggc agaaaacaag tagatttgac tcttcgtagg   8580
gaagaaatga ggattgagcg agaaacatta gcaaaaagat ccttcgtaac aagattttta   8640
catttctggt gttgaaggga aagatatgag ctatacagcg gaatttccat atcactcaga   8700
ttttgttatc taatttttc cttcccacgt ccgcgggaat ctgtgtatat tactgcatct   8760
agatatatgt tatcttatct tggcgcgtac atttaatttt caacgtattc tataagaaat   8820
tgcgggagtt tttttcatgt agatgatact gactgcacgc aaatataggc atgatttata   8880
ggcatgattt gatggctgta ccgataggaa cgctaagagt aacttcagaa tcgttatcct   8940
ggcggaaaaa attcatttgt aaactttaaa aaaaaaagcc aatatcccca aaattattaa   9000
gagcgcctcc attattaact aaaatttcac tcagcatcca caatgtatca ggtatctact   9060
acagatatta catgtggcga aaaagacaag aacaatgcaa tagcgcatca agaaaaaaca   9120
caaagctttc aatcaatgaa tcgaaaatgt cattaaaata gtatataaat tgaaactaag   9180
tcataaagct ataaaaagaa aatttattta aatgcaagat ttaaagtaaa ttcacggccc   9240
tgcaggcctc agctcttgtt ttgttctgca aataacttac ccatcttttt caaaacttta   9300
ggtgcaccct cctttgctag aataagttct atccaataca tcctatttgg atctgcttga   9360
gcttctttca tcacggatac gaattcattt tctgttctca caattttgga cacaactctg   9420
tcttccgttg ccccgaaact ttctggcagt tttgagtaat tccacatagg aatgtcatta   9480
taactctggt tcggaccatg aatttccctc tcaaccgtgt aaccatcgtt attaatgata   9540
aagcagattg ggtttatctt ctctctaatg gctagtccta attcttggac agtcagttgc   9600
aatgatccat ctccgataaa caataaatgt ctagattctt tatctgcaat ttggctgcct   9660
agagctgcgg ggaaagtgta tcctatagat ccccacaagg gttgaccaat aaaatgtgat   9720
```

```
ttcgatttca gaaatataga tgaggcaccg aagaaagaag tgccttgttc agccacgatc   9780
gtctcattac tttgggtcaa attttcgaca gcttgccaca gtctatcttg tgacaacagc   9840
gcgttagaag gtacaaaatc ttcttgcttt ttatctatgt acttgccttt atattcaatt   9900
tcggacaagt caagaagaga tgatatcagg gattcgaagt cgaaattttg gattctttcg   9960
ttgaaaattt taccttcatc gatattcaag gaaatcattt tattttcatt aagatggtga  10020
gtaaatgcac ccgtactaga atcggtaagc tttacaccca acataagaat aaaatcagca  10080
gattccacaa attccttcaa gtttggctct gacagagtac cgttgtaaat ccccaaaaat  10140
gagggcaatg cttcatcaac agatgattta ccaaagttca aagtagtaat aggtaactta  10200
gtctttgaaa taaactgagt aacagtcttc tctaggccga acgatataat ttcatggcct  10260
gtgattacaa ttggtttctt ggcattcttc agactttcct gtattttgtt cagaatctct  10320
tgatcagatg tattcgacgt ggaattttcc ttcttaagag gcaaggatgg tttttcagcc  10380
ttagcggcag ctacatctac aggtaaattg atgtaaaccg gctttctttc ctttagtaag  10440
gcagacaaca ctctatcaat ttcaacagtt gcattctcgg ctgtcaataa agtcctggca  10500
gcagtaaccg gttcgtgcat cttcataaag tgcttgaaat caccatcagc caacgtatgg  10560
tgaacaaact taccttcgtt ctgcactttc gaggtaggag atcccacgat ctcaacaaca  10620
ggcaggttct cagcatagga gcccgctaag ccattaactg cggataattc gccaacacca  10680
aatgtagtca agaatgccgc agccttttc gttcttgcgt acccgtcggc catataggag   10740
gcatttaact cattagcatt tcccacccat ttcatatctt tgtgtgaaat aatttgatct  10800
agaaattgca aattgtagtc acctggtact ccgaatattt cttctatacc taattcgtgt  10860
aatctgtcca acagatagtc acctactgta tacattttgt ttactagttt atgtgtgttt  10920
attcgaaact aagttcttgg tgttttaaaa ctaaaaaaaa gactaactat aaaagtagaa  10980
tttaagaagt ttaagaaata gatttacaga attacaatca atacctaccg tctttatata  11040
cttattagtc aagtagggga ataatttcag ggaactggtt tcaacctttt ttttcagctt  11100
tttccaaatc agagagagca gaaggtaata gaaggtgtaa gaaaatgaga tagatacatg  11160
cgtgggtcaa ttgccttgtg tcatcattta ctccaggcag gttgcatcac tccattgagg  11220
ttgtgcccgt tttttgcctg tttgtgcccc tgttctctgt agttgcgcta agagaatgga  11280
cctatgaact gatggttggt gaagaaaaca atattttggt gctgggattc tttttttttc  11340
tggatgccag cttaaaaagc gggctccatt atatttagtg gatgccagga ataaactgtt  11400
cacccagaca cctacgatgt tatatattct gtgtaacccg ccccctattt tgggcatgta  11460
cgggttacag cagaattaaa aggctaattt tttgactaaa taaagttagg aaaatcacta  11520
ctattaatta tttacgtatt ctttgaaatg gcagtattga taatgataaa ctcgaactga  11580
aaaagcgtgt tttttattca aaatgattct aactccctta cgtaatcaag gaatcttttt  11640
gccttggcct ccgcgtcatt aaacttcttg ttgttgacgc taacattcaa cgctagtata  11700
tattcgtttt tttcaggtaa gttcttttca acgggtctta ctgatgaggc agtcgcgtct  11760
gaacctgtta agaggtcaaa tatgtcttct tgaccgtacg tgtcttgcat gttattagct  11820
ttgggaattt gcatcaagtc ataggaaaat ttaaatcttg gctctcttgg gctcaaggtg  11880
acaaggtcct cgaaaatagg gcgcgcccca ccgcggtgga gctccagctt ttgttccctt  11940
tagtgagggt taattgcgcg cttggcgtaa tcatggtcat agctgtttcc tgtgtgaaat  12000
tgttatccgc tcacaattcc acacaacata cgagccggaa gcataaagtg taaagcctgg  12060
ggtgcctaat gagtgagcta actcacatta attgcgttgc gctcactgcc cgctttccag  12120
```

```
tcgggaaacc tgtcgtgcca gctgcattaa tgaatcggcc aacgcgcggg gagaggcggt  12180
ttgcgtattg ggcgctcttc cgcttcctcg ctcactgact cgctgcgctc ggtcgttcgg  12240
ctgcggcgag cggtatcagc tcactcaaag gcggtaatac ggttatccac agaatcaggg  12300
gataacgcag gaaagaacat gtgagcaaaa ggccagcaaa aggccaggaa ccgtaaaaag  12360
gccgcgttgc tggcgttttt ccataggctc cgcccccctg acgagcatca caaaaatcga  12420
cgctcaagtc agaggtggcg aaacccgaca ggactataaa gataccaggc gtttccccct  12480
ggaagctccc tcgtgcgctc tcctgttccg accctgccgc ttaccggata cctgtccgcc  12540
tttctccctt cgggaagcgt ggcgctttct catagctcac gctgtaggta tctcagttcg  12600
gtgtaggtcg ttcgctccaa gctgggctgt gtgcacgaac cccccgttca gcccgaccgc  12660
tgcgccttat ccggtaacta tcgtcttgag tccaacccgg taagacacga cttatcgcca  12720
ctggcagcag ccactggtaa caggattagc agagcgaggt atgtaggcgg tgctacagag  12780
ttcttgaagt ggtggcctaa ctacggctac actagaagaa cagtatttgg tatctgcgct  12840
ctgctgaagc cagttacctt cggaaaaaga gttggtagct cttgatccgg caaacaaacc  12900
accgctggta gcggtggttt ttttgtttgc aagcagcaga ttacgcgcag aaaaaaagga  12960
tctcaagaag atcctttgat cttttctacg gggtctgacg ctcagtggaa cgaaaactca  13020
cgttaaggga ttttggtcat gagattatca aaaaggatct tcacctagat ccttttaaat  13080
taaaaatgaa gttttaaatc aatctaaagt atatatgagt aaacttggtc tgacagttac  13140
caatgcttaa tcagtgaggc acctatctca gcgatctgtc tatttcgttc atccatagtt  13200
gcctgactcc ccgtcgtgta gataactacg atacgggagg gcttaccatc tggccccagt  13260
gctgcaatga taccgcgaga cccacgctca ccggctccag atttatcagc aataaaccag  13320
ccagccggaa gggccgagcg cagaagtggt cctgcaactt tatccgcctc catccagtct  13380
attaattgtt gccgggaagc tagagtaagt agttcgccag ttaatagttt gcgcaacgtt  13440
gttgccattg ctacaggcat cgtggtgtca cgctcgtcgt ttggtatggc ttcattcagc  13500
tccggttccc aacgatcaag gcgagttaca tgatccccca tgttgtgcaa aaaagcggtt  13560
agctccttcg gtcctccgat cgttgtcaga agtaagttgg ccgcagtgtt atcactcatg  13620
gttatggcag cactgcataa ttctcttact gtcatgccat ccgtaagatg cttttctgtg  13680
actggtgagt actcaaccaa gtcattctga gaatagtgta tgcggcgacc gagttgctct  13740
tgcccggcgt caatacggga taataccgcg ccacatagca gaactttaaa agtgctcatc  13800
attggaaaac gttcttcggg gcgaaaactc tcaaggatct taccgctgtt gagatccagt  13860
tcgatgtaac ccactcgtgc acccaactga tcttcagcat cttttacttt caccagcgtt  13920
tctgggtgag caaaaacagg aaggcaaaat gccgcaaaaa agggaataag ggcgacacgg  13980
aaatgttgaa tactcatact cttccttttt caatattatt gaagcattta tcagggttat  14040
tgtctcatga gcggatacat atttgaatgt atttagaaaa ataaacaaat aggggttccg  14100
cgcacatttc cccgaaaagt gccacctgaa cgaagcatct gtgcttcatt ttgtagaaca  14160
aaaatgcaac gcgagagcgc taatttttca aacaaagaat ctgagctgca tttttacaga  14220
acagaaatgc aacgcgaaag cgctatttta ccaacgaaga atctgtgctt catttttgta  14280
aaacaaaaat gcaacgcgag agcgctaatt tttcaaacaa agaatctgag ctgcattttt  14340
acagaacaga aatgcaacgc gagagcgcta ttttaccaac aaagaatcta tacttctttt  14400
ttgttctaca aaaatgcatc ccgagagcgc tatttttcta acaaagcatc ttagattact  14460
tttttctcc tttgtgcgct ctataatgca gtctcttgat aactttttgc actgtaggtc  14520
```

```
cgttaaggtt agaagaaggc tactttggtg tctattttct cttccataaa aaaagcctga  14580

ctccacttcc cgcgtttact gattactagc gaagctgcgg gtgcattttt tcaagataaa  14640

ggcatccccg attatattct ataccgatgt ggattgcgca tactttgtga acagaaagtg  14700

atagcgttga tgattcttca ttggtcagaa aattatgaac ggtttcttct attttgtctc  14760

tatatactac gtataggaaa tgtttacatt ttcgtattgt tttcgattca ctctatgaat  14820

agttcttact acaatttttt tgtctaaaga gtaatactag agataaacat aaaaaatgta  14880

gaggtcgagt ttagatgcaa gttcaaggag cgaaaggtgg atgggtaggt tatataggga  14940

tatagcacag agatatatag caaagagata cttttgagca atgtttgtgg aagcggtatt  15000

cgcaatattt tagtagctcg ttacagtccg gtgcgttttt ggtttttga aagtgcgtct  15060

tcagagcgct tttggttttc aaaagcgctc tgaagttcct atactttcta gagaatagga  15120

acttcggaat aggaacttca aagcgtttcc gaaaacgagc gcttccgaaa atgcaacgcg  15180

agctgcgcac atacagctca ctgttcacgt cgcacctata tctgcgtgtt gcctgtatat  15240

atatatacat gagaagaacg gcatagtgcg tgtttatgct taaatgcgta cttatatgcg  15300

tctatttatg taggatgaaa ggtagtctag tacctcctgt gatattatcc cattccatgc  15360

ggggtatcgt atgcttcctt cagcactacc ctttagctgt tctatatgct gccactcctc  15420

aattggatta gtctcatcct tcaatgctat catttccttt gatattggat catactaaga  15480

aaccattatt atcatgacat taacctataa aaataggcgt atcacgaggc cctttcgtc   15539
```

<210> SEQ ID NO 3
<211> LENGTH: 4586
<212> TYPE: DNA
<213> ORGANISM: Artificial sequence
<220> FEATURE:
<223> OTHER INFORMATION: Template

<400> SEQUENCE: 3

```
gggtaccgag ctcgaattca ctggccgtcg ttttacaacg tcgtgactgg gaaaaccctg     60

gcgttaccca acttaatcgc cttgcagcac atcccccttt cgccagctgg cgtaatagcg    120

aagaggcccg caccgatcgc ccttcccaac agttgcgcag cctgaatggc gaatggcgcc    180

tgatgcggta ttttctcctt acgcatctgt gcggtatttc acaccgcata tggtgcactc    240

tcagtacaat ctgctctgat gccgcatagt taagccagcc ccgacacccg ccaacacccg    300

ctgacgcgcc ctgacgggct tgtctgctcc cggcatccgc ttacagacaa gctgtgaccg    360

tctccgggag ctgcatgtgt cagaggtttt caccgtcatc accgaaacgc gcgagacgaa    420

agggcctcgt gatacgccta tttttatagg ttaatgtcat gataataatg gtttcttaga    480

cgtcaggtgg cacttttcgg ggaaatgtgc gcggaacccc tatttgttta tttttctaaa    540

tacattcaaa tatgtatccg ctcatgagac aataaccctg ataaatgctt caataatatt    600

gaaaaaggaa gagtatgagt attcaacatt tccgtgtcgc ccttattccc ttttttgcgg    660

cattttgcct tcctgttttt gctcacccag aaacgctggt gaaagtaaaa gatgctgaag    720

atcagttggg tgcacgagtg ggttacatcg aactggatct caacagcggt aagatccttg    780

agagttttcg ccccgaagaa cgttttccaa tgatgagcac ttttaaagtt ctgctatgtg    840

gcgcggtatt atcccgtatt gacgccgggc aagagcaact cggtcgccgc atacactatt    900

ctcagaatga cttggttgag tactcaccag tcacagaaaa gcatcttacg gatggcatga    960

cagtaagaga attatgcagt gctgccataa ccatgagtga taacactgcg gccaacttac   1020

ttctgacaac gatcggagga ccgaaggagc taaccgcttt tttgcacaac atgggggatc   1080
```

```
atgtaactcg ccttgatcgt tgggaaccgg agctgaatga agccatacca aacgacgagc   1140

gtgacaccac gatgcctgta gcaatggcaa caacgttgcg caaactatta actggcgaac   1200

tacttactct agcttcccgg caacaattaa tagactggat ggaggcggat aaagttgcag   1260

gaccacttct gcgctcggcc cttccggctg gctggtttat tgctgataaa tctggagccg   1320

gtgagcgtgg gtctcgcggt atcattgcag cactggggcc agatggtaag ccctcccgta   1380

tcgtagttat ctacacgacg gggagtcagg caactatgga tgaacgaaat agacagatcg   1440

ctgagatagg tgcctcactg attaagcatt ggtaactgtc agaccaagtt tactcatata   1500

tactttagat tgatttaaaa cttcattttt aatttaaaag gatctaggtg aagatccttt   1560

ttgataatct catgaccaaa atcccttaac gtgagttttc gttccactga gcgtcagacc   1620

ccgtagaaaa gatcaaagga tcttcttgag atcctttttt tctgcgcgta atctgctgct   1680

tgcaaacaaa aaaaccaccg ctaccagcgg tggtttgttt gccggatcaa gagctaccaa   1740

ctctttttcc gaaggtaact ggcttcagca gagcgcagat accaaatact gtccttctag   1800

tgtagccgta gttaggccac cacttcaaga actctgtagc accgcctaca tacctcgctc   1860

tgctaatcct gttaccagtg gctgctgcca gtggcgataa gtcgtgtctt accgggttgg   1920

actcaagacg atagttaccg gataaggcgc agcggtcggg ctgaacgggg ggttcgtgca   1980

cacagcccag cttggagcga acgacctaca ccgaactgag atacctacag cgtgagctat   2040

gagaaagcgc cacgcttccc gaagggagaa aggcggacag gtatccggta agcggcaggg   2100

tcggaacagg agagcgcacg agggagcttc caggggggaaa cgcctggtat ctttatagtc   2160

ctgtcgggtt tcgccacctc tgacttgagc gtcgattttt gtgatgctcg tcaggggggc   2220

ggagcctatg gaaaaacgcc agcaacgcgg cctttttacg gttcctggcc ttttgctggc   2280

cttttgctca catgttcttt cctgcgttat cccctgattc tgtggataac cgtattaccg   2340

cctttgagtg agctgatacc gctcgccgca gccgaacgac cgagcgcagc gagtcagtga   2400

gcgaggaagc ggaagagcgc ccaatacgca aaccgcctct ccccgcgcgt tggccgattc   2460

attaatgcag ctggcacgac aggtttcccg actggaaagc gggcagtgag cgcaacgcaa   2520

ttaatgtgag ttagctcact cattaggcac cccaggcttt acactttatg cttccggctc   2580

gtatgttgtg tggaattgtg agcggataac aatttcacac aggaaacagc tatgaccatg   2640

attacgccaa gcttgcatgc ctgcaggtcg actctagagg atccccgcat tgcggattac   2700

gtattctaat gttcagataa cttcgtatag catacattat acgaagttat ctagggattc   2760

ataaccattt tctcaatcga attacacaga acacaccgta caaacctctc tatcataact   2820

acttaatagt cacacacgta ctcgtctaaa tacacatcat cgtcctacaa gttcatcaaa   2880

gtgttggaca gacaactata ccagcatgga tctcttgtat cggttctttt ctcccgctct   2940

ctcgcaataa caatgaacac tgggtcaatc atagcctaca caggtgaaca gagtagcgtt   3000

tatacagggt ttatacggtg attcctacgg caaaaatttt tcatttctaa aaaaaaaaag   3060

aaaaattttt ctttccaacg ctagaaggaa aagaaaaatc taattaaatt gatttggtga   3120

ttttctgaga gttccctttt tcatatatcg aattttgaat ataaaaggag atcgaaaaaa   3180

tttttctatt caatctgttt tctggtttta tttgatagtt tttttgtgta ttattattat   3240

ggattagtac tggtttatat gggtttttct gtataacttc tttttatttt agtttgttta   3300

atcttatttt gagttacatt atagttccct aactgcaaga gaagtaacat taaaactcga   3360

gatgggtaag gaaaagactc acgtttcgag gccgcgatta aattccaaca tggatgctga   3420

tttatatggg tataaatggg ctcgcgataa tgtcgggcaa tcaggtgcga caatctatcg   3480
```

```
attgtatggg aagcccgatg cgccagagtt gtttctgaaa catggcaaag gtagcgttgc   3540

caatgatgtt acagatgaga tggtcagact aaactggctg acggaattta tgcctcttcc   3600

gaccatcaag cattttatcc gtactcctga tgatgcatgg ttactcacca ctgcgatccc   3660

cggcaaaaca gcattccagg tattagaaga atatcctgat tcaggtgaaa atattgttga   3720

tgcgctggca gtgttcctgc gccggttgca ttcgattcct gtttgtaatt gtccttttaa   3780

cagcgatcgc gtatttcgtc tcgctcaggc gcaatcacga atgaataacg gtttggttga   3840

tgcgagtgat tttgatgacg agcgtaatgg ctggcctgtt gaacaagtct ggaaagaaat   3900

gcataagctt ttgccattct caccggattc agtcgtcact catggtgatt tctcacttga   3960

taaccttatt tttgacgagg ggaaattaat aggttgtatt gatgttggac gagtcggaat   4020

cgcagaccga taccaggatc ttgccatcct atggaactgc ctcggtgagt tttctccttc   4080

attacagaaa cggctttttc aaaaatatgg tattgataat cctgatatga ataaattgca   4140

gtttcatttg atgctcgatg agtttttcta agtttaactt gatactacta gatttttctc   4200

cttcatttat aaaatttttg gttataattg aagctttaga agtatgaaaa aatccttttt   4260

tttcattctt tgcaaccaaa ataagaagct tcttttattc attgaaatga tgaatataaa   4320

cctaacaaaa gaaaaagact cgaatatcaa acattaaaaa aaaataaaag aggttatctg   4380

ttttcccatt tagttggagt ttgcattttc taatagatag aactctcaat taatgtggat   4440

ttagtttctc tgttcgtttt tttttgtttt gttctcactg tatttacatt tctatttagt   4500

atttagttat tcatataatc tataacttcg tatagcatac attatacgaa gttatccagt   4560

gatgatacaa cgagttagcc aaggtg                                         4586
```

<210> SEQ ID NO 4
<211> LENGTH: 80
<212> TYPE: DNA
<213> ORGANISM: Artificial sequence
<220> FEATURE:
<223> OTHER INFORMATION: Primer

<400> SEQUENCE: 4

```
ttccggtttc tttgaaattt ttttgattcg gtaatctccg agcagaagga gcattgcgga     60

ttacgtattc taatgttcag                                                 80
```

<210> SEQ ID NO 5
<211> LENGTH: 81
<212> TYPE: DNA
<213> ORGANISM: Artificial sequence
<220> FEATURE:
<223> OTHER INFORMATION: Primer

<400> SEQUENCE: 5

```
gggtaataac tgatataatt aaattgaagc tctaatttgt gagtttagta caccttggct     60

aactcgttgt atcatcactg g                                               81
```

<210> SEQ ID NO 6
<211> LENGTH: 38
<212> TYPE: DNA
<213> ORGANISM: Artificial sequence
<220> FEATURE:
<223> OTHER INFORMATION: Primer

<400> SEQUENCE: 6

```
gcctcgagtt ttaatgttac ttctcttgca gttaggga                             38
```

<210> SEQ ID NO 7
<211> LENGTH: 31
<212> TYPE: DNA
<213> ORGANISM: Artificial sequence
<220> FEATURE:
<223> OTHER INFORMATION: Primer

<400> SEQUENCE: 7
gctaaattcg agtgaaacac aggaagacca g 31

<210> SEQ ID NO 8
<211> LENGTH: 90
<212> TYPE: DNA
<213> ORGANISM: Artificial sequence
<220> FEATURE:
<223> OTHER INFORMATION: Primer

<400> SEQUENCE: 8
gtattttggt agattcaatt ctctttccct ttccttttcc ttcgctcccc ttccttatca 60
gcattgcgga ttacgtattc taatgttcag 90

<210> SEQ ID NO 9
<211> LENGTH: 90
<212> TYPE: DNA
<213> ORGANISM: Artificial sequence
<220> FEATURE:
<223> OTHER INFORMATION: Primer

<400> SEQUENCE: 9
ttggttgggg gaaaaagagg caacaggaaa gatcagaggg ggaggggggg ggagagtgtc 60
accttggcta actcgttgta tcatcactgg 90

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
tcggtgcggg cctcttcgct a 21

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
aatgtgagtt agctcactca t 21

<210> SEQ ID NO 12
<211> LENGTH: 57
<212> TYPE: DNA
<213> ORGANISM: Artificial sequence
<220> FEATURE:
<223> OTHER INFORMATION: Primer

<400> SEQUENCE: 12
aattggatcc ggcgcgccgt ttaaacggcc ggccaatgtg gctgtggttt cagggtc 57

<210> SEQ ID NO 13
<211> LENGTH: 49
<212> TYPE: DNA
<213> ORGANISM: Artificial sequence
<220> FEATURE:
<223> OTHER INFORMATION: Primer

<400> SEQUENCE: 13
aatttctaga ttaattaagc ggccgcaagg ccatgaagct ttttctttc 49

<210> SEQ ID NO 14
<211> LENGTH: 24
<212> TYPE: DNA
<213> ORGANISM: Artificial sequence
<220> FEATURE:
<223> OTHER INFORMATION: Primer

<400> SEQUENCE: 14
ttctcgacgt gggccttttt cttg 24

<210> SEQ ID NO 15
<211> LENGTH: 49
<212> TYPE: DNA
<213> ORGANISM: Artificial sequence
<220> FEATURE:
<223> OTHER INFORMATION: Primer

<400> SEQUENCE: 15
tgcagcttta aataatcggt gtcactactt tgccttcgtt tatcttgcc 49

<210> SEQ ID NO 16
<211> LENGTH: 49
<212> TYPE: DNA
<213> ORGANISM: Artificial sequence
<220> FEATURE:
<223> OTHER INFORMATION: Primer

<400> SEQUENCE: 16
gagcaggcaa gataaacgaa ggcaaagtag tgacaccgat tatttaaag 49

<210> SEQ ID NO 17
<211> LENGTH: 49
<212> TYPE: DNA
<213> ORGANISM: Artificial sequence
<220> FEATURE:
<223> OTHER INFORMATION: Primer

<400> SEQUENCE: 17
tatggaccct gaaaccacag ccacattgta accaccacga cggttgttg 49

<210> SEQ ID NO 18
<211> LENGTH: 49
<212> TYPE: DNA
<213> ORGANISM: Artificial sequence
<220> FEATURE:
<223> OTHER INFORMATION: Primer

<400> SEQUENCE: 18
tttagcaaca accgtcgtgg tggttacaat gtggctgtgg tttcagggt 49

<210> SEQ ID NO 19
<211> LENGTH: 49
<212> TYPE: DNA
<213> ORGANISM: Artificial sequence
<220> FEATURE:
<223> OTHER INFORMATION: Primer

<400> SEQUENCE: 19
ccagaaaccc tatacctgtg tggacgtaag gccatgaagc tttttcttt 49

<210> SEQ ID NO 20
<211> LENGTH: 49
<212> TYPE: DNA
<213> ORGANISM: Artificial sequence
<220> FEATURE:
<223> OTHER INFORMATION: Primer

<400> SEQUENCE: 20
attggaaaga aaaagcttca tggccttacg tccacacagg tatagggtt 49

<210> SEQ ID NO 21
<211> LENGTH: 22
<212> TYPE: DNA
<213> ORGANISM: Artificial sequence
<220> FEATURE:
<223> OTHER INFORMATION: Primer

<400> SEQUENCE: 21
cataagaaca cctttggtgg ag 22

<210> SEQ ID NO 22
<211> LENGTH: 22
<212> TYPE: DNA
<213> ORGANISM: Artificial sequence
<220> FEATURE:
<223> OTHER INFORMATION: Primer

<400> SEQUENCE: 22
aggattatca ttcataagtt tc 22

<210> SEQ ID NO 23
<211> LENGTH: 23
<212> TYPE: DNA
<213> ORGANISM: Artificial sequence
<220> FEATURE:
<223> OTHER INFORMATION: Primer

<400> SEQUENCE: 23
ttcttggagc tgggacatgt ttg 23

<210> SEQ ID NO 24
<211> LENGTH: 22
<212> TYPE: DNA
<213> ORGANISM: Artificial sequence
<220> FEATURE:
<223> OTHER INFORMATION: Primer

<400> SEQUENCE: 24
tgatgatatt tcataaataa tg 22

<210> SEQ ID NO 25
<211> LENGTH: 23
<212> TYPE: DNA
<213> ORGANISM: Artificial sequence
<220> FEATURE:
<223> OTHER INFORMATION: Primer

<400> SEQUENCE: 25
atgcgtccat ctttacagtc ctg 23

<210> SEQ ID NO 26
<211> LENGTH: 22
<212> TYPE: DNA
<213> ORGANISM: Artificial sequence
<220> FEATURE:
<223> OTHER INFORMATION: Primer

<400> SEQUENCE: 26

```
tacgtacgga ccaatcgaag tg                                                22


<210> SEQ ID NO 27
<211> LENGTH: 49
<212> TYPE: DNA
<213> ORGANISM: Artificial sequence
<220> FEATURE:
<223> OTHER INFORMATION: Primer

<400> SEQUENCE: 27

aattcgtttg agtacactac taatggcttt gttggcaata tgtttttgc                   49


<210> SEQ ID NO 28
<211> LENGTH: 49
<212> TYPE: DNA
<213> ORGANISM: Artificial sequence
<220> FEATURE:
<223> OTHER INFORMATION: Primer

<400> SEQUENCE: 28

atatagcaaa aacatattgc caacaaagcc attagtagtg tactcaaac                   49


<210> SEQ ID NO 29
<211> LENGTH: 49
<212> TYPE: DNA
<213> ORGANISM: Artificial sequence
<220> FEATURE:
<223> OTHER INFORMATION: Primer

<400> SEQUENCE: 29

tatggaccct gaaaccacag ccacattctt gttatttata aaaagacac                   49


<210> SEQ ID NO 30
<211> LENGTH: 49
<212> TYPE: DNA
<213> ORGANISM: Artificial sequence
<220> FEATURE:
<223> OTHER INFORMATION: Primer

<400> SEQUENCE: 30

ctcccgtgtc tttttataaa taacaagaat gtggctgtgg tttcagggt                   49


<210> SEQ ID NO 31
<211> LENGTH: 49
<212> TYPE: DNA
<213> ORGANISM: Artificial sequence
<220> FEATURE:
<223> OTHER INFORMATION: Primer

<400> SEQUENCE: 31

taccgtaggc gtccttagga aagatagaag gccatgaagc tttttcttt                   49


<210> SEQ ID NO 32
<211> LENGTH: 49
<212> TYPE: DNA
<213> ORGANISM: Artificial sequence
<220> FEATURE:
<223> OTHER INFORMATION: Primer

<400> SEQUENCE: 32

attggaaaga aaaagcttca tggccttcta tctttcctaa ggacgccta                   49


<210> SEQ ID NO 33
<211> LENGTH: 21
<212> TYPE: DNA
<213> ORGANISM: Artificial sequence
```

<220> FEATURE:
<223> OTHER INFORMATION: Primer

<400> SEQUENCE: 33
ttattgtttg gcatttgtag c 21

<210> SEQ ID NO 34
<211> LENGTH: 22
<212> TYPE: DNA
<213> ORGANISM: Artificial sequence
<220> FEATURE:
<223> OTHER INFORMATION: Primer

<400> SEQUENCE: 34
ccaagcatct cataaaccta tg 22

<210> SEQ ID NO 35
<211> LENGTH: 22
<212> TYPE: DNA
<213> ORGANISM: Artificial sequence
<220> FEATURE:
<223> OTHER INFORMATION: Primer

<400> SEQUENCE: 35
tgtgcagatg cagatgtgag ac 22

<210> SEQ ID NO 36
<211> LENGTH: 17
<212> TYPE: DNA
<213> ORGANISM: Artificial sequence
<220> FEATURE:
<223> OTHER INFORMATION: Primer

<400> SEQUENCE: 36
agttattgat accgtac 17

<210> SEQ ID NO 37
<211> LENGTH: 19
<212> TYPE: DNA
<213> ORGANISM: Artificial sequence
<220> FEATURE:
<223> OTHER INFORMATION: Primer

<400> SEQUENCE: 37
cgagataccg taggcgtcc 19

<210> SEQ ID NO 38
<211> LENGTH: 24
<212> TYPE: DNA
<213> ORGANISM: Artificial sequence
<220> FEATURE:
<223> OTHER INFORMATION: Primer

<400> SEQUENCE: 38
ttatgtatgc tcttctgact tttc 24

<210> SEQ ID NO 39
<211> LENGTH: 49
<212> TYPE: DNA
<213> ORGANISM: Artificial sequence
<220> FEATURE:
<223> OTHER INFORMATION: Primer

<400> SEQUENCE: 39
aataattaga gattaaatcg ctcatttttt gccagtttct tcaggcttc 49

<210> SEQ ID NO 40
<211> LENGTH: 49
<212> TYPE: DNA
<213> ORGANISM: Artificial sequence
<220> FEATURE:
<223> OTHER INFORMATION: Primer

<400> SEQUENCE: 40
agcctgaaga aactggcaaa aaatgagcga tttaatctct aattattag 49

<210> SEQ ID NO 41
<211> LENGTH: 49
<212> TYPE: DNA
<213> ORGANISM: Artificial sequence
<220> FEATURE:
<223> OTHER INFORMATION: Primer

<400> SEQUENCE: 41
tatggaccct gaaaccacag ccacattttt caatcattgg agcaatcat 49

<210> SEQ ID NO 42
<211> LENGTH: 49
<212> TYPE: DNA
<213> ORGANISM: Artificial sequence
<220> FEATURE:
<223> OTHER INFORMATION: Primer

<400> SEQUENCE: 42
taaaatgatt gctccaatga ttgaaaaatg tggctgtggt ttcagggtc 49

<210> SEQ ID NO 43
<211> LENGTH: 49
<212> TYPE: DNA
<213> ORGANISM: Artificial sequence
<220> FEATURE:
<223> OTHER INFORMATION: Primer

<400> SEQUENCE: 43
accgtaggtg ttgtttggga aagtggaagg ccatgaagct tttctttc 49

<210> SEQ ID NO 44
<211> LENGTH: 49
<212> TYPE: DNA
<213> ORGANISM: Artificial sequence
<220> FEATURE:
<223> OTHER INFORMATION: Primer

<400> SEQUENCE: 44
ttggaaagaa aaagcttcat ggccttccac tttcccaaac aacacctac 49

<210> SEQ ID NO 45
<211> LENGTH: 23
<212> TYPE: DNA
<213> ORGANISM: Artificial sequence
<220> FEATURE:
<223> OTHER INFORMATION: Primer

<400> SEQUENCE: 45
ttattgctta gcgttggtag cag 23

<210> SEQ ID NO 46
<211> LENGTH: 21
<212> TYPE: DNA
<213> ORGANISM: Artificial sequence
<220> FEATURE:
<223> OTHER INFORMATION: Primer

<400> SEQUENCE: 46
tttttggtgg ttccggcttc c 21

<210> SEQ ID NO 47
<211> LENGTH: 22
<212> TYPE: DNA
<213> ORGANISM: Artificial sequence
<220> FEATURE:
<223> OTHER INFORMATION: Primer

<400> SEQUENCE: 47
aaagttggca tagcggaaac tt 22

<210> SEQ ID NO 48
<211> LENGTH: 16
<212> TYPE: DNA
<213> ORGANISM: Artificial sequence
<220> FEATURE:
<223> OTHER INFORMATION: Primer

<400> SEQUENCE: 48
gtcattgaca ccatct 16

<210> SEQ ID NO 49
<211> LENGTH: 19
<212> TYPE: DNA
<213> ORGANISM: Artificial sequence
<220> FEATURE:
<223> OTHER INFORMATION: Primer

<400> SEQUENCE: 49
agagataccg taggtgttg 19

<210> SEQ ID NO 50
<211> LENGTH: 33
<212> TYPE: DNA
<213> ORGANISM: Artificial sequence
<220> FEATURE:
<223> OTHER INFORMATION: Primer

<400> SEQUENCE: 50
aattggcgcg ccatgaaagc tctggtttat cac 33

<210> SEQ ID NO 51
<211> LENGTH: 49
<212> TYPE: DNA
<213> ORGANISM: Artificial sequence
<220> FEATURE:
<223> OTHER INFORMATION: Primer

<400> SEQUENCE: 51
tgaatcatga gttttatgtt aattagctca ggcagcgcct gcgttcgag 49

<210> SEQ ID NO 52
<211> LENGTH: 49
<212> TYPE: DNA
<213> ORGANISM: Artificial sequence
<220> FEATURE:
<223> OTHER INFORMATION: Primer

<400> SEQUENCE: 52
atcctctcga acgcaggcgc tgcctgagct aattaacata aaactcatg 49

<210> SEQ ID NO 53
<211> LENGTH: 34
<212> TYPE: DNA
<213> ORGANISM: Artificial sequence
<220> FEATURE:
<223> OTHER INFORMATION: Primer

<400> SEQUENCE: 53
aattgtttaa acaagtaaat aaattaatca gcat 34

<210> SEQ ID NO 54
<211> LENGTH: 49
<212> TYPE: DNA
<213> ORGANISM: Artificial sequence
<220> FEATURE:
<223> OTHER INFORMATION: Primer

<400> SEQUENCE: 54
acacaataca ataacaagaa gaacaaaatg aaagctctgg tttatcacg 49

<210> SEQ ID NO 55
<211> LENGTH: 49
<212> TYPE: DNA
<213> ORGANISM: Artificial sequence
<220> FEATURE:
<223> OTHER INFORMATION: Primer

<400> SEQUENCE: 55
agcgtataca tctgttggga aagtagaagg ccatgaagct tttctttc 49

<210> SEQ ID NO 56
<211> LENGTH: 49
<212> TYPE: DNA
<213> ORGANISM: Artificial sequence
<220> FEATURE:
<223> OTHER INFORMATION: Primer

<400> SEQUENCE: 56
ttggaaagaa aaagcttcat ggccttctac tttcccaaca gatgtatac 49

<210> SEQ ID NO 57
<211> LENGTH: 22
<212> TYPE: DNA
<213> ORGANISM: Artificial sequence
<220> FEATURE:
<223> OTHER INFORMATION: Primer

<400> SEQUENCE: 57
ttattgttta gcgttagtag cg 22

<210> SEQ ID NO 58
<211> LENGTH: 72
<212> TYPE: DNA
<213> ORGANISM: Artificial sequence
<220> FEATURE:
<223> OTHER INFORMATION: Primer

<400> SEQUENCE: 58
cataatcaat ctcaaagaga acaacacaat acaataacaa gaagaacaaa atgaaagctc 60
tggtttatca cg 72

<210> SEQ ID NO 59
<211> LENGTH: 21
<212> TYPE: DNA
<213> ORGANISM: Artificial sequence
<220> FEATURE:
<223> OTHER INFORMATION: Primer

<400> SEQUENCE: 59
taggcataat caccgaagaa g 21

<210> SEQ ID NO 60
<211> LENGTH: 21
<212> TYPE: DNA
<213> ORGANISM: Artificial sequence
<220> FEATURE:
<223> OTHER INFORMATION: Primer

<400> SEQUENCE: 60
aaaatggtaa gcagctgaaa g 21

<210> SEQ ID NO 61
<211> LENGTH: 17
<212> TYPE: DNA
<213> ORGANISM: Artificial sequence
<220> FEATURE:
<223> OTHER INFORMATION: Primer

<400> SEQUENCE: 61
agttgttaga actgttg 17

<210> SEQ ID NO 62
<211> LENGTH: 19
<212> TYPE: DNA
<213> ORGANISM: Artificial Sequence
<220> FEATURE:
<223> OTHER INFORMATION: oBP553

<400> SEQUENCE: 62
gacgatagcg tatacatct 19

<210> SEQ ID NO 63
<211> LENGTH: 22
<212> TYPE: DNA
<213> ORGANISM: Artificial sequence
<220> FEATURE:
<223> OTHER INFORMATION: Primer

<400> SEQUENCE: 63
cttagcctct agccatagcc at 22

<210> SEQ ID NO 64
<211> LENGTH: 23
<212> TYPE: DNA
<213> ORGANISM: Artificial sequence
<220> FEATURE:
<223> OTHER INFORMATION: Primer

<400> SEQUENCE: 64
ttagttttgc tggccgcatc ttc 23

<210> SEQ ID NO 65
<211> LENGTH: 21
<212> TYPE: DNA
<213> ORGANISM: Artificial sequence
<220> FEATURE:
<223> OTHER INFORMATION: Primer

<400> SEQUENCE: 65
cccattaata tactattgag a 21

<210> SEQ ID NO 66
<211> LENGTH: 7523
<212> TYPE: DNA
<213> ORGANISM: Artificial sequence
<220> FEATURE:
<223> OTHER INFORMATION: Plasmid

<400> SEQUENCE: 66

```
ccagcttttg ttccctttag tgagggttaa ttgcgcgctt ggcgtaatca tggtcatagc     60
tgtttcctgt gtgaaattgt tatccgctca caattccaca caacatagga gccggaagca    120
taaagtgtaa agcctggggt gcctaatgag tgaggtaact cacattaatt gcgttgcgct    180
cactgcccgc tttccagtcg ggaaacctgt cgtgccagct gcattaatga atcggccaac    240
gcgcggggag aggcggtttg cgtattgggc gctcttccgc ttcctcgctc actgactcgc    300
tgcgctcggt cgttcggctg cggcgagcgg tatcagctca ctcaaaggcg gtaatacggt    360
tatccacaga atcaggggat aacgcaggaa agaacatgtg agcaaaaggc cagcaaaagg    420
ccaggaaccg taaaaaggcc gcgttgctgg cgtttttcca taggctccgc ccccctgacg    480
agcatcacaa aaatcgacgc tcaagtcaga ggtggcgaaa cccgacagga ctataaagat    540
accaggcgtt tccccctgga agctccctcg tgcgctctcc tgttccgacc ctgccgctta    600
ccggatacct gtccgccttt ctcccttcgg gaagcgtggc gctttctcat agctcacgct    660
gtaggtatct cagttcggtg taggtcgttc gctccaagct gggctgtgtg cacgaacccc    720
ccgttcagcc cgaccgctgc gccttatccg gtaactatcg tcttgagtcc aacccggtaa    780
gacacgactt atcgccactg gcagcagcca ctggtaacag gattagcaga gcgaggtatg    840
taggcggtgc tacagagttc ttgaagtggt ggcctaacta cggctacact agaaggacag    900
tatttggtat ctgcgctctg ctgaagccag ttaccttcgg aaaaagagtt ggtagctctt    960
gatccggcaa acaaaccacc gctggtagcg gtggtttttt tgtttgcaag cagcagatta   1020
cgcgcagaaa aaaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactccccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
ccgcctccat ccagtctatt aattgttgcc gggaagctag agtaagtagt tcgccagtta   1500
atagtttgcg caacgttgtt gccattgcta caggcatcgt ggtgtcacgc tcgtcgtttg   1560
gtatggcttc attcagctcc ggttcccaac gatcaaggcg agttacatga tcccccatgt   1620
tgtgcaaaaa agcggttagc tccttcggtc ctccgatcgt tgtcagaagt aagttggccg   1680
cagtgttatc actcatggtt atggcagcac tgcataattc tcttactgtc atgccatccg   1740
taagatgctt ttctgtgact ggtgagtact caaccaagtc attctgagaa tagtgtatgc   1800
ggcgaccgag ttgctcttgc ccggcgtcaa tacgggataa taccgcgcca catagcagaa   1860
ctttaaaagt gctcatcatt ggaaaacgtt cttcggggcg aaaactctca aggatcttac   1920
cgctgttgag atccagttcg atgtaaccca ctcgtgcacc caactgatct tcagcatctt   1980
ttactttcac cagcgtttct gggtgagcaa aaacaggaag gcaaaatgcc gcaaaaaagg   2040
gaataagggc gacacggaaa tgttgaatac tcatactctt cctttttcaa tattattgaa   2100
gcatttatca gggttattgt ctcatgagcg gatacatatt tgaatgtatt tagaaaaata   2160
aacaaatagg ggttccgcgc acatttcccc gaaaagtgcc acctgaacga agcatctgtg   2220
cttcattttg tagaacaaaa atgcaacgcg agagcgctaa tttttcaaac aaagaatctg   2280
agctgcattt ttacagaaca gaaatgcaac gcgaaagcgc tattttacca acgaagaatc   2340
```

```
tgtgcttcat ttttgtaaaa caaaaatgca acgcgagagc gctaattttt caaacaaaga   2400
atctgagctg catttttaca gaacagaaat gcaacgcgag agcgctattt taccaacaaa   2460
gaatctatac ttcttttttg ttctacaaaa atgcatcccg agagcgctat ttttctaaca   2520
aagcatctta gattactttt tttctccttt gtgcgctcta taatgcagtc tcttgataac   2580
tttttgcact gtaggtccgt taaggttaga agaaggctac tttggtgtct attttctctt   2640
ccataaaaaa agcctgactc cacttcccgc gtttactgat tactagcgaa gctgcgggtg   2700
catttttttca agataaaggc atccccgatt atattctata ccgatgtgga ttgcgcatac   2760
tttgtgaaca gaaagtgata gcgttgatga ttcttcattg gtcagaaaat tatgaacggt   2820
ttcttctatt ttgtctctat atactacgta taggaaatgt ttacattttc gtattgtttt   2880
cgattcactc tatgaatagt tcttactaca attttttttgt ctaaagagta atactagaga   2940
taaacataaa aaatgtagag gtcgagttta gatgcaagtt caaggagcga aaggtggatg   3000
ggtaggttat atagggatat agcacagaga tatatagcaa agagatactt ttgagcaatg   3060
tttgtggaag cggtattcgc aatattttag tagctcgtta cagtccggtg cgtttttggt   3120
tttttgaaag tgcgtcttca gagcgctttt ggttttcaaa agcgctctga agttcctata   3180
ctttctagag aataggaact tcggaatagg aacttcaaag cgtttccgaa aacgagcgct   3240
tccgaaaatg caacgcgagc tgcgcacata cagctcactg ttcacgtcgc acctatatct   3300
gcgtgttgcc tgtatatata tatacatgag aagaacggca tagtgcgtgt ttatgcttaa   3360
atgcgtactt atatgcgtct atttatgtag gatgaaaggt agtctagtac ctcctgtgat   3420
attatcccat tccatgcggg gtatcgtatg cttccttcag cactaccctt tagctgttct   3480
atatgctgcc actcctcaat tggattagtc tcatccttca atgctatcat ttcctttgat   3540
attggatcat ctaagaaacc attattatca tgacattaac ctataaaaat aggcgtatca   3600
cgaggccctt tcgtctcgcg cgtttcggtg atgacggtga aaacctctga cacatgcagc   3660
tcccggagac ggtcacagct tgtctgtaag cggatgccgg gagcagacaa gcccgtcagg   3720
gcgcgtcagc gggtgttggc gggtgtcggg gctggcttaa ctatgcggca tcagagcaga   3780
ttgtactgag agtgcaccat aaattcccgt tttaagagct tggtgagcgc taggagtcac   3840
tgccaggtat cgtttgaaca cggcattagt cagggaagtc ataacacagt cctttcccgc   3900
aattttcttt ttctattact cttggcctcc tctagtacac tctatatttt tttatgcctc   3960
ggtaatgatt ttcatttttt tttttcccct agcggatgac tctttttttt tcttagcgat   4020
tggcattatc acataatgaa ttatacatta tataaagtaa tgtgatttct tcgaagaata   4080
tactaaaaaa tgagcaggca agataaacga aggcaaagat gacagagcag aaagccctag   4140
taaagcgtat tacaaatgaa accaagattc agattgcgat ctctttaaag ggtggtcccc   4200
tagcgataga gcactcgatc ttcccagaaa aagaggcaga agcagtagca gaacaggcca   4260
cacaatcgca agtgattaac gtccacacag gtatagggtt tctggaccat atgatacatg   4320
ctctggccaa gcattccggc tggtcgctaa tcgttgagtg cattggtgac ttacacatag   4380
acgaccatca caccactgaa gactgcggga ttgctctcgg tcaagctttt aaagaggccc   4440
tactggcgcg tggagtaaaa aggtttggat caggatttgc gcctttggat gaggcacttt   4500
ccagagcggt ggtagatctt tcgaacaggc cgtacgcagt tgtcgaactt ggtttgcaaa   4560
gggagaaagt aggagatctc tcttgcgaga tgatcccgca ttttcttgaa agctttgcag   4620
aggctagcag aattaccctc cacgttgatt gtctgcgagg caagaatgat catcaccgta   4680
gtgagagtgc gttcaaggct cttgcggttg ccataagaga agccacctcg cccaatggta   4740
```

```
ccaacgatgt tccctccacc aaaggtgttc ttatgtagtg acaccgatta tttaaagctg   4800

cagcatacga tatatataca tgtgtatata tgtataccta tgaatgtcag taagtatgta   4860

tacgaacagt atgatactga agatgacaag gtaatgcatc attctatacg tgtcattctg   4920

aacgaggcgc gctttccttt tttctttttg ctttttcttt ttttttctct tgaactcgac   4980

ggatctatgc ggtgtgaaat accgcacaga tgcgtaagga gaaaataccg catcaggaaa   5040

ttgtaaacgt taatattttg ttaaaattcg cgttaaattt ttgttaaatc agctcatttt   5100

ttaaccaata ggccgaaatc ggcaaaatcc cttataaatc aaaagaatag accgagatag   5160

ggttgagtgt tgttccagtt tggaacaaga gtccactatt aaagaacgtg gactccaacg   5220

tcaaagggcg aaaaaccgtc tatcagggcg atggcccact acgtgaacca tcaccctaat   5280

caagtttttt ggggtcgagg tgccgtaaag cactaaatcg gaaccctaaa gggagccccc   5340

gatttagagc ttgacgggga aagccggcga acgtggcgag aaaggaaggg aagaaagcga   5400

aaggagcggg cgctagggcg ctggcaagtg tagcggtcac gctgcgcgta accaccacac   5460

ccgccgcgct taatgcgccg ctacagggcg cgtcgcgcca ttcgccattc aggctgcgca   5520

actgttggga agggcgatcg gtgcgggcct cttcgctatt acgccagctg gcgaaagggg   5580

gatgtgctgc aaggcgatta agttgggtaa cgccagggtt ttcccagtca cgacgttgta   5640

aaacgacggc cagtgagcgc gcgtaatacg actcactata gggcgaattg ggtaccgggc   5700

ccccctcga ggtattagaa gccgccgagc gggcgacagc cctccgacgg aagactctcc   5760

tccgtgcgtc ctcgtcttca ccggtcgcgt tcctgaaacg cagatgtgcc tcgcgccgca   5820

ctgctccgaa caataaagat tctacaatac tagcttttat ggttatgaag aggaaaaatt   5880

ggcagtaacc tggccccaca aaccttcaaa ttaacgaatc aaattaacaa ccataggatg   5940

ataatgcgat tagtttttta gccttatttc tggggtaatt aatcagcgaa gcgatgattt   6000

ttgatctatt aacagatata taaatggaaa agctgcataa ccactttaac taatactttc   6060

aacattttca gtttgtatta cttcttattc aaatgtcata aaagtatcaa caaaaaattg   6120

ttaatatacc tctatacttt aacgtcaagg agaaaaatgt ccaatttact gcccgtacac   6180

caaaatttgc ctgcattacc ggtcgatgca acgagtgatg aggttcgcaa gaacctgatg   6240

gacatgttca gggatcgcca ggcgttttct gagcatacct ggaaaatgct tctgtccgtt   6300

tgccggtcgt gggcggcatg gtgcaagttg aataaccgga aatggtttcc cgcagaacct   6360

gaagatgttc gcgattatct tctatatctt caggcgcgcg gtctggcagt aaaaactatc   6420

cagcaacatt tgggccagct aaacatgctt catcgtcggt ccgggctgcc acgaccaagt   6480

gacagcaatg ctgtttcact ggttatgcgg cggatccgaa aagaaaacgt tgatgccggt   6540

gaacgtgcaa aacaggctct agcgttcgaa cgcactgatt tcgaccaggt tcgttcactc   6600

atggaaaata gcgatcgctg ccaggatata cgtaatctgg catttctggg gattgcttat   6660

aacaccctgt tacgtatagc cgaaattgcc aggatcaggg ttaaagatat ctcacgtact   6720

gacggtggga gaatgttaat ccatattggc agaacgaaaa cgctggttag caccgcaggt   6780

gtagagaagg cacttagcct gggggtaact aaactggtcg agcgatggat ttccgtctct   6840

ggtgtagctg atgatccgaa taactacctg ttttgccggg tcagaaaaaa tggtgttgcc   6900

gcgccatctg ccaccagcca gctatcaact cgcgccctgg aagggatttt tgaagcaact   6960

catcgattga tttacggcgc taaggatgac tctggtcaga gatacctggc ctggtctgga   7020

cacagtgccc gtgtcggagc cgcgcgagat atggcccgcg ctggagtttc aataccggag   7080

atcatgcaag ctggtggctg gaccaatgta aatattgtca tgaactatat ccgtaacctg   7140
```

```
gatagtgaaa caggggcaat ggtgcgcctg ctggaagatg gcgattagga gtaagcgaat   7200

ttcttatgat ttatgatttt tattattaaa taagttataa aaaaaataag tgtatacaaa   7260

ttttaaagtg actcttaggt tttaaaacga aaattcttat tcttgagtaa ctctttcctg   7320

taggtcaggt tgctttctca ggtatagcat gaggtcgctc ttattgacca cacctctacc   7380

ggcatgccga gcaaatgcct gcaaatcgct ccccatttca cccaattgta gatatgctaa   7440

ctccagcaat gagttgatga atctcggtgt gtattttatg tcctcagagg acaacacctg   7500

tggtccgcca ccgcggtgga gct                                           7523
```

<210> SEQ ID NO 67
<211> LENGTH: 15456
<212> TYPE: DNA
<213> ORGANISM: Artificial sequence
<220> FEATURE:
<223> OTHER INFORMATION: Template

<400> SEQUENCE: 67

```
aaagagtaat actagagata aacataaaaa atgtagaggt cgagtttaga tgcaagttca     60

aggagcgaaa ggtggatggg taggttatat agggatatag cacagagata tatagcaaag    120

agatactttt gagcaatgtt tgtggaagcg gtattcgcaa tattttagta gctcgttaca    180

gtccggtgcg tttttggttt tttgaaagtg cgtcttcaga gcgcttttgg ttttcaaaag    240

cgctctgaag ttcctatact ttctagagaa taggaacttc ggaataggaa cttcaaagcg    300

tttccgaaaa cgagcgcttc cgaaaatgca acgcgagctg cgcacataca gctcactgtt    360

cacgtcgcac ctatatctgc gtgttgcctg tatatatata tacatgagaa gaacggcata    420

gtgcgtgttt atgcttaaat gcgtacttat atgcgtctat ttatgtagga tgaaaggtag    480

tctagtacct cctgtgatat tatcccattc catgcggggt atcgtatgct tccttcagca    540

ctacccttta gctgttctat atgctgccac tcctcaattg gattagtctc atccttcaat    600

gctatcattt cctttgatat tggatcatac taagaaacca ttattatcat gacattaacc    660

tataaaaata ggcgtatcac gaggcccttt cgtctcgcgc gtttcggtga tgacggtgaa    720

aacctctgac acatgcagct cccggagacg gtcacagctt gtctgtaagc ggatgccggg    780

agcagacaag cccgtcaggg cgcgtcagcg ggtgttggcg ggtgtcgggg ctggcttaac    840

tatgcggcat cagagcagat tgtactgaga gtgcaccata aattcccgtt ttaagagctt    900

ggtgagcgct aggagtcact gccaggtatc gtttgaacac ggcattagtc agggaagtca    960

taacacagtc ctttcccgca attttctttt tctattactc ttggcctcct ctagtacact   1020

ctatattttt ttatgcctcg gtaatgattt tcattttttt ttttccacct agcggatgac   1080

tctttttttt tcttagcgat tggcattatc acataatgaa ttatacatta tataaagtaa   1140

tgtgatttct tcgaagaata tactaaaaaa tgagcaggca agataaacga aggcaaagat   1200

gacagagcag aaagccctag taaagcgtat tacaaatgaa accaagattc agattgcgat   1260

ctctttaaag ggtggtcccc tagcgataga gcactcgatc ttcccagaaa aagaggcaga   1320

agcagtagca gaacaggcca cacaatcgca agtgattaac gtccacacag gtatagggtt   1380

tctggaccat atgatacatg ctctggccaa gcattccggc tggtcgctaa tcgttgagtg   1440

cattggtgac ttacacatag acgaccatca caccactgaa gactgcggga ttgctctcgg   1500

tcaagctttt aaagaggccc taggggccgt gcgtggagta aaaaggtttg gatcaggatt   1560

tgcgcctttg gatgaggcac tttccagagc ggtggtagat ctttcgaaca ggccgtacgc   1620

agttgtcgaa cttggtttgc aaagggagaa agtaggagat ctctcttgcg agatgatccc   1680
```

```
gcattttctt gaaagctttg cagaggctag cagaattacc ctccacgttg attgtctgcg   1740
aggcaagaat gatcatcacc gtagtgagag tgcgttcaag gctcttgcgg ttgccataag   1800
agaagccacc tcgcccaatg gtaccaacga tgttccctcc accaaaggtg ttcttatgta   1860
gtgacaccga ttatttaaag ctgcagcata cgatatatat acatgtgtat atatgtatac   1920
ctatgaatgt cagtaagtat gtatacgaac agtatgatac tgaagatgac aaggtaatgc   1980
atcattctat acgtgtcatt ctgaacgagg cgcgctttcc tttttctttt ttgctttttc   2040
tttttttttc tcttgaactc gacggatcta tgcggtgtga aataccgcac agatgcgtaa   2100
ggagaaaata ccgcatcagg aaattgtaag cgttaatatt ttgttaaaat tcgcgttaaa   2160
tttttgttaa atcagctcat tttttaacca ataggccgaa atcggcaaaa tcccttataa   2220
atcaaaagaa tagaccgaga tagggttgag tgttgttcca gtttggaaca agagtccact   2280
attaaagaac gtggactcca acgtcaaagg gcgaaaaacc gtctatcagg gcgatggccc   2340
actacgtgaa ccatcaccct aatcaagttt tttggggtcg aggtgccgta aagcactaaa   2400
tcggaaccct aaagggagcc cccgatttag agcttgacgg ggaaagccgg cgaacgtggc   2460
gagaaaggaa gggaagaaag cgaaaggagc gggcgctagg gcgctggcaa gtgtagcggt   2520
cacgctgcgc gtaaccacca cacccgccgc gcttaatgcg ccgctacagg gcgcgtccat   2580
tcgccattca ggctgcgcaa ctgttgggaa gggcgcggtg cgggcctctt cgctattacg   2640
ccagctggcg aaagggggat gtgctgcaag gcgattaagt tgggtaacgc cagggttttc   2700
ccagtcacga cgttgtaaaa cgacggccag tgagcgcgcg taatacgact cactataggg   2760
cgaattgggt accgggcccc ccctcgaggt cgacggcgcg ccactggtag agagcgactt   2820
tgtatgcccc aattgcgaaa cccgcgatat ccttctcgat tctttagtac ccgaccagga   2880
caaggaaaag gaggtcgaaa cgtttttgaa gaaacaagag gaactacacg gaagctctaa   2940
agatggcaac cagccagaaa ctaagaaaat gaagttgatg gatccaactg gcaccgctgg   3000
cttgaacaac aataccagcc ttccaacttc tgtaaataac ggcggtacgc cagtgccacc   3060
agtaccgtta cctttcggta tacctccttt ccccatgttt ccaatgccct tcatgcctcc   3120
aacggctact atcacaaatc ctcatcaagc tgacgcaagc cctaagaaat gaataacaat   3180
actgacagta ctaaataatt gcctacttgg cttcacatac gttgcatacg tcgatataga   3240
taataatgat aatgacagca ggattatcgt aatacgtaat agctgaaaat ctcaaaaatg   3300
tgtgggtcat tacgtaaata atgataggaa tgggattctt ctatttttcc tttttccatt   3360
ctagcagccg tcgggaaaac gtggcatcct ctctttcggg ctcaattgga gtcacgctgc   3420
cgtgagcatc ctctctttcc atatctaaca actgagcacg taaccaatgg aaaagcatga   3480
gcttagcgtt gctccaaaaa agtattggat ggttaatacc atttgtctgt tctcttctga   3540
ctttgactcc tcaaaaaaaa aaatctacaa tcaacagatc gcttcaatta cgccctcaca   3600
aaaacttttt tccttcttct tcgcccacgt taaattttat ccctcatgtt gtctaacgga   3660
tttctgcact tgatttatta taaaaagaca aagacataat acttctctat caatttcagt   3720
tattgttctt ccttgcgtta ttcttctgtt cttctttttc ttttgtcata tataaccata   3780
accaagtaat acatattcaa actagtatga ctgacaaaaa aactcttaaa gacttaagaa   3840
atcgtagttc tgtttacgat tcaatggtta aatcacctaa tcgtgctatg ttgcgtgcaa   3900
ctggtatgca agatgaagac tttgaaaaac ctatcgtcgg tgtcatttca acttgggctg   3960
aaaacacacc ttgtaatatc cacttacatg actttggtaa actagccaaa gtcggtgtta   4020
aggaagctgg tgcttggcca gttcagttcg gaacaatcac ggtttctgat ggaatcgcca   4080
```

```
tgggaaccca aggaatgcgt ttctccttga catctcgtga tattattgca gattctattg   4140

aagcagccat gggaggtcat aatgcggatg cttttgtagc cattggcggt tgtgataaaa   4200

acatgcccgg ttctgttatc gctatggcta acatggatat cccagccatt tttgcttacg   4260

gcggaacaat tgcacctggt aatttagacg gcaaagatat cgatttagtc tctgtctttg   4320

aaggtgtcgg ccattggaac cacggcgata tgaccaaaga agaagttaaa gctttggaat   4380

gtaatgcttg tcccggtcct ggaggctgcg gtggtatgta tactgctaac acaatggcga   4440

cagctattga agttttggga cttagccttc cgggttcatc ttctcacccg gctgaatccg   4500

cagaaaagaa agcagatatt gaagaagctg gtcgcgctgt tgtcaaaatg ctcgaaatgg   4560

gcttaaaacc ttctgacatt ttaacgcgtg aagcttttga agatgctatt actgtaacta   4620

tggctctggg aggttcaacc aactcaaccc ttcacctctt agctattgcc catgctgcta   4680

atgtggaatt gacacttgat gatttcaata ctttccaaga aaaagttcct catttggctg   4740

atttgaaacc ttctggtcaa tatgtattcc aagaccttta caaggtcgga ggggtaccag   4800

cagttatgaa atatctcctt aaaaatggct tccttcatgg tgaccgtatc acttgtactg   4860

gcaaaacagt cgctgaaaat ttgaaggctt ttgatgattt aacacctggt caaaaggtta   4920

ttatgccgct tgaaaatcct aaacgtgaag atggtccgct cattattctc catggtaact   4980

tggctccaga cggtgccgtt gccaaagttt ctggtgtaaa agtgcgtcgt catgtcggtc   5040

ctgctaaggt ctttaattct gaagaagaag ccattgaagc tgtcttgaat gatgatattg   5100

ttgatggtga tgttgttgtc gtacgttttg taggaccaaa gggcggtcct ggtatgcctg   5160

aaatgctttc cctttcatca atgattgttg gtaaagggca aggtgaaaaa gttgcccttc   5220

tgacagatgg ccgcttctca ggtggtactt atggtcttgt cgtgggtcat atcgctcctg   5280

aagcacaaga tggcggtcca atcgcctacc tgcaaacagg agacatagtc actattgacc   5340

aagacactaa ggaattacac tttgatatct ccgatgaaga gttaaaacat cgtcaagaga   5400

ccattgaatt gccaccgctc tattcacgcg gtatccttgg taaatatgct cacatcgttt   5460

cgtctgcttc taggggagcc gtaacagact tttggaagcc tgaagaaact ggcaaaaaat   5520

gttgtcctgg ttgctgtggt taagcggccg cgttaattca aattaattga tatagttttt   5580

taatgagtat tgaatctgtt tagaaataat ggaatattat ttttatttat ttatttatat   5640

tattggtcgg ctcttttctt ctgaaggtca atgacaaaat gatatgaagg aaataatgat   5700

ttctaaaatt ttacaacgta agatattttt acaaaagcct agctcatctt ttgtcatgca   5760

ctattttact cacgcttgaa attaacggcc agtccactgc ggagtcattt caaagtcatc   5820

ctaatcgatc tatcgttttt gatagctcat tttggagttc gcgattgtct tctgttattc   5880

acaactgttt taatttttat ttcattctgg aactcttcga gttctttgta aagtctttca   5940

tagtagctta ctttatcctc caacatattt aacttcatgt caatttcggc tcttaaattt   6000

tccacatcat caagttcaac atcatctttt aacttgaatt tattctctag ctcttccaac   6060

caagcctcat tgctccttga tttactggtg aaaagtgata cactttgcgc gcaatccagg   6120

tcaaaacttt cctgcaaaga attcaccaat ttctcgacat catagtacaa tttgttttgt   6180

tctcccatca caatttaata tacctgatgg attcttatga agcgctgggt aatggacgtg   6240

tcactctact tcgccttttt ccctactcct tttagtacgg aagacaatgc taataaataa   6300

gagggtaata ataatattat taatcggcaa aaaagattaa acgccaagcg tttaattatc   6360

agaaagcaaa cgtcgtacca atccttgaat gcttcccaat tgtatattaa gagtcatcac   6420

agcaacatat tcttgttatt aaattaatta ttattgattt ttgatattgt ataaaaaaac   6480
```

```
caaatatgta taaaaaaagt gaataaaaaa taccaagtat ggagaaatat attagaagtc   6540
tatacgttaa accacccggg cccccccctcg aggtcgacgg tatcgataag cttgatatcg   6600
aattcctgca gcccggggga tccactagtt ctagagcggc cgctctagaa ctagtaccac   6660
aggtgttgtc ctctgaggac ataaaataca caccgagatt catcaactca ttgctggagt   6720
tagcatatct acaattgggt gaaatgggga gcgatttgca ggcatttgct cggcatgccg   6780
gtagaggtgt ggtcaataag agcgacctca tgctatacct gagaaagcaa cctgacctac   6840
aggaaagagt tactcaagaa taagaatttt cgttttaaaa cctaagagtc actttaaaat   6900
ttgtatacac ttattttttt tataacttat ttaataataa aaatcataaa tcataagaaa   6960
ttcgcttact cttaattaat caggcagcgc ctgcgttcga gaggatgatc ttcatcgcct   7020
tctccttggc gccattgagg aatacctgat aggcgtgctc gatctcggcc agctcgaagc   7080
gatgggtaat catcttcttc aacggaagct tgtcggtcga ggcgaccttc atcagcatgg   7140
gcgtcgtgtt cgtgttcacc agtcccgtgg tgatcgtcag gttcttgatc cagagcttct   7200
gaatctcgaa gtcaaccttg acgccatgca cgccgacgtt ggcgatgtgc gcgccgggct   7260
tgacgatctc ctggcagatg tcccaagtcg ccggtatgcc caccgcctcg atcgcaacat   7320
cgactccctc tgccgcaatc ctatgcacgg cttcgacaac gttctccgtg ccggagttga   7380
tggtgtgcgt tgccccgagc tccttggcga gctggaggcg attctcgtcc atgtcgatca   7440
cgatgatggt cgagggggag tagaactggg cggtcaacag tacggacatg ccgacggggc   7500
ccgcgccgac aatagccacc gcatcgcccg gctggacatt cccatactgg acgccgattt   7560
cgtggccggt gggcaggatg tcgctcagca ggacggcgat ttcgtcgtca attgtctggg   7620
ggatcttgta gaggctgttg tcggcatgcg ggatgcggac gtattcggcc tgcacgccat   7680
cgatcatgta acccaggatc cacccgccgt cgcggcaatg ggagtaaagc tgcttcttgc   7740
agtagtcgca cgagccgcaa gaagtgacgc aggaaatcag gaccttgtcg cctttcttga   7800
actgcgtgac actctcgccc acttcctcga tgacgcctac cccttcatgg cccaggatgc   7860
gcccgtcggc gacctctgga ttcttgcctt tgtagatgcc gagatccgtg ccgcagatcg   7920
tggtcttcaa aacccgtact actacatccg tgggcttttg aagggtgggc ttgggcttgt   7980
cttcaagcga gatcttgtgg tcaccgtgat aaaccagagc tttcatcctc agctattgta   8040
atatgtgtgt ttgtttggat tattaagaag aataattaca aaaaaaatta caaaggaagg   8100
taattacaac agaattaaga aaggacaaga aggaggaaga gaatcagttc attatttctt   8160
ctttgttata taacaaaccc aagtagcgat ttggccatac attaaaagtt gagaaccacc   8220
ctccctggca acagccacaa ctcgttacca ttgttcatca cgatcatgaa actcgctgtc   8280
agctgaaatt tcacctcagt ggatctctct ttttattctt catcgttcca ctaacctttt   8340
tccatcagct ggcagggaac ggaaagtgga atcccattta gcgagcttcc tcttttcttc   8400
aagaaaagac gaagcttgtg tgtgggtgcg cgcgctagta tctttccaca ttaagaaata   8460
taccataaag gttacttaga catcactatg gctatatata tatatatata tatatatgta   8520
acttagcacc atcgcgcgtg catcactgca tgtgttaacc gaaaagtttg gcgaacactt   8580
caccgacacg gtcatttaga tctgtcgtct gcattgcacg tcccttagcc ttaaatccta   8640
ggcgggagca ttctcgtgta attgtgcagc ctgcgtagca actcaacata gcgtagtcta   8700
cccagttttt caagggttta tcgttagaag attctccctt ttcttcctgc tcacaaatct   8760
taaagtcata cattgcacga ctaaatgcaa gcatgcggat cccccgggct gcaggaattc   8820
gatatcaagc ttatcgatac cgtcgactgg ccattaatct ttcccatatt agatttcgcc   8880
```

```
aagccatgaa agttcaagaa aggtctttag acgaattacc cttcatttct caaactggcg   8940
tcaagggatc ctggtatggt tttatcgttt tatttctggt tcttatagca tcgttttgga   9000
cttctctgtt cccattaggc ggttcaggag ccagcgcaga atcattcttt gaaggatact   9060
tatcctttcc aattttgatt gtctgttacg ttggacataa actgtatact agaaattgga   9120
ctttgatggt gaaactagaa gatatggatc ttgataccgg cagaaaacaa gtagatttga   9180
ctcttcgtag ggaagaaatg aggattgagc gagaaacatt agcaaaaaga tccttcgtaa   9240
caagattttt acatttctgg tgttgaaggg aaagatatga gctatacagc ggaatttcca   9300
tatcactcag attttgttat ctaatttttt ccttcccacg tccgcgggaa tctgtgtata   9360
ttactgcatc tagatatatg ttatcttatc ttggcgcgta catttaattt tcaacgtatt   9420
ctataagaaa ttgcgggagt ttttttcatg tagatgatac tgactgcacg caaatatagg   9480
catgatttat aggcatgatt tgatggctgt accgatagga acgctaagag taacttcaga   9540
atcgttatcc tggcggaaaa aattcatttg taaactttaa aaaaaaaagc caatatcccc   9600
aaaattatta agagcgcctc cattattaac taaaatttca ctcagcatcc acaatgtatc   9660
aggtatctac tacagatatt acatgtggcg aaaaagacaa gaacaatgca atagcgcatc   9720
aagaaaaaac acaaagcttt caatcaatga atcgaaaatg tcattaaaat agtatataaa   9780
ttgaaactaa gtcataaagc tataaaaaga aaatttattt aaatgcaaga tttaaagtaa   9840
attcacggcc ctgcaggcct cagctcttgt tttgttctgc aaataactta cccatctttt   9900
tcaaaacttt aggtgcaccc tcctttgcta gaataagttc tatccaatac atcctatttg   9960
gatctgcttg agcttctttc atcacggata cgaattcatt ttctgttctc acaattttgg  10020
acacaactct gtcttccgtt gccccgaaac tttctggcag ttttgagtaa ttccacatag  10080
gaatgtcatt ataactctgg ttcggaccat gaatttccct ctcaaccgtg taaccatcgt  10140
tattaatgat aaagcagatt gggtttatct tctctctaat ggctagtcct aattcttgga  10200
cagtcagttg caatgatcca tctccgataa acaataaatg tctagattct ttatctgcaa  10260
tttggctgcc tagagctgcg gggaaagtgt atcctataga tccccacaag ggttgaccaa  10320
taaaatgtga tttcgatttc agaaatatag atgaggcacc gaagaaagaa gtgccttgtt  10380
cagccacgat cgtctcatta ctttgggtca aattttcgac agcttgccac agtctatctt  10440
gtgacaacag cgcgttagaa ggtacaaaat cttcttgctt tttatctatg tacttgcctt  10500
tatattcaat ttcggacaag tcaagaagag atgatatcag ggattcgaag tcgaaatttt  10560
ggattctttc gttgaaaatt ttaccttcat cgatattcaa ggaaatcatt ttattttcat  10620
taagatggtg agtaaatgca cccgtactag aatcggtaag ctttacaccc aacataagaa  10680
taaaatcagc agattccaca aattccttca agtttggctc tgacagagta ccgttgtaaa  10740
tccccaaaaa tgagggcaat gcttcatcaa cagatgattt accaaagttc aaagtagtaa  10800
taggtaactt agtctttgaa ataaactgag taacagtctt ctctaggccg aacgatataa  10860
tttcatggcc tgtgattaca attggtttct tggcattctt cagactttcc tgtattttgt  10920
tcagaatctc ttgatcagat gtattcgacg tggaattttc cttcttaaga ggcaaggatg  10980
gtttttcagc cttagcggca gctacatcta caggtaaatt gatgtaaacc ggctttcttt  11040
cctttagtaa ggcagacaac actctatcaa tttcaacagt tgcattctcg gctgtcaata  11100
aagtcctggc agcagtaacc ggttcgtgca tcttcataaa gtgcttgaaa tcaccatcag  11160
ccaacgtatg gtgaacaaac ttaccttcgt tctgcacttt cgaggtagga gatcccacga  11220
tctcaacaac aggcaggttc tcagcatagg agcccgctaa gccattaact gcggataatt  11280
```

```
cgccaacacc aaatgtagtc aagaatgccg cagccttttt cgttcttgcg tacccgtcgg  11340
ccatatagga ggcatttaac tcattagcat ttcccaccca tttcatatct ttgtgtgaaa  11400
taatttgatc tagaaattgc aaattgtagt cacctggtac tccgaatatt tcttctatac  11460
ctaattcgtg taatctgtcc aacagatagt cacctactgt atacattttg tttactagtt  11520
tatgtgtgtt tattcgaaac taagttcttg gtgttttaaa actaaaaaaa agactaacta  11580
taaaagtaga atttaagaag tttaagaaat agatttacag aattacaatc aatacctacc  11640
gtctttatat acttattagt caagtagggg aataatttca gggaactggt ttcaaccttt  11700
tttttcagct ttttccaaat cagagagagc agaaggtaat agaaggtgta agaaaatgag  11760
atagatacat gcgtgggtca attgccttgt gtcatcattt actccaggca ggttgcatca  11820
ctccattgag gttgtgcccg ttttttgcct gtttgtgccc ctgttctctg tagttgcgct  11880
aagagaatgg acctatgaac tgatggttgg tgaagaaaac aatattttgg tgctgggatt  11940
cttttttttt ctggatgcca gcttaaaaag cgggctccat tatatttagt ggatgccagg  12000
aataaactgt tcacccagac acctacgatg ttatatattc tgtgtaaccc gccccctatt  12060
ttgggcatgt acgggttaca gcagaattaa aaggctaatt ttttgactaa ataaagttag  12120
gaaaatcact actattaatt atttacgtat tctttgaaat ggcagtattg ataatgataa  12180
actcgaactg aaaaagcgtg ttttttattc aaaatgattc taactccctt acgtaatcaa  12240
ggaatctttt tgccttggcc tccgcgtcat taaacttctt gttgttgacg ctaacattca  12300
acgctagtat atattcgttt ttttcaggta agttcttttc aacgggtctt actgatgagg  12360
cagtcgcgtc tgaacctgtt aagaggtcaa atatgtcttc ttgaccgtac gtgtcttgca  12420
tgttattagc tttgggaatt tgcatcaagt cataggaaaa tttaaatctt ggctctcttg  12480
ggctcaaggt gacaaggtcc tcgaaaatag ggcgcgcccc accgcggtgg agctccagct  12540
tttgttccct ttagtgaggg ttaattgcgc gcttggcgta atcatggtca tagctgtttc  12600
ctgtgtgaaa ttgttatccg ctcacaattc cacacaacat acgagccgga agcataaagt  12660
gtaaagcctg gggtgcctaa tgagtgagct aactcacatt aattgcgttg cgctcactgc  12720
ccgctttcca gtcgggaaac ctgtcgtgcc agctgcatta atgaatcggc caacgcgcgg  12780
ggagaggcgg tttgcgtatt gggcgctctt ccgcttcctc gctcactgac tcgctgcgct  12840
cggtcgttcg gctgcggcga gcggtatcag ctcactcaaa ggcggtaata cggttatcca  12900
cagaatcagg ggataacgca ggaaagaaca tgtgagcaaa aggccagcaa aaggccagga  12960
accgtaaaaa ggccgcgttg ctggcgtttt tccataggct ccgcccccct gacgagcatc  13020
acaaaaatcg acgctcaagt cagaggtggc gaaacccgac aggactataa agataccagg  13080
cgtttccccc tggaagctcc ctcgtgcgct ctcctgttcc gaccctgccg cttaccggat  13140
acctgtccgc ctttctccct tcgggaagcg tggcgctttc tcatagctca cgctgtaggt  13200
atctcagttc ggtgtaggtc gttcgctcca agctgggctg tgtgcacgaa ccccccgttc  13260
agcccgaccg ctgcgcctta tccggtaact atcgtcttga gtccaacccg gtaagacacg  13320
acttatcgcc actggcagca gccactggta acaggattag cagagcgagg tatgtaggcg  13380
gtgctacaga gttcttgaag tggtggccta actacggcta cactagaaga acagtatttg  13440
gtatctgcgc tctgctgaag ccagttacct tcggaaaaag agttggtagc tcttgatccg  13500
gcaaacaaac caccgctggt agcggtggtt tttttgtttg caagcagcag attacgcgca  13560
gaaaaaaagg atctcaagaa gatcctttga tcttttctac ggggtctgac gctcagtgga  13620
acgaaaactc acgttaaggg attttggtca tgagattatc aaaaaggatc ttcacctaga  13680
```

```
tccttttaaa ttaaaaatga agttttaaat caatctaaag tatatatgag taaacttggt  13740
ctgacagtta ccaatgctta atcagtgagg cacctatctc agcgatctgt ctatttcgtt  13800
catccatagt tgcctgactc cccgtcgtgt agataactac gatacgggag ggcttaccat  13860
ctggccccag tgctgcaatg ataccgcgag acccacgctc accggctcca gatttatcag  13920
caataaacca gccagccgga agggccgagc gcagaagtgg tcctgcaact ttatccgcct  13980
ccatccagtc tattaattgt tgccgggaag ctagagtaag tagttcgcca gttaatagtt  14040
tgcgcaacgt tgttgccatt gctacaggca tcgtggtgtc acgctcgtcg tttggtatgg  14100
cttcattcag ctccggttcc caacgatcaa ggcgagttac atgatccccc atgttgtgca  14160
aaaaagcggt tagctccttc ggtcctccga tcgttgtcag aagtaagttg gccgcagtgt  14220
tatcactcat ggttatggca gcactgcata attctcttac tgtcatgcca tccgtaagat  14280
gcttttctgt gactggtgag tactcaacca agtcattctg agaatagtgt atgcggcgac  14340
cgagttgctc ttgcccggcg tcaatacggg ataataccgc gccacatagc agaactttaa  14400
aagtgctcat cattggaaaa cgttcttcgg ggcgaaaact ctcaaggatc ttaccgctgt  14460
tgagatccag ttcgatgtaa cccactcgtg cacccaactg atcttcagca tcttttactt  14520
tcaccagcgt ttctgggtga gcaaaaacag gaaggcaaaa tgccgcaaaa aagggaataa  14580
gggcgacacg gaaatgttga atactcatac tcttcctttt tcaatattat tgaagcattt  14640
atcagggtta ttgtctcatg agcggataca tatttgaatg tatttagaaa aataaacaaa  14700
taggggttcc gcgcacattt ccccgaaaag tgccacctga acgaagcatc tgtgcttcat  14760
tttgtagaac aaaaatgcaa cgcgagagcg ctaatttttc aaacaaagaa tctgagctgc  14820
atttttacag aacagaaatg caacgcgaaa gcgctatttt accaacgaag aatctgtgct  14880
tcatttttgt aaaacaaaaa tgcaacgcga gagcgctaat tttcaaaca aagaatctga  14940
gctgcatttt tacagaacag aaatgcaacg cgagagcgct attttaccaa caaagaatct  15000
atacttcttt tttgttctac aaaaatgcat cccgagagcg ctatttttct aacaaagcat  15060
cttagattac ttttttctc ctttgtgcgc tctataatgc agtctcttga taactttttg  15120
cactgtaggt ccgttaaggt tagaagaagg ctactttggt gtctattttc tcttccataa  15180
aaaaagcctg actccacttc ccgcgtttac tgattactag cgaagctgcg ggtgcatttt  15240
ttcaagataa aggcatcccc gattatattc tataccgatg tggattgcgc atactttgtg  15300
aacagaaagt gatagcgttg atgattcttc attggtcaga aaattatgaa cggtttcttc  15360
tattttgtct ctatatacta cgtataggaa atgtttacat tttcgtattg ttttcgattc  15420
actctatgaa tagttcttac tacaattttt ttgtct                            15456
```

<210> SEQ ID NO 68
<211> LENGTH: 1559
<212> TYPE: DNA
<213> ORGANISM: Artificial sequence
<220> FEATURE:
<223> OTHER INFORMATION: Template

<400> SEQUENCE: 68

```
gcattgcgga ttacgtattc taatgttcag taccgttcgt ataatgtatg ctatacgaag     60
ttatgcagat tgtactgaga gtgcaccata ccaccttttc aattcatcat ttttttttta    120
ttcttttttt tgatttcggt ttccttgaaa tttttttgat tcggtaatct ccgaacagaa    180
ggaagaacga aggaaggagc acagacttag attggtatat atacgcatat gtagtgttga    240
agaaacatga aattgcccag tattcttaac ccaactgcac agaacaaaaa cctgcaggaa    300
```

```
acgaagataa atcatgtcga aagctacata taaggaacgt gctgctactc atcctagtcc    360

tgttgctgcc aagctattta atatcatgca cgaaaagcaa acaaacttgt gtgcttcatt    420

ggatgttcgt accaccaagg aattactgga gttagttgaa gcattaggtc ccaaaatttg    480

tttactaaaa acacatgtgg atatcttgac tgatttttcc atggagggca cagttaagcc    540

gctaaaggca ttatccgcca agtacaattt tttactcttc gaagacagaa aatttgctga    600

cattggtaat acagtcaaat tgcagtactc tgcgggtgta tacagaatag cagaatgggc    660

agacattacg aatgcacacg gtgtggtggg cccaggtatt gttagcggtt tgaagcaggc    720

ggcagaagaa gtaacaaagg aacctagagg ccttttgatg ttagcagaat tgtcatgcaa    780

gggctcccta tctactggag aatatactaa gggtactgtt gacattgcga agagcgacaa    840

agattttgtt atcggcttta ttgctcaaag agacatgggt ggaagagatg aaggttacga    900

ttggttgatt atgacacccg gtgtgggttt agatgacaag ggagacgcat tgggtcaaca    960

gtatagaacc gtggatgatg tggtctctac aggatctgac attattattg ttggaagagg   1020

actatttgca aagggaaggg atgctaaggt agagggtgaa cgttacagaa aagcaggctg   1080

ggaagcatat ttgagaagat gcggccagca aaactaaaaa actgtattat aagtaaatgc   1140

atgtatacta aactcacaaa ttagagcttc aatttaatta tatcagttat taccctatgc   1200

ggtgtgaaat accgcacaga tgcgtaagga gaaaataccg catcaggaaa ttgtaaacgt   1260

taatattttg ttaaaattcg cgttaaattt ttgttaaatc agctcatttt ttaaccaata   1320

ggccgaaatc ggcaaaatcc cttataaatc aaaagaatag accgagatag ggttgagtgt   1380

tgttccagtt tggaacaaga gtccactatt aaagaacgtg gactccaacg tcaaagggcg   1440

aaaaaccgtc tatcagggcg atggcccact acgtgaacca tcaccctaat caagataact   1500

tcgtataatg tatgctatac gaacggtacc agtgatgata caacgagtta gccaaggtg    1559
```

<210> SEQ ID NO 69
<211> LENGTH: 2237
<212> TYPE: DNA
<213> ORGANISM: Artificial Sequence
<220> FEATURE:
<223> OTHER INFORMATION: PDC1 Fragment A-ilvDSm

<400> SEQUENCE: 69

```
ttatgtatgc tcttctgact tttcgtgtga tgaggctcgt ggaaaaaatg aataatttat     60

gaatttgaga acaattttgt gttgttacgg tattttacta tggaataatc aatcaattga    120

ggattttatg caaatatcgt ttgaatattt ttccgaccct ttgagtactt ttcttcataa    180

ttgcataata ttgtccgctg ccccttttc tgttagacgg tgtcttgatc tacttgctat     240

cgttcaacac caccttattt tctaactatt tttttttag ctcatttgaa tcagcttatg     300

gtgatggcac atttttgcat aaacctagct gtcctcgttg aacataggaa aaaaaaatat    360

ataaacaagg ctctttcact ctccttgcaa tcagatttgg gtttgttccc tttattttca    420

tatttcttgt catattcctt tctcaattat tattttctac tcataacctc acgcaaaata    480

acacagtcaa atcaatcaaa atgactgaca aaaaaactct taaagactta agaaatcgta    540

gttctgttta cgattcaatg gttaaatcac ctaatcgtgc tatgttgcgt gcaactggta    600

tgcaagatga agactttgaa aaacctatcg tcggtgtcat ttcaacttgg gctgaaaaca    660

caccttgtaa tatccactta catgactttg gtaaactagc caaagtcggt gttaaggaag    720

ctggtgcttg gccagttcag ttcggaacaa tcacggtttc tgatggaatc gccatgggaa    780

cccaaggaat gcgtttctcc ttgacatctc gtgatattat tgcagattct attgaagcag    840
```

```
ccatgggagg tcataatgcg gatgcttttg tagccattgg cggttgtgat aaaaacatgc    900
ccggttctgt tatcgctatg gctaacatgg atatcccagc catttttgct tacggcggaa    960
caattgcacc tggtaattta gacggcaaag atatcgattt agtctctgtc tttgaaggtg   1020
tcggccattg gaaccacggc gatatgacca aagaagaagt taaagctttg gaatgtaatg   1080
cttgtcccgg tcctggaggc tgcggtggta tgtatactgc taacacaatg gcgacagcta   1140
ttgaagtttt gggacttagc cttccgggtt catcttctca cccggctgaa tccgcagaaa   1200
agaaagcaga tattgaagaa gctggtcgcg ctgttgtcaa aatgctcgaa atgggcttaa   1260
aaccttctga cattttaacg cgtgaagctt ttgaagatgc tattactgta actatggctc   1320
tgggaggttc aaccaactca acccttcacc tcttagctat tgcccatgct gctaatgtgg   1380
aattgacact tgatgatttc aatactttcc aagaaaaagt tcctcatttg gctgatttga   1440
aaccttctgg tcaatatgta ttccaagacc tttacaaggt cggaggggta ccagcagtta   1500
tgaaatatct ccttaaaaat ggcttccttc atggtgaccg tatcacttgt actggcaaaa   1560
cagtcgctga aaatttgaag gcttttgatg atttaacacc tggtcaaaag gttattatgc   1620
cgcttgaaaa tcctaaacgt gaagatggtc cgctcattat tctccatggt aacttggctc   1680
cagacggtgc cgttgccaaa gtttctggtg taaaagtgcg tcgtcatgtc ggtcctgcta   1740
aggtctttaa ttctgaagaa gaagccattg aagctgtctt gaatgatgat attgttgatg   1800
gtgatgttgt tgtcgtacgt tttgtaggac caaagggcgg tcctggtatg cctgaaatgc   1860
tttccctttc atcaatgatt gttggtaaag ggcaaggtga aaaagttgcc cttctgacag   1920
atggccgctt ctcaggtggt acttatggtc ttgtcgtggg tcatatcgct cctgaagcac   1980
aagatggcgg tccaatcgcc tacctgcaaa caggagacat agtcactatt gaccaagaca   2040
ctaaggaatt acactttgat atctccgatg aagagttaaa acatcgtcaa gagaccattg   2100
aattgccacc gctctattca cgcggtatcc ttggtaaata tgctcacatc gtttcgtctg   2160
cttctagggg agccgtaaca gacttttgga agcctgaaga aactggcaaa aaatgagcga   2220
tttaatctct aattatt                                                  2237
```

<210> SEQ ID NO 70
<211> LENGTH: 4420
<212> TYPE: DNA
<213> ORGANISM: Artificial Sequence
<220> FEATURE:
<223> OTHER INFORMATION: PDC1 A-ilvDSm-BUC cassette

<400> SEQUENCE: 70

```
ttatgtatgc tcttctgact tttcgtgtga tgaggctcgt ggaaaaaatg aataatttat     60
gaatttgaga acaattttgt gttgttacgg tattttacta tggaataatc aatcaattga    120
ggattttatg caaatatcgt ttgaatattt ttccgaccct ttgagtactt ttcttcataa    180
ttgcataata ttgtccgctg cccctttttc tgttagacgg tgtcttgatc tacttgctat    240
cgttcaacac caccttattt tctaactatt ttttttttag ctcatttgaa tcagcttatg    300
gtgatggcac atttttgcat aaacctagct gtcctcgttg aacataggaa aaaaaaatat    360
ataaacaagg ctctttcact ctccttgcaa tcagatttgg gtttgttccc tttattttca    420
tatttcttgt catattcctt tctcaattat tattttctac tcataacctc acgcaaaata    480
acacagtcaa atcaatcaaa atgactgaca aaaaaactct taaagactta agaaatcgta    540
gttctgttta cgattcaatg gttaaatcac ctaatcgtgc tatgttgcgt gcaactggta    600
tgcaagatga agactttgaa aaacctatcg tcggtgtcat ttcaacttgg gctgaaaaca    660
```

```
caccttgtaa tatccactta catgactttg gtaaactagc caaagtcggt gttaaggaag    720

ctggtgcttg gccagttcag ttcggaacaa tcacggtttc tgatggaatc gccatgggaa    780

cccaaggaat gcgtttctcc ttgacatctc gtgatattat tgcagattct attgaagcag    840

ccatgggagg tcataatgcg gatgcttttg tagccattgg cggttgtgat aaaaacatgc    900

ccggttctgt tatcgctatg gctaacatgg atatcccagc catttttgct tacggcggaa    960

caattgcacc tggtaattta gacggcaaag atatcgattt agtctctgtc tttgaaggtg   1020

tcggccattg gaaccacggc gatatgacca aagaagaagt taaagctttg gaatgtaatg   1080

cttgtcccgg tcctggaggc tgcggtggta tgtatactgc taacacaatg gcgacagcta   1140

ttgaagtttt gggacttagc cttccgggtt catcttctca cccggctgaa tccgcagaaa   1200

agaaagcaga tattgaagaa gctggtcgcg ctgttgtcaa aatgctcgaa atgggcttaa   1260

aaccttctga cattttaacg cgtgaagctt ttgaagatgc tattactgta actatggctc   1320

tgggaggttc aaccaactca acccttcacc tcttagctat tgcccatgct gctaatgtgg   1380

aattgacact tgatgatttc aatactttcc aagaaaaagt tcctcatttg gctgatttga   1440

aaccttctgg tcaatatgta ttccaagacc tttacaaggt cggaggggta ccagcagtta   1500

tgaaatatct ccttaaaaat ggcttccttc atggtgaccg tatcacttgt actggcaaaa   1560

cagtcgctga aaatttgaag gcttttgatg atttaacacc tggtcaaaag gttattatgc   1620

cgcttgaaaa tcctaaacgt gaagatggtc cgctcattat tctccatggt aacttggctc   1680

cagacggtgc cgttgccaaa gtttctggtg taaaagtgcg tcgtcatgtc ggtcctgcta   1740

aggtctttaa ttctgaagaa gaagccattg aagctgtctt gaatgatgat attgttgatg   1800

gtgatgttgt tgtcgtacgt tttgtaggac caaagggcgg tcctggtatg cctgaaatgc   1860

tttccctttc atcaatgatt gttggtaaag ggcaaggtga aaaagttgcc cttctgacag   1920

atggccgctt ctcaggtggt acttatggtc ttgtcgtggg tcatatcgct cctgaagcac   1980

aagatggcgg tccaatcgcc tacctgcaaa caggagacat agtcactatt gaccaagaca   2040

ctaaggaatt acactttgat atctccgatg aagagttaaa acatcgtcaa gagaccattg   2100

aattgccacc gctctattca cgcggtatcc ttggtaaata tgctcacatc gtttcgtctg   2160

cttctagggg agccgtaaca gacttttgga agcctgaaga aactggcaaa aaatgagcga   2220

tttaatctct aattattagt taaagtttta taagcatttt tatgtaacga aaaataaatt   2280

ggttcatatt attactgcac tgtcacttac catggaaaga ccagacaaga agttgccgac   2340

agtctgttga attggcctgg ttaggcttaa gtctgggtcc gcttctttac aaatttggag   2400

aatttctctt aaacgatatg tatattcttt tcgttggaaa agatgtcttc caaaaaaaaa   2460

accgatgaat tagtggaacc aaggaaaaaa aaagaggtat ccttgattaa ggaacactgt   2520

ttaaacagtg tggtttccaa aaccctgaaa ctgcattagt gtaatagaag actagacacc   2580

tcgatacaaa taatggttac tcaattcaaa actgccagcg aattcgactc tgcaattgct   2640

caagacaagc tagttgtcgt agatttctac gccacttggt gcggtccatg taaaatgatt   2700

gctccaatga ttgaaaaatg tggctgtggt ttcagggtcc ataaagcttt tcaattcatc   2760

ttttttttt ttgttctttt ttttgattcc ggtttctttg aaattttttt gattcggtaa   2820

tctccgagca gaaggaagaa cgaaggaagg agcacagact tagattggta tatatacgca   2880

tatgtggtgt tgaagaaaca tgaaattgcc cagtattctt aacccaactg cacagaacaa   2940

aaacctgcag gaaacgaaga taaatcatgt cgaaagctac atataaggaa cgtgctgcta   3000

ctcatcctag tcctgttgct gccaagctat ttaatatcat gcacgaaaag caaacaaact   3060
```

```
tgtgtgcttc attggatgtt cgtaccacca aggaattact ggagttagtt gaagcattag   3120

gtcccaaaat ttgtttacta aaaacacatg tggatatctt gactgatttt tccatggagg   3180

gcacagttaa gccgctaaag gcattatccg ccaagtacaa ttttttactc ttcgaagaca   3240

gaaaatttgc tgacattggt aatacagtca aattgcagta ctctgcgggt gtatacagaa   3300

tagcagaatg ggcagacatt acgaatgcac acggtgtggt gggcccaggt attgttagcg   3360

gtttgaagca ggcggcggaa gaagtaacaa aggaacctag aggccttttg atgttagcag   3420

aattgtcatg caagggctcc ctagctactg gagaatatac taagggtact gttgacattg   3480

cgaagagcga caaagatttt gttatcggct ttattgctca aagagacatg ggtggaagag   3540

atgaaggtta cgattggttg attatgacac ccggtgtggg tttagatgac aagggagacg   3600

cattgggtca acagtataga accgtggatg atgtggtctc tacaggatct gacattatta   3660

ttgttggaag aggactattt gcaaagggaa gggatgctaa ggtagagggt gaacgttaca   3720

gaaaagcagg ctgggaagca tatttgagaa gatgcggcca gcaaaactaa aaaactgtat   3780

tataagtaaa tgcatgtata ctaaactcac aaattagagc ttcaatttaa ttatatcagt   3840

tattacccgg gaatctcggt cgtaatgatt tctataatga cgaaaaaaaa aaaattggaa   3900

agaaaaagct tcatggcctt ccactttccc aaacaacacc tacggtatct ctcaagtctt   3960

atggggttcc attggtttca ccactggtgc taccttgggt gctgctttcg ctgctgaaga   4020

aattgatcca aagaagagag ttatcttatt cattggtgac ggttctttgc aattgactgt   4080

tcaagaaatc tccaccatga tcagatgggg cttgaagcca tacttgttcg tcttgaacaa   4140

cgatggttac accattgaaa agttgattca cggtccaaag gctcaataca acgaaattca   4200

aggttgggac cacctatcct tgttgccaac tttcggtgct aaggactatg aaacccacag   4260

agtcgctacc accggtgaat gggacaagtt gacccaagac aagtctttca acgacaactc   4320

taagatcaga atgattgaaa tcatgttgcc agtcttcgat gctccacaaa acttggttga   4380

acaagctaag ttgactgctg ctaccaacgc taagcaataa                         4420
```

```
<210> SEQ ID NO 71
<211> LENGTH: 2686
<212> TYPE: DNA
<213> ORGANISM: Artificial Sequence
<220> FEATURE:
<223> OTHER INFORMATION: pUC19

<400> SEQUENCE: 71
```

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt cgagctcggt acccggggat    420

cctctagagt cgacctgcag gcatgcaagc ttggcgtaat catggtcata gctgtttcct    480

gtgtgaaatt gttatccgct cacaattcca cacaacatac gagccggaag cataaagtgt    540

aaagcctggg gtgcctaatg agtgagctaa ctcacattaa ttgcgttgcg ctcactgccc    600

gctttccagt cgggaaacct gtcgtgccag ctgcattaat gaatcggcca acgcgcgggg    660

agaggcggtt tgcgtattgg gcgctcttcc gcttcctcgc tcactgactc gctgcgctcg    720
```

```
gtcgttcggc tgcggcgagc ggtatcagct cactcaaagg cggtaatacg gttatccaca     780

gaatcagggg ataacgcagg aaagaacatg tgagcaaaag gccagcaaaa ggccaggaac     840

cgtaaaaagg ccgcgttgct ggcgtttttc cataggctcc gcccccctga cgagcatcac     900

aaaaatcgac gctcaagtca gaggtggcga aacccgacag gactataaag ataccaggcg     960

tttccccctg gaagctccct cgtgcgctct cctgttccga ccctgccgct taccggatac    1020

ctgtccgcct ttctcccttc gggaagcgtg gcgctttctc atagctcacg ctgtaggtat    1080

ctcagttcgg tgtaggtcgt tcgctccaag ctgggctgtg tgcacgaacc ccccgttcag    1140

cccgaccgct gcgccttatc cggtaactat cgtcttgagt ccaacccggt aagacacgac    1200

ttatcgccac tggcagcagc cactggtaac aggattagca gagcgaggta tgtaggcggt    1260

gctacagagt tcttgaagtg gtggcctaac tacggctaca ctagaaggac agtatttggt    1320

atctgcgctc tgctgaagcc agttaccttc ggaaaaagag ttggtagctc ttgatccggc    1380

aaacaaacca ccgctggtag cggtggtttt tttgtttgca agcagcagat tacgcgcaga    1440

aaaaaaggat ctcaagaaga tcctttgatc ttttctacgg ggtctgacgc tcagtggaac    1500

gaaaactcac gttaagggat tttggtcatg agattatcaa aaaggatctt cacctagatc    1560

cttttaaatt aaaaatgaag ttttaaatca atctaaagta tatatgagta aacttggtct    1620

gacagttacc aatgcttaat cagtgaggca cctatctcag cgatctgtct atttcgttca    1680

tccatagttg cctgactccc cgtcgtgtag ataactacga tacgggaggg cttaccatct    1740

ggccccagtg ctgcaatgat accgcgagac ccacgctcac cggctccaga tttatcagca    1800

ataaaccagc cagccggaag ggccgagcgc agaagtggtc ctgcaacttt atccgcctcc    1860

atccagtcta ttaattgttg ccgggaagct agagtaagta gttcgccagt taatagtttg    1920

cgcaacgttg ttgccattgc tacaggcatc gtggtgtcac gctcgtcgtt tggtatggct    1980

tcattcagct ccggttccca acgatcaagg cgagttacat gatcccccat gttgtgcaaa    2040

aaagcggtta gctccttcgg tcctccgatc gttgtcagaa gtaagttggc cgcagtgtta    2100

tcactcatgg ttatggcagc actgcataat tctcttactg tcatgccatc cgtaagatgc    2160

ttttctgtga ctggtgagta ctcaaccaag tcattctgag aatagtgtat gcggcgaccg    2220

agttgctctt gcccggcgtc aatacgggat aataccgcgc cacatagcag aactttaaaa    2280

gtgctcatca ttggaaaacg ttcttcgggg cgaaaactct caaggatctt accgctgttg    2340

agatccagtt cgatgtaacc cactcgtgca cccaactgat cttcagcatc ttttactttc    2400

accagcgttt ctgggtgagc aaaaacagga aggcaaaatg ccgcaaaaaa gggaataagg    2460

gcgacacgga aatgttgaat actcatactc ttcctttttc aatattattg aagcatttat    2520

cagggttatt gtctcatgag cggatacata tttgaatgta tttagaaaaa taaacaaata    2580

ggggttccgc gcacatttcc ccgaaaagtg ccacctgacg tctaagaaac cattattatc    2640

atgacattaa cctataaaaa taggcgtatc acgaggccct ttcgtc                   2686
```

<210> SEQ ID NO 72
<211> LENGTH: 3521
<212> TYPE: DNA
<213> ORGANISM: Artificial Sequence
<220> FEATURE:
<223> OTHER INFORMATION: PDC5 A-sadB-BUC cassette

<400> SEQUENCE: 72

```
aaggaaataa agcaaataac aataacacca ttattttaat ttttttttcta ttactgtcgc      60

taacacctgt atggttgcaa ccaggtgaga atccttctga tgcatacttt atgcgtttat     120
```

```
gcgttttgcg ccccttggaa aaaaattgat tctcatcgta aatgcatact acatgcgttt    180
atgggaaaag cctccatatc caaaggtcgc gtttctttta gaaaaactaa tacgtaaacc    240
tgcattaagg taagattata tcagaaaatg tgttgcaaga aatgcattat gcaatttttt    300
gattatgaca atctctcgaa agaaatttca tatgatgaga cttgaataat gcagcggcgc    360
ttgctaaaag aacttgtata taagagctgc cattctcgat caatatactg tagtaagtcc    420
tttcctctct ttcttattac acttatttca cataatcaat ctcaaagaga acaacacaat    480
acaataacaa gaagaacaaa atgaaagctc tggtttatca cggtgaccac aagatctcgc    540
ttgaagacaa gcccaagccc acccttcaaa agcccacgga tgtagtagta cgggttttga    600
agaccacgat ctgcggcacg gatctcggca tctacaaagg caagaatcca gaggtcgccg    660
acgggcgcat cctgggccat gaaggggtag gcgtcatcga ggaagtgggc gagagtgtca    720
cgcagttcaa gaaaggcgac aaggtcctga tttcctgcgt cacttcttgc ggctcgtgcg    780
actactgcaa gaagcagctt tactcccatt gccgcgacgg cgggtggatc ctgggttaca    840
tgatcgatgg cgtgcaggcc gaatacgtcc gcatcccgca tgccgacaac agcctctaca    900
agatccccca gacaattgac gacgaaatcg ccgtcctgct gagcgacatc ctgcccaccg    960
gccacgaaat cggcgtccag tatgggaatg tccagccggg cgatgcggtg gctattgtcg   1020
gcgcgggccc cgtcggcatg tccgtactgt tgaccgccca gttctactcc ccctcgacca   1080
tcatcgtgat cgacatggac gagaatcgcc tccagctcgc caaggagctc ggggcaacgc   1140
acaccatcaa ctccggcacg gagaacgttg tcgaagccgt gcataggatt gcggcagagg   1200
gagtcgatgt tgcgatcgag gcggtgggca taccggcgac ttgggacatc tgccaggaga   1260
tcgtcaagcc cggcgcgcac atcgccaacg tcggcgtgca tggcgtcaag gttgacttcg   1320
agattcagaa gctctggatc aagaacctga cgatcaccac gggactggtg aacacgaaca   1380
cgacgcccat gctgatgaag gtcgcctcga ccgacaagct tccgttgaag aagatgatta   1440
cccatcgctt cgagctggcc gagatcgagc acgcctatca ggtattcctc aatggcgcca   1500
aggagaaggc gatgaagatc atcctctcga acgcaggcgc tgcctgagct aattaacata   1560
aaactcatga ttcaacgttt gtgtattttt ttacttttga aggttataga tgtttaggta   1620
aataattggc atagatatag ttttagtata ataaatttct gatttggttt aaaatatcaa   1680
ctattttttt tcacatatgt tcttgtaatt acttttctgt cctgtcttcc aggttaaaga   1740
ttagcttcta atattttagg tggtttatta tttaatttta tgctgattaa tttatttact   1800
tgtttaaacg gccggccaat gtggctgtgg tttcagggtc cataaagctt ttcaattcat   1860
cttttttttt tttgttcttt tttttgattc cggtttcttt gaaatttttt tgattcggta   1920
atctccgagc agaaggaaga acgaaggaag gagcacagac ttagattggt atatatacgc   1980
atatgtggtg ttgaagaaac atgaaattgc ccagtattct taacccaact gcacagaaca   2040
aaaacctgca ggaaacgaag ataaatcatg tcgaaagcta catataagga acgtgctgct   2100
actcatccta gtcctgttgc tgccaagcta tttaatatca tgcacgaaaa gcaaacaaac   2160
ttgtgtgctt cattggatgt tcgtaccacc aaggaattac tggagttagt tgaagcatta   2220
ggtcccaaaa tttgtttact aaaaacacat gtggatatct tgactgattt ttccatggag   2280
ggcacagtta agccgctaaa ggcattatcc gccaagtaca atttttttact cttcgaagac   2340
agaaaatttg ctgacattgg taatacagtc aaattgcagt actctgcggg tgtatacaga   2400
atagcagaat gggcagacat tacgaatgca cacggtgtgg tgggcccagg tattgttagc   2460
ggtttgaagc aggcggcgga agaagtaaca aaggaaccta gaggcctttt gatgttagca   2520
```

```
gaattgtcat gcaagggctc cctagctact ggagaatata ctaagggtac tgttgacatt   2580
gcgaagagcg acaaagattt tgttatcggc tttattgctc aaagagacat gggtggaaga   2640
gatgaaggtt acgattggtt gattatgaca cccggtgtgg gtttagatga caagggagac   2700
gcattgggtc aacagtatag aaccgtggat gatgtggtct ctacaggatc tgacattatt   2760
attgttggaa gaggactatt tgcaaaggga agggatgcta aggtagaggg tgaacgttac   2820
agaaaagcag gctgggaagc atatttgaga agatgcggcc agcaaaacta aaaaactgta   2880
ttataagtaa atgcatgtat actaaactca caaattagag cttcaattta attatatcag   2940
ttattacccg ggaatctcgg tcgtaatgat ttctataatg acgaaaaaaa aaaaattgga   3000
aagaaaaagc ttcatggcct tctactttcc caacagatgt atacgctatc gtccaagtct   3060
tgtggggttc cattggtttc acagtcggcg ctctattggg tgctactatg gccgctgaag   3120
aacttgatcc aaagaagaga gttattttat tcattggtga cggttctcta caattgactg   3180
ttcaagaaat ctctaccatg attagatggg gtttgaagcc atacattttt gtcttgaata   3240
acaacggtta caccattgaa aaattgattc acggtcctca tgccgaatat aatgaaattc   3300
aaggttggga ccacttggcc ttattgccaa cttttggtgc tagaaactac gaaacccaca   3360
gagttgctac cactggtgaa tgggaaaagt tgactcaaga caaggacttc caagacaact   3420
ctaagattag aatgattgaa gttatgttgc cagtctttga tgctccacaa aacttggtta   3480
aacaagctca attgactgcc gctactaacg ctaaacaata a                      3521
```

<210> SEQ ID NO 73
<211> LENGTH: 1685
<212> TYPE: DNA
<213> ORGANISM: Artificial Sequence
<220> FEATURE:
<223> OTHER INFORMATION: gpd2::loxP-URA3-loxP cassette

<400> SEQUENCE: 73

```
gtattttggt agattcaatt ctctttccct ttccttttcc ttcgctcccc ttccttatca     60
gcattgcgga ttacgtattc taatgttcag ataacttcgt atagcataca ttatacgaag    120
ttatgcagat tgtactgaga gtgcaccata ccacagcttt tcaattcaat tcatcatttt    180
tttttattc tttttttttga tttcggtttc tttgaaattt ttttgattcg gtaatctccg   240
aacagaagga agaacgaagg aaggagcaca gacttagatt ggtatatata cgcatatgta    300
gtgttgaaga aacatgaaat tgcccagtat tcttaaccca actgcacaga acaaaaacct    360
gcaggaaacg aagataaatc atgtcgaaag ctacatataa ggaacgtgct gctactcatc    420
ctagtcctgt tgctgccaag ctatttaata tcatgcacga aaagcaaaca aacttgtgtg    480
cttcattgga tgttcgtacc accaaggaat tactggagtt agttgaagca ttaggtccca    540
aaatttgttt actaaaaaca catgtggata tcttgactga tttttccatg gagggcacag    600
ttaagccgct aaaggcatta tccgccaagt acaatttttt actcttcgaa gacagaaaat    660
ttgctgacat tggtaataca gtcaaattgc agtactctgc gggtgtatac agaatagcag    720
aatgggcaga cattacgaat gcacacggtg tggtgggccc aggtattgtt agcggtttga    780
agcaggcggc agaagaagta acaaaggaac ctagaggcct tttgatgtta gcagaattgt    840
catgcaaggg ctccctatct actggagaat atactaaggg tactgttgac attgcgaaga    900
gcgacaaaga ttttgttatc ggctttattg ctcaaagaga catgggtgga agagatgaag    960
gttacgattg gttgattatg acacccggtg tgggtttaga tgacaaggga gacgcattgg   1020
gtcaacagta tagaaccgtg gatgatgtgg tctctacagg atctgacatt attattgttg   1080
```

-continued

```
gaagaggact atttgcaaag ggaagggatg ctaaggtaga gggtgaacgt tacagaaaag   1140
caggctggga agcatatttg agaagatgcg gccagcaaaa ctaaaaaact gtattataag   1200
taaatgcatg tatactaaac tcacaaatta gagcttcaat ttaattatat cagttattac   1260
cctatgcggt gtgaaatacc gcacagatgc gtaaggagaa aataccgcat caggaaattg   1320
taaacgttaa tattttgtta aaattcgcgt taaatttttg ttaaatcagc tcatttttta   1380
accaataggc cgaaatcggc aaaatccctt ataaatcaaa agaatagacc gagatagggt   1440
tgagtgttgt tccagtttgg aacaagagtc cactattaaa gaacgtggac tccaacgtca   1500
aagggcgaaa aaccgtctat cagggcgatg gcccactacg tgaaccatca ccctaatcaa   1560
gataacttcg tatagcatac attatacgaa gttatccagt gatgatacaa cgagttagcc   1620
aaggtgacac tctccccccc cctcccccctc tgatctttcc tgttgcctct ttttccccca   1680
accaa                                                              1685
```